US012448630B2

(12) United States Patent
Chen et al.

(10) Patent No.: US 12,448,630 B2
(45) Date of Patent: Oct. 21, 2025

(54) CRISPR-Cas SYSTEMS AND USES THEREOF

(71) Applicant: Lumiere Therapeutics Co., Ltd., Jiangsu (CN)

(72) Inventors: Bohong Chen, Guangzhou (CN); Yang Hu, Guangzhou (CN); Yulin Yu, Guangzhou (CN); Wenqiong Tan, Guangzhou (CN); Shaoyun Lin, Guangzhou (CN); Wenchang Xu, Guangzhou (CN); Youyu Wu, Guangzhou (CN); Xiaojie Ma, Guangzhou (CN); Jiajun Yu, Guangzhou (CN); Jinshuai Sun, Guangzhou (CN)

(73) Assignee: Lumiere Therapeutics Co., Ltd., Jiangsu (CN)

( * ) Notice: Subject to any disclaimer, the term of this patent is extended or adjusted under 35 U.S.C. 154(b) by 0 days.

(21) Appl. No.: 18/820,460

(22) Filed: Aug. 30, 2024

(65) Prior Publication Data

US 2025/0146023 A1 May 8, 2025

(30) Foreign Application Priority Data

Nov. 6, 2023 (CN) ........................ 202311464815.0

(51) Int. Cl.

*C12N 9/22* (2006.01)
*C12N 9/78* (2006.01)
*C12N 15/11* (2006.01)
*C12N 15/90* (2006.01)

(52) U.S. Cl.

CPC ............... *C12N 15/90* (2013.01); *C12N 9/22* (2013.01); *C12N 9/78* (2013.01); *C12N 15/11* (2013.01); *C12Y 305/04004* (2013.01); *C12N 2310/20* (2017.05); *C12N 2310/531* (2013.01)

(58) Field of Classification Search

None
See application file for complete search history.

(56) References Cited

U.S. PATENT DOCUMENTS

2020/0063126 A1* 2/2020 Cheng .................... C12N 15/90
2023/0332119 A1* 10/2023 Chong ................... C12N 15/63

FOREIGN PATENT DOCUMENTS

WO WO-2022174099 A2 * 8/2022 ........... C12N 15/102
WO WO-2024156085 A1 * 8/2024

OTHER PUBLICATIONS

Huang et al., Structural basis for two metal-ion catalysis of DNA cleavage by Cas12i2. Nature Communications (2020), 11:5241, pp. 1-14 (Year: 2020).*

Yan et al., Functionally diverse type V CRISPR-Cas systems. Science (2019), 363: 88-91 (Year: 2019).*

Duan et al., An engineered Cas12i nuclease that is an efficient genome editing tool in animals and plants. The Innovation (2024), 5(2): 100564 (Year: 2024).*

Zhang et al., Mechanisms for target recognition and cleavage by the Cas12i RNA-guided endonuclease. Nature Structural and Molecular Biology (2020), 27: 1069-1076 (Year: 2020).*

Liu et al., Synthetic chimeric nucleases function for efficient genome editing. Nature Communications (2019), 10:5524, pp. 1-11 (Year: 2019).*

* cited by examiner

*Primary Examiner* — Abigail Vanhorn
*Assistant Examiner* — Catherine Konopka
(74) *Attorney, Agent, or Firm* — Sheppard, Mullin, Richter &Hampton LLP

(57) ABSTRACT

Disclosed herein are a Cas12i polypeptide and use thereof in a CRISPR-Cas system. Specifically disclosed herein are a Cas12i polypeptide, a Cas12i fusion polypeptide, a guide RNA, a complex formed by the Cas12i polypeptide or fusion polypeptide with the guide RNA, a nucleic acid, a vector, a vector system, a delivery system, a kit, a composition, and a method for modifying a nucleic acid using the components described above.

54 Claims, 40 Drawing Sheets

Specification includes a Sequence Listing.

| | |
|---|---|
| 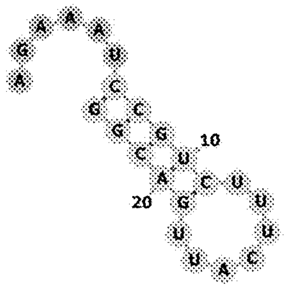 5'-AGAAATCCGTCTTTCATTGACGG-3' (SEQ ID NO. 7) | 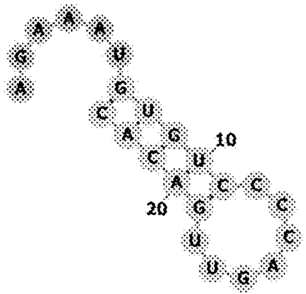 5'-AGAAATGTGTCCCCAGTTGACAC-3' (SEQ ID NO. 8) |
| Secondary structure of crRNA-1 (calculated by the minimum free energy (MFE) algorithm); the secondary structures of crRNA-1 to crRNA-8 are highly similar | Secondary structure of crRNA-2 |
| 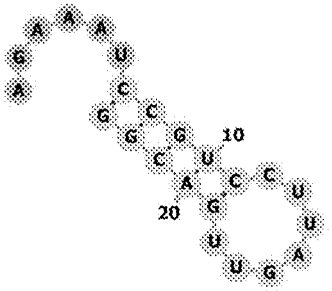 5'-AGAAATCCGTCCTTAGTTGACGG-3' (SEQ ID NO. 9) | 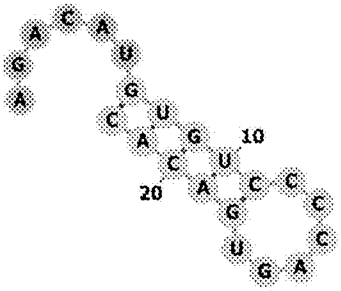 5'-AGACATGTGTCCCCAGTGACAC-3' (SEQ ID NO. 10) |
| Secondary structure of crRNA-3 | Secondary structure of crRNA-4 |
| 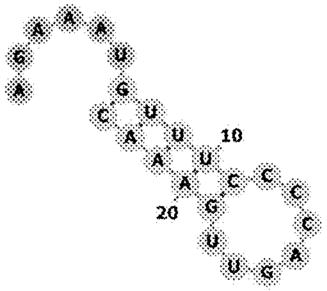 5'-AGAAATGTTTCCCCAGTTGAAAC-3' (SEQ ID NO. 11) | 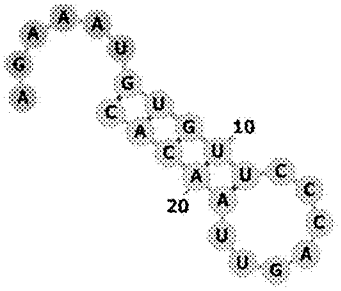 5'-AGAAATGTGTTCCCAGTTAACAC-3' (SEQ ID NO. 12) |
| Secondary structure of crRNA-5 | Secondary structure of crRNA-6 |
| 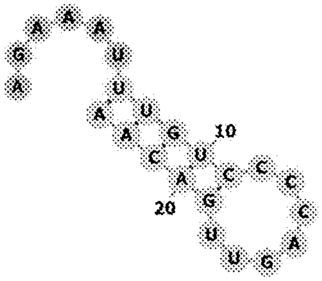 5'-AGAAATTTGTCCCCAGTTGACAA-3' (SEQ ID NO. 13) | 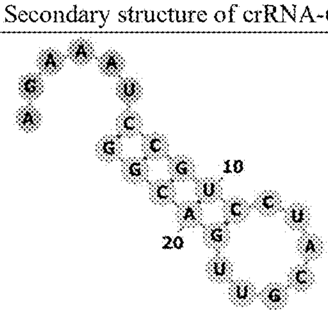 5'-AGAAATCCGTCCTACGTTGACGG-3' (SEQ ID NO.14) |
| Secondary structure of crRNA-7 | Secondary structure of crRNA-8 |

FIG. 1

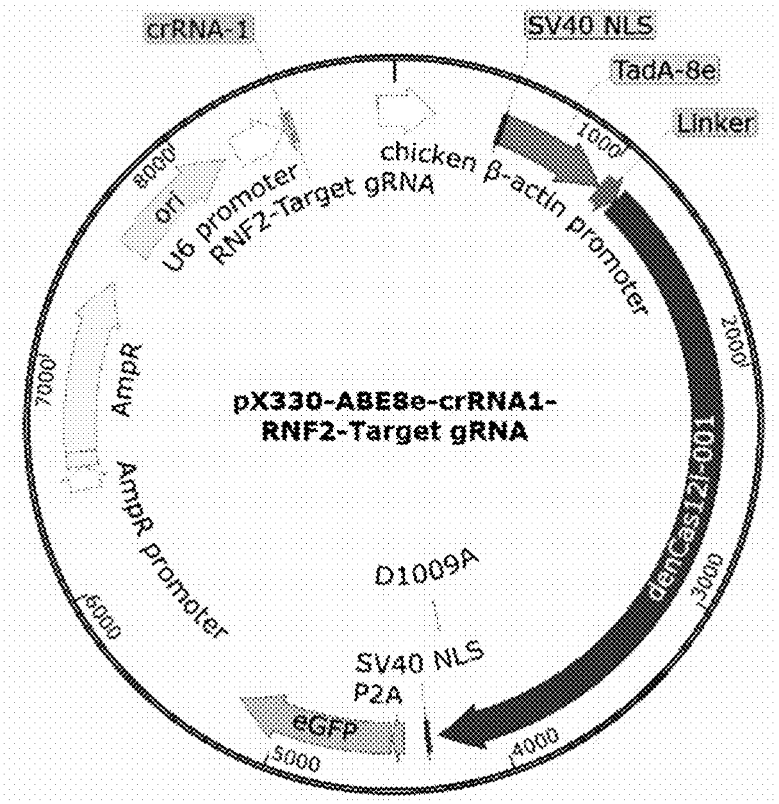
Vector 1
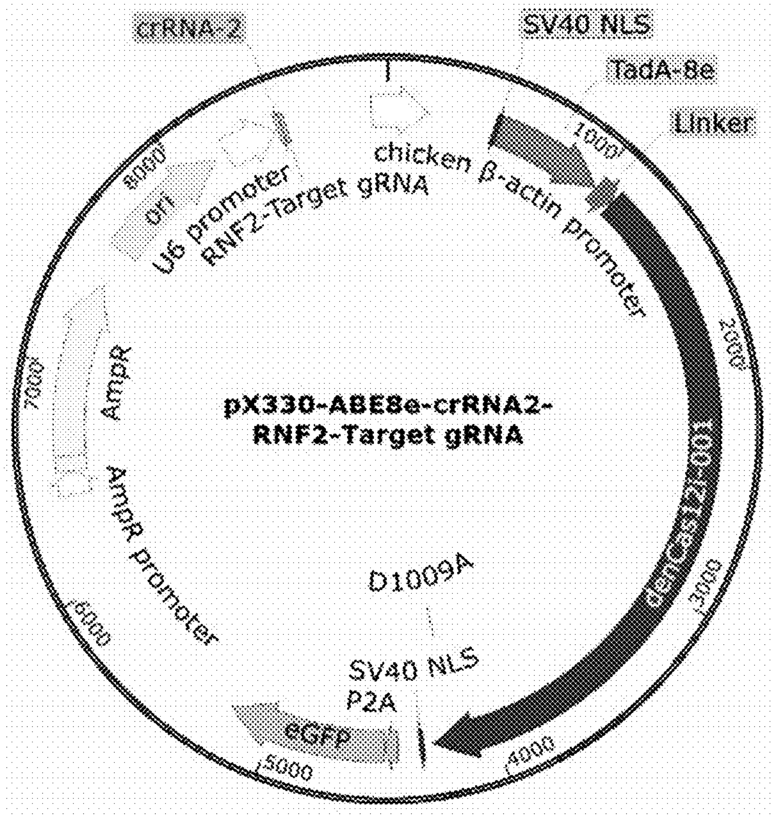
Vector 2
FIG. 2

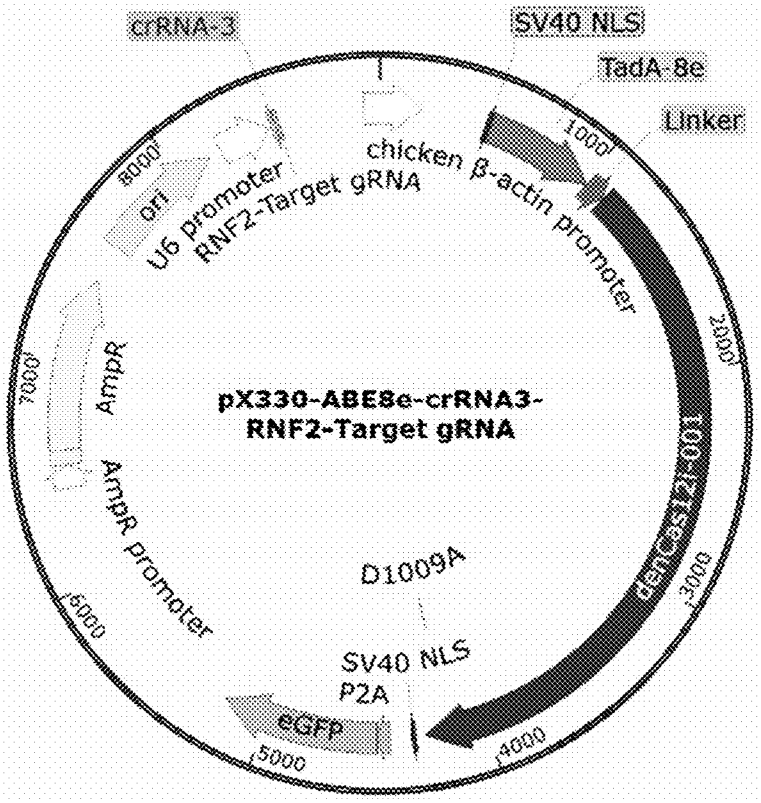
Vector 3
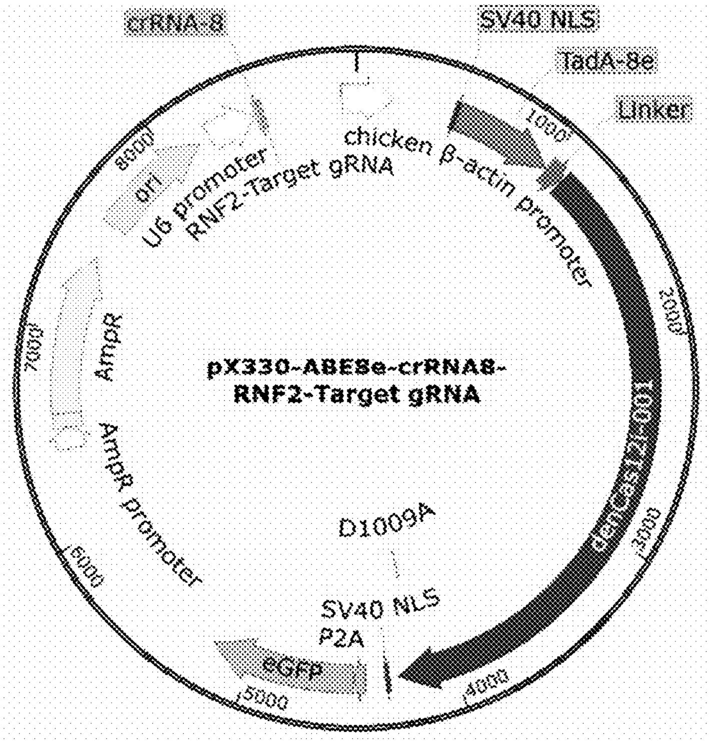
Vector 4
FIG. 2 (Con't)

5'-TTCAACATATCCAAACAAAT-3' (SEQ ID NO. 75)
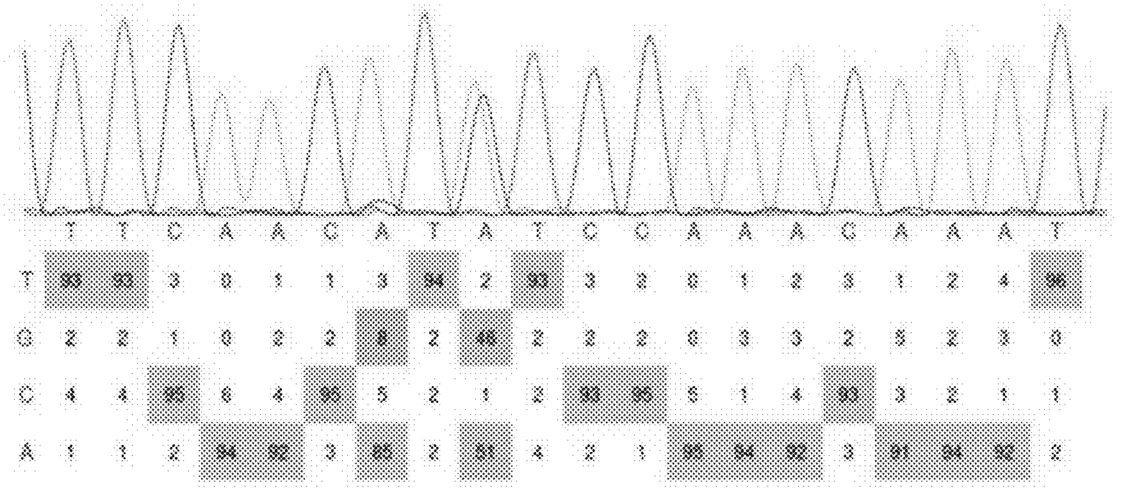
Sequencing results of cells transfected with pX330-ABE8e-crRNA1-RNF2-Target gRNA (vector 1)
5'-TTCAACATATCCAAACAAAT-3' (SEQ ID NO. 75)
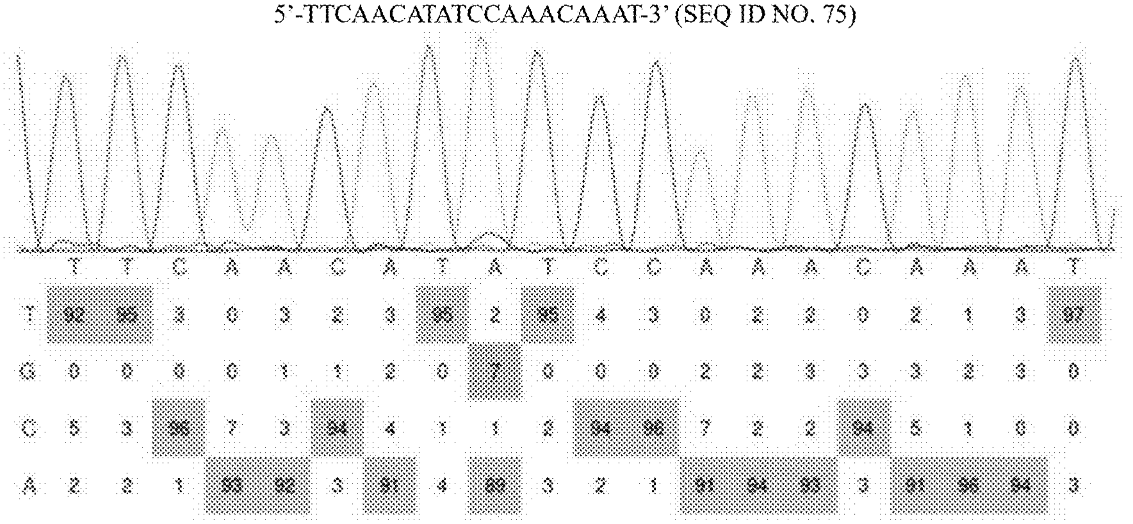
Sequencing results of cells transfected with pX330-ABE8e-crRNA2-RNF2-Target gRNA (vector 2)
FIG. 3

5'-TTCAACATATCCAAACAAAT-3' (SEQ ID NO. 75)
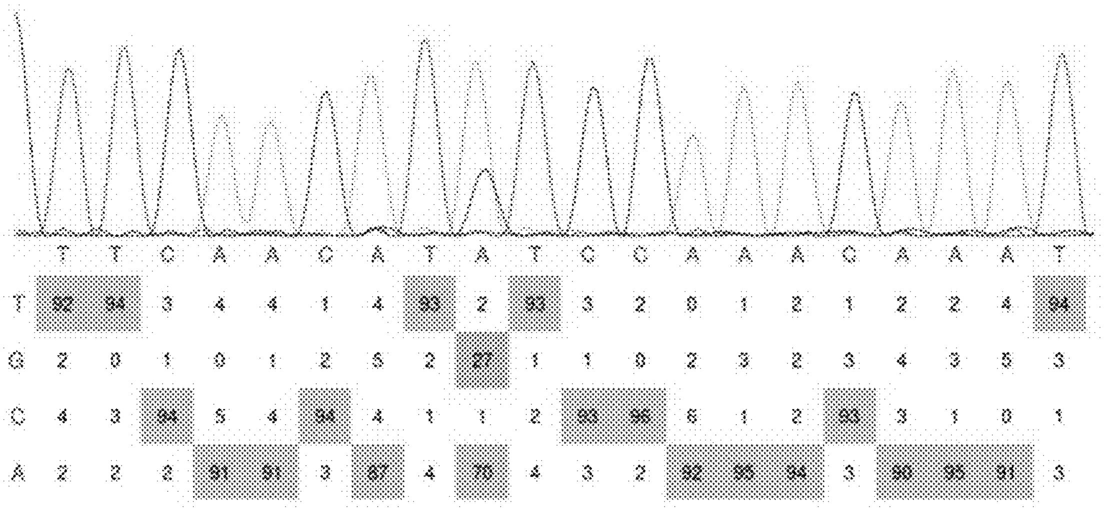
Sequencing results of cells transfected with pX330-ABE8e-crRNA3-RNF2-Target gRNA (vector 3)
5'-TTCAACATATCCAAACAAAT-3' (SEQ ID NO. 75)
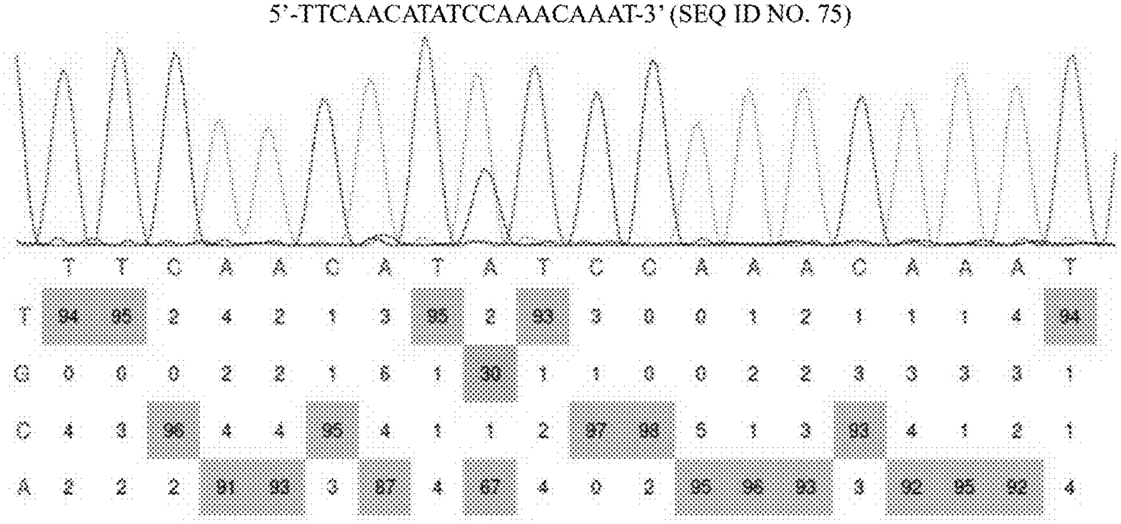
Sequencing results of cells transfected with pX330-ABE8e-crRNA8-RNF2-Target gRNA (vector 4)
FIG. 3 (Con't)

A
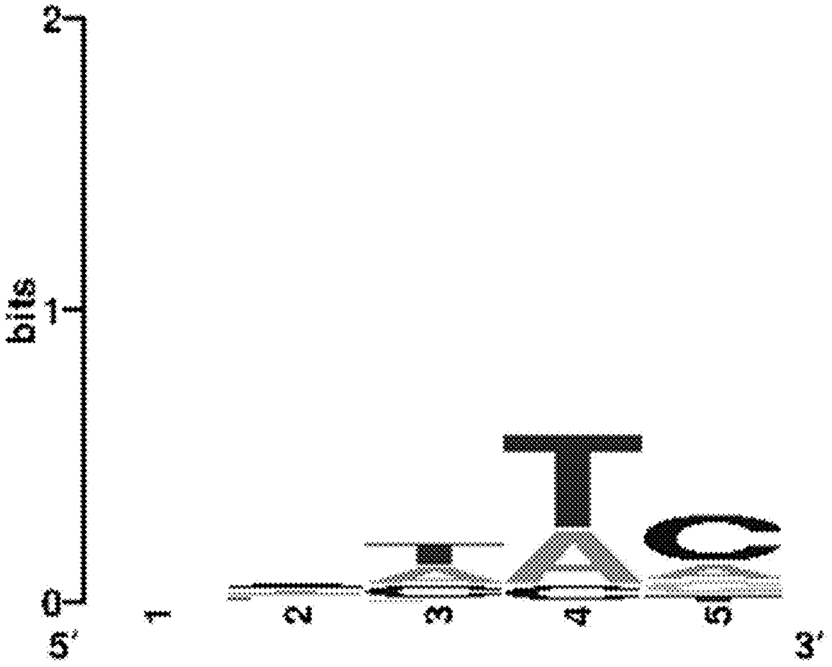
B
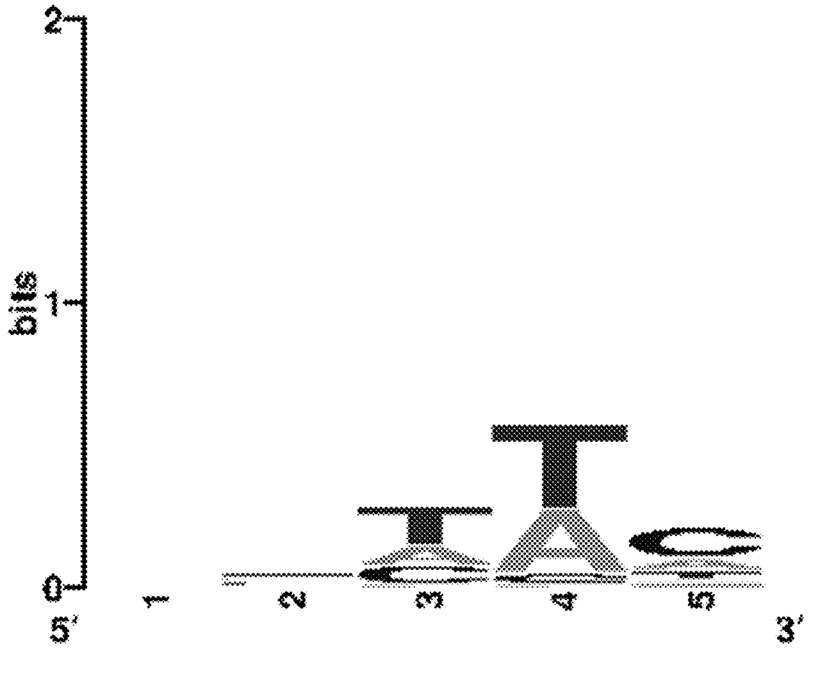
FIG. 4

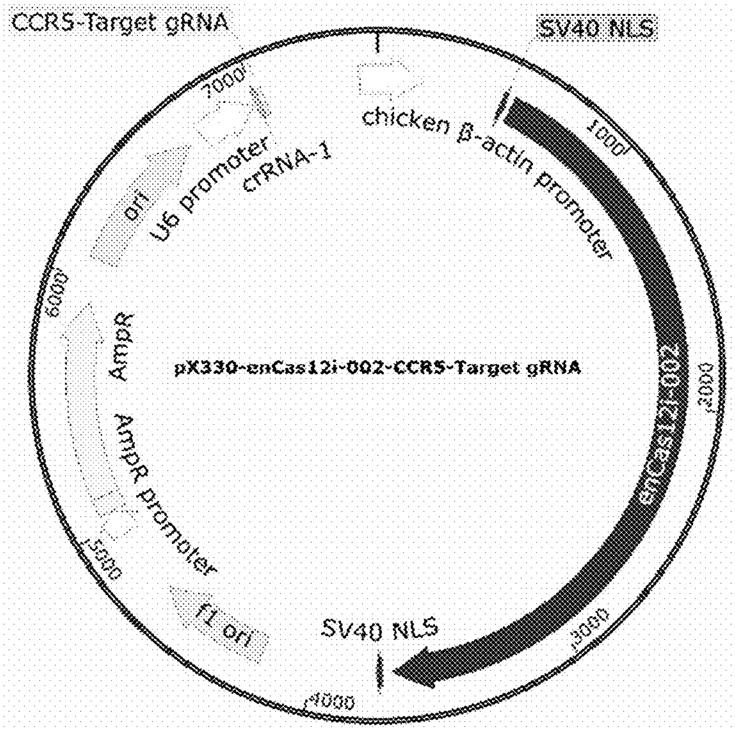
Vector 5
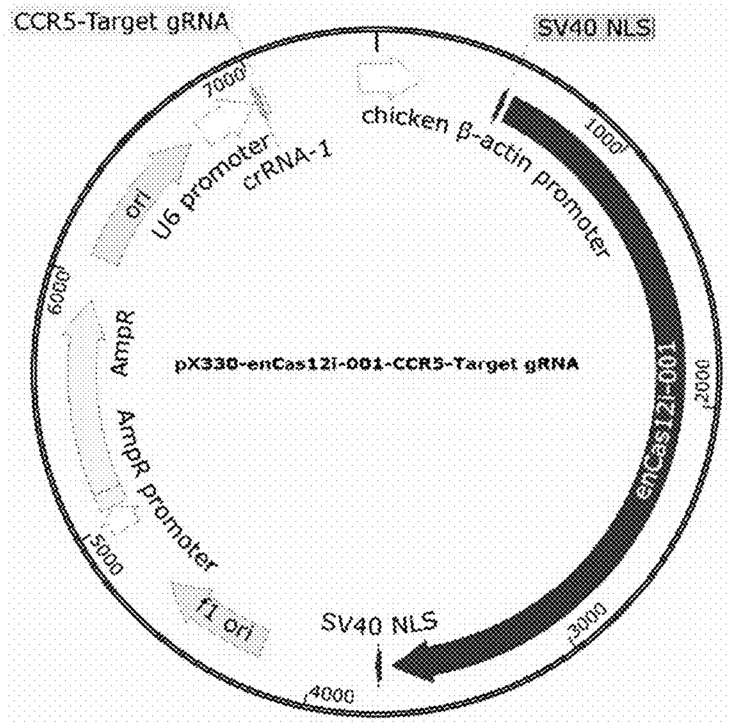
Vector 6
FIG. 5

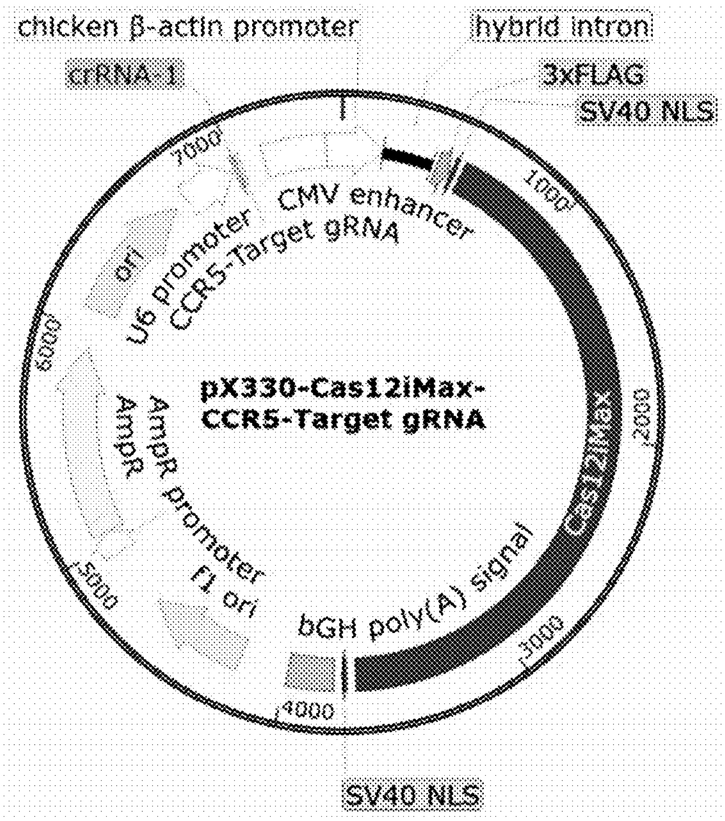
Vector 7
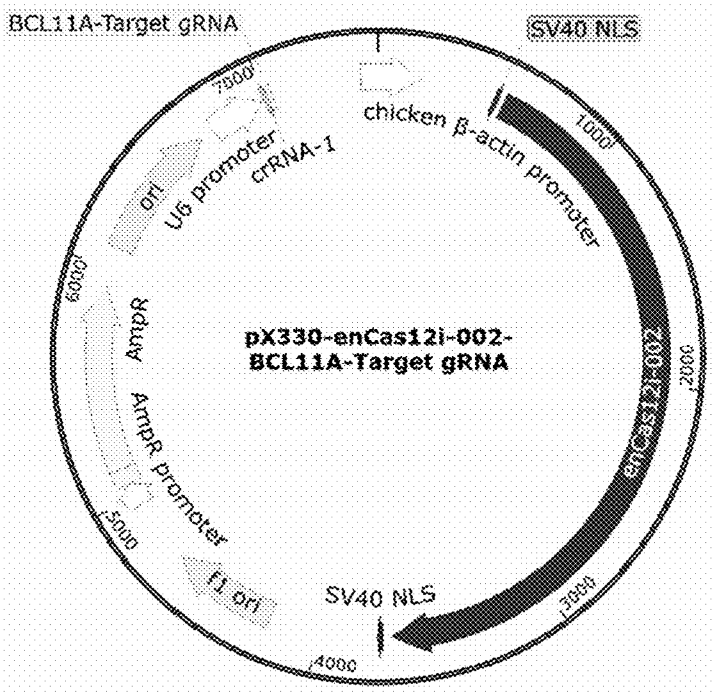
Vector 8
FIG. 5 (Con't)

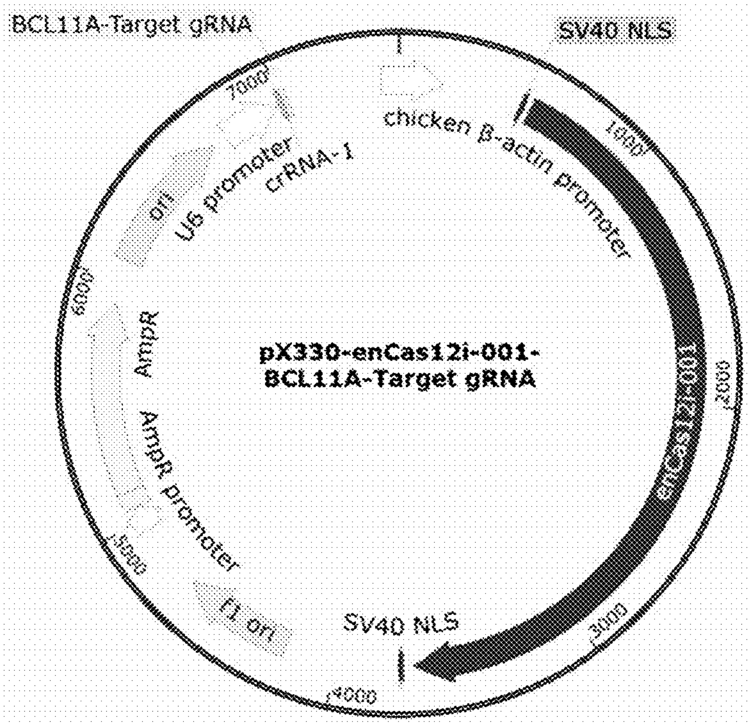
Vector 9
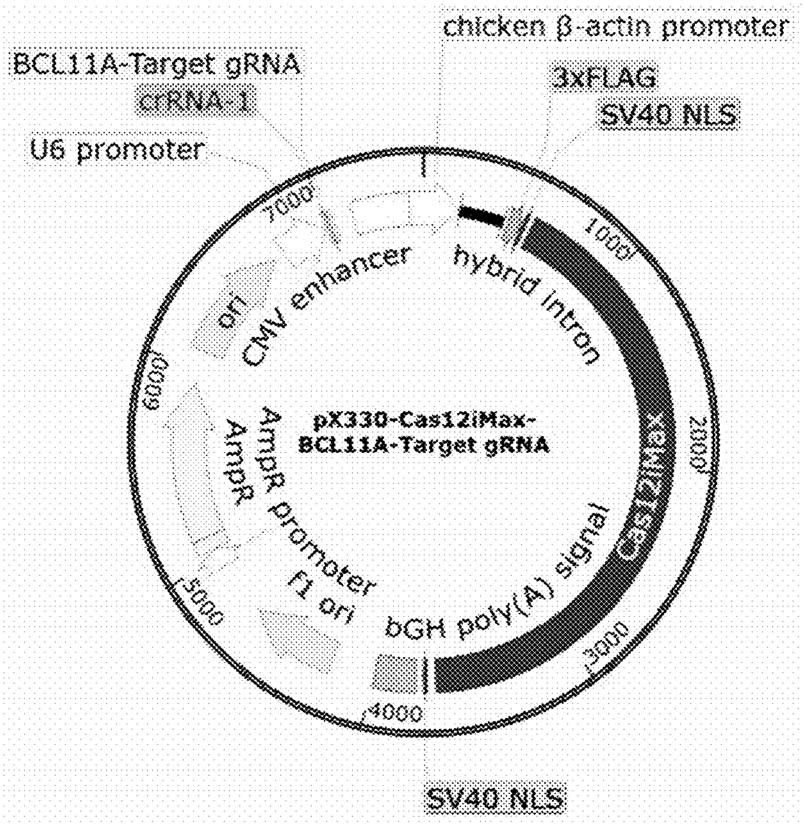
Vector 10
FIG. 5 (Con't)

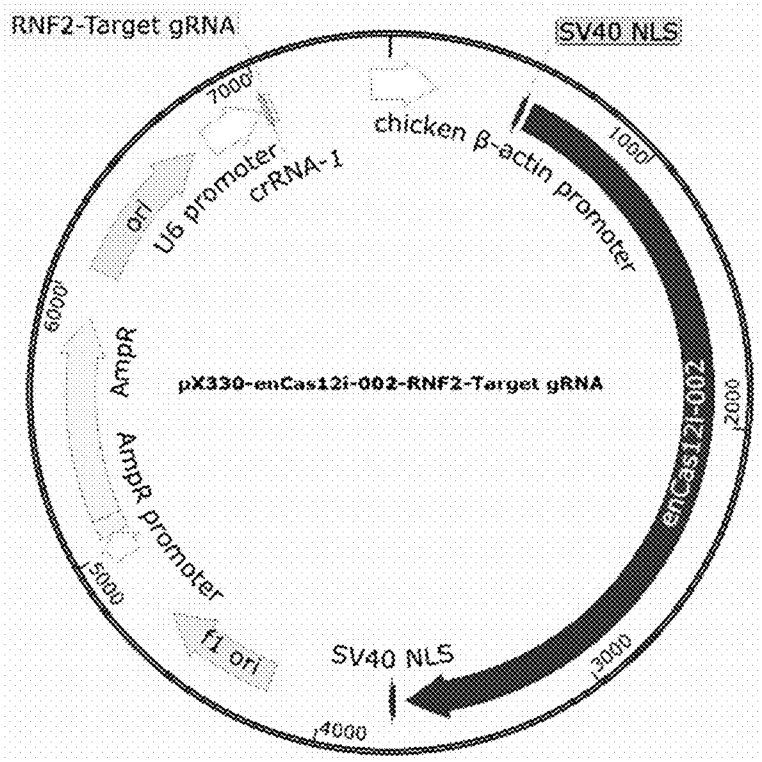
Vector 11
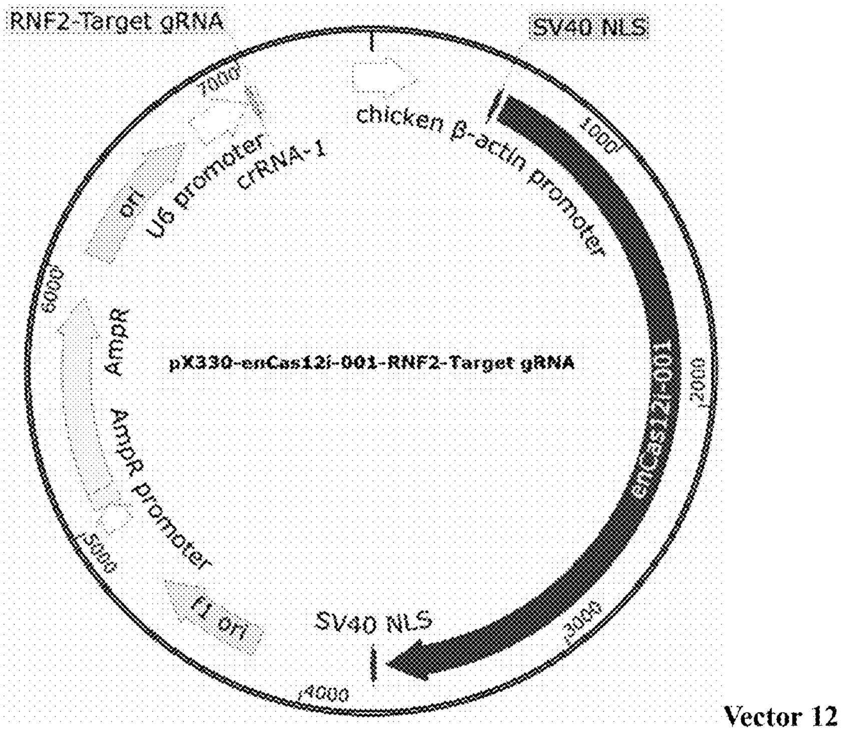
Vector 12
FIG. 6

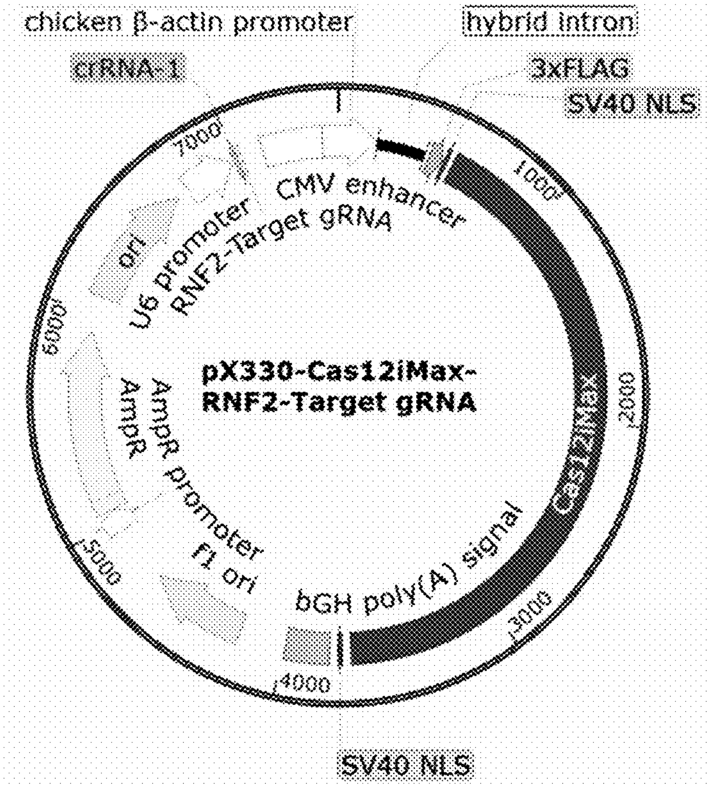
Vector 13
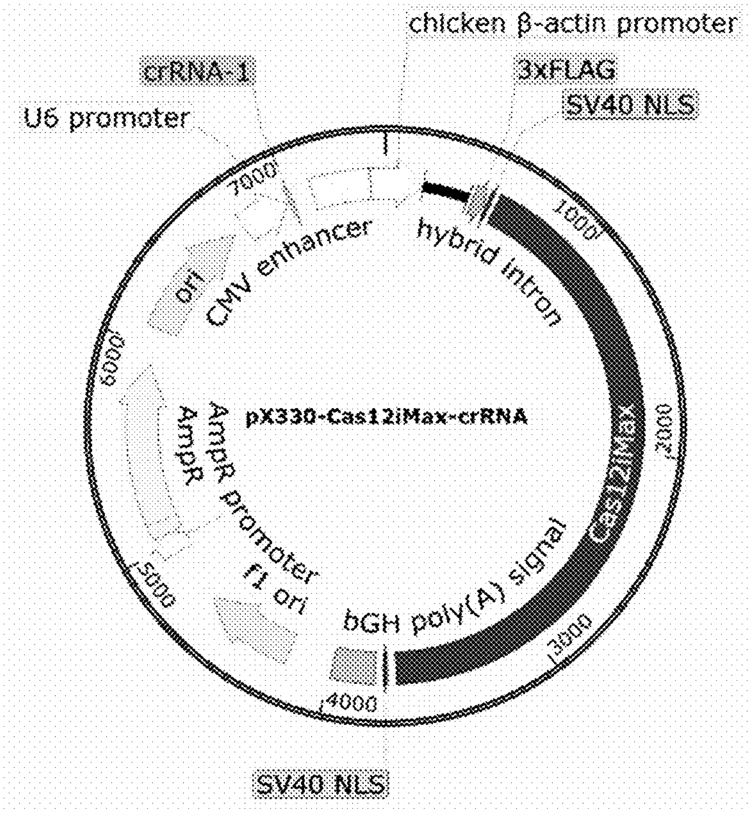
Vector 14
FIG. 6 (Con't)

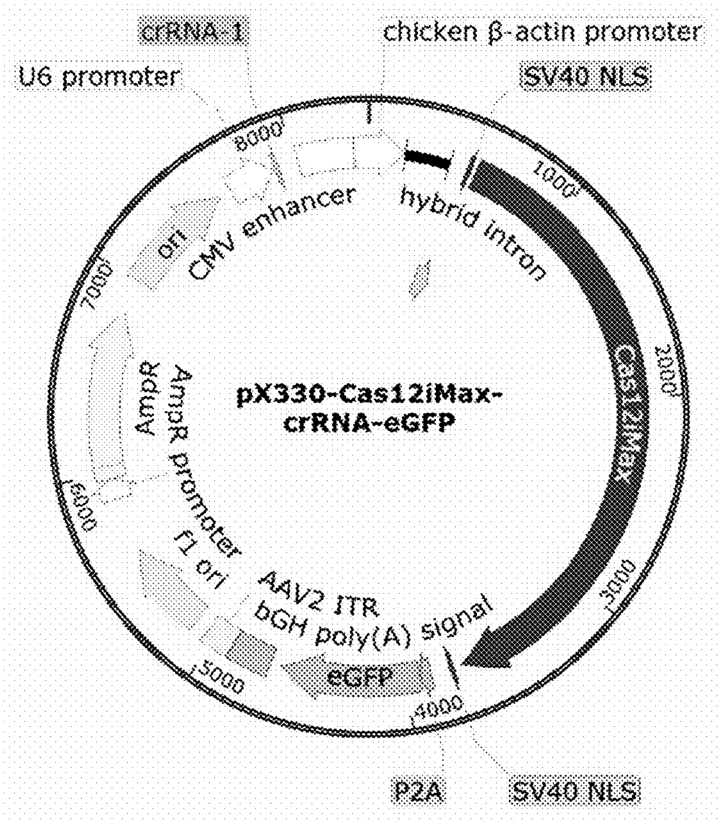
Vector 15
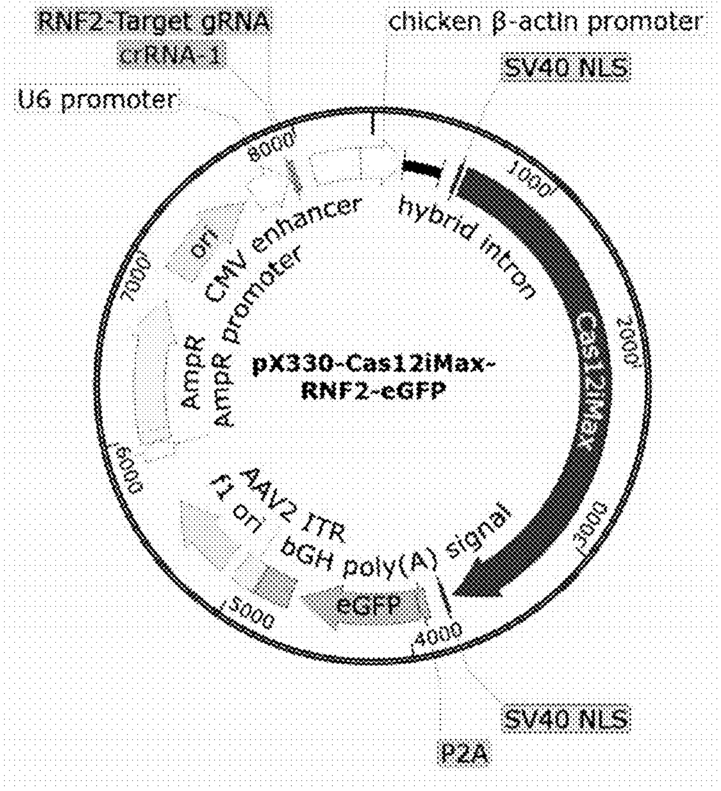
Vector 16
FIG. 8

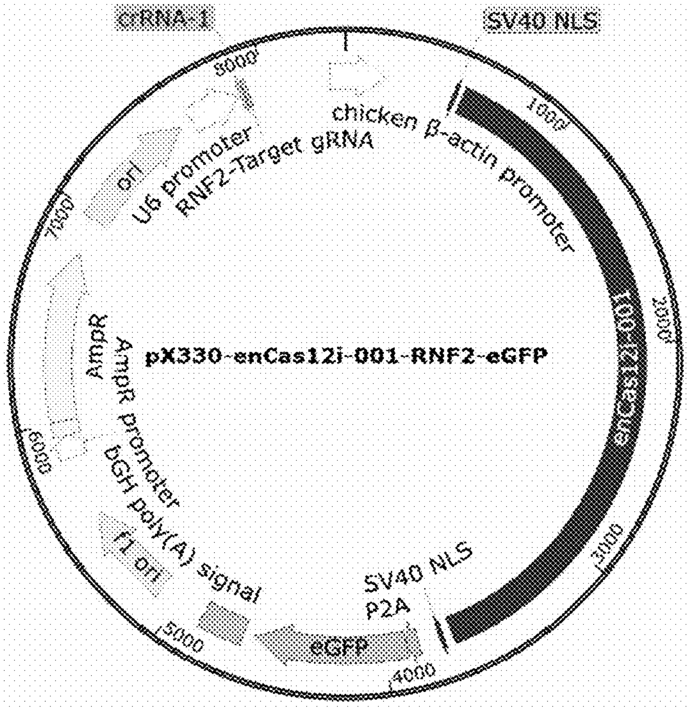
Vector 17
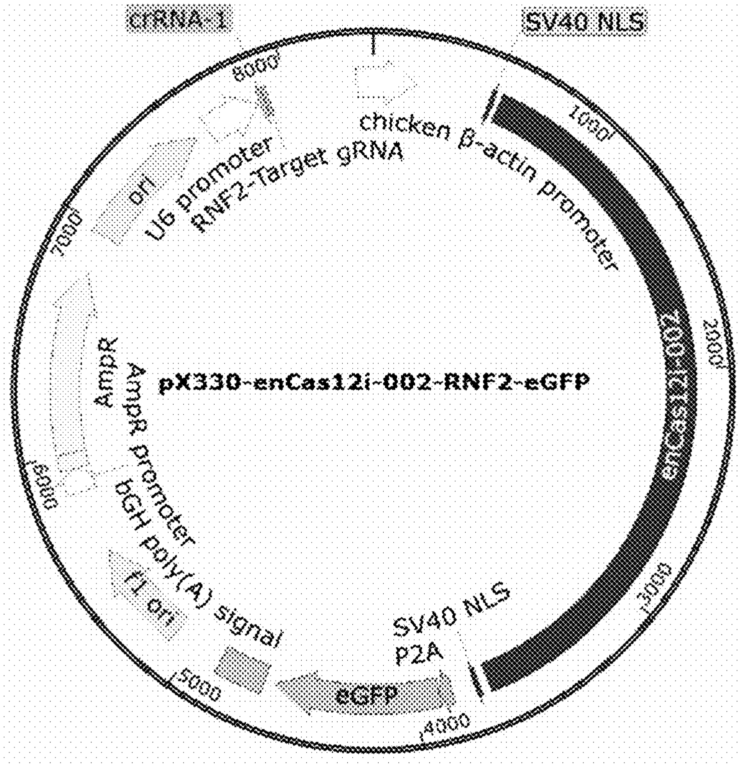
Vector 18
FIG. 8 (Con't)

5'-

AGTCATGGTGTTCTTCAACATATCCAAACAAATTGGGCACATTAATTCACTGTGTAGACTTCGAGGT

G-3' (SEQ ID NO: 99)

Sequencing results of cells transfected with vector 15

5'-
AGTCATGGTGTTCTTCAACATATCCAATTTATTTATTCTTCTACAACTACCCACAAAACCTAAACCTT
CTG-3' (SEQ ID NO: 100)

Sequencing results of cells transfected with vector 16

5'-

GTCATGGTGTTCTTCAACATATCCAAATTGTTTAGACTTCTTAAATTAAACACAATACCTAAATCTTCTACC-

3' (SEQ ID NO: 101)

Sequencing results of cells transfected with vector 17

5'-

TAGTCATGGTGTTCTTCAACATATCCAAATTGTGTAGACATCTACAAGAAACCAGTATACCTCAATCTCAT-

3' (SEQ ID NO: 102)

Sequencing results of cells transfected with vector 18

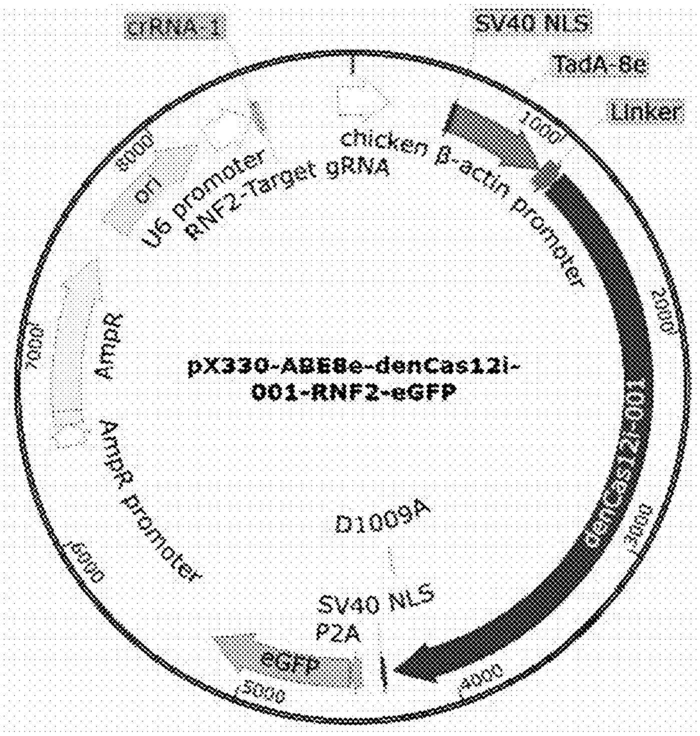
Vector 19
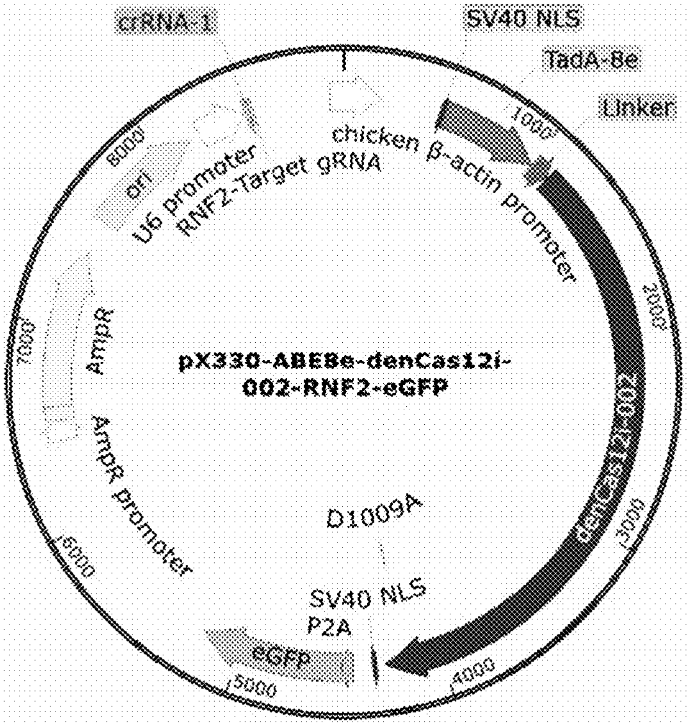
Vector 20
FIG. 11

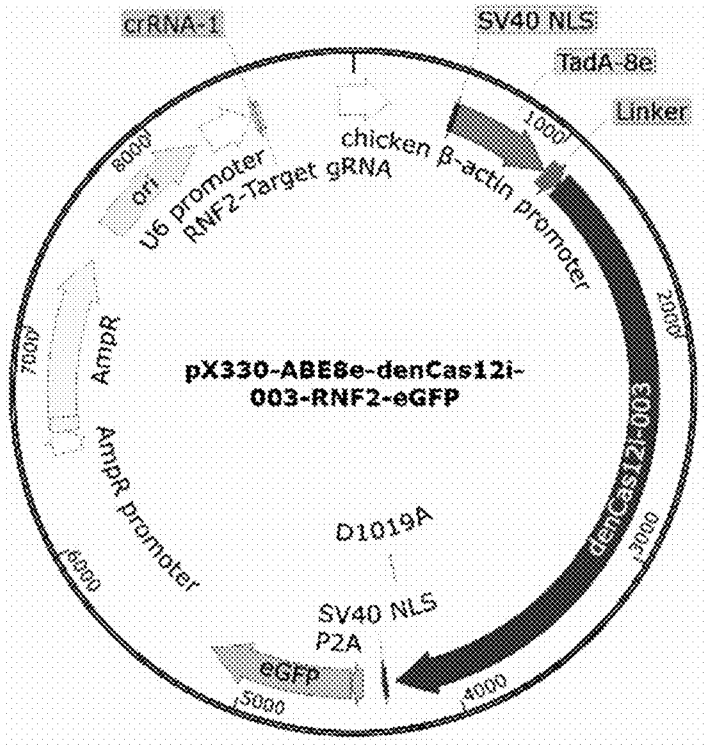
Vector 21
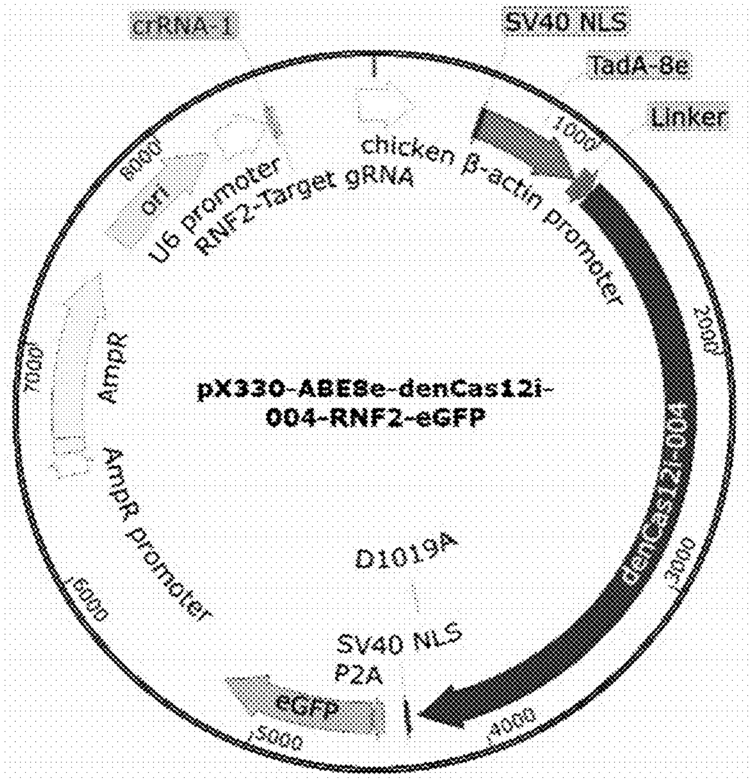
Vector 22
FIG. 11 (Con't)

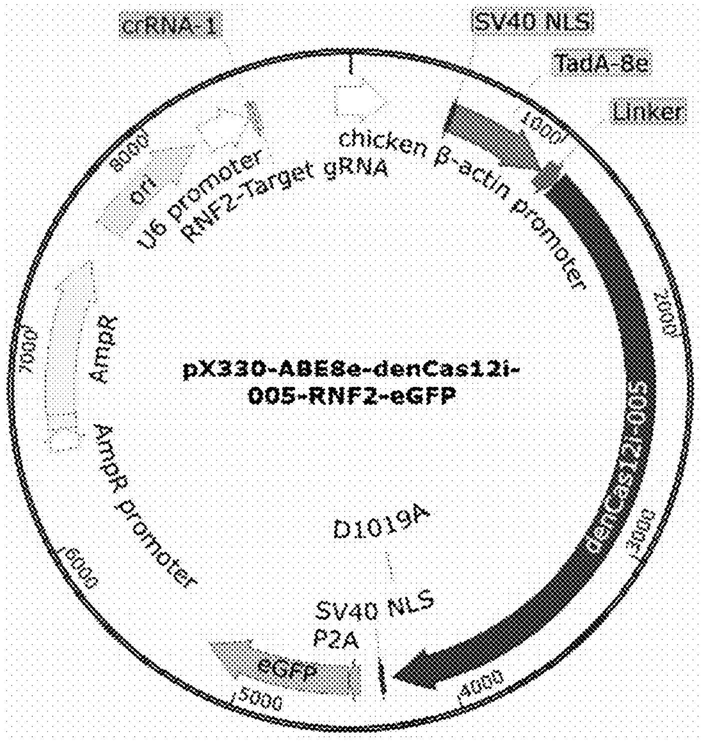
Vector 23
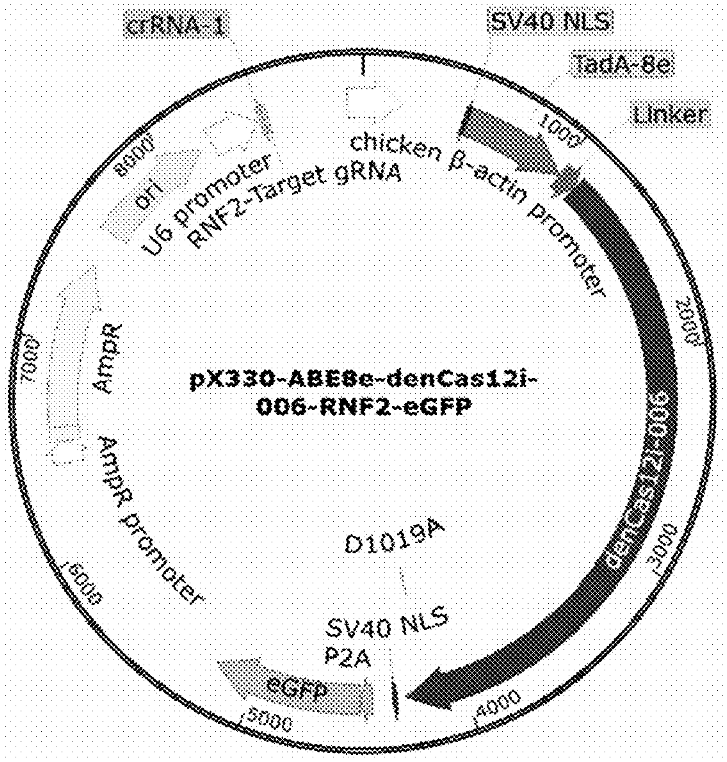
Vector 24
FIG. 11 (Con't)

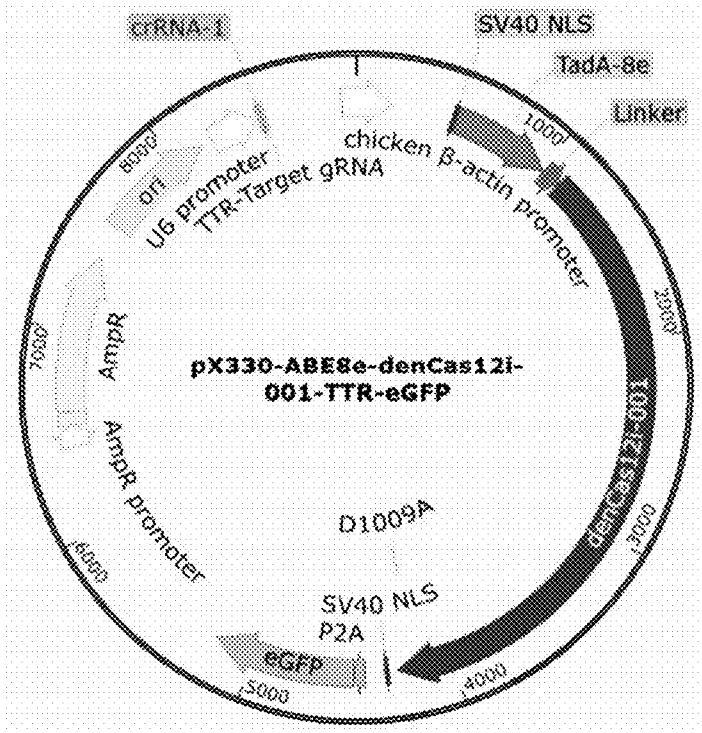
Vector 25
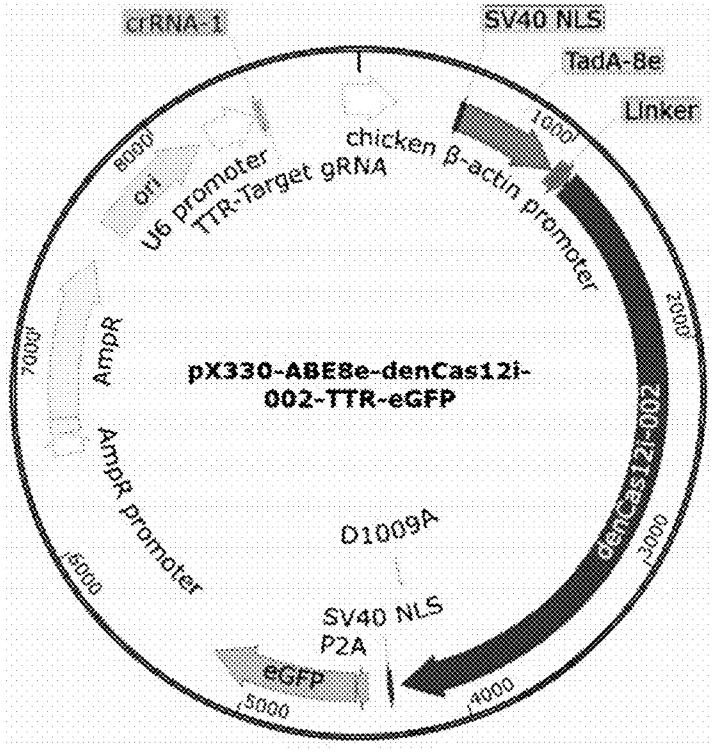
Vector 26
FIG. 12

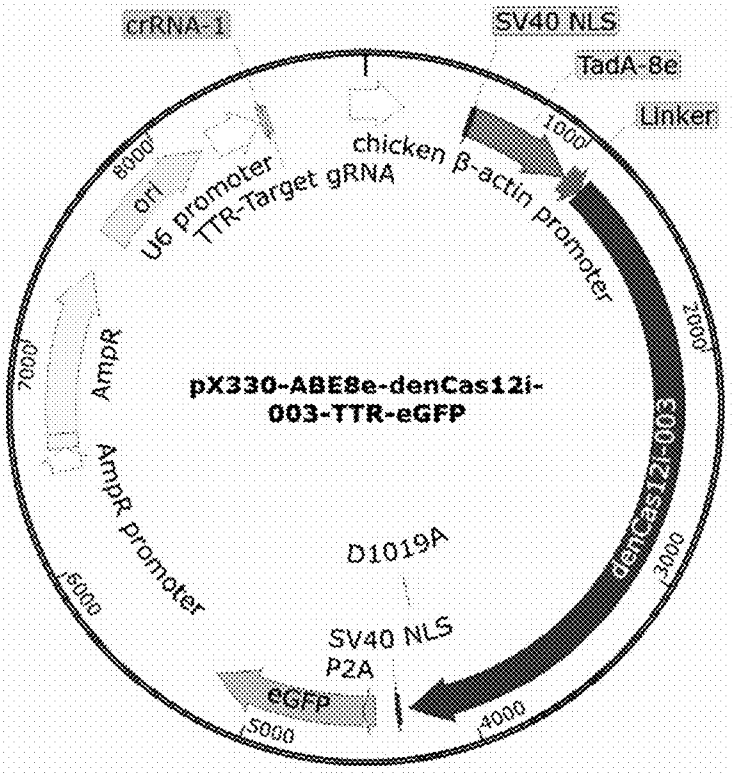
Vector 27
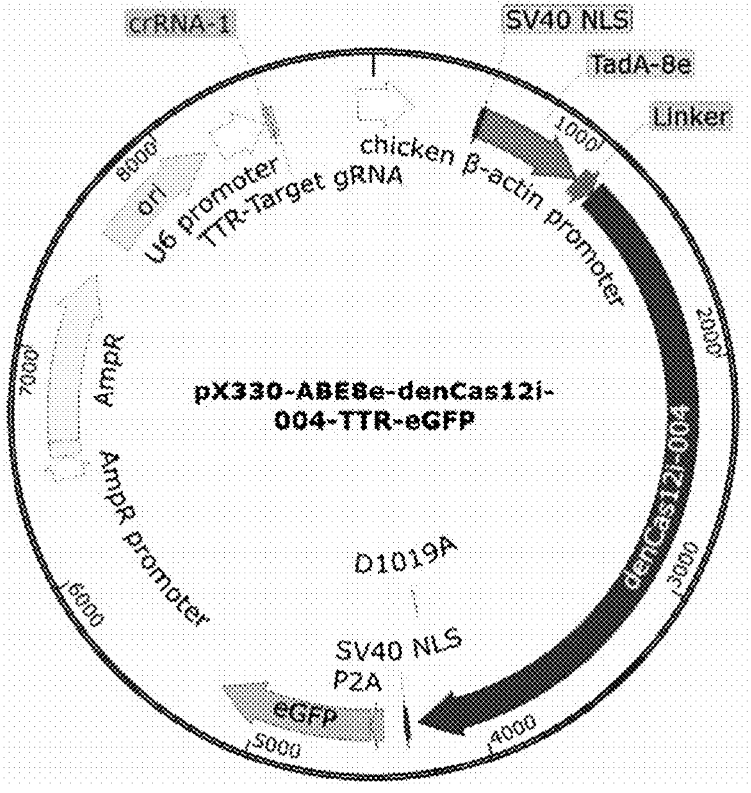
Vector 28
FIG. 12 (Con't)

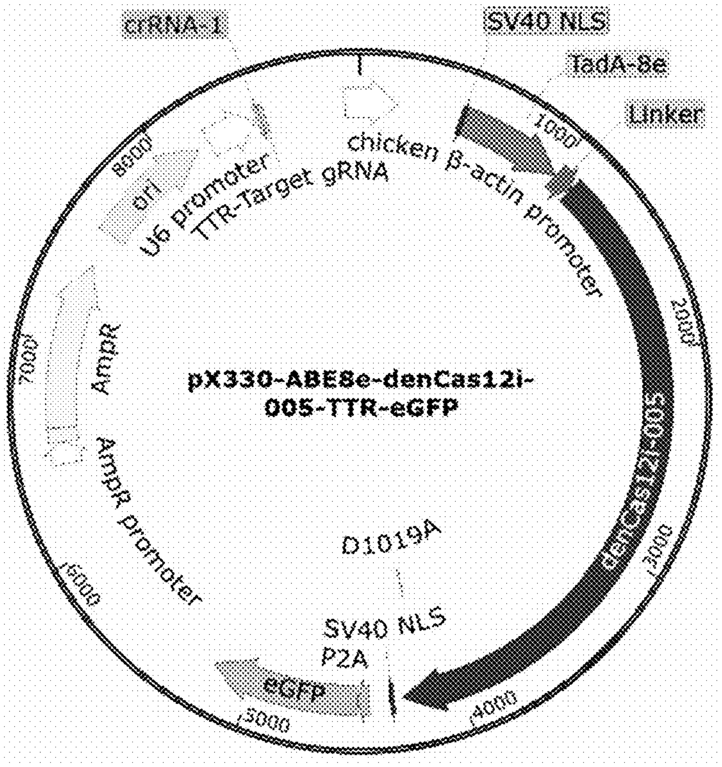
Vector 29
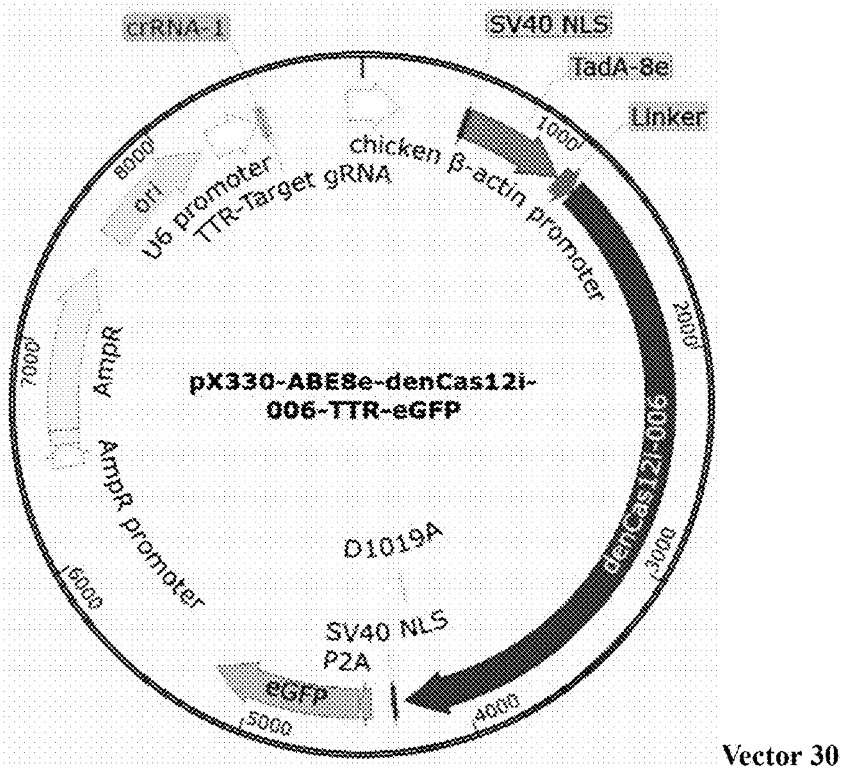
Vector 30
FIG. 12 (Con't)

5'-TTCAACATATCCAAACAAAT-3' (SEQ ID NO: 75)
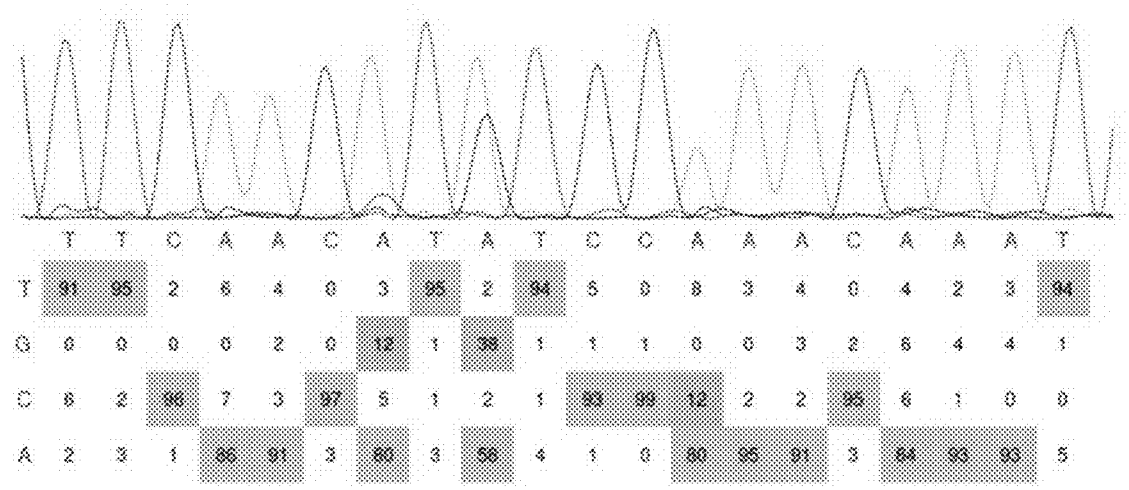
Sequencing results of cells transfected with vector 21
5'-TTCAACATATCCAAACAAAT-3' (SEQ ID NO: 75)
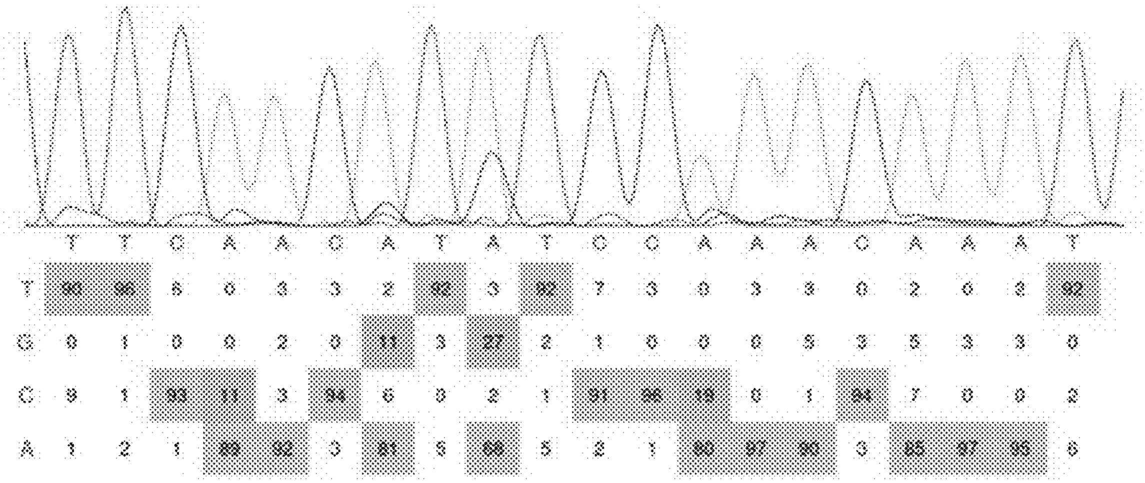
Sequencing results of cells transfected with vector 22
FIG. 13 (Con't)

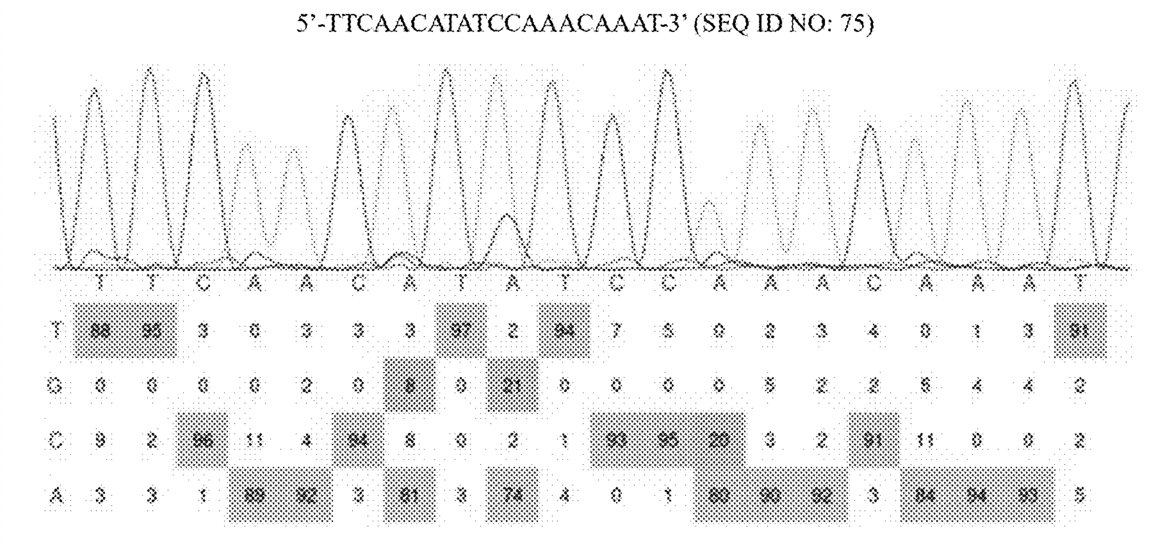
Sequencing results of cells transfected with vector 23
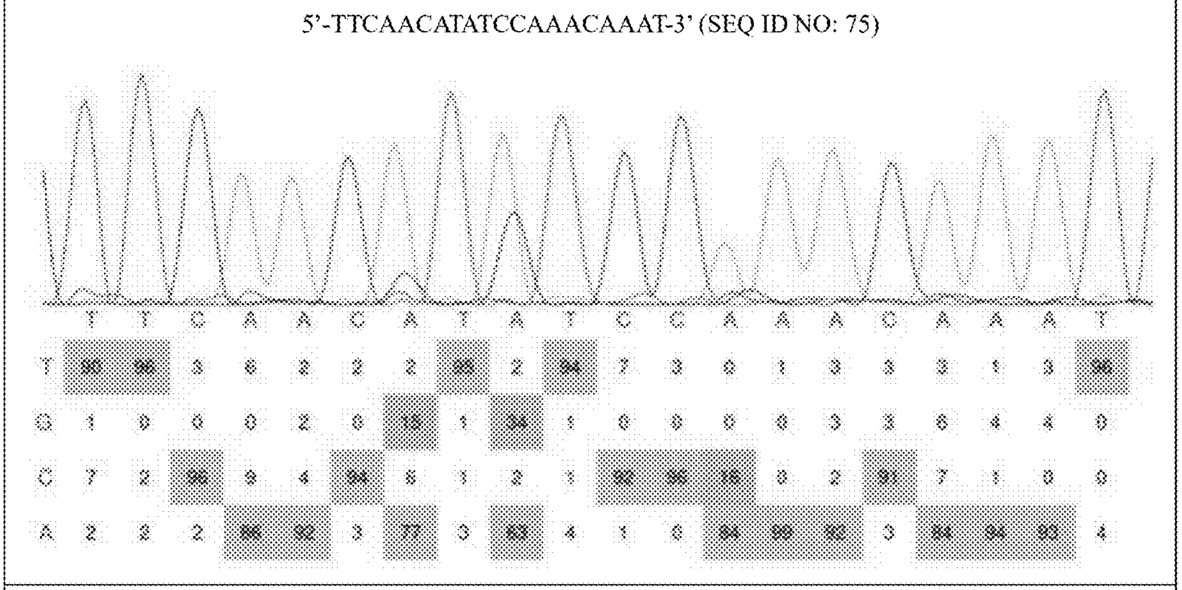
Sequencing results of cells transfected with vector 24
FIG. 14

5'-TTGTATAATAGGAAAGGGAA-3' (SEQ ID NO: 84)
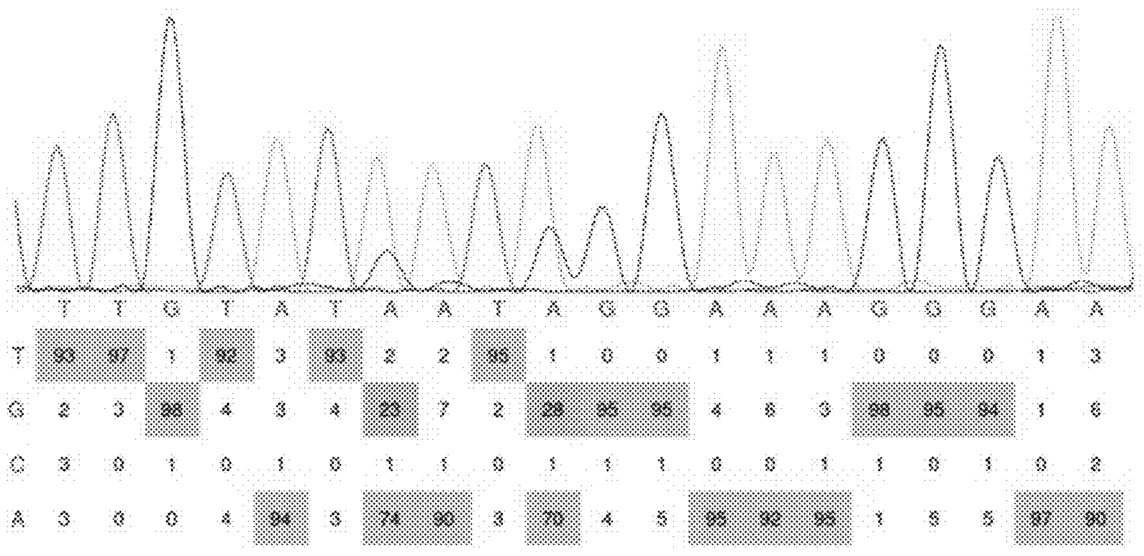
Sequencing results of cells transfected with vector 25
5'-TTGTATAATAGGAAAGGGAA-3' (SEQ ID NO: 84)
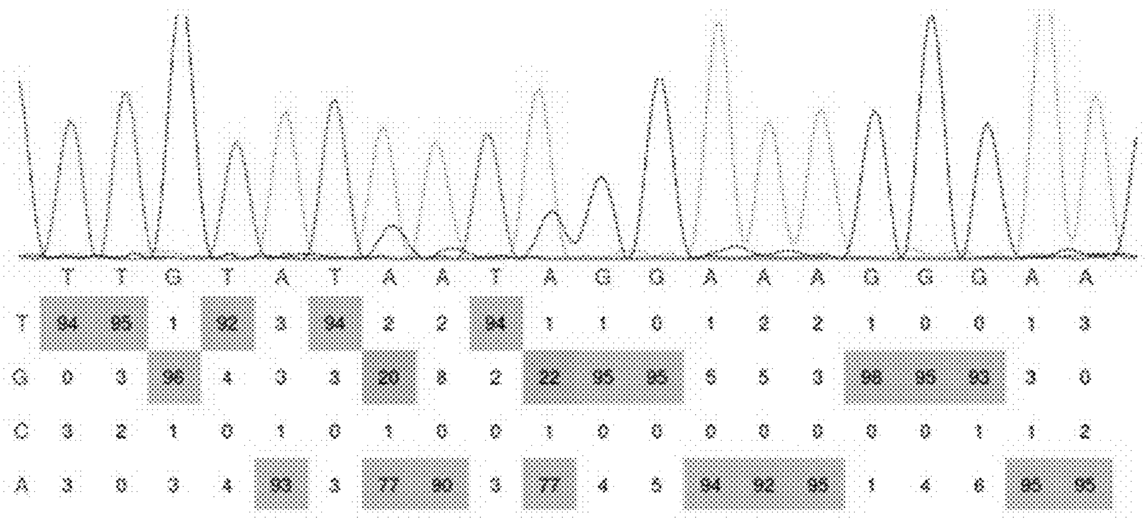
Sequencing results of cells transfected with vector 26
FIG. 14 (Con't)

5'-TTGTATAATAGGAAAGGGAA-3' (SEQ ID NO: 84)
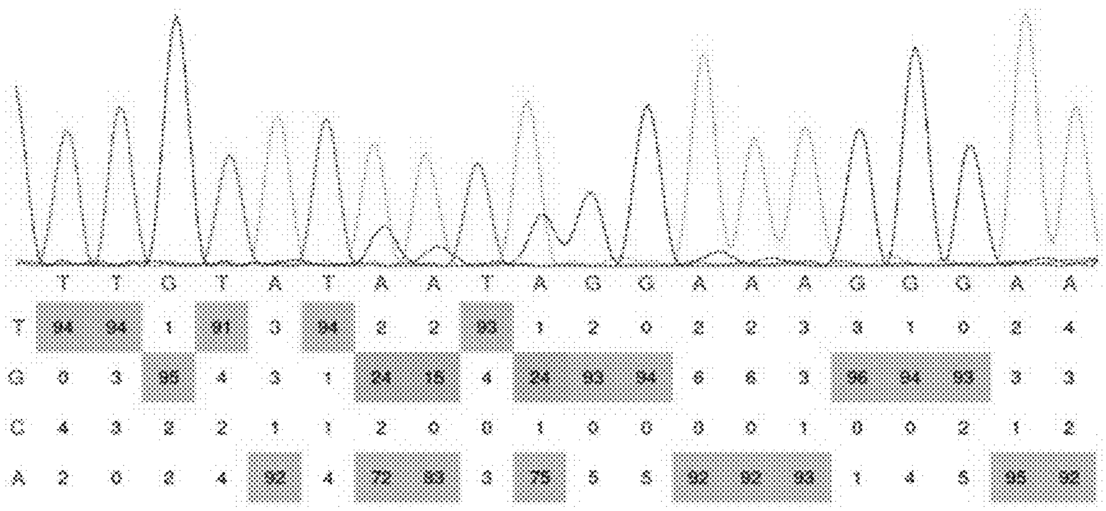
Sequencing results of cells transfected with vector 27
5'-TTGTATAATAGGAAAGGGAA-3' (SEQ ID NO: 84)
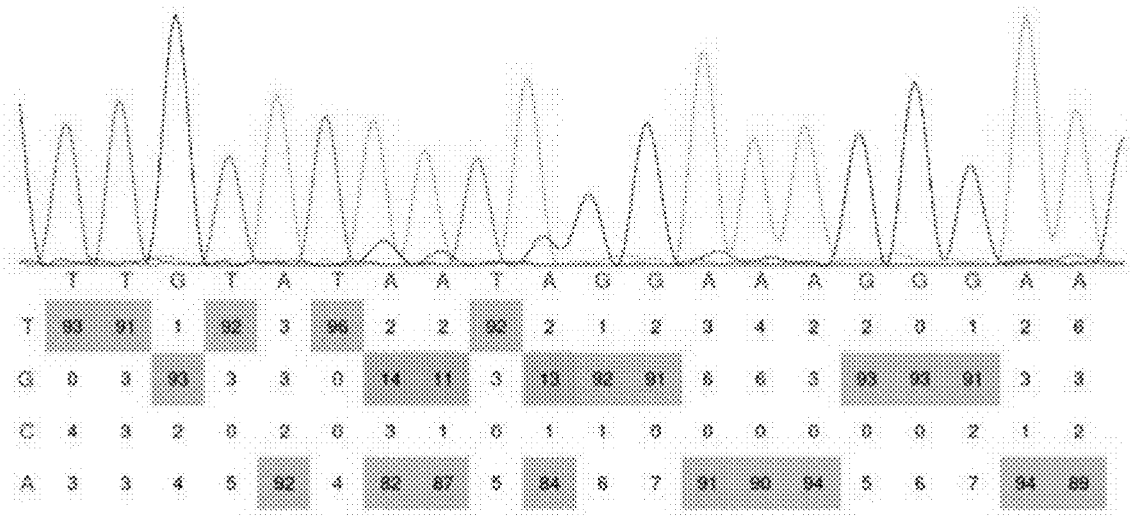
Sequencing results of cells transfected with vector 28
FIG. 15

5'-TTGTATAATAGGAAAGGGAA-3' (SEQ ID NO: 84)
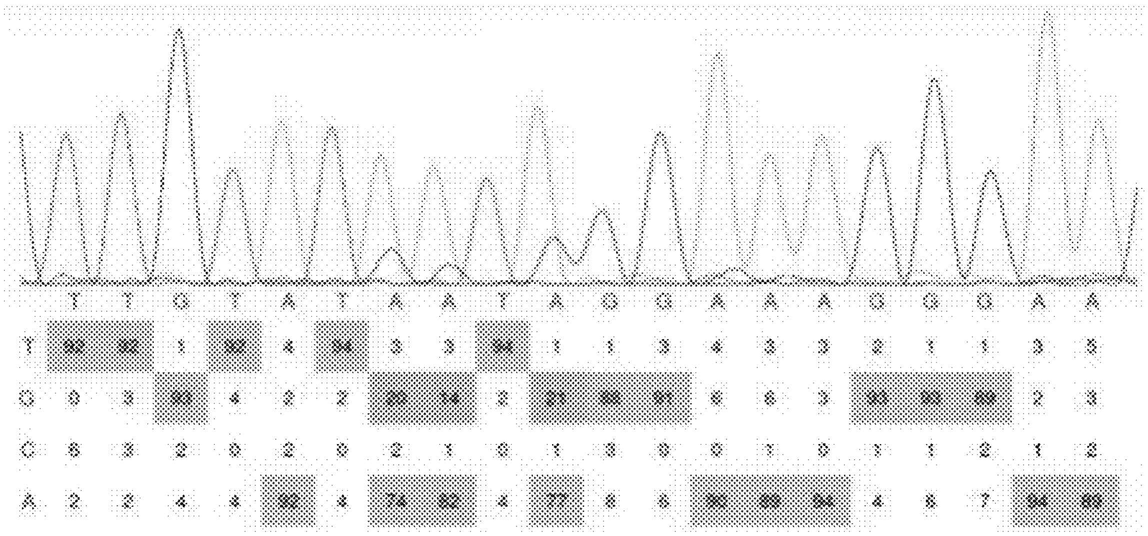
Sequencing results of cells transfected with vector 29
5'-TTGTATAATAGGAAAGGGAA-3' (SEQ ID NO: 84)
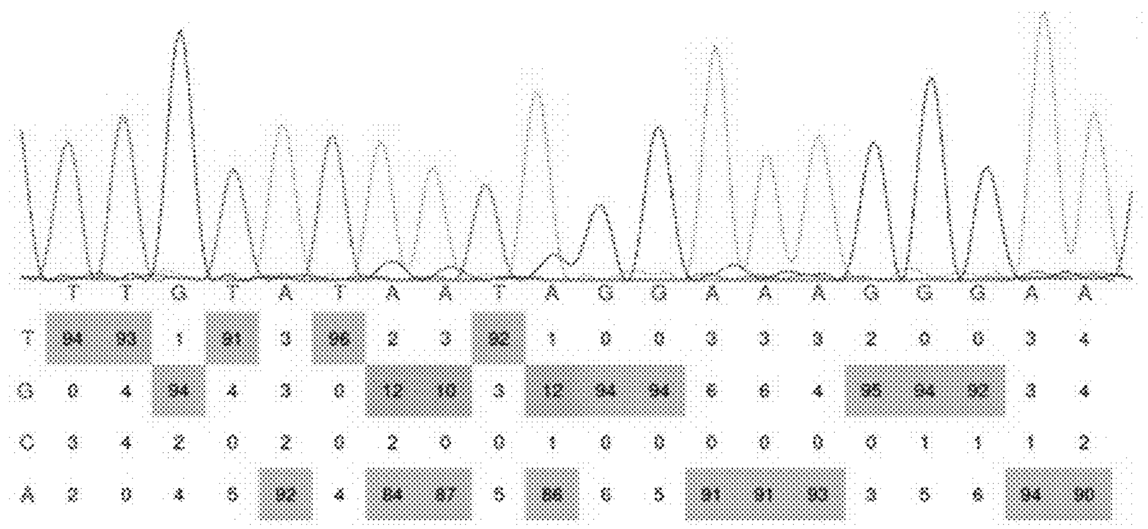
Sequencing results of cells transfected with vector 30
FIG. 15 (Con't)

5'-
TCTTCAACATATCCTAATTGTTTGTGCTTCGACTTTTCAACACTATACCTCAATCTTCAACCACTGTTT
CTTGGCC-3' (SEQ ID NO: 103)

Sequencing results of cells transfected with pX330-enCas12i-001-N229R-RNF2-eGFP

5'-TCTTCAACATATCCTAATTGTTTGTGCTTCGACTTTTCAACACTATACCTCAATCTTCAACCACTGTTTCTTGGCCAACAGTAATTG-3' (SEQ ID NO: 104)
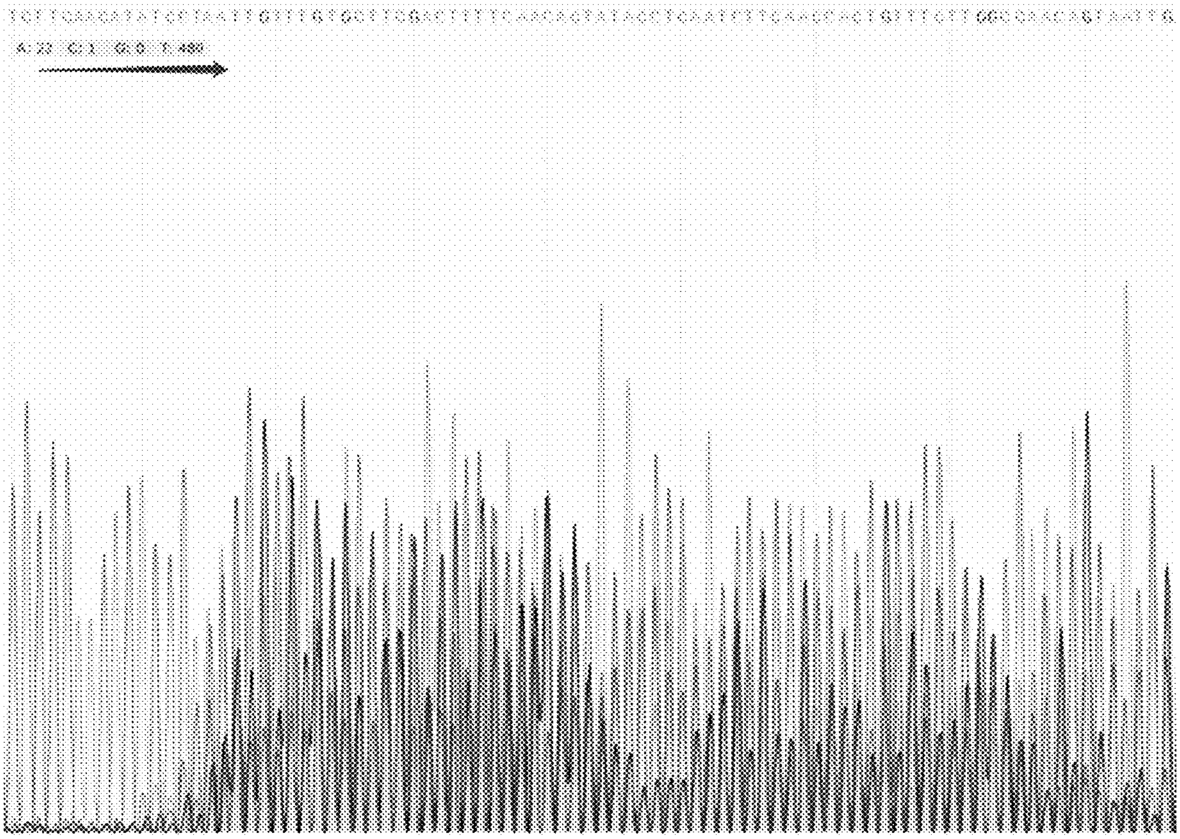
Sequencing results of cells transfected with pX330-enCas12i-001-D924R-RNF2-eGFP
FIG. 16 (Con't)

5'-
CTTCAACATATCCAAACTGTTTGGGCTCCTTAATTCAAAGAGTATATTTAAATGTTATACCTTTGTTTC
TTAGCCAACAG-3' (SEQ ID NO: 105)

Sequencing results of cells transfected with pX330-enCas12i-001-S925R-RNF2-eGFP

5'-TTCAACATATCCAAACAAAT-3' (SEQ ID NO: 75)
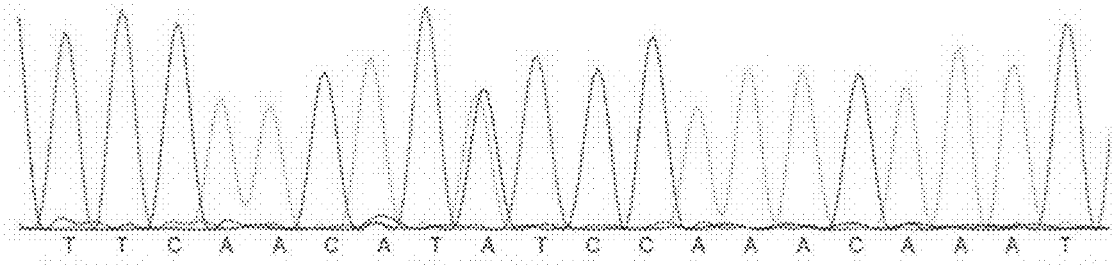
| | T | T | C | A | A | C | A | T | A | T | C | C | A | A | A | C | A | A | A | T |
|---|---|---|---|---|---|---|---|---|---|---|---|---|---|---|---|---|---|---|---|---|
| T | 93 | 96 | 4 | 5 | 3 | 2 | 3 | 94 | 2 | 93 | 2 | 3 | 0 | 3 | 3 | 0 | 2 | 2 | 3 | 96 |
| G | 0 | 0 | 1 | 0 | 2 | 0 | 7 | 2 | 50 | 1 | 1 | 1 | 0 | 3 | 3 | 4 | 4 | 2 | 3 | 0 |
| C | 5 | 3 | 94 | 6 | 4 | 95 | 4 | 2 | 0 | 3 | 95 | 94 | 6 | 1 | 2 | 93 | 4 | 1 | 1 | 1 |
| A | 1 | 2 | 1 | 88 | 91 | 3 | 86 | 3 | 49 | 3 | 2 | 1 | 94 | 93 | 92 | 3 | 91 | 95 | 93 | 3 |
Sequencing results of RNF2 target edited by ABE constructed by denCas12i-001-N229R
5'-TTCAACATATCCAAACAAAT-3' (SEQ ID NO: 75)
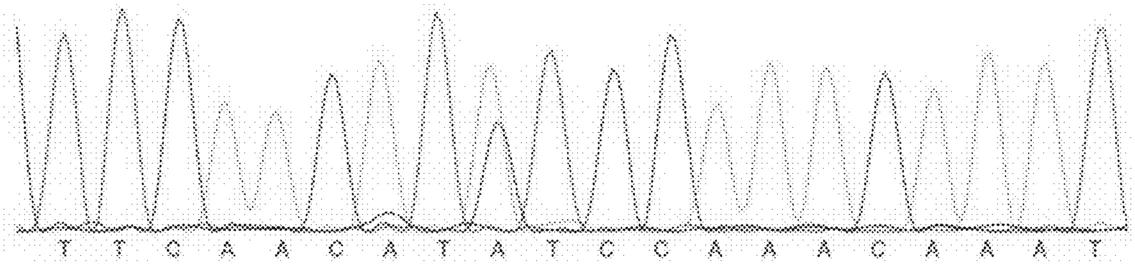
| | T | T | C | A | A | C | A | T | A | T | C | C | A | A | A | C | A | A | A | T |
|---|---|---|---|---|---|---|---|---|---|---|---|---|---|---|---|---|---|---|---|---|
| T | 93 | 94 | 2 | 5 | 0 | 0 | 2 | 95 | 2 | 92 | 2 | 3 | 0 | 2 | 4 | 0 | 1 | 1 | 3 | 95 |
| G | 2 | 2 | 3 | 0 | 2 | 0 | 9 | 1 | 38 | 1 | 0 | 0 | 2 | 3 | 2 | 3 | 4 | 4 | 2 | 0 |
| C | 4 | 2 | 94 | 5 | 3 | 97 | 4 | 2 | 3 | 2 | 97 | 97 | 4 | 1 | 2 | 94 | 4 | 0 | 1 | 1 |
| A | 1 | 2 | 1 | 90 | 94 | 3 | 85 | 2 | 58 | 5 | 1 | 0 | 94 | 94 | 92 | 3 | 91 | 95 | 95 | 4 |
Sequencing results of RNF2 target edited by ABE constructed by denCas12i-001-D924R
FIG. 18

5'-TTCAACATATCCAAACAAAT-3' (SEQ ID NO: 75)
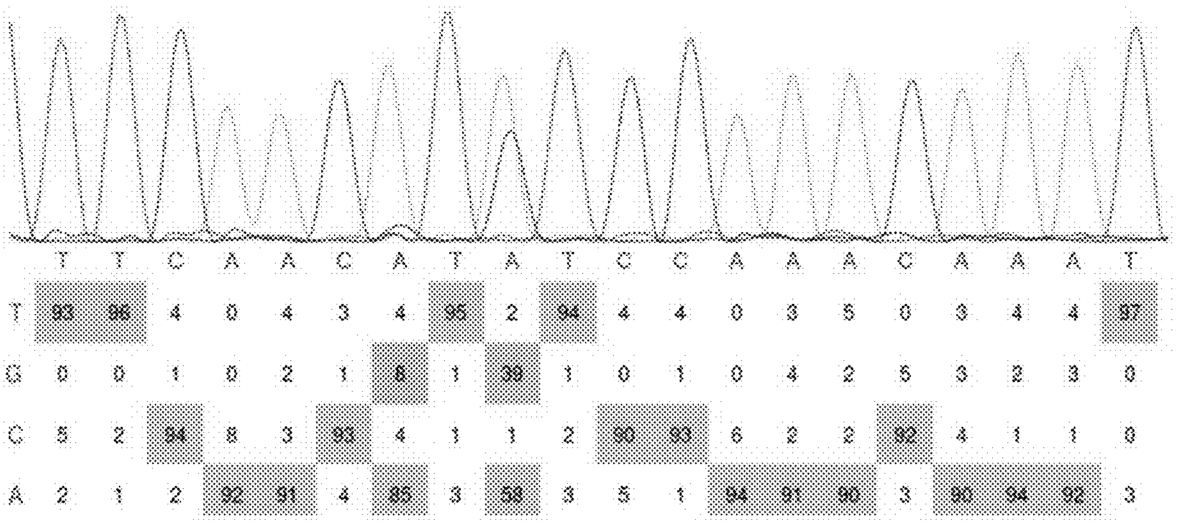
Sequencing results of RNF2 target edited by ABE constructed by denCas12i-001-S925R
FIG. 18 (Con't)

5'-TTGTATAATAGGAAAGGGAA-3' (SEQ ID NO: 84)
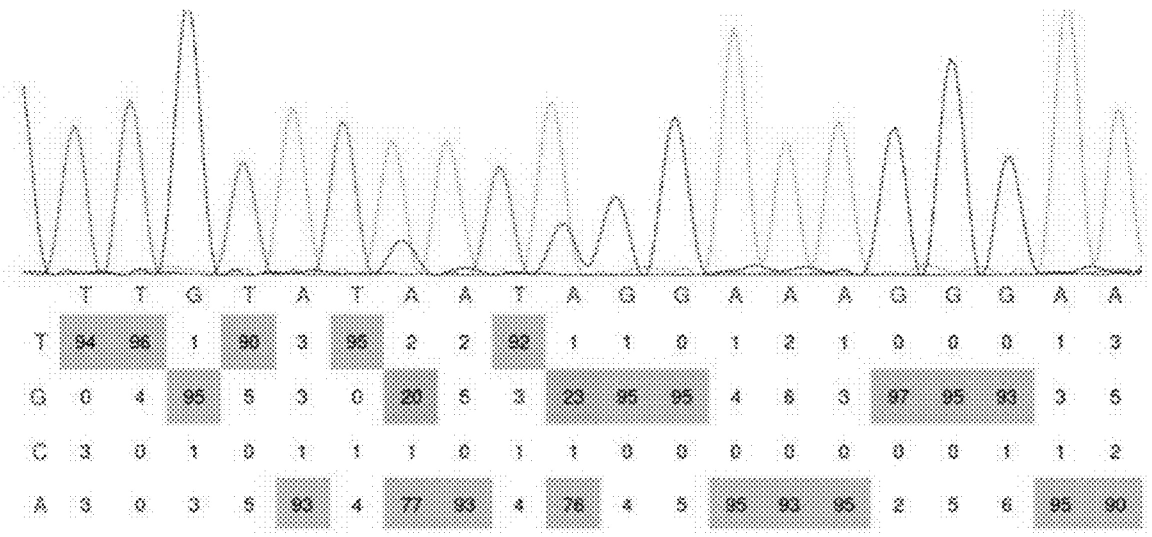
Sequencing results of TTR target edited by ABE constructed by denCas12i-001-N229R
5'-TTGTATAATAGGAAAGGGAA-3' (SEQ ID NO: 84)
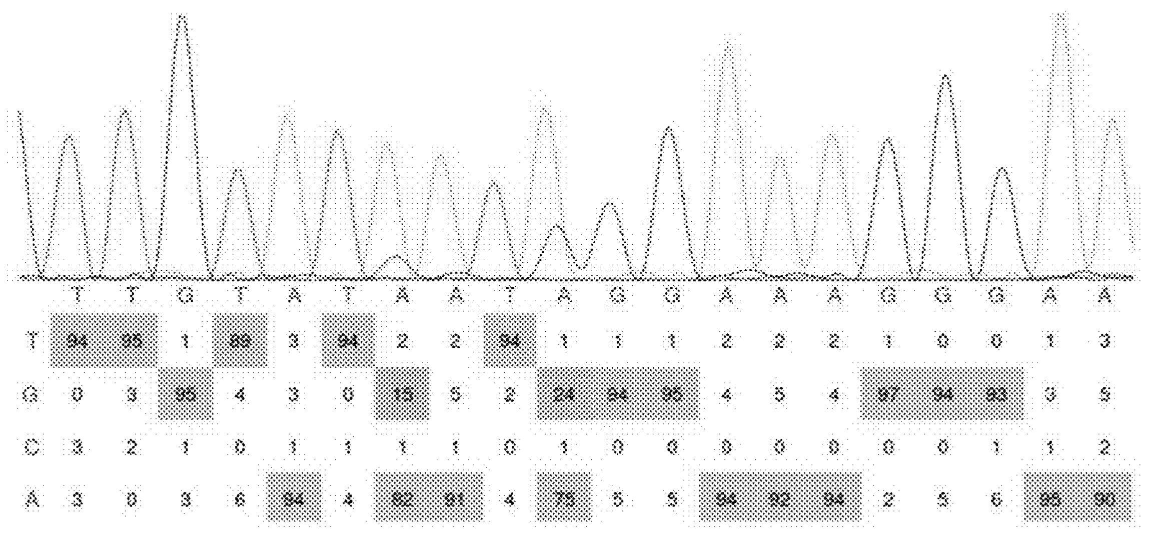
Sequencing results of TTR target edited by ABE constructed by denCas12i-001-D924R
FIG. 19

5'-TTGTATAATAGGAAAGGGAA-3' (SEQ ID NO: 84)
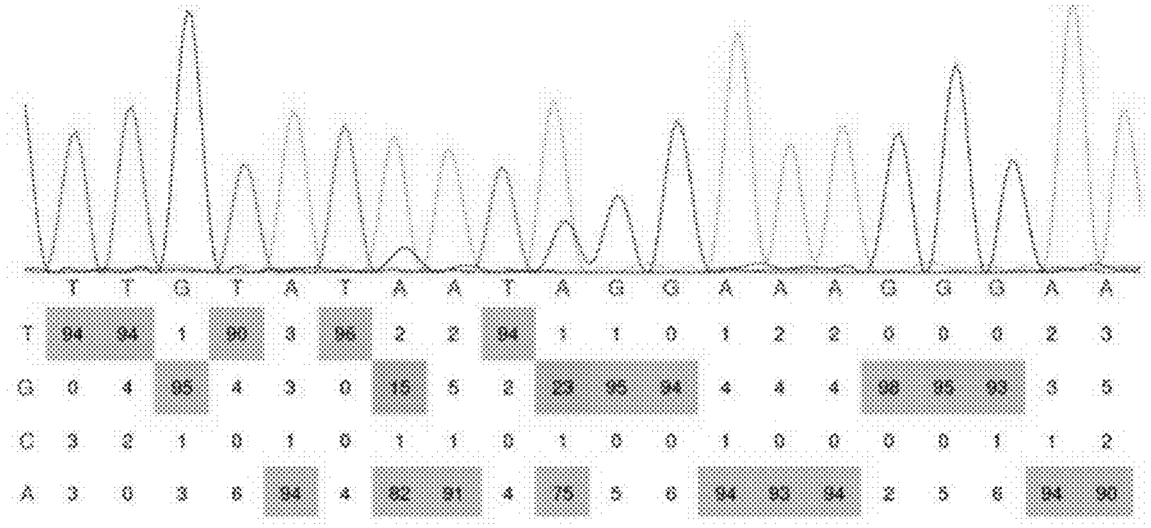
Sequencing results of TTR target edited by ABE constructed by denCas12i-001-S925R
FIG. 19 (Con't)
5'-TTCTCTATCACTGATAGGGAGTG-3' (SEQ ID NO. 98)
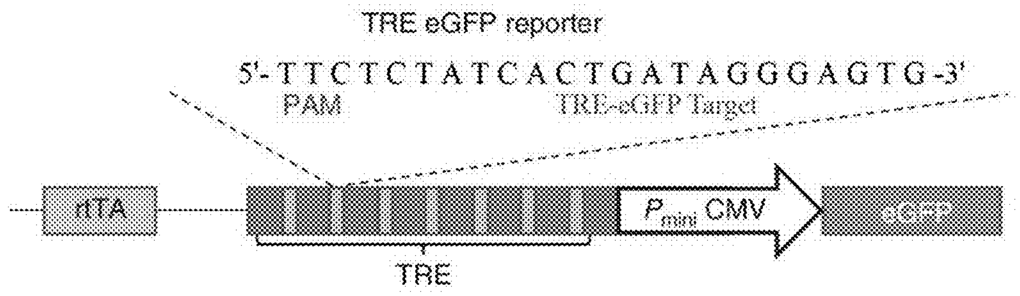
FIG. 20A

CRISPR-Cas SYSTEMS AND USES THEREOF

CROSS REFERENCE TO RELATED APPLICATIONS

The present application claims priority of Chinese Application No. CN 202311464815.0, filed Nov. 6, 2023, the content of which is incorporated herein by reference in its entirety.

REFERENCE TO AN ELECTRONIC SEQUENCE LISTING

The contents of the electronic sequence listing (39D198842USP.xml; Size: 137,645 bytes; and Date of Creation: Dec. 2, 2024) is herein incorporated by reference in its entirety.

TECHNICAL FIELD

The present invention relates to the field of nucleic acid editing and in particular to the technical field of clustered regularly interspaced short palindromic repeats (CRISPR). Specifically, the present invention relates to Cas effector proteins, fusion proteins comprising such proteins, and nucleic acid molecules encoding the same. The present invention further relates to complexes and compositions for nucleic acid editing (e.g., gene or genome editing) comprising the protein or the fusion protein of the present invention, or the nucleic acid molecule encoding the same. The present invention further relates to a method for nucleic acid editing (e.g., gene or genome editing) using the protein or the fusion protein of the present invention.

BACKGROUND

Clustered regularly interspaced short palindromic repeats (CRISPR) and CRISPR-associated (Cas) genes (collectively referred to as CRISPR-Cas or CRISPR/Cas systems) are adaptive immune systems in archaea and bacteria that defend specific species against foreign genetic elements. The CRISPR-Cas system is a high-efficiency and cost-effective genome editing technology that can be widely applied to prokaryotes and eukaryotes. To date, based on the outstanding functional and evolutionary modularity of this system, CRISPR-Cas systems including six types (types I-VI) and two classes (class 1 and class 2) have been characterized. In class 2 of CRISPR-Cas systems, the CRISPR-Cas9 system is the most widely applied. A traditional CRISPR-Cas9 system consists of a Cas9 nuclease and an engineered sgRNA. The latter is responsible for guiding Cas9 to a target site and causing a double-stranded DNA break (DSB), and then the break site is repaired through endogenous pathways such as non-homologous end joining (NHEJ) and homologous recombination repair (HDR). The CRISPR-Cas9 system has been utilized for somatic cell editing, synchronous multi-site editing, single-base editing, and the like, providing a broad prospect for biomedical research.

However, the current CRISPR-Cas9 system has several limitations, including its large molecular weight that limits its efficient delivery in vivo. Thus, developing a new CRISPR/Cas system that is more robust and has versatile good performance is of great significance to the development of biotechnology.

SUMMARY

One aspect of the present invention provides an engineered chimeric Cas12i polypeptide comprising a Nuc domain, wherein the Nuc domain is derived from a Nuc domain of a first Cas12i polypeptide, a non-Nuc domain moiety of the engineered chimeric Cas12i polypeptide is derived from a non-Nuc domain moiety of a second Cas12i polypeptide, the first Cas12i polypeptide has no more than 80% sequence identity to the second Cas12i polypeptide, and the engineered chimeric Cas12i polypeptide is capable of binding to and optionally cleaving a nucleic acid.

In a preferred embodiment, the engineered chimeric Cas12i polypeptide: (i) comprises an amino acid sequence having at least 95% sequence identity to the amino acid sequence set forth in SEQ ID NO: 1 or 2; or (ii) comprises an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2.

In some other embodiments, the present invention provides an engineered chimeric Cas12i polypeptide capable of binding to and optionally cleaving the nucleic acid, wherein the engineered chimeric Cas12i polypeptide: (i) comprises an amino acid sequence having at least 95% sequence identity to the amino acid sequence set forth in any one of SEQ ID NOs: 3 to 6; or (ii) comprises an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6.

In some other embodiments, the present invention provides an engineered chimeric Cas12i polypeptide capable of binding to and optionally cleaving the nucleic acid, wherein the engineered chimeric Cas12i polypeptide comprises, from N-terminus to C-terminus, a first peptide segment, a second peptide segment, and a third peptide segment connected in sequence, wherein:

- the first peptide segment comprises an amino acid sequence having at least 80% sequence identity to the amino acid sequence of aa 1 to 897 of SEQ ID NO: 1 or aa 1 to 895 of SEQ ID NO: 3;
- the second peptide segment comprises an amino acid sequence having at least 80% sequence identity to the amino acid sequence set forth in any one of SEQ ID NOs: 67 to 72; and
- the third peptide segment comprises an amino acid sequence having at least 80% sequence identity to the amino acid sequence of aa 1008 to 1044 of SEQ ID NO: 1 or aa 1016 to 1054 of SEQ ID NO: 3.

In some embodiments, the engineered chimeric Cas12i polypeptide is mutated to have one or more of the following characteristics: (i) partial or complete inactivation of nucleic acid cleavage activity, or an enhancement of nucleic acid cleavage activity; and (ii) an enhancement of nucleic acid binding activity.

In some embodiments, the engineered chimeric Cas12i polypeptide, according to the sequence numbering set forth in SEQ ID NO: 1, has an amino acid substitution, preferably with alanine, at position D1009.

In some embodiments, the engineered chimeric Cas12i polypeptide, according to the sequence numbering set forth in SEQ ID NO: 1, has an amino acid substitution, preferably with lysine, arginine, or histidine, more preferably with arginine, at position N229.

In some embodiments, the engineered chimeric Cas12i polypeptide (i) comprises an amino acid sequence having at least 95% sequence identity to the amino acid sequence set forth in SEQ ID NO: 1; or (ii) comprises an amino acid sequence having at least 80% sequence identity to the amino acid sequences of aa 1 to 897 and aa 1008 to 1044 of SEQ ID NO: 1 and having at least 80% sequence identity to the amino acid sequence of aa 898 to 1007 of SEQ ID NO: 1 or 2; and the engineered chimeric Cas12i polypeptide has an amino acid substitution, preferably with lysine, arginine, or histidine, more preferably with arginine, at least one of the two positions D924 and S925.

In another aspect of the present invention, provided is a CRISPR-Cas system comprising: (a) a Cas12i polypeptide being any one of the engineered chimeric Cas12i polypeptides provided by the present invention; and (b) a guide RNA complexed with the Cas12i polypeptide to guide the Cas12i polypeptide to bind to a target nucleic acid.

In some embodiments, the guide RNA comprises a guide segment hybridizing with the target nucleic acid and a repeat segment binding to the Cas12i polypeptide, and the guide RNA does not comprise and does not bind to a tracrRNA.

In some embodiments, in the CRISPR-Cas system, the repeat segment of the guide RNA comprises the nucleotide sequence set forth in any one of SEQ ID NOs: 7 to 14 or a nucleotide sequence having 1 to 10 nucleotide substitutions, deletions, and/or insertions compared with the nucleotide sequence set forth in any one of SEQ ID NOs: 7 to 14; preferably, the repeat segment of the guide RNA is the nucleotide sequence set forth in any one of SEQ ID NOs: 7 to 14.

Another aspect of the present invention provides a fusion polypeptide comprising a Cas12i polypeptide fused to one or more heterologous polypeptides, wherein the Cas12i polypeptide is any one of the engineered chimeric Cas12i polypeptides provided by the present invention.

In a preferred embodiment, in the fusion polypeptide, the one or more heterologous polypeptides are each independently an epitope tag or a nuclear localization signal, or have one or more of the following enzymatic activities: reverse transcriptase activity, nuclease activity, methyltransferase activity, demethylase activity, acetyltransferase activity, deacetylase activity, kinase activity, phosphatase activity, ubiquitin ligase activity, deubiquitination activity, adenylation activity, deadenylation activity, SUMOylation activity, deSUMOylation activity, ribosylation activity, deribosylation activity, myristoylation activity, demyristoylation activity, glycosylation activity (e.g., from an O-GlcNAc transferase) and deglycosylation activity, DNA repair activity, DNA damage activity, deaminase activity, dismutase activity, alkylation activity, depurination activity, oxidation activity, pyrimidine dimer formation activity, integrase activity, transposase activity, recombinase activity, polymerase activity, ligase activity, helicase activity, photolyase activity, and glycosylase activity. In a preferred embodiment, the enzymatic activity domain has one or more of the following enzymatic activities: deaminase activity, methyltransferase activity, demethylase activity, acetyltransferase activity, and deacetylase activity. In a preferred embodiment, the one or more heterologous polypeptides are each independently a transcriptional repression domain, a transcriptional activation domain, or a deaminase domain.

In a preferred embodiment, in the fusion polypeptide, the transcriptional activation domain comprises a domain formed by an enzyme selected from the following: a transcriptional activator, a histone lysine methyltransferase, a histone lysine demethylase, a histone acetyltransferase, and a DNA demethylase; preferably, the transcriptional repression domain comprises a domain selected from the following: a transcriptional repressor, a ZIM3 domain, a KOX1 repression domain, a Mad mSIN3 interaction domain (SID), an ERF repressor domain (ERD), an SRDX repression domain, a histone lysine methyltransferase, a histone lysine demethylase, a histone lysine deacetylase, a DNA methylase, and a peripheral recruitment element. In a preferred embodiment, the transcriptional activation domain comprises VP64; P65; RTA; truncated P65; truncated RTA; or one or more fusion forms thereof or therebetween. In a preferred embodiment, the transcriptional repression domain is selected from a KRAB catalytic domain, a DNA methyltransferase, or a combination thereof.

In a preferred embodiment, a structure of the fusion polypeptide is selected from:

$NH_2$-[Cas12i]-[transcriptional regulatory domain]-COOH;

$NH_2$-[transcriptional regulatory domain]-[Cas12i]—COOH;

$NH_2$-[Cas12i]-[transcriptional activation domain]-COOH;

$NH_2$-[transcriptional activation domain]-[Cas12i]—COOH;

$NH_2$—[NLS]-[Cas12i]-[transcriptional activation domain]-COOH;

$NH_2$-[Cas12i]-[transcriptional activation domain]-[NLS]—COOH;

$NH_2$—[NLS]-[Cas12i]-[transcriptional activation domain]-[NLS]—COOH;

$NH_2$—[NLS]-[transcriptional activation domain]-[Cas12i]—COOH;

$NH_2$-[transcriptional activation domain]-[Cas12i]-[NLS]—COOH;

$NH_2$—[NLS]-[transcriptional activation domain]-[Cas12i]-[NLS]—COOH;

$NH_2$-[Cas12i]-[VP64-P65-RTA fusion protein and a truncated fusion protein thereof]-COOH;

$NH_2$—[VP64-P65-RTA fusion protein and a truncated fusion protein thereof]-[Cas12i]—COOH;

$NH_2$—[NLS]-[Cas12i]-[VP64-P65-RTA fusion protein and a truncated fusion protein thereof]-COOH;

$NH_2$-[Cas12i]-[VP64-P65-RTA fusion protein and a truncated fusion protein thereof]-[NLS]—COOH;

$NH_2$—[NLS]-[Cas12i]-[VP64-P65-RTA fusion protein and a truncated fusion protein thereof]-[NLS]—COOH;

$NH_2$—[NLS]-[VP64-P65-RTA fusion protein and a truncated fusion protein thereof]-[Cas12i]—COOH;

$NH_2$—[VP64-P65-RTA fusion protein and a truncated fusion protein thereof]-[Cas12i]-[NLS]—COOH;

$NH_2$—[NLS]-[Cas12i]-[VP64-P65-RTA fusion protein and a truncated fusion protein thereof]-[NLS]—COOH;

$NH_2$-[Cas12i]-[transcriptional inhibition domain]-COOH;

$NH_2$-[transcriptional inhibition domain]-[Cas12i]—COOH;

$NH_2$—[NLS]-[Cas12i]-[transcriptional inhibition domain]-COOH;

$NH_2$-[Cas12i]-[transcriptional inhibition domain]-[NLS]—COOH;

$NH_2$—[NLS]-[Cas12i]-[transcriptional inhibition domain]-[NLS]—COOH;

$NH_2$—[NLS]-[transcriptional inhibition domain]-[Cas12i]—COOH;

$NH_2$-[transcriptional inhibition domain]-[Cas12i]-[NLS]—COOH;

$NH_2$—[NLS]-[transcriptional inhibition domain]-[Cas12i]-[NLS]—COOH;

$NH_2$-[Cas12i]-[first transcriptional inhibition domain]-[second transcriptional inhibition domain]-COOH;

$NH_2$-[Cas12i]-[second transcriptional inhibition domain]-[first transcriptional inhibition domain]-COOH;

$NH_2$-[first transcriptional inhibition domain]-[second transcriptional inhibition domain]-[Cas12i]—COOH;

$NH_2$-[second transcriptional inhibition domain]-[first transcriptional inhibition domain]-[Cas12i]—COOH;

$NH_2$-[first transcriptional inhibition domain]-[Cas12i]-[second transcriptional inhibition domain]-COOH;

$NH_2$-[second transcriptional inhibition domain]-[Cas12i]-[first transcriptional inhibition domain]-COOH;

$NH_2$—[NLS]-[Cas12i]-[KRAB catalytic domain]-[DNMT3A-DNMT3L]-COOH;

$NH_2$-[Cas12i]-[KRAB catalytic domain]-[DNMT3A-DNMT3L]-[NLS]—COOH;

$NH_2$—[NLS]-[Cas12i]-[KRAB catalytic domain]-[DNMT3A-DNMT3L]-[NLS]—COOH;

$NH_2$—[NLS]-[KRAB catalytic domain]-[DNMT3A-DNMT3L]-[Cas12i]—COOH;

$NH_2$—[KRAB catalytic domain]-[DNMT3A-DNMT3L]-[Cas12i]-[NLS]—COOH;

$NH_2$—[NLS]-[KRAB catalytic domain]-[DNMT3A-DNMT3L]-[Cas12i]-[NLS]—COOH;

$NH_2$—[NLS]-[KRAB catalytic domain]-[Cas12i]-[DNMT3A-DNMT3L]-COOH;

$NH_2$—[KRAB catalytic domain]-[Cas12i]-[DNMT3A-DNMT3L]-[NLS]—COOH;

$NH_2$—[NLS]-[KRAB catalytic domain]-[Cas12i]-[DNMT3A-DNMT3L]-[NLS]—COOH;

$NH_2$—[NLS]-[DNMT3A-DNMT3L]-[Cas12i]-[KRAB catalytic domain]-COOH;

$NH_2$-[DNMT3A-DNMT3L]-[Cas12i]-[KRAB catalytic domain]-[NLS]—COOH; and $NH_2$—[NLS]-[DNMT3A-DNMT3L]-[Cas12i]-[KRAB catalytic domain]-[NLS]—COOH.

In some embodiments, in the fusion polypeptide, the deaminase domain comprises an adenosine deaminase domain, a cytidine deaminase domain, or a combination thereof. In a preferred embodiment, the cytidine deaminase is selected from an activation-induced cytidine deaminase (AID), an apolipoprotein B mRNA editing complex (APOBEC), and PmCDA1. In a preferred embodiment, the adenosine deaminase domain is TadA, ecTadA, saTadA, ecTadA7.10, TadA-8c, TadA8.17, TadA8.20, TadA9, or a combination thereof.

In a preferred embodiment, a structure of the fusion polypeptide is selected from:

$NH_2$-[adenosine deaminase domain]-[Cas12i]—COOH;

$NH_2$-[Cas12i]-[adenosine deaminase domain]-COOH;

$NH_2$-[first adenosine deaminase domain]-[second adenosine deaminase domain]-[Cas12i]—COOH;

$NH_2$-[first adenosine deaminase domain]-[Cas12i]-[second adenosine deaminase domain]-COOH;

$NH_2$-[Cas12i]-[first adenosine deaminase domain]-[second adenosine deaminase domain]-COOH;

$NH_2$-[second adenosine deaminase domain]-[first adenosine deaminase domain]-[Cas12i]—COOH;

$NH_2$-[second adenosine deaminase domain]-[Cas12i]-[first adenosine deaminase domain]-COOH;

$NH_2$-[Cas12i]-[second adenosine deaminase domain]-[first adenosine deaminase domain]-COOH;

$NH_2$-[adenosine deaminase domain]-[Cas12i]-[NLS]—COOH;

$NH_2$-[Cas12i]-[adenosine deaminase domain]-[NLS]—COOH;

$NH_2$—[NLS]-[adenosine deaminase domain]-[Cas12i]—COOH;

$NH_2$—[NLS]-[Cas12i]-[adenosine deaminase domain]-COOH;

$NH_2$—[NLS]-[adenosine deaminase domain]-[Cas12i]-[NLS]—COOH;

$NH_2$—[NLS]-[Cas12i]-[adenosine deaminase domain]-[NLS]—COOH;

$NH_2$-[cytidine deaminase domain]-[Cas12i]-[uracil glycosylase inhibitor (UGI)]—COOH;

$NH_2$-[uracil glycosylase inhibitor (UGI)]-[Cas12i]-[cytidine deaminase domain]-COOH;

$NH_2$—[NLS]-[cytidine deaminase domain]-[Cas12i]-[uracil glycosylase inhibitor (UGI)]—COOH;

$NH_2$—[NLS]-[uracil glycosylase inhibitor (UGI)]-[Cas12i]-[cytidine deaminase domain]-COOH;

$NH_2$-[cytidine deaminase domain]-[Cas12i]-[uracil glycosylase inhibitor (UGI)]-[NLS]—COOH;

$NH_2$-[uracil glycosylase inhibitor (UGI)]-[Cas12i]-[cytidine deaminase domain]-[NLS]—COOH;

$NH_2$—[NLS]-[cytidine deaminase domain]-[Cas12i]-[uracil glycosylase inhibitor (UGI)]-[NLS]—COOH; and $NH_2$—[NLS]-[uracil glycosylase inhibitor (UGI)]-[Cas12i]-[cytidine deaminase domain]-[NLS]—COOH.

Another aspect of the present invention provides a complex comprising any one of the fusion polypeptides provided by the present invention and a guide RNA, wherein the guide RNA is complexed with the fusion polypeptide to guide the fusion polypeptide to bind to a target nucleic acid. In a preferred embodiment, in the complex, the guide RNA comprises a guide segment hybridizing with the target nucleic acid and a repeat segment binding to the fusion polypeptide, and the guide RNA does not comprise and does not bind to a tracrRNA. In a preferred embodiment, in the complex, the repeat segment of the guide RNA comprises the nucleotide sequence set forth in any one of SEQ ID NOs: 7 to 14 or a nucleotide sequence having 1 to 10 nucleotide substitutions, deletions, and/or insertions compared with the nucleotide sequence set forth in any one of SEQ ID NOs: 7 to 14; preferably, the repeat segment of the guide RNA is the nucleotide sequence set forth in any one of SEQ ID NOs: 7 to 14.

In a preferred embodiment, the complex is an epigenetic editor. In a preferred embodiment, the complex is a base editor.

Another aspect of the present invention provides a nucleic acid comprising a polynucleotide encoding any one of the fusion polypeptides or Cas12i polypeptides provided by the present invention. In a preferred embodiment, the polynucleotide is codon-optimized for expression in a prokaryotic or eukaryotic cell. In a preferred embodiment, the polynucleotide comprises or is the nucleotide sequence set forth in any one of SEQ ID NOs: 59 to 64.

Another aspect of the present invention provides a nucleic acid comprising a guide RNA or a nucleotide sequence encoding the guide RNA, wherein the guide RNA comprises a repeat segment comprising the nucleotide sequence set forth in any one of SEQ ID NOs: 7 to 14 or a nucleotide sequence having 1 to 10 nucleotide substitutions, deletions, and/or insertions compared with the nucleotide sequence set forth in any one of SEQ ID NOs: 7 to 14; preferably, the repeat segment of the guide RNA is the nucleotide sequence set forth in any one of SEQ ID NOs: 7 to 14. In a preferred embodiment, the guide RNA does not comprise and does not bind to a tracrRNA. In a preferred embodiment, the nucleic acid is a DNA or an mRNA.

Another aspect of the present invention provides a vector comprising any one of the nucleic acids provided by the present invention. In a preferred embodiment, the vector is a plasmid or a viral vector. In a preferred embodiment, the viral vector is an adeno-associated virus vector, an adenovirus vector, a retrovirus vector, a lentivirus vector, or a herpes simplex virus vector.

Another aspect of the present invention provides a vector system comprising a first vector and a second vector different from the first vector, wherein the first vector comprises the polynucleotide encoding any one of the fusion polypeptides or Cas12i polypeptides provided by the present invention; the second vector comprises a guide RNA or a nucleotide sequence encoding the guide RNA. In a preferred embodiment, the first vector and the second vector are each independently a plasmid or a viral vector. In a preferred embodiment, the viral vector is an adeno-associated virus vector, an adenovirus vector, a retrovirus vector, a lentivirus vector, or a herpes simplex virus vector.

Another aspect of the present invention provides a delivery system comprising any one of the Cas12i polypeptides provided by the present invention, any one of the CRISPR-Cas systems provided by the present invention, any one of the fusion polypeptides provided by the present invention, any one of the complexes provided by the present invention, any one of the nucleic acids provided by the present invention, any one of the vectors provided by the present invention, or any one of the vector systems provided by the present invention. In a preferred embodiment, the delivery system comprises a liposome, a nanoparticle, or an exosome.

Another aspect of the present invention provides a cell comprising any one of the Cas12i polypeptides provided by the present invention, any one of the CRISPR-Cas systems provided by the present invention, any one of the fusion polypeptides provided by the present invention, any one of the complexes provided by the present invention, any one of the nucleic acids provided by the present invention, any one of the vectors provided by the present invention, any one of the vector systems provided by the present invention, or any one of the delivery systems provided by the present invention. In a preferred embodiment, the cell is a eukaryotic cell. In a preferred embodiment, the cell is a human cell.

Another aspect of the present invention provides a composition or a kit comprising any one of the Cas12i polypeptides provided by the present invention, any one of the CRISPR-Cas systems provided by the present invention, any one of the fusion polypeptides provided by the present invention, any one of the complexes provided by the present invention, any one of the nucleic acids provided by the present invention, any one of the vectors provided by the present invention, any one of the vector systems provided by the present invention, any one of the delivery systems provided by the present invention, or any one of the cells provided by the present invention; and a pharmaceutically acceptable carrier.

Another aspect of the present invention provides a method for modifying a target nucleic acid, comprising contacting the target nucleic acid with any one of the CRISPR-Cas systems provided by the present invention, any one of the complexes provided by the present invention, any one of the vector systems provided by the present invention, or any one of the delivery systems provided by the present invention, wherein the contacting results in a modification of the target nucleic acid. In a preferred embodiment, the modification comprises increasing or decreasing expression of a target sequence in the target nucleic acid. In a preferred embodiment, the modification comprises deaminating a target adenine or a target cytosine in the target nucleic acid to achieve base pair conversion. In a preferred embodiment, the target nucleic acid is selected from: a double-stranded DNA, a single-stranded DNA, an RNA, a genomic DNA, and an extrachromosomal DNA. In a preferred embodiment, the contacting occurs outside a cell in vitro, inside a cultured cell, or inside an in-vivo cell. In a preferred embodiment, the cell is a eukaryotic cell, more preferably a human cell.

BRIEF DESCRIPTION OF THE DRAWINGS

FIG. 1 shows diagrams of the secondary structures of predicted crRNAs of the chimeric Cas12i polypeptide of the present invention.

FIG. 2 shows maps of recombinant vectors of an editor formed by the denCas12i-001 of the present invention with an adenine deaminase TadA-8e.

FIG. 3 shows the editing efficiency of each adenine base editor on the RNF2 target.

FIG. 4 shows PAM base preference results for the chimeric Cas12i effector proteins of the present invention.

FIG. 5 and FIG. 6 show schematic diagrams of vectors in which the eukaryotic codon-optimized nucleotides of the enCas12i-001 and enCas12i-002 effector proteins are constructed in eukaryotic expression vectors.

FIG. 8 shows schematic diagrams of vectors in which the eukaryotic codon-optimized nucleotides of the enCas12i-001, enCas12i-002, and Cas12i$^{Max}$ effector proteins are constructed in eukaryotic expression vectors.

FIG. 11 and FIG. 12 show schematic diagrams of recombinant vectors of base editors targeting the RNF2 and TTR genes constructed with the denCas12i of the present invention and TadA8e.

FIG. 13, FIG. 14, and FIG. 15 show the editing activity of the base editors of the present invention in eukaryotic cells by sequencing results.

FIG. 18 and FIG. 19 show the editing activity of mutants of the enCas12i effector protein of the present invention in eukaryotic cells by sequencing results.

DETAILED DESCRIPTION

Definitions

Figure 7:
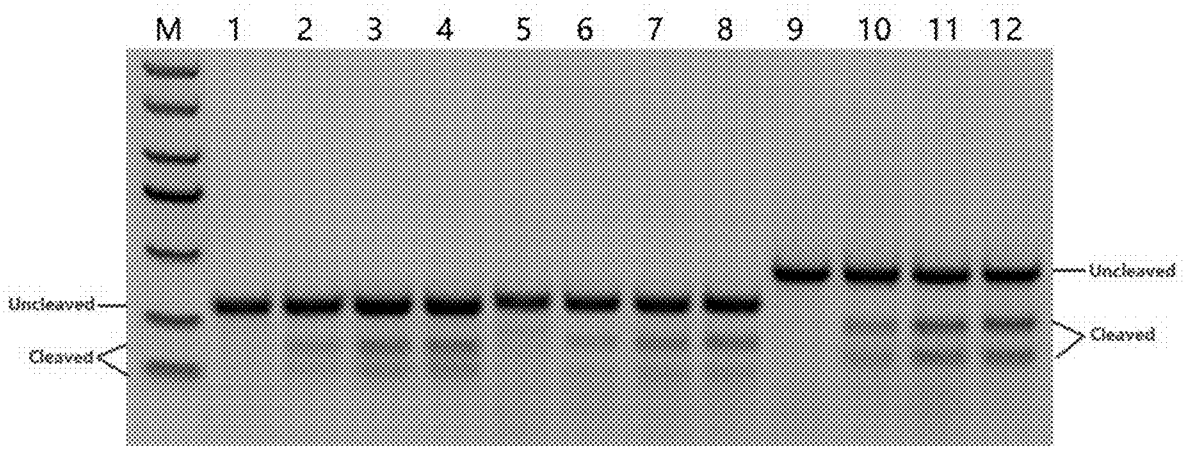
FIG. 7 shows an electrophoretogram of cleavage results for PCR products as detected by agarose gel electrophoresis analysis.

The terms "polynucleotide" and "nucleic acid" as used interchangeably herein refer to a polymeric form of nucleotides (ribonucleotides or deoxyribonucleotides) of any length. Thus, these terms include, but are not limited to, a single-, double- or multi-stranded DNA or RNA, a genomic DNA, a cDNA, a DNA-RNA hybrid, or a polymer comprising purine and pyrimidine bases or other natural, chemically or biochemically modified, non-natural, or derivatized nucleotide bases.

"Hybridizable" or "complementary" or "substantially complementary" means that a nucleic acid (e.g., RNA or DNA) comprises a nucleotide sequence that enables it, under in-vitro and/or in-vivo conditions of appropriate temperature and solution ionic strength, to non-covalently bind (i.e., forming Watson-Crick base pairs and/or G/U base pairs), "anneal" or "hybridize" to another nucleic acid in a sequence-specific, antiparallel manner (i.e., the nucleic acid specifically binds to the complementary nucleic acid). Standard Watson-Crick base pairing includes: adenine (A) pairing with thymine (T), adenine (A) pairing with uracil (U), and guanine (G) pairing with cytosine (C) [DNA and RNA]. In addition, for hybridization between two RNA molecules (e.g., dsRNAs), and for hybridization of a DNA molecule with an RNA molecule (e.g., when a DNA target nucleic acid base pairs with a guide RNA, etc.): guanine (G) may also base-pair with uracil (U). For example, G/U base pairing is at least part of the reason for the genetic code degeneracy (i.e., redundancy) in the context of a tRNA anticodon base pairing with a codon in an mRNA. Thus, in the context of the present invention, guanine (G) (e.g., in a dsRNA duplex of a guide RNA molecule; a guide RNA base pairing with a target nucleic acid, etc.) is considered complementary to uracil (U) and adenine (A). For example, when a G/U base pair can be generated at a given nucleotide position in a dsRNA duplex of a guide RNA molecule, the position is not considered non-complementary, but is considered complementary.

Hybridization requires that the two nucleic acids comprise complementary sequences, although mismatches between bases are possible. The conditions suitable for hybridization between two nucleic acids depend on the length of the nucleic acids and the degree of complementarity, as well as variables well-known in the art. The greater the degree of complementarity between two nucleotide sequences, the greater the value of the melting temperature (Tm) for hybrids of nucleic acids having those sequences. For hybridization between nucleic acids having complementarity of short sequence segments (e.g., complementarity over 35 or less, 30 or less, 25 or less, 22 or less, 20 or less, or 18 or less nucleotides), the position of mismatches may become important (see Sambrook et al., supra, 11.7-11.8). Generally, the length of a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). According to factors such as the length of a complementary region and the degree of complementarity, the temperature, the salt concentration of a wash solution, and other conditions may be adjusted as necessary.

It is understood that the sequence of a polynucleotide does not need to be 100% complementary to the sequence of its target nucleic acid in order to be specifically hybridizable or hybridizable. In addition, a polynucleotide may hybridize over one or more segments such that intermediate segments or adjacent segments are not involved in a hybridization event (e.g., bulge, loop structure, or hairpin structure, etc.). A polynucleotide may have 60% or more, 65% or more, 70% or more, 75% or more, 80% or more, 85% or more, 90% or more, 95% or more, 98% or more, 99% or more, 99.5% or more, or 100% sequence complementarity to a target region in a target nucleic acid sequence with which it hybridizes. For example, an antisense nucleic acid in which 18 of 20 nucleotides of the antisense compound are complementary to a target region and thus will specifically hybridize will represent 90% complementarity. In this example, the remaining non-complementary nucleotides may be clustered with or interspersed among complementary nucleotides and need not be contiguous to each other or to the complementary nucleotides. Any convenient method can be used to determine the percentage of complementarity between specific nucleic acid sequence segments in a nucleic acid. Exemplary methods include BLAST programs (basic local alignment search tools) and PowerBLAST programs, Gap programs (e.g., using default settings), and the like.

The terms "peptide", "polypeptide", and "protein" as used interchangeably herein refer to polymeric forms of amino acids (which may include coding and non-coding amino acids, chemically or biochemically modified or derivatized amino acids) of any length, as well as polypeptides having modified peptide backbones.

As used herein, "binding" (e.g., with respect to an RNA-binding domain of a polypeptide, binding to a target nucleic acid, etc.) refers to a non-covalent interaction between macromolecules (e.g., between a protein and a nucleic acid; between a Cas12i polypeptide/guide RNA complex and a target nucleic acid; etc.). While in the state of non-covalent interaction, the macromolecules are said to be "associated" or "interacting" or "binding" (e.g., when a molecule X is said to interact with a molecule Y, it means that the molecule X binds to the molecule Y in a non-covalent manner). Not all components of the binding interaction need to be sequence-specific (e.g., contacting with phosphate residues in a DNA backbone), but some portions of the binding interaction may be sequence-specific. The binding interaction is generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, and increased binding affinity is correlated with a lower $K_D$.

"Binding domain" means a protein domain capable of non-covalent binding to another molecule. The binding domain may bind to, for example, a DNA molecule (DNA-binding domain), an RNA molecule (RNA-binding domain), and/or a protein molecule (protein-binding domain). In the case of a protein having a protein-binding domain, in some embodiments, it can bind to itself (to form a homodimer, homotrimer, etc.) and/or it can bind to one or more regions of a different protein.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine-glycine, and asparaginc-glutamine.

When a polynucleotide or polypeptide has a certain percentage of "sequence identity" to another polynucleotide or polypeptide, it means that the bases or amino acids have the same percentage when aligned, and they are at the same relative positions when the two sequences are compared. Sequence identity can be determined in many different ways. To determine sequence identity, sequences may be aligned using a variety of convenient methods and computer programs (e.g., BLAST, T-COFFEE, MUSCLE, MAFFT, etc.) available on the world wide web sites including ncbi.nlm-.nili.gov/BLAST, cbi.ac.uk/Tools/msa/tcoffee/, ebi.ac.uk/Tools/msa/muscle/, and mafft.cbrc.jp/alignment/software/. The term "sequence identity" as used herein refers to the degree of sequence similarity on a nucleotide-by-nucleotide basis or on an amino acid-by-amino acid basis within a comparison window. Thus, "percentage of sequence identity" is calculated as follows: by comparing two optimally aligned sequences within a comparison window, the number of positions at which identical nucleic acid bases (e.g., A, T, C, G, or I) or identical amino acid residues (e.g., Ala, Pro, Ser, Thr, Gly, Val, Leu, Ile, Phe, Tyr, Trp, Lys, Arg, His, Asp, Glu, Asn, Gln, Cys, and Met) occur in the two sequences is determined to generate the number of matched positions, the number of matched positions is divided by the total number of positions in the comparison window (i.e., the window size), and the result is multiplied by 100 to give the percentage of sequence identity.

In the present invention, when the sequences to be aligned are two non-contiguous sequences, the calculation of sequence identity is obtained based on the alignment results of the two sequences. For example, "having at least 80% sequence identity to the amino acid sequences of aa 1 to 897 and aa 1008 to 1044 of SEQ ID NO: 1" refers to: (i) having at least 80% sequence identity to the amino acid sequence of aa 1 to 897 of SEQ ID NO: 1 and having at least 80% sequence identity to the amino acid sequence of aa 1008 to 1044 of SEQ ID NO: 1; or (ii) having less than or higher than 80% sequence identity to the amino acid sequence of aa 1 to 897 of SEQ ID NO: 1 and having higher than or less than 80% sequence identity to the amino acid sequence of aa 1008 to 1044 of SEQ ID NO: 1, but having at least 80% sequence identity over a total of 934 amino acids of aa 1 to 897 and aa 1008 to 1044.

The term "at least 80%" in the present invention refers to any value from 80% to 100%, for example, 80%, 85%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, or 100%. The term "at least 95%" in the present invention refers to any value from 95% to 100%, for example, 95%, 95.5%, 96%, 96.5%, 97%, 97.5%, 98%, 98.5%, 99%, 99.5%, or 100%.

A DNA sequence "encoding" a specific RNA is a DNA nucleotide sequence that is transcribed into an RNA. A DNA polynucleotide may encode an RNA that is translated into a protein (mRNA) (thus both a DNA and an mRNA encode a protein), or a DNA polynucleotide may encode an RNA that is not translated into a protein (e.g., tRNA, rRNA, microRNA (miRNA), "non-coding" RNA (ncRNA), guide RNA, etc.).

A "protein coding sequence" or a sequence encoding a specific protein or polypeptide is a nucleotide sequence that, when placed under the control of appropriate regulatory sequences, is transcribed into an mRNA (in the case of DNA) and translated in vitro or in vivo (in the case of mRNA) into a polypeptide.

The terms "DNA regulatory sequence", "control element", and "regulatory element" as used interchangeably herein refer to transcriptional and translational control sequences that provide and/or regulate the transcription of a non-coding sequence (e.g., guide RNA) or coding sequence (e.g., Cas12i polypeptide, Cas12i fusion polypeptide, etc.) and/or regulate the translation of an encoded polypeptide, for example, promoters, enhancers, polyadenylation signals, terminators, protein degradation signals, and the like.

As used herein, a "promoter" or a "promoter sequence" is a DNA regulatory region capable of binding to an RNA polymerase and initiating transcription of a downstream (3' direction) coding or non-coding sequence. For the purposes of the present invention, the promoter sequence binds at its 3' end by a transcription start site and extends upstream (5' direction) of the sequence segment to comprise the minimum number of bases or elements required to initiate transcription at detectable levels above the background. Within the promoter sequence, the transcription start site and a protein-binding domain will be found, which are responsible for the binding of the RNA polymerase. Eukaryotic promoters often, but not always, comprise "TATA" boxes and "CAT" boxes. Various promoters, including inducible promoters, may be used to drive expression of the various vectors of the present invention.

The term "naturally occurring" or "unmodified" or "wild-type" as used herein as applied to a nucleic acid, a polypeptide, a cell, or an organism refers to a nucleic acid, a polypeptide, a cell, or an organism that is present in nature. For example, a polypeptide or polynucleotide sequence present in an organism that can be isolated from a source in nature is naturally occurring.

The term "fusion" as used herein as applied to a nucleic acid or a polypeptide refers to two components defined by structures derived from different sources. For example, when "fusion" is used in the context of a fusion polypeptide (e.g., fusion Cas12i protein), the fusion polypeptide comprises amino acid sequences derived from different polypeptides. The fusion polypeptide may comprise a modified or naturally occurring polypeptide sequence (e.g., a first amino acid sequence from a modified or unmodified Cas12i protein; and a second amino acid sequence from a modified or unmodified protein other than the Cas12i protein, etc.). Similarly, "fusion" in the context of a polynucleotide encoding a fusion polypeptide comprises nucleotide sequences derived from different coding regions (e.g., a first nucleotide sequence encoding a modified or unmodified Cas12i protein; and a second nucleotide sequence encoding a polypeptide other than the Cas12i protein).

The term "fusion polypeptide" refers to a polypeptide generally made through human intervention, by combining (i.e., "fusing") two otherwise separated segments of an amino acid sequence.

As used herein, "heterologous" means nucleotide or polypeptide sequences that are not present together in a natural nucleic acid or protein. For example, in some embodiments, in the fusion protein of the present invention, a moiety of a chimeric Cas12i polypeptide (or a variant thereof) can be fused to an amino acid sequence from a protein other than the source from which the chimeric Cas12i polypeptide is derived, or to an amino acid sequence from another organism. As another example, a fusion Cas12i polypeptide may comprise all or a moiety of a chimeric Cas12i polypeptide (or a variant thereof) fused to a heterologous polypeptide, the heterologous polypeptide being a polypeptide from a protein other than the source from which the chimeric Cas12i polypeptide is derived, or being a polypeptide from another organism. The heterologous polypeptide may exhibit activity that the chimeric Cas12i protein or the fusion Cas12i protein also exhibits (e.g., enzymatic activity) (e.g., biotin ligase activity; nuclear localization; etc.). A heterologous nucleic acid sequence may be linked to a nucleic acid sequence (or a variant thereof) (e.g., by genetic engineering) to generate a nucleotide sequence encoding a fusion polypeptide (fusion protein).

As used herein, "recombinant" means that a specific nucleic acid (DNA or RNA) is the product of various combinations of cloning, restriction, polymerase chain reaction (PCR), and/or ligation steps resulting in a construct having a structural coding or non-coding sequence that are distinguishable from endogenous nucleic acids found in a natural system. A DNA sequence encoding a polypeptide may be assembled from cDNA fragments or from a series of synthetic oligonucleotides to provide a synthetic nucleic acid capable of being expressed by a recombinant transcriptional unit contained in a cell or in a cell-free transcription and translation system. A genomic DNA comprising the relevant sequences may also be used to form a recombinant gene or a transcriptional unit. Sequences of non-translated DNA may be present at the 5' end or 3' end of an open reading frame, wherein such sequences do not interfere with the manipulation or expression of the coding region, and may indeed act to regulate the production of a desired product by various mechanisms. Alternatively, non-translated DNA sequences encoding RNA (e.g., guide RNA) may also be considered recombinant. Thus, for example, the term "recombinant" nucleic acid refers to a non-naturally occurring nucleic acid that is, for example, made through human intervention by artificially combining two otherwise separated segments of a sequence. Such an artificial combination is often accomplished by chemical synthesis means or by artificial manipulation of isolated segments of nucleic acids (e.g., by genetic engineering techniques). This is generally done by replacing a codon with a codon encoding the same amino acid, a conservative amino acid, or a non-conservative amino acid. Alternatively, such manipulation is performed to join together nucleic acid segments having desired functions to generate a desired combination of functions. Such an artificial combination is often accomplished by chemical synthesis means or by artificial manipulation of isolated segments of nucleic acids (e.g., by genetic engineering techniques). When a recombinant polynucleotide encodes a polypeptide, the sequence encoding the polypeptide may be naturally occurring ("wild-type") or may be a variant (e.g., a mutant) of the naturally occurring sequence. An example of such a case is a DNA (recombinant) encoding a wild-type protein, wherein the DNA sequence is codon-optimized for expression of the protein in a cell (e.g., a eukaryotic cell) in which the protein does not naturally occur (e.g., expression of a CRISPR/Cas RNA-guided polypeptide such as Cas12i (e.g., chimeric Cas12i; fusion Cas12i, etc.) in a eukaryotic cell). Thus, a codon-optimized DNA may be recombinant and non-naturally occurring, while the protein encoded by the DNA may have a wild-type amino acid sequence.

Thus, the term "recombinant" polypeptide does not necessarily refer to a polypeptide whose amino acid sequence is not naturally occurring. In contrast, a "recombinant" polypeptide is encoded by a recombinant non-naturally occurring DNA sequence, but the amino acid sequence of the polypeptide may be naturally occurring ("wild-type") or non-naturally occurring (e.g., a variant, a mutant, etc.). Thus, a "recombinant" polypeptide is the result of human intervention, but may have a naturally occurring amino acid sequence.

A "vector" or "expression vector" is a replicon, such as a plasmid, a phage, a virus, an artificial chromosome, or a cosmid, to which another DNA segment (i.e., "insert") may be attached in order to bring about the replication of the attached segment in a cell.

An "expression cassette" comprises a DNA coding sequence operably linked to a promoter. "Operably linked" refers to a juxtaposition, wherein the components are in a relationship permitting them to function in their intended manner. For example, a promoter is operably linked to a coding sequence (or the coding sequence can also be considered operably linked to the promoter) if the promoter affects its transcription or expression.

The terms "recombinant expression vector" and "DNA construct" as used interchangeably herein refer to a DNA molecule comprising a vector and an insert. Recombinant expression vectors are generally generated for the purpose of expressing and/or propagating the insert or for the construction of other recombinant nucleotide sequences. The insert may or may not be operably linked to a promoter sequence and may or may not be operably linked to a DNA regulatory sequence.

A cell is "genetically modified" or "transformed" or "transfected" with an exogenous DNA or an exogenous RNA, e.g., a recombinant expression vector, when such DNA has been introduced inside the cell. The presence of the exogenous DNA results in a permanent or transient genetic change. The transforming DNA may or may not be integrated (covalently linked) into the genome of the cell. In cells such as prokaryotic cells, yeast cells, and mammalian cells, the transforming DNA may be maintained on an episomal element such as a plasmid. With respect to eukaryotic cells, a stably transformed cell is one in which the transforming DNA is gradually integrated into a chromosome such that it is inherited by daughter cells through chromosomal replication. This stability is shown by the ability of the eukaryotic cell to establish cell lines or clones comprising a population of daughter cells containing the transforming DNA. A "clone" is a population of cells derived from a single cell or a common ancestor by mitosis. A "cell line" is a clone of a primary cell capable of stable growth in vitro for many generations.

Suitable methods for genetic modification (also referred to as "transformation") include, for example, viral or phage infection, transfection, conjugation, protoplast fusion, lipofection, electroporation, calcium phosphate precipitation, polyethyleneimine (PEI)-mediated transfection, DEAE-dextran-mediated transfection, liposome-mediated transfection, particle gun technology, calcium phosphate precipitation, direct microinjection, nanoparticle-mediated nucleic acid delivery, and the like. The choice of method of genetic modification generally depends on the type of the cell to be transformed and the circumstances under which the transformation occurs (e.g., in vitro, ex vivo, or in vivo).

As used herein, a "target nucleic acid" is a polynucleotide (e.g., DNA, such as genomic DNA) that comprises a site ("target site" or "target sequence") targeted by an RNA-guided endonuclease polypeptide (e.g., chimeric Cas12i; fusion Cas12i, etc.). The target sequence is the sequence with which the guide sequence of a Cas12i guide RNA (e.g., a dual Cas12i guide RNA or a single-molecule Cas12i guide RNA) will hybridize. Suitable hybridization conditions include physiological conditions normally present in a cell. For a double-stranded target nucleic acid, the strand of the target nucleic acid that is complementary to and hybridizes with the guide RNA is referred to as the "complementary strand" or "target strand"; while the strand of the target nucleic acid that is complementary to the "target strand" (and thus not complementary to the guide RNA) is referred to as the "non-target strand" or "non-complementary strand".

As used herein, the terms "treatment", "treating", and the like refer to obtaining a desired pharmacological and/or physiological effect. The effect may be prophylactic in terms of completely or partially preventing a disease or symptoms thereof, and/or may be therapeutic in terms of a partial or complete cure for the disease and/or side effects attributable to the disease. As used herein, "treatment" encompasses any treatment of a disease in a mammal (e.g., human) and includes: (a) preventing the occurrence of the disease in a subject who may be predisposed to the disease but has not yet been diagnosed with the disease; (b) inhibiting the disease, i.e. arresting its development; and (c) relieving the disease, i.e., causing regression of the disease.

The terms "individual", "subject", "host", and "patient" as used interchangeably herein refer to an individual organism, for example, a mammal, including, but not limited to, rodents, apes, humans, non-human primates, ungulates, felines, canines, bovines, sheep, mammalian farm animals, mammalian sport animals, and mammalian pets.

Chimeric Cas12i Polypeptide

One aspect of the present invention provides an engineered chimeric Cas12i polypeptide comprising a Nuc domain, wherein the Nuc domain is derived from a Nuc domain of a first Cas12i polypeptide, a non-Nuc domain moiety of the engineered chimeric Cas12i polypeptide is derived from a non-Nuc domain moiety of a second Cas12i polypeptide, the first Cas12i polypeptide has no more than 80% sequence identity to the second Cas12i polypeptide, and the engineered chimeric Cas12i polypeptide is capable of binding to a nucleic acid and optionally cleaving the nucleic acid.

In some embodiments, the first Cas12i polypeptide and the second Cas12i polypeptide have the same two-lobe partition structure, for example, both comprise a recognition lobe (REC lobe) and a nuclease lobe (NUC lobe). For example, the recognition lobe is divided into two Helical-I domains (including the first Helical-I and the second Helical-I), a PI domain (PAM-interacting domain), and a Helical-II domain, while the nuclease lobe consists of a WED domain (wedge domain, including WED-I and WED-II), a RuvC nuclease domain, and other three domains: a Helical-III domain, a BH (Bridge Hinge) domain, and a Nuc domain; the RuvC nuclease domain is divided into 3 moieties (including RuvC-I, RuvC-II, and RuvC-III) that are not contiguous in sequence. In some embodiments, the first Cas12i polypeptide and the second Cas12i polypeptide lack HNH nuclease domains and do not comprise zinc finger domains commonly found in eukaryotes (Cys2/His2 zinc fingers, Cys2/Cys2 zinc fingers, etc.).

In some embodiments, the first Cas12i polypeptide and the second Cas12i polypeptide sequentially comprise, from N-terminus to C-terminus, WED-I, first Helical-I, PI, second Helical-I, Helical-II, WED-II, RuvC-I, Helical-III, BH, RuvC-II, Nuc, and RuvC-III domains. In addition, the chimeric Cas12i polypeptide sequentially comprises, from N-terminus to C-terminus, WED-I, first Helical-I, PI, second Helical-I, Helical-II, WED-II, RuvC-I, Helical-III, BH, RuvC-II, Nuc, and RuvC-III domains.

The first Cas12i polypeptide and the second Cas12i polypeptide may be independently selected from those Cas12i polypeptides disclosed in WO2023138685A1, WO2023078314A1, WO2023039534A2, U.S. Pat. No. 11,649,444B1, or WO2022247873A1, the disclosures of which are incorporated herein by reference in their entirety.

In some embodiments, the engineered chimeric Cas12i polypeptide comprises or is an amino acid sequence having at least 95% sequence identity to the amino acid sequence set forth in SEQ ID NO: 1 or 2. For example, the engineered chimeric Cas12i polypeptide comprises or is an amino acid sequence having at least 95%, 96%, 97%, 98%, 99%, or 100% sequence identity to the amino acid sequence set forth in SEQ ID NO: 1. For example, the engineered chimeric Cas12i polypeptide comprises or is an amino acid sequence having at least 95%, 96%, 97%, 98%, 99%, or 100% sequence identity to the amino acid sequence set forth in SEQ ID NO: 2.

In some embodiments, the engineered chimeric Cas12i polypeptide comprises or is an amino acid sequence having at least 95% sequence identity to the amino acid sequence set forth in any one of SEQ ID NOs: 3 to 6. For example, the engineered chimeric Cas12i polypeptide comprises or is an amino acid sequence having at least 95%, 96%, 97%, 98%, 99%, or 100% sequence identity to the amino acid sequence set forth in SEQ ID NO: 3. For example, the engineered chimeric Cas12i polypeptide comprises or is an amino acid sequence having at least 95%, 96%, 97%, 98%, 99%, or 100% sequence identity to the amino acid sequence set forth in SEQ ID NO: 4. For example, the engineered chimeric Cas12i polypeptide comprises or is an amino acid sequence having at least 95%, 96%, 97%, 98%, 99%, or 100% sequence identity to the amino acid sequence set forth in SEQ ID NO: 5. For example, the engineered chimeric Cas12i polypeptide comprises or is an amino acid sequence having at least 95%, 96%, 97%, 98%, 99%, or 100% sequence identity to the amino acid sequence set forth in SEQ ID NO: 6.

In some embodiments, the engineered chimeric Cas12i polypeptide comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2.

For example, the engineered chimeric Cas12i polypeptide comprises or is an amino acid sequence having at least 80%, 85%, 90%, 95%, 96%, 97%, 98%, 99%, or 100% sequence identity to the amino acid sequences of aa 1 to 897 and aa 1008 to 1044 of SEQ ID NO: 1 and having at least 80%, 85%, 90%, 95%, 96%, 97%, 98%, 99%, or 100% sequence identity to the amino acid sequence of aa 898 to 1007 of SEQ ID NO: 1. For example, the engineered chimeric Cas12i polypeptide comprises or is an amino acid sequence having at least 80%, 85%, 90%, 95%, 96%, 97%, 98%, 99%, or 100% sequence identity to the amino acid sequences of aa 1 to 897 and aa 1008 to 1044 of SEQ ID NO: 2 and having at least 80%, 85%, 90%, 95%, 96%, 97%, 98%, 99%, or 100% sequence identity to the amino acid sequence of aa 898 to 1007 of SEQ ID NO: 2.

In some embodiments, the engineered chimeric Cas12i polypeptide comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6.

For example, the engineered chimeric Cas12i polypeptide comprises or is an amino acid sequence having at least 80%, 85%, 90%, 95%, 96%, 97%, 98%, 99%, or 100% sequence identity to the amino acid sequences of aa 1 to 895 and aa 1016 to 1054 of SEQ ID NO: 3 and having at least 80%, 85%, 90%, 95%, 96%, 97%, 98%, 99%, or 100% sequence identity to the amino acid sequence of aa 896 to 1015 of SEQ ID NO: 3. For example, the engineered chimeric Cas12i polypeptide comprises or is an amino acid sequence having at least 80%, 85%, 90%, 95%, 96%, 97%, 98%, 99%, or 100% sequence identity to the amino acid sequences of aa 1 to 895 and aa 1016 to 1054 of SEQ ID NO: 4 and having at least 80%, 85%, 90%, 95%, 96%, 97%, 98%, 99%, or 100% sequence identity to the amino acid sequence of aa 896 to 1015 of SEQ ID NO: 4. For example, the engineered chimeric Cas12i polypeptide comprises or is an amino acid sequence having at least 80%, 85%, 90%, 95%, 96%, 97%, 98%, 99%, or 100% sequence identity to the amino acid sequences of aa 1 to 895 and aa 1016 to 1054 of SEQ ID NO: 5 and having at least 80%, 85%, 90%, 95%, 96%, 97%, 98%, 99%, or 100% sequence identity to the amino acid sequence of aa 896 to 1015 of SEQ ID NO: 5. For example, the engineered chimeric Cas12i polypeptide comprises or is an amino acid sequence having at least 80%, 85%, 90%, 95%, 96%, 97%, 98%, 99%, or 100% sequence identity to the amino acid sequences of aa 1 to 895 and aa 1016 to 1054 of SEQ ID NO: 6 and having at least 80%, 85%, 90%, 95%, 96%, 97%, 98%, 99%, or 100% sequence identity to the amino acid sequence of aa 896 to 1015 of SEQ ID NO: 6.

In some embodiments, the present invention provides an engineered chimeric Cas12i polypeptide capable of binding to a nucleic acid and optionally cleaving the nucleic acid, wherein the engineered chimeric Cas12i polypeptide comprises, from N-terminus to C-terminus, a first peptide segment, a second peptide segment, and a third peptide segment connected in sequence, wherein: the first peptide segment comprises or is an amino acid sequence having at least 80%, 85%, 90%, 95%, 96%, 97%, 98%, 99%, or 100% sequence identity to the amino acid sequence of aa 1 to 897 of SEQ ID NO: 1 or aa 1 to 895 of SEQ ID NO: 3; the second peptide segment comprises or is an amino acid sequence having at least 80%, 85%, 90%, 95%, 96%, 97%, 98%, 99%, or 100% sequence identity to the amino acid sequence set forth in any one of SEQ ID NOs: 67 to 72; and the third peptide segment comprises or is an amino acid sequence having at least 80%, 85%, 90%, 95%, 96%, 97%, 98%, 99%, or 100% sequence identity to the amino acid sequence of aa 1008 to 1044 of SEQ ID NO: 1 or aa 1016 to 1054 of SEQ ID NO: 3.

In some embodiments, the present invention provides an engineered chimeric Cas12i polypeptide capable of binding to a nucleic acid and optionally cleaving the nucleic acid, wherein the engineered chimeric Cas12i polypeptide comprises, from N-terminus to C-terminus, a first peptide segment, a second peptide segment, and a third peptide segment connected in sequence, wherein: the first peptide segment comprises or is an amino acid sequence having at least 80%, 85%, 90%, 95%, 96%, 97%, 98%, 99%, or 100% sequence identity to the amino acid sequence of aa 1 to 897 of SEQ ID NO: 1; the second peptide segment comprises or is an amino acid sequence having at least 80%, 85%, 90%, 95%, 96%, 97%, 98%, 99%, or 100% sequence identity to the amino acid sequence set forth in any one of SEQ ID NOs: 67 to 72; and the third peptide segment comprises or is an amino acid sequence having at least 80%, 85%, 90%, 95%, 96%, 97%, 98%, 99%, or 100% sequence identity to the amino acid sequence of aa 1008 to 1044 of SEQ ID NO: 1.

In some embodiments, the present invention provides an engineered chimeric Cas12i polypeptide capable of binding to a nucleic acid and optionally cleaving the nucleic acid, wherein the engineered chimeric Cas12i polypeptide comprises, from N-terminus to C-terminus, a first peptide segment, a second peptide segment, and a third peptide segment connected in sequence, wherein: the first peptide segment comprises or is an amino acid sequence having at least 80%, 85%, 90%, 95%, 96%, 97%, 98%, 99%, or 100% sequence identity to the amino acid sequence of aa 1 to 897 of SEQ ID NO: 1; the second peptide segment comprises or is an amino acid sequence having at least 80%, 85%, 90%, 95%, 96%, 97%, 98%, 99%, or 100% sequence identity to the amino acid sequence set forth in any one of SEQ ID NOs: 67 to 72; and the third peptide segment comprises or is an amino acid sequence having at least 80%, 85%, 90%, 95%, 96%, 97%, 98%, 99%, or 100% sequence identity to the amino acid sequence of aa 1016 to 1054 of SEQ ID NO: 3.

In some embodiments, the present invention provides an engineered chimeric Cas12i polypeptide capable of binding to a nucleic acid and optionally cleaving the nucleic acid, wherein the engineered chimeric Cas12i polypeptide comprises, from N-terminus to C-terminus, a first peptide segment, a second peptide segment, and a third peptide segment connected in sequence, wherein: the first peptide segment comprises or is an amino acid sequence having at least 80%, 85%, 90%, 95%, 96%, 97%, 98%, 99%, or 100% sequence identity to the amino acid sequence of aa 1 to 895 of SEQ ID NO: 3; the second peptide segment comprises or is an amino acid sequence having at least 80%, 85%, 90%, 95%, 96%, 97%, 98%, 99%, or 100% sequence identity to the amino acid sequence set forth in any one of SEQ ID NOs: 67 to 72; and the third peptide segment comprises or is an amino acid sequence having at least 80%, 85%, 90%, 95%, 96%, 97%, 98%, 99%, or 100% sequence identity to the amino acid sequence of aa 1008 to 1044 of SEQ ID NO: 1.

In some embodiments, the present invention provides an engineered chimeric Cas12i polypeptide capable of binding to a nucleic acid and optionally cleaving the nucleic acid, wherein the engineered chimeric Cas12i polypeptide comprises, from N-terminus to C-terminus, a first peptide segment, a second peptide segment, and a third peptide segment connected in sequence, wherein: the first peptide segment comprises or is an amino acid sequence having at least 80%, 85%, 90%, 95%, 96%, 97%, 98%, 99%, or 100% sequence identity to the amino acid sequence of aa 1 to 895 of SEQ ID NO: 3; the second peptide segment comprises or is an amino acid sequence having at least 80%, 85%, 90%, 95%, 96%, 97%, 98%, 99%, or 100% sequence identity to the amino acid sequence set forth in any one of SEQ ID NOs: 67 to 72; and the third peptide segment comprises or is an amino acid sequence having at least 80%, 85%, 90%, 95%, 96%, 97%, 98%, 99%, or 100% sequence identity to the amino acid sequence of aa 1016 to 1054 of SEQ ID NO: 3.

In some embodiments, the engineered chimeric Cas12i polypeptide (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6; and the engineered chimeric Cas12i polypeptide is mutated to have one or more of the following characteristics: (i) partial or complete inactivation of nucleic acid cleavage activity, or an enhancement of nucleic acid cleavage activity; and (ii) an enhancement of nucleic acid binding activity.

In some embodiments, the mutation results in substantially unchanged nucleic acid binding activity, guide RNA binding activity, and/or nucleic acid cleavage activity of the chimeric Cas12i polypeptide, for example, compared with a parent chimeric Cas12i polypeptide, an increase or a decrease in nucleic acid binding activity, guide RNA binding activity, and/or nucleic acid cleavage activity of about 10% or less, such as 1% to about 10%.

In some embodiments, the mutation results in an enhancement of nucleic acid binding activity of the chimeric Cas12i polypeptide, for example, compared with a parent chimeric Cas12i polypeptide, an enhancement of nucleic acid binding activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%.

In some embodiments, the mutation results in an enhancement of guide RNA binding activity of the chimeric Cas12i polypeptide, for example, compared with a parent chimeric Cas12i polypeptide, an enhancement of guide RNA binding activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%.

In some embodiments, the mutation results in a decrease in nucleic acid cleavage activity of the chimeric Cas12i polypeptide, for example, compared with a parent chimeric Cas12i polypeptide, a decrease in nucleic acid cleavage activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%. In some embodiments, the mutation results in a complete loss of nucleic acid cleavage activity of the chimeric Cas12i polypeptide.

In some embodiments, the mutation results in an enhancement of nucleic acid binding activity of the chimeric Cas12i polypeptide, for example, compared with a parent chimeric Cas12i polypeptide, an enhancement of nucleic acid binding activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%; an enhancement of guide RNA binding activity of the chimeric Cas12i polypeptide, for example, compared with a parent chimeric Cas12i polypeptide, an enhancement of guide RNA binding activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%; and a decrease in nucleic acid cleavage activity of the chimeric Cas12i polypeptide, for example, compared with a parent chimeric Cas12i polypeptide, a decrease in nucleic acid cleavage activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%, or a complete loss of nucleic acid cleavage activity.

In some embodiments, the chimeric Cas12i polypeptide (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and at least 80% sequence identity to the amino acid sequence of aa 896 to 1015 of any one of SEQ ID NOs: 3 to 6, and further having at least one (e.g., 1 to 10, such as 1, 2, 3, 4, 5, 6, 7, 8, 9, or 10) amino acid substitution, deletion, and/or insertion. In such embodiments, the at least one amino acid substitution, deletion, and/or insertion may result in substantially unchanged nucleic acid binding activity and/or nucleic acid cleavage activity of the chimeric Cas12i polypeptide, for example, compared with a parent chimeric Cas12i polypeptide, an increase or a decrease in nucleic acid binding activity, guide RNA binding activity, and/or nucleic acid cleavage activity of about 10% or less, such as 1% to about 10%. In such embodiments, the at least one amino acid substitution, deletion, and/or insertion may result in an enhancement of nucleic acid binding activity of the chimeric Cas12i polypeptide, for example, compared with a parent chimeric Cas12i polypeptide, an enhancement of nucleic acid binding activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%. In such embodiments, the at least one amino acid substitution, deletion, and/or insertion may result in an enhancement of guide RNA binding activity of the chimeric Cas12i polypeptide, for example, compared with a parent chimeric Cas12i polypeptide, an enhancement of guide RNA binding activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%. In such embodiments, the at least one amino acid substitution, deletion, and/or insertion may result in a decrease in nucleic acid cleavage activity of the chimeric Cas12i polypeptide, for example, compared with a parent chimeric Cas12i polypeptide, a decrease in nucleic acid cleavage activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%, or a complete loss of nucleic acid cleavage activity.

In some embodiments, the present invention provides a chimeric Cas12i polypeptide, which (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6, and according to the sequence numbering set forth in SEQ ID NO: 1, has an amino acid substitution at position D1009. In a preferred embodiment, D1009 is preferably substituted with alanine. In some embodiments, the substitution results in, compared with a parent chimeric Cas12i polypeptide, a decrease in nucleic acid cleavage activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%, or a complete loss of nucleic acid cleavage activity.

In some embodiments, the present invention provides a chimeric Cas12i polypeptide, which (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6, and according to the sequence numbering set forth in SEQ ID NO: 1, has an amino acid substitution at position N229. In a preferred embodiment, N229 is substituted with lysine, arginine, or histidine. In a more preferred embodiment, N229 is substituted with arginine.

In some embodiments, the present invention provides a chimeric Cas12i polypeptide, which (i) comprises or is an amino acid sequence having at least 95% sequence identity to the amino acid sequence set forth in SEQ ID NO: 1; or (ii) comprises or is an amino acid sequence having at least 80% sequence identity to the amino acid sequences of aa 1 to 897 and aa 1008 to 1044 of SEQ ID NO: 1 and having at least 80% sequence identity to the amino acid sequence of aa 898 to 1007 of SEQ ID NO: 1 or 2; and the chimeric Cas12i polypeptide has an amino acid substitution at least one of the two positions D924 and S925. In a preferred embodiment, at least one of the two positions D924 and S925 is substituted with lysine, arginine, or histidine. In a preferred embodiment, both positions D924 and S925 are substituted with lysine, arginine, or histidine. In a more preferred embodiment, at least one of the two positions D924 and S925 is substituted with arginine. In a more preferred embodiment, both positions D924 and S925 are substituted with arginine.

In a preferred embodiment, the present invention provides a chimeric Cas12i polypeptide, which (i) comprises or is an amino acid sequence having at least 95% sequence identity to the amino acid sequence set forth in SEQ ID NO: 1; or (ii) comprises or is an amino acid sequence having at least 80% sequence identity to the amino acid sequences of aa 1 to 897 and aa 1008 to 1044 of SEQ ID NO: 1 and having at least 80% sequence identity to the amino acid sequence of aa 898 to 1007 of SEQ ID NO: 1 or 2; and the chimeric Cas12i polypeptide has an amino acid substitution at least one of the three positions N229, D924, and S925. In a preferred embodiment, at least one of the three positions N229, D924, and S925 is substituted with lysine, arginine, or histidine. In a preferred embodiment, N229 is substituted with lysine, arginine, or histidine, and at least one of the two positions D924 and S925 is substituted with lysine, arginine, or histidine. In a preferred embodiment, N229, D924, and S925 are all substituted with lysine, arginine, or histidine. In a preferred embodiment, N229, D924, and S925 are all substituted with arginine.

In some embodiments, the chimeric Cas12i polypeptide comprises or is the amino acid sequences set forth in SEQ ID NOs: 1 to 6, referred to as "enCas12i-001", "enCas12i-002", "enCas12i-003", "enCas12i-004", "enCas12i-005", and "enCas12i-006", respectively. In some other embodiments, the chimeric Cas12i polypeptide has a D1009A or D1019A mutation based on the amino acid sequences set forth in SEQ ID NOs: 1 to 6, thereby forming "denCas12i", referred to as "denCas12i-001" (i.e., enCas12i-001 (D1009A)), "denCas12i-002" (i.e., enCas12i-002 (D1009A)), "denCas12i-003" (i.e., enCas12i-003 (D1019A)), "denCas12i-004" (i.e., enCas12i-004 (D1019A)), "denCas12i-005" (i.e., enCas12i-005 (D1019A)), and "denCas12i-006" (i.e., enCas12i-006 (D1019A)), respectively. In the present invention, these chimeric Cas12i polypeptides and mutants thereof are also referred to as "enCas12i polypeptides", "Cas12i polypeptides", "Cas12i effector proteins", and "enCas12i effector proteins", these terms being used interchangeably herein.

In some embodiments, a length of the amino acid (aa) sequence of the chimeric Cas12i polypeptide is 1000 to 1200, for example, 1000 to 1100, such as 1000 to 1080, 1000 to 1060, 1020 to 1060, 1030 to 1060, 1040 to 1060, 1050 to 1060, 1040, 1041, 1042, 1043, 1044, 1045, 1046, 1047, 1048, 1049, 1050, 1051, 1052, 1053, 1054, 1055, 1056, 1057, 1058, 1059, or 1060.

Guide RNA (gRNA)

Another aspect of the present invention provides a guide RNA. The guide RNA comprises a guide segment hybridizing with the target nucleic acid and a repeat segment binding to the chimeric Cas12i polypeptide. In some embodiments, the guide RNA does not comprise and does not bind to a tracrRNA.

The guide segment of the guide RNA is also referred to as a targeting segment, which comprises a nucleotide sequence (guide sequence) that is complementary to (and thus hybridizes with) a specific sequence (target site) within a target nucleic acid (e.g., target dsDNA, target ssRNA, target ssDNA, a complementary strand of a double-stranded target DNA, etc.). The repeat segment of the guide RNA, also referred to as a protein-binding segment ("protein-binding sequence" or crRNA), interacts with (binds to) the chimeric Cas12i polypeptide provided by the present invention. Site-specific binding of a target nucleic acid (e.g., genomic DNA, dsDNA, RNA, etc.) may occur at a position determined by base pairing complementarity between the guide RNA (guide sequence) and the target nucleic acid (e.g., the target sequence of the target locus).

In some embodiments, the percentage of complementarity between the guide sequence and the target site of the target nucleic acid is 60% or higher (e.g., 65% or higher, 70% or higher, 75% or higher, 80% or higher, 85% or higher, 90% or higher, 95% or higher, 97% or higher, 98% or higher, 99% or higher, or 100%). In some embodiments, the percentage of complementarity between the guide sequence and the target site of the target nucleic acid is 80% or higher (e.g., 85% or higher, 90% or higher, 95% or higher, 97% or higher, 98% or higher, 99% or higher, or 100%). In some embodiments, the percentage of complementarity between the guide sequence and the target site of the target nucleic acid is 90% or higher (e.g., 95% or higher, 97% or higher, 98% or higher, 99% or higher, or 100%). In some embodiments, the percentage of complementarity between the guide sequence and the target site of the target nucleic acid is 100%. In some embodiments, the percentage of complementarity between the guide sequence and the target site of the target nucleic acid over seven contiguous nucleotides at the 3'-most end of the target site of the target nucleic acid is 100%.

In some embodiments, the percentage of complementarity between the guide sequence and the target site of the target nucleic acid over 17 or more (e.g., 18 or more, 19 or more, 20 or more, 21 or more, or 22 or more) contiguous nucleotides is 60% or higher (e.g., 70% or higher, 75% or higher, 80% or higher, 85% or higher, 90% or higher, 95% or higher, 97% or higher, 98% or higher, 99% or higher, or 100%). In some embodiments, the percentage of complementarity between the guide sequence and the target site of the target nucleic acid over 17 or more (e.g., 18 or more, 19 or more, 20 or more, 21 or more, or 22 or more) contiguous nucleotides is 80% or higher (e.g., 85% or higher, 90% or higher, 95% or higher, 97% or higher, 98% or higher, 99% or higher, or 100%). In some embodiments, the percentage of complementarity between the guide sequence and the target site of the target nucleic acid over 17 or more (e.g., 18 or more, 19 or more, 20 or more, 21 or more, or 22 or more) contiguous nucleotides is 90% or higher (e.g., 95% or higher, 97% or higher, 98% or higher, 99% or higher, or 100%). In some embodiments, the percentage of complementarity between the guide sequence and the target site of the target nucleic acid over 17 or more (e.g., 18 or more, 19 or more, 20 or more, 21 or more, or 22 or more) contiguous nucleotides is 100%.

In some embodiments, the percentage of complementarity between the guide sequence and the target site of the target nucleic acid over 19 or more (e.g., 20 or more, 21 or more, or 22 or more) contiguous nucleotides is 60% or higher (e.g., 70% or higher, 75% or higher, 80% or higher, 85% or higher, 90% or higher, 95% or higher, 97% or higher, 98% or higher, 99% or higher, or 100%). In some embodiments, the percentage of complementarity between the guide sequence and the target site of the target nucleic acid over 19 or more (e.g., 20 or more, 21 or more, or 22 or more) contiguous nucleotides is 80% or higher (e.g., 85% or higher, 90% or higher, 95% or higher, 97% or higher, 98% or higher, 99% or higher, or 100%). In some embodiments, the percentage of complementarity between the guide sequence and the target site of the target nucleic acid over 19 or more (e.g., 20 or more, 21 or more, or 22 or more) contiguous nucleotides is 90% or higher (e.g., 95% or higher, 97% or higher, 98% or higher, 99% or higher, or 100%). In some embodiments, the percentage of complementarity between the guide sequence and the target site of the target nucleic acid over 19 or more (e.g., 20 or more, 21 or more, or 22 or more) contiguous nucleotides is 100%.

In some embodiments, the percentage of complementarity between the guide sequence and the target site of the target nucleic acid over 17-25 contiguous nucleotides is 60% or higher (e.g., 70% or higher, 75% or higher, 80% or higher, 85% or higher, 90% or higher, 95% or higher, 97% or higher, 98% or higher, 99% or higher, or 100%). In some embodiments, the percentage of complementarity between the guide sequence and the target site of the target nucleic acid over 17-25 contiguous nucleotides is 80% or higher (e.g., 85% or higher, 90% or higher, 95% or higher, 97% or higher, 98% or higher, 99% or higher, or 100%). In some embodiments, the percentage of complementarity between the guide sequence and the target site of the target nucleic acid over 17-25 contiguous nucleotides is 90% or higher (e.g., 95% or higher, 97% or higher, 98% or higher, 99% or higher, or 100%). In some embodiments, the percentage of complementarity between the guide sequence and the target site of the target nucleic acid over 17-25 contiguous nucleotides is 100%.

In some embodiments, the percentage of complementarity between the guide sequence and the target site of the target nucleic acid over 19-25 contiguous nucleotides is 60% or higher (e.g., 70% or higher, 75% or higher, 80% or higher, 85% or higher, 90% or higher, 95% or higher, 97% or higher, 98% or higher, 99% or higher, or 100%). In some embodiments, the percentage of complementarity between the guide sequence and the target site of the target nucleic acid over 19-25 contiguous nucleotides is 80% or higher (e.g., 85% or higher, 90% or higher, 95% or higher, 97% or higher, 98% or higher, 99% or higher, or 100%). In some embodiments, the percentage of complementarity between the guide sequence and the target site of the target nucleic acid over 19-25 contiguous nucleotides is 90% or higher (e.g., 95% or higher, 97% or higher, 98% or higher, 99% or higher, or 100%). In some embodiments, the percentage of complementarity between the guide sequence and the target site of the target nucleic acid over 19-25 contiguous nucleotides is 100%.

In some embodiments, the guide sequence has a length in the range of 17-30 nucleotides (nt) (e.g., 17-25, 17-22, 17-20, 19-30, 19-25, 19-22, 19-20, 20-30, 20-25, or 20-22 nt). In some embodiments, the guide sequence has a length in the range of 17-25 nucleotides (nt) (e.g., 17-22, 17-20, 19-25, 19-22, 19-20, 20-25, or 20-22 nt). In some embodiments, the guide sequence has a length of 17 or more nt (e.g., 18 or more, 19 or more, 20 or more, 21 or more, or 22 or more nt; 19 nt, 20 nt, 21 nt, 22 nt, 23 nt, 24 nt, 25 nt, etc.). In some embodiments, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some embodiments, the guide sequence has a length of 17 nt. In some embodiments, the guide sequence has a length of 18 nt. In some embodiments, the guide sequence has a length of 19 nt. In some embodiments, the guide sequence has a length of 20 nt. In some embodiments, the guide sequence has a length of 21 nt. In some embodiments, the guide sequence has a length of 22 nt. In some embodiments, the guide sequence has a length of 23 nt. In some embodiments, the guide sequence has a length of 15 to 50 nucleotides (e.g., 15 nucleotides (nt) to 20 nt, 20 nt to 25 nt, 25 nt to 30 nt, 30 nt to 35 nt, 35 nt to 40 nt, 40 nt to 45 nt, or 45 nt to 50 nt).

In some embodiments of the present invention, the repeat segment (protein-binding segment) of the guide RNA is a single nucleotide sequence that does not complementarily pair with a tracrRNA or otherwise bind to a tracrRNA. Thus, the formed CRISPR-Cas system or complex does not comprise a tracrRNA.

Specifically, a length of the sequence of the repeat segment may be 15 to 100 nt, for example, 20-80 nt, 20-50 nt, or 20 to 40 nt, such as 20, 21, 22, 23, 24, 25, 26, 27, 28, 29, 30, 31, 32, 33, 34, 35, 36, 37, 38, 39, or 40 nt.

In some embodiments, the repeat segment of the guide RNA comprises or is the nucleotide sequence set forth in any one of SEQ ID NOs: 7 to 14 or a nucleotide sequence having 1 to 10 (e.g., 1, 2, 3, 4, 5, 6, 7, 8, 9, or 10) nucleotide substitutions, deletions, and/or insertions compared with the nucleotide sequence set forth in any one of SEQ ID NOs: 7 to 14.

In such embodiments, the at least one nucleotide substitution, deletion, and/or insertion may result in substantially unchanged chimeric Cas12i polypeptide binding activity of the repeat segment, for example, compared with a parent nucleotide sequence, an increase or a decrease in chimeric Cas12i polypeptide binding activity of about 10% or less, such as 1% to about 10%. In such embodiments, the at least one nucleotide substitution, deletion, and/or insertion may result in an enhancement of chimeric Cas12i polypeptide binding activity, for example, compared with a parent nucleotide sequence, an enhancement of chimeric Cas12i polypeptide binding activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%. In such embodiments, the at least one nucleotide substitution, deletion, and/or insertion may result in a decrease in chimeric Cas12i polypeptide binding activity, for example, compared with a parent nucleotide sequence, a decrease in chimeric Cas12i polypeptide binding activity of at least 10%, such as 10% to 500%, 10% to 100%, 10% to 200%, 10% to 300%, 10% to 50%, 10% to 30%, 10% to 20%, 50% to 100%, 50% to 200%, 50% to 300%, 100% to 200%, or 200% to 300%. Any nucleotide sequence that retains chimeric Cas12i polypeptide binding activity after the at least one nucleotide substitution, deletion, and/or insertion is within the scope of the present invention.

In some embodiments, the repeat segment of the guide RNA comprises or is the nucleotide sequence set forth in SEQ ID NO: 7. In some embodiments, the repeat segment of the guide RNA comprises or is the nucleotide sequence set forth in SEQ ID NO: 8. In some embodiments, the repeat segment of the guide RNA comprises or is the nucleotide sequence set forth in SEQ ID NO: 9. In some embodiments, the repeat segment of the guide RNA comprises or is the nucleotide sequence set forth in SEQ ID NO: 10. In some embodiments, the repeat segment of the guide RNA comprises or is the nucleotide sequence set forth in SEQ ID NO: 11. In some embodiments, the repeat segment of the guide RNA comprises or is the nucleotide sequence set forth in SEQ ID NO: 12. In some embodiments, the repeat segment of the guide RNA comprises or is the nucleotide sequence set forth in SEQ ID NO: 13. In some embodiments, the repeat segment of the guide RNA comprises or is the nucleotide sequence set forth in SEQ ID NO: 14. The secondary structure of the repeat segment of the guide RNA is calculated using the minimum free energy (MFE) algorithm as shown in FIG. 1.

In some embodiments, the repeat segment of the guide RNA may comprise a palindromic region that may form stem and stem-loop structures. In some embodiments, the palindromic region comprises a stem structure formed by 5 to 15 base pairs (bp), for example, 8 to 12 bp or 10 to 15 bp, such as 7, 8, 9, 10, 11, 12, 13, 14, or 15 bp. In some embodiments, not all nucleotides in the stem structure are paired, and thus the stem structure may comprise a bulge. The term "bulge" is used herein to mean a segment of nucleotides (which may be one nucleotide) that does not contribute to the stem structure but is surrounded at the 5' end and 3' end by contributing nucleotides, thus, the bulge is considered a moiety of the stem structure. In some embodiments, the stem structure comprises 1 or more bulges (e.g., 2 or more, 3 or more, or 4 or more bulges). In some embodiments, the stem structure comprises 2 or more bulges (e.g., 3 or more or 4 or more bulges). In some embodiments, the stem structure comprises 1-5 bulges (e.g., 1-4, 1-3, 2-5, 2-4, or 2-3 bulges).

In some embodiments, the guide RNA comprises or is the nucleotide sequence set forth in any one of SEQ ID NOs: 15 to 22 or a reverse complementary sequence thereof, wherein N is any nucleotide (A, G, C, U, or T), and n is an integer from 15 to 40, for example, 15 to 30, 15 to 20, 17 to 25, 17 to 22, 18 to 22, 18 to 20, 20 to 25, or 25 to 30, and may be, for example, 15, 16, 17, 18, 19, 20, 21, 22, 23, 24, 25, 26, 27, 28, 29, or 30. In some embodiments, the guide RNA comprises or is the nucleotide sequence set forth in SEQ ID NO: 15 or a reverse complementary sequence thereof, wherein N is any nucleotide (A, G, C, U, or T), and n is an integer from 15 to 40. In some embodiments, the guide RNA comprises or is the nucleotide sequence set forth in SEQ ID NO: 16 or a reverse complementary sequence thereof, wherein N is any nucleotide (A, G, C, U, or T), and n is an integer from 15 to 40. In some embodiments, the guide RNA comprises or is the nucleotide sequence set forth in SEQ ID NO: 17 or a reverse complementary sequence thereof, wherein N is any nucleotide (A, G, C, U, or T), and n is an integer from 15 to 40. In some embodiments, the guide RNA comprises or is the nucleotide sequence set forth in SEQ ID NO: 18 or a reverse complementary sequence thereof, wherein N is any nucleotide (A, G, C, U, or T), and n is an integer from 15 to 40. In some embodiments, the guide RNA comprises or is the nucleotide sequence set forth in SEQ ID NO: 19 or a reverse complementary sequence thereof, wherein N is any nucleotide (A, G, C, U, or T), and n is an integer from 15 to 40. In some embodiments, the guide RNA comprises or is the nucleotide sequence set forth in SEQ ID NO: 20 or a reverse complementary sequence thereof, wherein N is any nucleotide (A, G, C, U, or T), and n is an integer from 15 to 40. In some embodiments, the guide RNA comprises or is the nucleotide sequence set forth in SEQ ID NO: 21 or a reverse complementary sequence thereof, wherein N is any nucleotide (A, G, C, U, or T), and n is an integer from 15 to 40. In some embodiments, the guide RNA comprises or is the nucleotide sequence set forth in SEQ ID NO: 22 or a reverse complementary sequence thereof, wherein N is any nucleotide (A, G, C, U, or T), and n is an integer from 15 to 40.

In the present invention, the guide RNA may be modified. In some embodiments, the guide RNA has one or more modifications (e.g., base modifications, backbone modifications, etc.) to provide new or enhanced characteristics (e.g., improved stability) to the nucleic acid. Suitable nucleic acid modifications include, but are not limited to: 2'-O methyl modified nucleotides, 2'-fluoro modified nucleotides, locked nucleic acid (LNA) modified nucleotides, peptide nucleic acid (PNA) modified nucleotides, nucleotides having phosphorothioate bonds, and 5' caps (e.g., 7-methylguanosine cap (m7G)).

For example, the modification comprises an aptamer. Aptamers are synthetic oligonucleotides binding to specific target molecules; for example, nucleotide molecules that have been engineered by repeated rounds of in-vitro selection or SELEX (systematic evolution of ligands by exponential enrichment) to bind to different molecules, targeting entities such as small molecules, proteins, nucleic acids, and even cells, tissues, and organisms. Aptamers can provide antibody-like molecular recognition properties and elicit little immunogenicity in therapeutic applications.

CRISPR-Cas12i System

The CRISPR/Cas effector polypeptide (e.g., chimeric Cas12i protein) interacts with (binds to) a corresponding guide RNA (e.g., chimeric Cas12i guide RNA) to form a ribonucleoprotein (RNP) complex that is targeted to a specific site within a target nucleic acid (e.g., target DNA) by base pairing between the guide RNA and a target sequence within the target nucleic acid molecule. The guide RNA comprises a nucleotide sequence (guide sequence) complementary to a sequence (target site) of the target nucleic acid. Thus, the chimeric Cas12i protein forms a complex with the chimeric Cas12i guide RNA, and the guide RNA provides sequence specificity for the RNP complex by the guide sequence. In other words, the chimeric Cas12i protein is guided to a target site (e.g., stabilized at the target site) within a target nucleic acid sequence (e.g., a chromosomal sequence or an extrachromosomal sequence, such as an episomal sequence, a minicircle sequence, a mitochondrial sequence, a chloroplast sequence, etc.) by virtue of its association with the guide RNA.

Thus, one aspect of the present invention provides a CRISPR-Cas system comprising: (a) a Cas12i polypeptide being any one of the engineered chimeric Cas12i polypeptides provided by the present invention; and (b) a guide RNA complexed with the Cas12i polypeptide to guide the Cas12i polypeptide to bind to a target nucleic acid.

In some embodiments, in the CRISPR-Cas system provided by the present invention, the Cas12i polypeptide is any one of the chimeric Cas12i polypeptides described above in the section "Chimeric Cas12i polypeptide". In some embodiments, in the CRISPR-Cas system provided by the present invention, the guide RNA is any one of the guide RNAs described above in the section "Guide RNA (gRNA)".

In some specific embodiments, the present invention provides a CRISPR-Cas system comprising: (a) a Cas12i polypeptide comprising or being an amino acid sequence having at least 95% sequence identity to the amino acid sequence set forth in any one of SEQ ID NOs: 1 to 6; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising a Nuc domain, wherein the Nuc domain is derived from a Nuc domain of a first Cas12i polypeptide, a non-Nuc domain moiety of the engineered chimeric Cas12i polypeptide is derived from a non-Nuc domain moiety of a second Cas12i polypeptide, the first Cas12i polypeptide has no more than 80% sequence identity to the second Cas12i polypeptide, and the engineered chimeric Cas12i polypeptide is capable of binding to a nucleic acid and optionally cleaving the nucleic acid; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising or being an amino acid sequence having at least 95% sequence identity to the amino acid sequence set forth in any one of SEQ ID NOs: 1 to 6; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising or being an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising or being an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising or being an amino acid sequence having at least 95% sequence identity to the amino acid sequence set forth in any one of SEQ ID NOs: 1 to 6 and according to the sequence numbering set forth in SEQ ID NO: 1, having an amino acid substitution, preferably with alanine, at position D1009; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising or being an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2 and according to the sequence numbering set forth in SEQ ID NO: 1, having an amino acid substitution, preferably with alanine, at position D1009; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising or being an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6 and according to the sequence numbering set forth in SEQ ID NO: 1, having an amino acid substitution, preferably with alanine, at position D1009; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising or being an amino acid sequence having at least 95% sequence identity to the amino acid sequence set forth in any one of SEQ ID NOs: 1 to 6 and according to the sequence numbering set forth in SEQ ID NO: 1, having an amino acid substitution, preferably with lysine, arginine, or histidine, more preferably with arginine, at position N229; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising or being an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2 and according to the sequence numbering set forth in SEQ ID NO: 1, having an amino acid substitution, preferably with lysine, arginine, or histidine, more preferably with arginine, at position N229; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide comprising or being an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6 and according to the sequence numbering set forth in SEQ ID NO: 1, having an amino acid substitution, preferably with lysine, arginine, or histidine, more preferably with arginine, at position N229; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide, which comprises or is an amino acid sequence having at least 95% sequence identity to the amino acid sequence set forth in SEQ ID NO: 1 and has an amino acid substitution, preferably with lysine, arginine, or histidine, more preferably with arginine, at least one of the three positions N229, D924, and S925; and (b) a guide RNA complexed with the Cas12i polypeptide to guide the Cas12i polypeptide to bind to a target nucleic acid.

In some specific embodiments, the present invention provides a CRISPR-Cas system comprising: (a) a Cas12i polypeptide, which comprises or is an amino acid sequence having at least 80% sequence identity to the amino acid sequences of aa 1 to 897 and aa 1008 to 1044 of SEQ ID NO: 1 and having at least 80% sequence identity to the amino acid sequence of aa 898 to 1007 of SEQ ID NO: 1 or 2 and has an amino acid substitution, preferably with lysine, arginine, or histidine, more preferably with arginine, at least one of the three positions N229, D924, and S925; and (b) a guide RNA complexed with the Cas12i polypeptide to guide the Cas12i polypeptide to bind to a target nucleic acid.

In some specific embodiments, in any one of the CRISPR-Cas systems described above, the guide RNA comprises a guide segment hybridizing with the target nucleic acid and a repeat segment binding to the Cas12i polypeptide, and the guide RNA does not comprise and does not bind to a tracrRNA.

In some specific embodiments, in any one of the CRISPR-Cas systems described above, the repeat segment of the guide RNA comprises or is the nucleotide sequence set forth in any one of SEQ ID NOs: 7 to 14 or a nucleotide sequence having 1 to 10 nucleotide substitutions, deletions, and/or insertions compared with the nucleotide sequence set forth in any one of SEQ ID NOs: 7 to 14.

In some specific embodiments, in any one of the CRISPR-Cas systems described above, the repeat segment of the guide RNA is the nucleotide sequence set forth in any one of SEQ ID NOs: 7 to 14.

In some specific embodiments, in any one of the CRISPR-Cas systems described above, the guide RNA comprises or is the nucleotide sequence set forth in any one of SEQ ID NOs: 15 to 22.

The chimeric Cas12i polypeptide binds to a target nucleic acid at a target sequence defined by the complementarity region between the RNA targeting the target nucleic acid and the target nucleic acid. Site-specific binding of a double-stranded target nucleic acid occurs at a position determined by both: (i) base pairing complementarity between the guide RNA and the target nucleic acid; and (ii) a protospacer adjacent motif (PAM) in the target nucleic acid.

The process of the CRISPR-Cas12i system of the present invention recognizing and binding to a target nucleic acid requires the involvement of a short conservative sequence upstream/downstream of the target sequence, i.e., a protospacer adjacent motif (PAM). The gRNA mediates recognition of a PAM at the 5' end of the target sequence by the Cas12i protein. When the PAM exhibits a specific base composition characteristic, a DNA double strand near the target sequence is catalyzed to unwind, and a targeting segment (guide segment) of the guide RNA hybridizes with a targeting strand in the DNA double strand by base complementary pairing to form an RNA-DNA heteroduplex complex, which then binds to a target nucleic acid strand. It is found after experimental testing that the PAM sequence of the chimeric Cas12i polypeptide of the present invention is 5'-TTN (N=A, T, C, or G), 5'-ATN (N=A, T, C, or G), 5'-TAN (N=A, T, C, or G), or 5'-AAN (N=A, T, C, or G).

Fusion Polypeptide

Another aspect of the present invention provides a fusion polypeptide comprising a chimeric Cas12i polypeptide fused to one or more heterologous polypeptides, wherein the chimeric Cas12i polypeptide comprises a Nuc domain; the Nuc domain is derived from a Nuc domain of a first Cas12i polypeptide; a non-Nuc domain moiety of the engineered chimeric Cas12i polypeptide is derived from a non-Nuc domain moiety of a second Cas12i polypeptide; the first Cas12i polypeptide has no more than 80% sequence identity to the second Cas12i polypeptide; and the engineered chimeric Cas12i polypeptide is capable of binding to a nucleic acid, and preferably the chimeric Cas12i does not cleave the nucleic acid or only cleaves a single strand of the nucleic acid.

In some embodiments, the present invention provides a fusion polypeptide comprising a Cas12i polypeptide fused to one or more heterologous polypeptides, wherein the Cas12i polypeptide is any one of the chimeric Cas12i polypeptides described above in the section "Chimeric Cas12i polypeptide".

In some embodiments, the present invention provides a fusion polypeptide comprising a Cas12i polypeptide fused to one or more heterologous polypeptides, wherein the Cas12i polypeptide comprises or is an amino acid sequence having at least 95% sequence identity to the amino acid sequence set forth in any one of SEQ ID NOs: 1 to 6.

In some embodiments, the present invention provides a fusion polypeptide comprising a Cas12i polypeptide fused to one or more heterologous polypeptides, wherein the Cas12i polypeptide comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2.

In some embodiments, the present invention provides a fusion polypeptide with a Cas12i polypeptide fused to one or more heterologous polypeptides, wherein the Cas12i polypeptide comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6.

In some embodiments, the present invention provides a fusion polypeptide comprising a Cas12i polypeptide fused to one or more heterologous polypeptides, wherein the Cas12i polypeptide comprises or is an amino acid sequence having at least 95% sequence identity to the amino acid sequence set forth in any one of SEQ ID NOs: 1 to 6, and according to the sequence numbering set forth in SEQ ID NO: 1, has an amino acid substitution, preferably with alanine, at position D1009.

In some embodiments, the present invention provides a fusion polypeptide comprising a Cas12i polypeptide fused to one or more heterologous polypeptides, wherein the Cas12i polypeptide comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2, and according to the sequence numbering set forth in SEQ ID NO: 1, has an amino acid substitution, preferably with alanine, at position D1009.

In some embodiments, the present invention provides a fusion polypeptide comprising a Cas12i polypeptide fused to one or more heterologous polypeptides, wherein the Cas12i polypeptide comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6, and according to the sequence numbering set forth in SEQ ID NO: 1, has an amino acid substitution, preferably with alanine, at position D1009.

In some embodiments, the present invention provides a fusion polypeptide comprising a Cas12i polypeptide fused to one or more heterologous polypeptides, wherein the Cas12i polypeptide (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of SEQ ID NOs: 3 to 6, and according to the sequence numbering set forth in SEQ ID NO: 1, has an amino acid substitution, preferably with alanine, at position D1009; and the one or more heterologous polypeptides are independently selected from an epitope tag and a nuclear localization signal, or have one or more of the following enzymatic activities: reverse transcriptase activity, nuclease activity, methyltransferase activity, demethylase activity, acetyltransferase activity, deacetylase activity, kinase activity, phosphatase activity, ubiquitin ligase activity, deubiquitination activity, adenylation activity, deadenylation activity, SUMOylation activity, deSUMOylation activity, ribosylation activity, deribosylation activity, myristoylation activity, demyristoylation activity, glycosylation activity (e.g., from an O-GlcNAc transferase) and deglycosylation activity, DNA repair activity, DNA damage activity, deaminase activity, dismutase activity, alkylation activity, depurination activity, oxidation activity, pyrimidine dimer formation activity, integrase activity, transposase activity, recombinase activity, polymerase activity, ligase activity, helicase activity, photolyase activity, and glycosylase activity.

In some embodiments, the present invention provides a fusion polypeptide comprising a Cas12i polypeptide fused to one or more heterologous polypeptides, wherein the Cas12i polypeptide (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6, and according to the sequence numbering set forth in SEQ ID NO: 1, has an amino acid substitution, preferably with alanine, at position D1009; and the one or more heterologous polypeptides are independently selected from an epitope tag and a nuclear localization signal, or have one or more of the following enzymatic activities: deaminase activity, methyltransferase activity, demethylase activity, acetyltransferase activity, and deacetylase activity.

In some embodiments, the present invention provides a fusion polypeptide comprising a Cas12i polypeptide fused to one or more heterologous polypeptides, wherein the Cas12i polypeptide (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6, and according to the sequence numbering set forth in SEQ ID NO: 1, has an amino acid substitution, preferably with alanine, at position D1009; the one or more heterologous polypeptides are each independently a transcriptional repression domain (also referred to as transcriptional inhibition domain herein), a transcriptional activation domain, or a deaminase domain.

In a specific embodiment, the present invention provides a fusion polypeptide comprising a Cas12i polypeptide fused to a transcriptional repression domain, wherein the Cas12i polypeptide (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6, and according to the sequence numbering set forth in SEQ ID NO: 1, has an amino acid substitution, preferably with alanine, at position D1009.

In a specific embodiment, the present invention provides a fusion polypeptide comprising a Cas12i polypeptide fused to a transcriptional activation domain, wherein the Cas12i polypeptide (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6, and according to the sequence numbering set forth in SEQ ID NO: 1, has an amino acid substitution, preferably with alanine, at position D1009.

In a specific embodiment, the present invention provides a fusion polypeptide comprising a Cas12i polypeptide fused to a deaminase domain, wherein the Cas12i polypeptide (i) comprises or is an amino acid sequence having at least 95% sequence identity to the amino acid sequence set forth in any one of SEQ ID NOs: 1 to 6; (ii) comprises or is an amino acid sequence having at least 80% sequence identity to the amino acid sequences of aa 1 to 897 and aa 1008 to 1044 of SEQ ID NO: 1 or 2 and having at least 80% sequence identity to the amino acid sequence of aa 898 to 1007 of SEQ ID NO: 1 or 2; or (iii) comprises or is an amino acid sequence having at least 80% sequence identity to the amino acid sequences of aa 1 to 895 and aa 1016 to 1054 of any one of SEQ ID NOs: 3 to 6 and having at least 80% sequence identity to the amino acid sequence of aa 896 to 1015 of any one of SEQ ID NOs: 3 to 6, and according to the sequence numbering set forth in SEQ ID NO: 1, has an amino acid substitution, preferably with alanine, at position D1009.

Examples of proteins (or fragments thereof) that can be used to increase transcription include, but are not limited to: transcriptional activators such as VP16, VP64, VP48, VP160, p65 subdomain (e.g., from NFkB), and EDLL activation domain and/or TAL activation domain (e.g., for activity in plants); histone lysine methyltransferases such as SET1A, SET1B, MLL1-5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as TET1CD, TET1, DME, DML1, DML2, ROS1, and the like.

Examples of proteins (or fragments thereof) that can be used to decrease transcription include, but are not limited to: transcriptional repressors such as Krüppel-associated box (KRAB or SKD); ZIM3 domain; KOX1 repression domain; Mad mSIN3 interaction domain (SID); ERF repressor domain (ERD), SRDX repression domain (e.g., for repression in animals), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaIDNA m5c-methyltransferase (M.HhaI), DNA methyltransferase 1 (DNMT1), DNA methyltransferase 3a (DNMT3a), DNA methyltransferase 3b (DNMT3b), DNA methyltransferase 3 L (DNMT3L), DNA methyltransferase 3c (DNMT3c), METI, DRM3, ZMET2, CMT1, CMT2, and the like; and peripheral recruitment elements such as lamin A, lamin B, and the like.

In some embodiments, the heterologous polypeptide may also be selected from a molecule having an enzymatic activity that modifies a target nucleic acid (e.g., ssRNA, dsRNA, ssDNA, or dsDNA), wherein the enzymatic activity includes, but is not limited to: nuclease activity such as that provided by a restriction enzyme (e.g., FokI nuclease); methyltransferase activity such as that provided by a methyltransferase (e.g., HhaIDNAm5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2, etc.); demethylase activity such as that provided by a demethylase (e.g., TET1CD, TET1, DME, DML1, DML2, ROS1, etc.); DNA repair activity; DNA damage activity; deamination activity such as that provided by a deaminase (e.g., a cytosine deaminase such as rat APOBEC1); dismutase activity; alkylation activity; depurination activity; oxidation activity; pyrimidine dimer formation activity; integrase activity such as that provided by an integrase and/or a resolvase (e.g., Gin invertase such as an hyperactive mutant of the Gin invertase, GinH106Y; human immunodeficiency virus type 1 integrase (IN); Tn3 resolvase, etc.); transposase activity; recombinase activity such as that provided by a recombinase (e.g., a catalytic domain of Gin recombinase); polymerase activity; ligase activity; helicase activity; photolyase activity; and glycosylase activity).

In some embodiments, the heterologous polypeptide may also be selected from a molecule having an enzymatic activity that modifies a protein associated with a target nucleic acid (e.g., ssRNA, dsRNA, ssDNA, or dsDNA), such as a histone, an RNA-binding protein, a DNA-binding protein, or the like, wherein the enzymatic activity includes, but is not limited to: methyltransferase activity such as that provided by a histone methyltransferase (HMT), an autosomal histone lysine methyltransferase 2 (G9A, also known as KMT1C and EHMT2), SUV39H2, ESET/SETDB1 or the like, SET1A, SET1B, MLL1 to 5, ASH1, SYMD2, NSD1, DOT1L, Pr-SET7/8, SUV4-20H1, EZH2, or RIZ1); demethylase activity such as that provided by a histone demethylase (e.g., lysine demethylase 1A (KDM1A, also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, etc.); acetyltransferase activity such as that provided by a histone acetyltransferase (e.g., a catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, etc.); deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, etc.); kinase activity; phosphatase activity; ubiquitin ligase activity; deubiquitination activity; adenylation activity; deadenylation activity; SUMOylation activity; deSUMOylation activity; ribosylation activity; deribosylation activity; myristoylation activity; and demyristoylation activity.

In some embodiments, the heterologous polypeptide is selected from an epitope tag. Such epitope tags are existing conventional tags including, but not limited to, His, V5, FLAG, HA, Myc, VSV-G, Trx, and the like, and those skilled in the art know how to select an appropriate epitope tag according to the desired purpose (e.g., purification, detection, or tracking).

In some embodiments, the heterologous polypeptide is selected from a sequence of a reporter gene; such reporter genes are well-known to those skilled in the art, examples of which include, but are not limited to, GST, HRP, CAT, GFP, HcRed, DsRed, CFP, YFP, BFP, and the like.

In some embodiments, the heterologous polypeptide is selected from a domain capable of binding to a DNA molecule or an intracellular molecule, such as the maltose-binding protein (MBP), the DNA-binding domain (DBD) of Lex A, the DBD of GAL4, or the like.

In some embodiments, the heterologous polypeptide may also be an enzyme with a detectable signal, a radioisotope, a member of a specific binding pair, a fluorophore, a fluorescent protein, a quantum dot, or the like.

In some embodiments, the Cas12i fusion polypeptide provided by the present invention comprises: i) the chimeric Cas12i polypeptide provided by the present invention; and ii) a nuclease. Suitable nucleases include, but are not limited to, a homing nuclease polypeptide; a Fok1 polypeptide; a transcriptional activator-like effector nuclease (TALEN) polypeptide; a MegaTAL polypeptide; a meganuclease polypeptide; a zinc finger nuclease (ZFN); an ARCUS nuclease; and the like. The meganuclease can be engineered from an LADLIDADG homing endonuclease (LHE). The MegaTAL polypeptide may comprise a TALE DNA-binding domain and an engineered meganuclease.

In some embodiments, the Cas12i fusion polypeptide comprises: i) the chimeric Cas12i polypeptide provided by the present invention; and ii) a reverse transcriptase polypeptide. In certain cases, the chimeric Cas12i polypeptide has no catalytic activity. Suitable reverse transcriptases include, for example, murine leukemia virus reverse transcriptase; Rous sarcoma virus reverse transcriptase; human immunodeficiency virus type I reverse transcriptase; Moloney murine leukemia virus reverse transcriptase; and the like.

In some embodiments, the Cas12i fusion polypeptide provided by the present invention comprises: i) the chimeric Cas12i polypeptide provided by the present invention; and ii) a deaminase. Suitable deaminases include adenosine deaminases (e.g., TadA deaminases such as TadA, ecTadA, saTadA, ecTadA7.10, TadA-8c, TadA8.17, TadA8.20, TadA9, or a combination thereof, etc.) or cytidine deaminases (e.g., AID, APOBEC3G, etc.). A suitable adenosine deaminase is any enzyme capable of deaminating adenosine in DNA. In some embodiments, the deaminase is a TadA deaminase.

In some embodiments, a suitable adenosine deaminase comprises or is an amino acid sequence having at least 80%, at least 85%, at least 90%, at least 95%, at least 98%, at least 99%, or 100% amino acid sequence identity to the amino acid sequence set forth in any one of SEQ ID NOs: 23 to 31.

Suitable cytidine deaminases include any enzyme capable of deaminating cytidine in DNA. In some embodiments, the cytidine deaminase is a deaminase from the apolipoprotein B mRNA-editing complex (APOBEC) family of deaminases. In some embodiments, the deaminase of the APOBEC family is selected from the group consisting of: APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In some embodiments, the cytidine deaminase is an activation-induced deaminase (AID).

In some embodiments, a suitable cytidine deaminase comprises or is an amino acid sequence having at least 80%, at least 85%, at least 90%, at least 95%, at least 98%, at least 99%, or 100% amino acid sequence identity to the amino acid sequence set forth in any one of SEQ ID NOs: 32 to 34.

In some embodiments, the Cas12i fusion polypeptide comprises: i) the chimeric Cas12i polypeptide provided by the present invention; and ii) a transcriptional factor. The transcriptional factor may comprise: i) a DNA-binding domain; and ii) a transcriptional activator. The transcriptional factor may comprise: i) a DNA-binding domain; and ii) a transcriptional repressor. Suitable transcriptional factors include polypeptides comprising a transcriptional activator or transcriptional repressor domain (e.g., Krüppel-associated box (KRAB or SKD)); Mad mSIN3 interaction domain (SID); ERF repressor domain (ERD) and the like; zinc finger-based artificial transcriptional factors; TALE-based artificial transcriptional factors; and the like. In some embodiments, the transcriptional factor includes a VP64 polypeptide (transcriptional activation). In certain cases, the transcriptional factor includes a Krüppel-associated box (KRAB) polypeptide (transcriptional inhibition). In some embodiments, the transcriptional factor includes a Mad mSIN3 interaction domain (SID) polypeptide (transcriptional repression). In some embodiments, the transcriptional factor includes an ERF repressor domain (ERD) polypeptide (transcriptional repression). In some embodiments, the transcriptional factor includes DNMT3A-DNMT3L (transcriptional repression). In some embodiments, the transcriptional factor is a transcriptional activator, wherein the transcriptional activator is GAL4-VP16. In some embodiments, the transcriptional factor is a transcriptional activator, wherein the transcriptional activator is VP64; P65; RTA; truncated P65; truncated RTA; or one or more fusion forms thereof or therebetween.

In some embodiments, the Cas12i fusion polypeptide provided by the present invention comprises: i) the chimeric Cas12i polypeptide provided by the present invention; and ii) a recombinase. Suitable recombinases include, for example, a Cre recombinase; a Hin recombinase; a Tre recombinase; an FLP recombinase; and the like.

In some embodiments, the heterologous polypeptide provides subcellular localization, i.e., the heterologous polypeptide contains a subcellular localization sequence (e.g., a nuclear localization signal (NLS) for targeting the nucleus, a sequence for retaining the fusion protein outside the nucleus (e.g., a nuclear export sequence (NES)), a sequence for retaining the fusion protein in the cytoplasm, a mitochondrial localization signal for targeting the mitochondrion, a chloroplast localization signal for targeting the chloroplast, an ER retention signal, etc.). In some embodiments, the Cas12i fusion polypeptide does not comprise an NLS, such that the protein does not target the nucleus (which may be advantageous, for example, when the target nucleic acid is an RNA present in the cytosol).

In some embodiments, the Cas12i fusion polypeptide comprises (in a fusion manner) a nuclear localization signal (NLS) (e.g., in some embodiments, 2 or more, 3 or more, 4 or more, or 5 or more NLSs). Thus, in some embodiments, the Cas12i fusion polypeptide comprises one or more NLSs (e.g., 2 or more, 3 or more, 4 or more, or 5 or more NLSs). In some embodiments, one or more NLSs (2 or more, 3 or more, 4 or more, or 5 or more NLSs) are positioned at or near (e.g., within 50 amino acids) the N-terminus and/or the C-terminus. In some embodiments, one or more NLSs (2 or more, 3 or more, 4 or more, or 5 or more NLSs) are positioned at or near (e.g., within 50 amino acids) the N-terminus. In some embodiments, one or more NLSs (2 or more, 3 or more, 4 or more, or 5 or more NLSs) are positioned at or near (e.g., within 50 amino acids) the C-terminus. In some embodiments, one or more NLSs (3 or more, 4 or more, or 5 or more NLSs) are positioned at or near (e.g., within 50 amino acids) both the N-terminus and the C-terminus. In some embodiments, one or more NLSs are positioned at the N-terminus, and one or more NLSs are positioned at the C-terminus. Specifically, a connection order of the nuclear localization signal (NLS) may be: $NH_2$-[enCas12i]-[NLS]—COOH; or $NH_2$—[NLS]-[enCas12i]—COOH, wherein]-[indicates an optionally present linker peptide as defined below (the same applies hereinafter).

In some embodiments, the Cas12i fusion polypeptide comprises (in a fusion manner) 1 to 10 NLSs (e.g., 1-9, 1-8, 1-7, 1-6, 1-5, 2-10, 2-9, 2-8, 2-7, 2-6, or 2-5 NLSs). In some embodiments, the Cas12i fusion polypeptide comprises (in a fusion manner) 2 to 5 NLSs (e.g., 2-4 or 2-3 NLSs).

Non-limiting examples of NLSs include the amino acid sequence set forth in any one of SEQ ID NOs: 35 to 50.

In some embodiments, the Cas12i fusion polypeptide comprises a "protein transduction domain" or PTD (also known as cell-penetrating peptide (CPP)), which refers to a polypeptide, polynucleotide, carbohydrate, or organic or inorganic compound that facilitates traversing a lipid bilayer, micelle, cell membrane, organelle membrane or vesicle membrane. The PTD, when linked to another molecule (which may range from a small polar molecule to a large macromolecule and/or a nanoparticle), facilitates the molecule traversing a membrane, for example, from the extracellular space into the intracellular space, or from the cytosol into the organelle. In some embodiments, the PTD is covalently linked to the amino terminus of the chimeric Cas12i polypeptide to generate a fusion protein. In some embodiments, the PTD is covalently linked to the carboxy terminus of the chimeric Cas12i polypeptide to generate a fusion protein. In some embodiments, the PTD is inserted at a suitable insertion site within the Cas12i fusion polypeptide (i.e., not at the N-terminus or C-terminus of the Cas12i fusion polypeptide). In some embodiments, the Cas12i fusion polypeptide comprises (is conjugated to or fused to) one or more PTDs (e.g., two or more, three or more, or four or more PTDs). In some embodiments, the PTD comprises a nuclear localization signal (NLS) (e.g., in some embodiments, 2 or more, 3 or more, 4 or more, or 5 or more NLSs).

In some embodiments, the Cas12i polypeptide may be fused to a heterologous polypeptide via one or more linker polypeptides (also called linker peptides). The linker polypeptide may have any one of a variety of amino acid sequences. The proteins may be linked via a spacer peptide, which generally has flexibility, but other chemical bonds are not excluded. Suitable linkers include polypeptides with a length between 4 to 40 amino acids or a length between 4 to 25 amino acids. These linkers may be generated by using synthetic, linker-encoding oligonucleotides to couple the proteins, or may be encoded by fusion protein-encoding nucleic acid sequences. Peptide linkers having a certain degree of flexibility may be used. The linker peptides may actually have any amino acid sequence; it should be noted that a preferred linker will have a sequence that results in an overall flexible peptide. Small amino acids (such as glycine and alanine) are used to generate flexible peptides. The generation of such sequences is routine to those skilled in the art. A variety of different linkers are commercially available and are considered suitable for use.

Examples of linker polypeptides include glycine polymers (G) n, glycine-serine polymers, glycine-alanine polymers, and alanine-serine polymers. Exemplary linkers may comprise amino acid sequences including, but not limited to, GGSG, GGSGG (SEQ ID NO: 51), GSGSG (SEQ ID NO: 52), GSGGG (SEQ ID NO: 53), GGGSG (SEQ ID NO: 54), GSSSG (SEQ ID NO: 55), SGGSGGSGGS (SEQ ID NO: 87), and the like. The linker peptides may also be various XTEN linkers and the like. The XTEN linker has a length of about 16-80 amino acids, and may be an XTEN16 linker or an XTEN80 linker (SEQ ID NO: 86). More specifically, the linker peptide includes, but is not limited to, the amino acid sequences set forth in SEQ ID NOs: 56 to 58, 83, and 86. Those skilled in the art will recognize that the design of a peptide conjugated to any desired element may include a linker that is fully or partially flexible, such that the linker may include a flexible linker as well as one or more moieties that confer a less flexible structure.

In some embodiments, the present invention provides a fusion polypeptide for forming an epigenetic editor, comprising or being an amino acid sequence having at least 80% sequence identity to the amino acid sequence set forth in any one of SEQ ID NOs: 88 to 93.

In some embodiments, the present invention provides a fusion polypeptide for forming a base editor, comprising or being an amino acid sequence having at least 80% sequence identity to the amino acid sequence set forth in any one of SEQ ID NOs: 94 to 97.

Cas12i Fusion Protein: gRNA Complex

Another aspect of the present invention provides a complex comprising any one of the Cas12i fusion polypeptides provided by the present invention and any one of the guide RNAs provided by the present invention, wherein the guide RNA is complexed with the fusion polypeptide to guide the fusion polypeptide to bind to a target nucleic acid.

In some embodiments, the complex is an epigenetic editor comprising any one of the chimeric Cas12i polypeptides of the present invention fused to a transcriptional activation domain or a transcriptional inhibition domain (collectively referred to as transcriptional regulatory domains), and any one of the guide RNAs provided by the present invention. Preferably, there are at least 2 transcriptional inhibition domains, which may be 2 identical/different transcriptional inhibition domains, 3 identical/different transcriptional inhibition domains, 4 identical/different transcriptional inhibition domains, 5 identical/different transcriptional inhibition domains, 6 identical/different transcriptional inhibition domains, 7 identical/different transcriptional inhibition domains, 8 identical/different transcriptional inhibition domains, 9 identical/different transcriptional inhibition domains, or 10 identical/different transcriptional inhibition domains. Specifically, there may be two transcriptional inhibition domains, including a first transcriptional inhibition domain and a second transcriptional inhibition domain; the first transcriptional inhibition domain and the second transcriptional inhibition domain may be the same transcriptional inhibition domain, or the first transcriptional inhibition domain and the second transcriptional inhibition domain may be different transcriptional inhibition domains.

Specifically, there may be more than two transcriptional inhibition domains, and these transcriptional inhibition domains are linked to the N-terminus or/and the C-terminus of the chimeric Cas12i (e.g., enCas12i-001, enCas12i-002, enCas12i-003, enCas12i-004, enCas12i-005, enCas12i-006, denCas12i-001, or denCas12i-002, preferably denCas12i-001 or denCas12i-002) protein after being connected in tandem via linker peptides.

The transcriptional inhibition domain may include a DNA methyltransferase (e.g., DNMT1, DNMT3A, DNMT3B, DNMT3L, or any functional variant or fragment thereof), an RYBP (RING1 and YY1 binding protein) catalytic domain and homologs thereof, a YAF2 catalytic domain and homologs thereof, a KRAB catalytic domain, an MBD2 catalytic domain and homologs thereof, an MeCP2 catalytic domain and homologs thereof, an RBBP4 catalytic domain and homologs thereof, a CDYL2 catalytic domain and homologs thereof, an HP1α catalytic domain and homologs thereof, an HP1β (CBX1) catalytic domain and homologs thereof, a TOX catalytic domain and homologs thereof, a TOX3 catalytic domain and homologs thereof, a TOX4 catalytic domain and homologs thereof, an SCMH1 catalytic domain and homologs thereof, an SCMH2 catalytic domain and homologs thereof, a CBX8 catalytic domain and homologs thereof, an HDAC5 catalytic domain and homologs thereof, an 12BP1 catalytic domain and homologs thereof, an EZH2 catalytic domain and homologs thereof, an SUZ12 catalytic domain and homologs thereof, an SIN3A catalytic domain and homologs thereof, an RING2 catalytic domain and homologs thereof, and a SetDB1 catalytic domain and homologs thereof.

Specifically, the KRAB catalytic domain may be selected from ZIM3 KRAB, ZNF554, ZNF264, ZNF324, ZNF354A, ZNF189, ZNF543, ZFP82, ZNF669, ZNF582, KOX1-MeCP2, ZNF30, ZNF680, ZNF331, ZNF33A, ZNF528, ZNF320, ZNF350, ZNF175, ZNF214, ZNF184, ZNF8, ZNF596, KOX1, ZNF37A, ZNF394, ZNF610, ZNF273, ZNF34, ZNF250, ZNF98, ZNF675, ZNF213, NLuc, ZFP28-2, ZNF224, ZNF257, ZIM2 KRAB, ZNF566, ZNF595, ZNF419, ZNF254, ZNF557, ZNF785, ZNF140, ZNF764, ZNF45, ZNF816, ZNF729, ZNF28-1, ZNF547, ZFP1, ZNF677, ZNF41, ZNF14, ZNF490, ZNF436, or ZNF18. Preferably, the KRAB catalytic domain may be ZIM3 KRAB, ZNF554, ZNF264, ZNF324, ZNF354A, ZNF189, ZNF543, ZFP82, ZNF669, ZNF582, KOX1-MeCP2, ZNF30, ZNF680, ZNF331, ZNF33A, ZNF528, ZNF320, ZNF350, ZNF175, ZNF214, ZNF184, ZNF8, ZNF596, KOX1, ZIM2 KRAB, ZNF566, ZNF595, ZNF419, ZNF254, ZNF557, ZNF785, ZNF140, ZNF764, ZNF45, ZNF816, ZNF729, ZNF28-1, ZNF547, ZFP1, or ZNF677.

Specifically, the targeting segment of the gRNA of the chimeric Cas12i (e.g., denCas12i-001 or denCas12i-002) protein provided by the present invention can act on 3000 bp (preferably between 200-500 bp) upstream of the transcription start site (TSS) of the target nucleic acid, so that the epigenetic editor acts on regulatory elements such as promoters, enhancers, silencers, and the like of the target gene.

In a specific embodiment, the structure of the fusion polypeptide used for the epigenetic editor of the present invention is selected from any one of the following structures, wherein the Cas12i represents any one of the chimeric Cas12i polypeptides provided by the present invention, including but not limited to enCas12i-001, enCas12i-002, enCas12i-003, enCas12i-004, enCas12i-005, enCas12i-006, denCas12i-001, or denCas12i-002:

$NH_2$-[Cas12i]-[transcriptional regulatory domain]-COOH;

$NH_2$-[transcriptional regulatory domain]-[Cas12i]—COOH;

$NH_2$-[Cas12i]-[transcriptional activation domain]-COOH;

$NH_2$-[transcriptional activation domain]-[Cas12i]—COOH;

$NH_2$—[NLS]-[Cas12i]-[transcriptional activation domain]-COOH;

$NH_2$-[Cas12i]-[transcriptional activation domain]-[NLS]—COOH;

$NH_2$—[NLS]-[Cas12i]-[transcriptional activation domain]-[NLS]—COOH;

$NH_2$—[NLS]-[transcriptional activation domain]-[Cas12i]—COOH;

$NH_2$-[transcriptional activation domain]-[Cas12i]-[NLS]—COOH;

$NH_2$—[NLS]-[transcriptional activation domain]-[Cas12i]-[NLS]—COOH;

$NH_2$-[Cas12i]-[VP64-P65-RTA fusion protein and a truncated fusion protein thereof]-COOH;

$NH_2$—[VP64-P65-RTA fusion protein and a truncated fusion protein thereof]-[Cas12i]—COOH;

$NH_2$—[NLS]-[Cas12i]-[VP64-P65-RTA fusion protein and a truncated fusion protein thereof]-COOH;

$NH_2$-[Cas12i]-[VP64-P65-RTA fusion protein and a truncated fusion protein thereof]-[NLS]—COOH;

$NH_2$—[NLS]-[Cas12i]-[VP64-P65-RTA fusion protein and a truncated fusion protein thereof]-[NLS]—COOH;

$NH_2$—[NLS]-[VP64-P65-RTA fusion protein and a truncated fusion protein thereof]-[Cas12i]—COOH;

$NH_2$—[VP64-P65-RTA fusion protein and a truncated fusion protein thereof]-[Cas12i]-[NLS]—COOH;

$NH_2$—[NLS]-[Cas12i]-[VP64-P65-RTA fusion protein and a truncated fusion protein thereof]-[NLS]—COOH;

$NH_2$-[Cas12i]-[transcriptional inhibition domain]-COOH;

$NH_2$-[transcriptional inhibition domain]-[Cas12i]—COOH;

$NH_2$—[NLS]-[Cas12i]-[transcriptional inhibition domain]-COOH;

$NH_2$-[Cas12i]-[transcriptional inhibition domain]-[NLS]—COOH;

$NH_2$—[NLS]-[Cas12i]-[transcriptional inhibition domain]-[NLS]—COOH;

$NH_2$—[NLS]-[transcriptional inhibition domain]-[Cas12i]—COOH;

$NH_2$-[transcriptional inhibition domain]-[Cas12i]-[NLS]—COOH;

$NH_2$—[NLS]-[transcriptional inhibition domain]-[Cas12i]-[NLS]—COOH;

$NH_2$-[Cas12i]-[first transcriptional inhibition domain]-[second transcriptional inhibition domain]-COOH;

$NH_2$-[Cas12i]-[second transcriptional inhibition domain]-[first transcriptional inhibition domain]-COOH;

$NH_2$-[first transcriptional inhibition domain]-[second transcriptional inhibition domain]-[Cas12i]—COOH;

$NH_2$-[second transcriptional inhibition domain]-[first transcriptional inhibition domain]-[Cas12i]—COOH;

$NH_2$-[first transcriptional inhibition domain]-[Cas12i]-[second transcriptional inhibition domain]-COOH;

$NH_2$-[second transcriptional inhibition domain]-[Cas12i]-[first transcriptional inhibition domain]-COOH;

$NH_2$—[NLS]-[Cas12i]-[KRAB catalytic domain]-[DNMT3A-DNMT3L]-COOH;

$NH_2$-[Cas12i]-[KRAB catalytic domain]-[DNMT3A-DNMT3L]-[NLS]—COOH;

$NH_2$—[NLS]-[Cas12i]-[KRAB catalytic domain]-[DNMT3A-DNMT3L]-[NLS]—COOH;

$NH_2$—[NLS]-[KRAB catalytic domain]-[DNMT3A-DNMT3L]-[Cas12i]—COOH;

$NH_2$—[KRAB catalytic domain]-[DNMT3A-DNMT3L]-[Cas12i]-[NLS]—COOH;

$NH_2$—[NLS]-[KRAB catalytic domain]-[DNMT3A-DNMT3L]-[Cas12i]-[NLS]—COOH;

$NH_2$—[NLS]-[KRAB catalytic domain]-[Cas12i]-[DNMT3A-DNMT3L]-COOH;

$NH_2$—[KRAB catalytic domain]-[Cas12i]-[DNMT3A-DNMT3L]-[NLS]—COOH;

$NH_2$—[NLS]-[KRAB catalytic domain]-[Cas12i]-[DNMT3A-DNMT3L]-[NLS]—COOH;

$NH_2$—[NLS]-[DNMT3A-DNMT3L]-[Cas12i]-[KRAB catalytic domain]-COOH;

$NH_2$-[DNMT3A-DNMT3L]-[Cas12i]-[KRAB catalytic domain]-[NLS]—COOH; and $NH_2$—[NLS]-[DNMT3A-DNMT3L]-[Cas12i]-[KRAB catalytic domain]-[NLS]—COOH.

In some embodiments, the complex is a base editor comprising any one of the chimeric Cas12i polypeptides of the present invention fused to a deaminase domain, and any one of the guide RNAs provided by the present invention.

In a specific embodiment, the base editor provided by the present invention includes an adenine base editor (ABE) and a cytosine base editor (CBE).

In ABEs, the fusion of the adenosine deaminase domain to the chimeric Cas12i protein enables the conversion of A·T base pairs to G·C base pairs. In some embodiments, the base editor provided by the present invention comprises a first adenosine deaminase domain and a second adenosine deaminase domain, which may be identical or different adenosine deaminase domains. The adenosine deaminase domains include, but are not limited to: TadA and various variants thereof (e.g., ecTadA, saTadA, ecTadA7.10, TadA-8c, TadA8.17, TadA8.20, TadA9, etc.).

In CBEs, the cytidine deaminase domain APOBEC/AID is fused to the chimeric Cas12i protein and one or more uracil glycosylase inhibitors (UGIs), so as to improve the accuracy and efficiency of base editing in CBEs, converting C·G base pairs to T·A base pairs.

In a specific embodiment, the structure of the fusion polypeptide used for the base editor of the present invention is selected from any one of the following structures, wherein the Cas12i represents any one of the chimeric Cas12i polypeptides provided by the present invention, including but not limited to enCas12i-001, enCas12i-002, enCas12i-003, enCas12i-004, enCas12i-005, enCas12i-006, denCas12i-001, or denCas12i-002:

$NH_2$-[adenosine deaminase domain]-[Cas12i]—COOH;

$NH_2$-[Cas12i]-[adenosine deaminase domain]-COOH;

$NH_2$-[first adenosine deaminase domain]-[second adenosine deaminase domain]-[Cas12i]—COOH;

$NH_2$-[first adenosine deaminase domain]-[Cas12i]-[second adenosine deaminase domain]-COOH;

$NH_2$-[Cas12i]-[first adenosine deaminase domain]-[second adenosine deaminase domain]-COOH;

$NH_2$-[second adenosine deaminase domain]-[first adenosine deaminase domain]-[Cas12i]—COOH;

$NH_2$-[second adenosine deaminase domain]-[Cas12i]-[first adenosine deaminase domain]-COOH;

$NH_2$-[Cas12i]-[second adenosine deaminase domain]-[first adenosine deaminase domain]-COOH;

$NH_2$-[adenosine deaminase domain]-[Cas12i]-[NLS]—COOH;

$NH_2$-[Cas12i]-[adenosine deaminase domain]-[NLS]—COOH;

$NH_2$—[NLS]-[adenosine deaminase domain]-[Cas12i]—COOH;

$NH_2$—[NLS]-[Cas12i]-[adenosine deaminase domain]-COOH;

$NH_2$—[NLS]-[adenosine deaminase domain]-[Cas12i]-[NLS]—COOH;

$NH_2$—[NLS]-[Cas12i]-[adenosine deaminase domain]-[NLS]—COOH;

$NH_2$—[NLS]-[adenosine deaminase domain]-[Cas12i]-[NLS]—COOH;

$NH_2$-[cytidine deaminase domain]-[Cas12i]-[uracil glycosylase inhibitor (UGI)]—COOH;

$NH_2$-[uracil glycosylase inhibitor (UGI)]-[Cas12i]-[cytidine deaminase domain]-COOH;

$NH_2$—[NLS]-[cytidine deaminase domain]-[Cas12i]-[uracil glycosylase inhibitor (UGI)]—COOH;

$NH_2$—[NLS]-[uracil glycosylase inhibitor (UGI)]-[Cas12i]-[cytidine deaminase domain]-COOH;

$NH_2$-[cytidine deaminase domain]-[Cas12i]-[uracil glycosylase inhibitor (UGI)]-[NLS]—COOH;

$NH_2$-[uracil glycosylase inhibitor (UGI)]-[Cas12i]-[cytidine deaminase domain]-[NLS]—COOH;

$NH_2$—[NLS]-[cytidine deaminase domain]-[Cas12i]-[uracil glycosylase inhibitor (UGI)]-[NLS]—COOH; and $NH_2$—[NLS]-[uracil glycosylase inhibitor (UGI)]-[Cas12i]-[cytidine deaminase domain]-[NLS]—COOH.

In some embodiments, the present invention provides an epigenetic editor comprising a complex formed by a fusion protein and a gRNA, wherein the fusion protein comprises or is an amino acid sequence having at least 80% sequence identity to the amino acid sequence set forth in any one of SEQ ID NOs: 88 to 93.

In some embodiments, the present invention provides a base editor comprising a complex formed by a fusion protein and a gRNA, wherein the fusion protein comprises or is an amino acid sequence having at least 80% sequence identity to the amino acid sequence set forth in any one of SEQ ID NOs: 94 to 97.

Nucleic Acid

Another aspect of the present invention provides a variety of nucleic acids.

In some embodiments, the present invention provides a nucleic acid comprising a nucleotide sequence encoding any one of the chimeric Cas12i polypeptides or any one of the Cas12i fusion polypeptides provided by the present invention.

In some embodiments, the present invention provides a nucleic acid comprising any one of the guide RNAs provided by the present invention or a nucleotide sequence encoding the guide RNA.

In some embodiments, the nucleotide sequence encoding the chimeric Cas12i polypeptide or the fusion polypeptide of the present invention is codon-optimized. This type of optimization may require a mutation in the nucleotide sequence encoding the chimeric Cas12i polypeptide or the fusion polypeptide to mimic the codon preference of the intended host organism or cell when simultaneously encoding the same protein. Thus, the codons may be changed, but the encoded protein remains unchanged. For example, if the intended target cell is a human cell, a human codon-optimized nucleotide sequence encoding the chimeric Cas12i polypeptide or the fusion polypeptide may be used. As another non-limiting example, if the intended host cell is a mouse cell, a mouse codon-optimized nucleotide sequence encoding the chimeric Cas12i polypeptide or the fusion polypeptide may be generated. As another non-limiting example, if the intended host cell is a plant cell, a plant codon-optimized nucleotide sequence encoding the chimeric Cas12i polypeptide or the fusion polypeptide may be generated. As another non-limiting example, if the intended host cell is an insect cell, an insect codon-optimized nucleotide sequence encoding the chimeric Cas12i polypeptide or the fusion polypeptide may be generated.

In some embodiments, the nucleic acid is a DNA. In some embodiments, the nucleic acid is an mRNA. In some embodiments, the nucleic acid is a RNA.

In some embodiments, the nucleic acid encoding the chimeric Cas12i polypeptide comprises or is the nucleotide sequence set forth in any one of SEQ ID NOs: 59 to 64. In some embodiments, the nucleic acid encoding the chimeric Cas12i polypeptide comprises or is the nucleotide sequence set forth in SEQ ID NO: 59. In some embodiments, the nucleic acid encoding the chimeric Cas12i polypeptide comprises or is the nucleotide sequence set forth in SEQ ID NO: 60. In some embodiments, the nucleic acid encoding the chimeric Cas12i polypeptide comprises or is the nucleotide sequence set forth in SEQ ID NO: 61. In some embodiments, the nucleic acid encoding the chimeric Cas12i polypeptide comprises or is the nucleotide sequence set forth in SEQ ID NO: 62. In some embodiments, the nucleic acid encoding the chimeric Cas12i polypeptide comprises or is the nucleotide sequence set forth in SEQ ID NO: 63. In some embodiments, the nucleic acid encoding the chimeric Cas12i polypeptide comprises or is the nucleotide sequence set forth in SEQ ID NO: 64.

Vector and Vector System

Another aspect of the present invention provides a variety of vectors comprising any one of the nucleic acids provided by the present invention.

In some embodiments, the present invention provides a vector comprising a nucleic acid, wherein the nucleic acid comprises a nucleotide sequence encoding any one of the chimeric Cas12i polypeptides or any one of the Cas12i fusion polypeptides provided by the present invention.

In some embodiments, the present invention provides a vector comprising a nucleic acid, wherein the nucleic acid comprises a guide RNA or a nucleotide sequence encoding the guide RNA.

In some embodiments, the present invention provides a vector comprising a nucleic acid, wherein the nucleic acid comprises a nucleotide sequence encoding any one of the chimeric Cas12i polypeptides or any one of the Cas12i fusion polypeptides provided by the present invention, and the nucleic acid comprises a guide RNA or a nucleotide sequence encoding the guide RNA.

In some embodiments, the present invention provides a vector system comprising one or more identical vectors, each of the vectors comprising a nucleic acid, wherein the nucleic acid comprises a nucleotide sequence encoding any one of the chimeric Cas12i polypeptides or any one of the Cas12i fusion polypeptides provided by the present invention, and the nucleic acid comprises a guide RNA or a nucleotide sequence encoding the guide RNA.

In some embodiments, the present invention provides a vector system comprising a first vector and a second vector different from the first vector, wherein the first vector comprises a nucleic acid comprising a nucleotide sequence encoding any one of the chimeric Cas12i polypeptides or any one of the Cas12i fusion polypeptides provided by the present invention; the second vector comprises a nucleic acid comprising a guide RNA or a nucleotide sequence encoding the guide RNA.

Suitable vectors include liposomes, plasmids, particles, exosomes, microvesicles, gene guns, or viral vectors. Examples of viral vectors include adeno-associated virus vectors, adenovirus vectors, retrovirus vectors, lentivirus vectors, or herpes simplex virus vectors. In some embodiments, the vector of the present invention is a recombinant adeno-associated virus (AAV) vector. In some embodiments, the vector of the present invention is a recombinant lentivirus vector. In some embodiments, the vector of the present invention is a recombinant retrovirus vector. The vector may be an expression vector or a replication vector.

Depending on the host/vector system used, any one of a variety of suitable transcriptional and translational control elements including constitutive promoters and inducible promoters, transcriptional enhancer elements, transcriptional terminators, and the like may be used in the vector. In some embodiments, the nucleotide sequence encoding the guide RNA is operably linked to a control element, e.g., a transcriptional control element, such as a promoter. In some embodiments, the nucleotide sequence encoding the chimeric Cas12i polypeptide or the Cas12i fusion polypeptide is operably linked to a control element, e.g., a transcriptional control element, such as a promoter.

The transcriptional control element may be a promoter. In some embodiments, the promoter is a constitutively active promoter. In some embodiments, the promoter is a regulatable promoter. In some embodiments, the promoter is an inducible promoter. In some embodiments, the promoter is a tissue-specific promoter. In some embodiments, the promoter is a cell type-specific promoter. In some embodiments, the transcriptional control element (e.g., the promoter) is functional in the targeted cell type or targeted cell population. For example, in some embodiments, the transcriptional control element may be functional in eukaryotic cells (e.g., hematopoietic stem cells (e.g., mobilized peripheral blood (mPB) CD34(+) cells, bone marrow (BM) CD34 (+) cells, etc.)).

Non-limiting examples of eukaryotic promoters (promoters that are functional in eukaryotic cells) include EF1α, cytomegalovirus (CMV) immediate early promoters, and those from herpes simplex virus (HSV) thymidine kinase, early and late SV40, long terminal repeats (LTRs) of retroviruses, and mouse metallothionein-I. Selection of an appropriate vector and promoter is well within the capabilities of those of ordinary skill in the art. The expression vector may also contain a ribosome binding site for translation initiation and a transcriptional terminator. The expression vector may also comprise an appropriate sequence for amplification of expression. The expression vector may also comprise a nucleotide sequence encoding a protein tag (e.g., a 6×His tag, a hemagglutinin tag, a fluorescent protein, etc.), wherein the protein tag can be fused to the chimeric Cas12i polypeptide, thereby producing the Cas12i fusion polypeptide.

In some embodiments, the nucleotide sequence encoding the guide RNA and/or the Cas12i fusion polypeptide is operably linked to an inducible promoter. In some embodiments, the nucleotide sequence encoding the guide RNA and/or the Cas12i fusion protein is operably linked to a constitutive promoter. The promoter may be a constitutively active promoter (i.e., a promoter that is constitutively in the active/"ON" state); it may be an inducible promoter (i.e., a promoter whose state (active/"ON" or inactive/"OFF") is controlled by an external stimulus such as the presence of a particular temperature, compound or protein); it may be a spatially restricted promoter (i.e., a transcriptional control element, an enhancer, etc.) (e.g., a tissue-specific promoter, a cell type-specific promoter, etc.); and it may be a temporally restricted promoter (i.e., a promoter that is in the "ON" state or the "OFF" state during a particular stage of embryonic development or during a particular stage of a biological process (e.g., the hair follicle cycle in a mouse)).

Suitable promoters may be derived from viruses and may thus be referred to as viral promoters, or they may be derived from any organism, including prokaryotes or eukaryotes. Suitable promoters may be used to drive expression by any RNA polymerase (e.g., pol I, pol II, or pol III). Exemplary promoters include, but are not limited to, an SV40 early promoter, a mouse mammary tumor virus long terminal repeat (LTR) promoter; an adenovirus major late promoter (Ad MLP); a herpes simplex virus (HSV) promoter, a cytomegalovirus (CMV) promoter such as CMV immediate early (CMVIE) promoter region, a Rous sarcoma virus (RSV) promoter, a human U6 small nuclear promoter (U6), an enhanced U6 promoter, a human H1 promoter (H1), and the like.

In some embodiments, the nucleotide sequence encoding the guide RNA is operably linked to (under the control of) a promoter operable in a eukaryotic cell (e.g., a U6 promoter, an enhanced U6 promoter, an H1 promoter, etc.). As understood by those of ordinary skill in the art, when an RNA (e.g., a guide RNA) is expressed from a nucleic acid (e.g., an expression vector) using a U6 promoter (e.g., in a eukaryotic cell) or another PolIII promoter, the RNA may need to be mutated if there are several contiguous Ts (encoding Us in the RNA). This is because a string of Ts (e.g., 5 Ts) in DNA can act as a terminator for polymerase III (PolIII). Thus, in order to ensure transcription of the guide RNA in a eukaryotic cell, it may sometimes be necessary to modify the sequence encoding the guide RNA to eliminate the effects of the Ts. In some embodiments, the nucleotide sequence encoding the Cas12i polypeptide is operably linked to a promoter operable in a eukaryotic cell (e.g., a CMV promoter, an EF1α promoter, an estrogen receptor-regulated promoter, etc.).

Examples of inducible promoters include, but are not limited to, a T7 RNA polymerase promoter, polymerase promoter, an isopropyl-β-D-thiogalactopyranoside (IPTG)-regulated promoter, a lactose-induced promoter, a heat shock promoter, a tetracycline-regulated promoter, a steroid-regulated promoter, a metal-regulated promoter, an estrogen receptor-regulated promoter, and the like. Thus, inducible promoters can be regulated by molecules including, but not limited to, doxycycline; estrogen and/or estrogen analogs; IPTG; and the like.

In some embodiments, the promoter is a reversible promoter. Suitable reversible promoters, including reversible inducible promoters, are known in the art. Such reversible promoters may be isolated and derived from many organisms, such as eukaryotes and prokaryotes. Modification of reversible promoters derived from a first organism for use in a second organism (e.g., a first prokaryote and a second eukaryote, a first eukaryote and a second prokaryote, etc.) is well-known in the art. Such reversible promoters and systems based on such reversible promoters but also comprising additional control proteins include, but are not limited to, alcohol-regulated promoters (e.g., the alcohol dehydrogenase I (alcA) gene promoter, promoters responsive to alcohol transactivator protein (AlcR), etc.), tetracycline-regulated promoters (e.g., promoter systems including Tet activators, TetON, TetOFF, etc.), steroid-regulated promoters (e.g., rat glucocorticoid receptor promoter system, human estrogen receptor promoter system, retinoid promoter system, thyroid promoter system, ecdysone promoter system, mifepristone promoter system, etc.), metal-regulated promoters (e.g., metallothionein promoter system, etc.), pathogen-related regulatory promoters (e.g., salicylic acid-regulated promoters, ethylene-regulated promoters, benzothiadiazole-regulated promoters, etc.), temperature-regulated promoters (e.g., heat shock inducible promoters (e.g., HSP-70, HSP-90, soybean heat shock promoters, etc.)), light-regulated promoters, synthetic inducible promoters, and the like.

RNA polymerase III (pol III) promoters can be used to drive expression of non-protein-coding RNA molecules (e.g., guide RNAs). In some embodiments, a suitable promoter is a Pol III promoter. In some embodiments, the Pol III promoter is operably linked to a nucleotide sequence encoding the guide RNA (gRNA). In some embodiments, the Pol III promoter is operably linked to a nucleotide sequence encoding a CRISPR RNA (crRNA).

Non-limiting examples of Pol III promoters include a U6 promoter, an H1 promoter, a 5S promoter, an adenovirus 2 (Ad2) VAI promoter, a tRNA promoter, and a 7SK promoter. In some embodiments, the Pol III promoter is selected from the group consisting of: a U6 promoter, an H1 promoter, a 5S promoter, an adenovirus 2 (Ad2) VAI promoter, a tRNA promoter, and a 7SK promoter. In some embodiments, the guide RNA-encoding nucleotide sequence is operably linked to a promoter selected from the group consisting of a U6 promoter, an H1 promoter, a 5S promoter, an adenovirus 2 (Ad2) VAI promoter, a tRNA promoter, and a 7SK promoter.

Methods for introducing nucleic acids (e.g., those comprising one or more nucleic acids encoding the chimeric Cas12i polypeptide and/or the Cas12i guide RNA, etc.) into host cells are known in the art, and any convenient method can be used to introduce nucleic acids (e.g., expression constructs) into cells. Suitable methods include, for example, viral infection, transfection, lipofection, electroporation, calcium phosphate precipitation, polyethyleneimine (PEI)-mediated transfection, DEAE-dextran-mediated transfection, liposome-mediated transfection, particle gun technology, calcium phosphate precipitation, direct microinjection, nanoparticle-mediated nucleic acid delivery, and the like. Introduction of a recombinant expression vector into a cell may occur in any culture media and under any culture conditions that promote the survival of the cell. Introduction of a recombinant expression vector into a target cell may be performed in vivo or ex vivo. Introduction of a recombinant expression vector into a target cell may be performed in vitro. In some embodiments, the chimeric Cas12i polypeptide may be provided as an RNA. The RNA may be provided by direct chemical synthesis, or may be transcribed in vitro from a DNA (e.g., a DNA encoding the chimeric Cas12i polypeptide). Once synthesized, the RNA may be introduced into a cell by any of the well-known techniques for introducing nucleic acids into cells (e.g., microinjection, electroporation, transfection, etc.).

The vector may be provided directly to the target host cell. In other words, contacting the cell with a vector comprising the nucleic acid (e.g., a recombinant expression vector comprising a nucleic acid encoding the chimeric Cas12i guide RNA and a nucleic acid encoding the chimeric Cas12i polypeptide or the fusion polypeptide, etc.) allows the vector to be taken up by the cell. Methods for contacting cells with nucleic acid vectors as plasmids (including electroporation, calcium chloride transfection, microinjection, and lipofection) are well-known in the art. For viral vector delivery, cells can be brought into contact with viral particles comprising the subject viral expression vectors.

Retroviruses, such as lentiviruses, are suitable for use in the methods of the present invention. Commonly used retrovirus vectors are "defective", i.e., incapable of producing viral proteins required for productive infection. Moreover, replication of the vectors requires growth in a packaging cell line. To generate viral particles comprising the nucleic acids of interest, retroviral nucleic acids comprising the nucleic acids are packaged into viral capsids by a packaging cell line. Different packaging cell lines provide different envelope proteins (ecotropic, amphotropic, or xenotropic) to be incorporated into the capsids, and the envelope proteins determine the specificity of the viral particles for the cells (ecotropic for mouse and rat cells; amphotropic for most mammalian cell types, including human, dog and mouse cells; and xenotropic for most mammalian cell types other than murine cells). An appropriate packaging cell line can be used to ensure that the cells are targeted by the packaged viral particles. Methods for introducing the subject vector expression vectors into packaging cell lines and harvesting viral particles generated by the packaging cell lines are well-known in the art. Nucleic acids may also be introduced by direct microinjection (e.g., injection of RNA).

In some embodiments, the nucleic acid and the vector comprising the nucleic acid of the present invention comprise an insertion site for the guide sequence of interest. For example, the nucleic acid may comprise an insertion site for the guide sequence of interest, wherein the insertion site is immediately adjacent to a nucleotide sequence encoding a moiety of the chimeric Cas12i guide RNA, and when the guide sequence is changed to hybridize to a desired target sequence (e.g., a sequence that contributes to the chimeric Cas12i binding aspect of the guide RNA, i.e., a repeat segment), the moiety of the chimeric Cas12i guide RNA remains unchanged. Thus, in some embodiments, the nucleic acid (e.g., the expression vector) provided by the present invention comprises a nucleotide sequence encoding the chimeric Cas12i guide RNA, except that the moiety encoding the guide sequence moiety of the guide RNA is an insertion sequence (insertion site). The insertion site is any nucleotide sequence used for the insertion of the desired sequence. "Insertion sites" for use with various techniques are known to those of ordinary skill in the art, and any convenient insertion site can be used. The insertion site can be used in any method for manipulating a nucleic acid sequence. For example, in some embodiments, the insertion site is a multiple cloning site (MCS) (e.g., a site comprising one or more restriction enzyme recognition sequences), a site for ligation-independent cloning, a site for recombination-based cloning (e.g., att site-based recombination), a nucleotide sequence recognized by a CRISPR/Cas (e.g., Cas9)-based technique, and the like.

The insertion site may be of any desired length, and may depend on the type of insertion site (e.g., it may depend on whether the site comprises one or more restriction enzyme recognition sequences (and how many restriction enzyme recognition sequences the site comprises), whether the site comprises a target site for the CRISPR/Cas protein, etc.). In some embodiments, the length of the insertion site of the nucleic acid of the present invention is 3 or more nucleotides (nt) (e.g., 5 or more, 8 or more, 10 or more, 15 or more, 17 or more, 18 or more, 19 or more, 20 or more, or 25 or more, or 30 or more nt). In some embodiments, the insertion site of the nucleic acid of the present invention has a length in the range of 2 to 50 nucleotides (nt) (e.g., 2 to 40 nt, 2 to 30 nt, 2 to 25 nt, 2 to 20 nt, 5 to 50 nt, 5 to 40 nt, 5 to 30 nt, 5 to 25 nt, 5 to 20 nt, 10 to 50 nt, 10 to 40 nt, 10 to 30 nt, 10 to 25 nt, 10 to 20 nt, 17 to 50 nt, 17 to 40 nt, 17 to 30 nt, or 17 to 25 nt). In some embodiments, the insertion site of the present invention has a length in the range of 5 to 40 nt.

Delivery System

The Cas12i guide RNA (or a nucleic acid comprising a nucleotide sequence encoding the guide RNA) and/or the chimeric Cas12i polypeptide of the present invention (or a nucleic acid comprising a nucleotide sequence encoding the polypeptide) and/or the Cas12i fusion polypeptide of the present invention (or a nucleic acid comprising a nucleotide sequence encoding the Cas12i fusion polypeptide of the present invention) can be introduced into a host cell by any one of a variety of well-known methods.

Any one of a variety of compounds and methods can be used to deliver the Cas12i system of the present invention to a target cell. The Cas12i system may comprise: a) the chimeric Cas12i polypeptide and the Cas12i guide RNA of the present invention; b) the Cas12i fusion polypeptide and the Cas12i guide RNA of the present invention; c) an mRNA encoding the chimeric Cas12i polypeptide of the present invention; and the Cas12i guide RNA; d) an mRNA encoding the Cas12i fusion polypeptide of the present invention, and the Cas12i guide RNA; e) a recombinant expression vector comprising a nucleotide sequence encoding the Cas12i polypeptide of the present invention and a nucleotide sequence encoding the Cas12i guide RNA; f) a recombinant expression vector comprising a nucleotide sequence encoding the Cas12i fusion polypeptide of the present invention and the nucleotide sequence encoding the Cas12i guide RNA; g) a first recombinant expression vector comprising a nucleotide sequence encoding the chimeric Cas12i polypeptide of the present invention, and a second recombinant expression vector comprising the nucleotide sequence encoding the Cas12i guide RNA; h) a first recombinant expression vector comprising the nucleotide sequence encoding the Cas12i fusion polypeptide of the present invention, and a second recombinant expression vector comprising the nucleotide sequence encoding the Cas12i guide RNA; i) a recombinant expression vector comprising the nucleotide sequence encoding the chimeric Cas12i polypeptide of the present invention, a nucleotide sequence encoding a first Cas12i guide RNA, and a nucleotide sequence encoding a second Cas12i guide RNA; or j) a recombinant expression vector comprising the nucleotide sequence encoding the Cas12i fusion polypeptide of the present invention, a nucleotide sequence encoding a first Cas12i guide RNA, and a nucleotide sequence encoding a second Cas12i guide RNA; or a variant of one of (a) to (j). As a non-limiting example, the Cas12i system of the present invention can be combined with a lipid. As another non-limiting example, the Cas12i system of the present invention can be combined with or formulated into a particle.

Methods for introducing nucleic acids into host cells are known in the art, and any convenient method can be used to introduce the subject nucleic acids (e.g., expression constructs/vectors) into target cells (e.g., prokaryotic cells, eukaryotic cells, plant cells, animal cells, mammalian cells, human cells, etc.). Suitable methods include, for example, viral infection, transfection, conjugation, protoplast fusion, lipofection, electroporation, calcium phosphate precipitation, polyethyleneimine (PEI)-mediated transfection, DEAE-dextran-mediated transfection, liposome-mediated transfection, particle gun technology, calcium phosphate precipitation, direct microinjection, and nanoparticle-mediated nucleic acid delivery.

In some embodiments, the chimeric Cas12i polypeptide of the present invention is provided as a nucleic acid (e.g., an mRNA, a DNA, a plasmid, an expression vector, a viral vector, etc.) encoding the chimeric Cas12i polypeptide. In some embodiments, the chimeric Cas12i polypeptide of the present invention is provided directly as a protein (e.g., without the associated guide RNA, or with the associated guide RNA, i.e., as a ribonucleoprotein complex). The chimeric Cas12i polypeptide of the present invention can be introduced into (provided to) a cell by any convenient method; such methods are known to those of ordinary skill in the art. As an illustrative example, the chimeric Cas12i polypeptide of the present invention can be injected directly into a cell (e.g., with or without the Cas12i guide RNA or a nucleic acid encoding the Cas12i guide RNA, and with or without a donor polynucleotide). As another example, a pre-formed complex (RNP) of the chimeric Cas12i polypeptide and the Cas12i guide RNA of the present invention can be introduced into a cell (e.g., a eukaryotic cell) (e.g., by injection; by nuclear transfection; by a protein transduction domain (PTD) conjugated to one or more components, e.g., conjugated to the chimeric Cas12i protein, conjugated to the guide RNA, conjugated to the chimeric Cas12i polypeptide and the guide RNA of the present invention; etc.).

In some embodiments, the Cas12i fusion polypeptide (e.g., the Cas12i polypeptide fused to the heterologous polypeptide) is provided as a nucleic acid (e.g., an mRNA, a DNA, a plasmid, an expression vector, a viral vector, etc.) encoding the Cas12i fusion polypeptide. In some embodiments, the Cas12i fusion polypeptide of the present invention is provided directly as a protein (e.g., without the associated guide RNA, or with the associated guide RNA, i.e., as a ribonucleoprotein complex). The Cas12i fusion polypeptide of the present invention can be introduced into (provided to) a cell by any convenient method; such methods are known to those of ordinary skill in the art. As an illustrative example, the Cas12i fusion polypeptide of the present invention can be injected directly into a cell (e.g., with or without the nucleic acid encoding the Cas12i guide RNA, and with or without a donor polynucleotide). As another example, a pre-formed complex (RNP) of the Cas12i fusion polypeptide and the Cas12i guide RNA of the present invention can be introduced into a cell (e.g., by injection; by nuclear transfection; by a protein transduction domain (PTD) conjugated to one or more components, e.g., conjugated to the Cas12i fusion protein, conjugated to the guide RNA, conjugated to the Cas12i fusion polypeptide and the guide RNA of the present invention; etc.).

A recombinant expression vector comprising a nucleotide sequence encoding the chimeric Cas12i polypeptide of the present invention and/or the Cas12i guide RNA, an mRNA comprising the nucleotide sequence encoding the chimeric Cas12i polypeptide of the present invention, and the guide RNA may be delivered simultaneously using a particle or lipid envelope; for example, the chimeric Cas12i polypeptide and the Cas12i guide RNA, e.g., as a complex (e.g., a ribonucleoprotein (RNP) complex), may be delivered by a particle, such as a delivery particle comprising a lipid or lipoid and a hydrophilic polymer (e.g., a cationic lipid and a hydrophilic polymer), wherein, for example, the cationic lipid includes 1,2-dioleoyl-3-trimethylammonium-propane (DOTAP) or 1,2-ditetradecanoyl-sn-glycero-3-phosphocholine (DMPC), and/or the hydrophilic polymer includes ethylene glycol or polyethylene glycol (PEG); and/or the particle further includes cholesterol. For example, the particle may be formed using a multi-step method in which the chimeric Cas12i polypeptide and the Cas12i guide RNA are mixed together, e.g., in a molar ratio of 1:1, e.g., at room temperature, e.g., for 30 min, e.g., in sterile, nuclease-free 1× phosphate-buffered saline (PBS); and DOTAP, DMPC, PEG, and cholesterol suitable for use in the formulation are separately dissolved in an alcohol (e.g., 100% ethanol); and then the two solutions are mixed together to form the particle containing the complex).

The chimeric Cas12i polypeptide of the present invention (or an mRNA comprising a nucleotide sequence encoding the chimeric Cas12i polypeptide of the present invention; or a recombinant expression vector comprising the nucleotide sequence encoding the chimeric Cas12i polypeptide of the present invention) and/or the Cas12i guide RNA (or a nucleic acid, such as one or more expression vectors encoding the chimeric Cas12i guide RNA) may be delivered simultaneously using a particle or lipid envelope. For example, a biodegradable core-shell structured nanoparticle with a poly (β-amino ester) (PBAE) core encapsulated by a phospholipid bilayer shell may be used. In some embodiments, particles/nanoparticles based on self-assembling bioadhesive polymers are used; such particles/nanoparticles may be applied to oral delivery of peptides, intravenous delivery of peptides, and intranasal delivery of peptides, e.g., to the brain. Other embodiments, such as oral absorption and ocular delivery of hydrophobic drugs, are also contemplated. Molecular envelope technology, which involves an engineered polymer envelope that is protected and delivered to the site of disease, may be used. A dose of about 5 mg/kg may be used as a single dose or multiple doses, depending on various factors such as the target tissue.

In some embodiments, a lipid nanoparticle (LNP) is used to deliver the chimeric Cas12i polypeptide of the present invention, the Cas12i fusion polypeptide of the present invention, the RNP of the present invention, the nucleic acid of the present invention, or the Cas12i system of the present invention to a target cell. Negatively charged polymers (such as RNA) may be loaded into LNPs at low pH values (e.g., pH 4) where ionizable lipids exhibit a positive charge. However, at physiological pH values, the LNPs exhibit a low surface charge compatible with longer circulation times. Cationic lipids including 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinK-DMA), 1,2-dilinoleyl-4-(2-dimethylaminoethyl)-[1,3]-dioxolane (DLinKC2-DMA), (3-O-[2"-(methoxypolyethylene glycol 2000) succinoyl]-1,2-dimyristoyl-sn-glycol (PEG-S-DMG), and R-3-[(ω-methoxy-poly(ethylene glycol) 2000) carbamoyl]-1,2-dimyristyloxlpropyl-3-amine (PEG-C-DOMG) may be used. A nucleic acid (e.g., the Cas12i guide RNA; the nucleic acid of the present invention; etc.) may be encapsulated in LNPs containing DLinDAP, DLinDMA, DLinK-DMA, and DLinKC2-DMA (with a molar ratio of cationic lipid:DSPC:CHOL:PEGS-DMG or PEG-C-DOMG being 40:10:40:10). In some embodiments, 0.2% SP-DiOC18 is incorporated.

Spherical nucleic acid (SNA™) constructs and other nanoparticles (particularly gold nanoparticles) may be used to deliver the chimeric Cas12i polypeptide of the present invention, the Cas12i fusion polypeptide of the present invention, the RNP of the present invention, the nucleic acid of the present invention, or the Cas12i system of the present invention to target cells. Self-assembling nanoparticles with RNA can be constructed using polyethyleneimine (PEI) PEGylated with an Arg-Gly-Asp (RGD) peptide ligand attached at the distal end of the polyethylene glycol (PEG). Generally, "nanoparticle" refers to any particle having a diameter of less than 1000 nm. In some embodiments, nanoparticles suitable for delivering the Cas12i polypeptide of the present invention, the Cas12i fusion polypeptide of the present invention, the RNP of the present invention, the nucleic acid of the present invention, or the Cas12i system of the present invention to target cells have a diameter of 500 nm or less, e.g., 25 nm to 35 nm, 35 nm to 50 nm, 50 nm to 75 nm, 75 nm to 100 nm, 100 nm to 150 nm, 150 nm to 200 nm, 200 nm to 300 nm, 300 nm to 400 nm, or 400 nm to 500 nm. In some embodiments, nanoparticles suitable for delivering the chimeric Cas12i polypeptide of the present invention, the Cas12i fusion polypeptide of the present invention, the RNP of the present invention, the nucleic acid of the present invention, or the Cas12i system of the present invention to target cells have a diameter of 25 nm to 200 nm. In some embodiments, nanoparticles suitable for delivering the chimeric Cas12i polypeptide of the present invention, the Cas12i fusion polypeptide of the present invention, the RNP of the present invention, the nucleic acid of the present invention, or the Cas12i system of the present invention to target cells have a diameter of 100 nm or less. In some embodiments, nanoparticles suitable for delivering the chimeric Cas12i polypeptide of the present invention, the Cas12i fusion polypeptide of the present invention, the RNP of the present invention, the nucleic acid of the present invention, or the Cas12i system of the present invention to target cells have a diameter of 35 nm to 60 nm. Nanoparticles suitable for delivering the chimeric Cas12i polypeptide of the present invention, the Cas12i fusion polypeptide of the present invention, the RNP of the present invention, the nucleic acid of the present invention, or the Cas12i system of the present invention to target cells may be provided in different forms, e.g., as solid nanoparticles (e.g., metals (such as silver, gold, iron, and titanium), non-metals, lipid-based solids, or polymers), suspensions of nanoparticles, or combinations thereof. Metal, dielectric, and semiconductor nanoparticles, as well as hybrid structures (e.g., core-shell nanoparticles), may be prepared. Nanoparticles made of semiconductor materials may also be labeled as quantum dots if they are small enough (typically below 10 nm) for the quantization of electronic energy levels to occur. Such nano-scale particles are used in biomedical applications as drug carriers or imaging agents, and may be suitable for similar purposes in the present invention.

In some embodiments, an exosome is used to deliver the chimeric Cas12i polypeptide of the present invention, the Cas12i fusion polypeptide of the present invention, the RNP of the present invention, the nucleic acid of the present invention, or the Cas12i system of the present invention to a target cell. Exosomes are endogenous nanovesicles that transport RNAs and proteins, and can deliver RNA to the brain and other target organs. In some embodiments, a liposome is used to deliver the chimeric Cas12i polypeptide of the present invention, the Cas12i fusion polypeptide of the present invention, the RNP of the present invention, the nucleic acid of the present invention, or the Cas12i system of the present invention to a target cell. Liposomes are spherical vesicle structures composed of a uni- or multilamellar lipid bilayer surrounding an inner aqueous compartment and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be accelerated by applying force in the form of shaking by using a homogenizer, an ultrasonic disruptor, or an extrusion device. Several other additives may be added to liposomes in order to modify their structures and properties. For example, cholesterol or sphingomyelin may be added to the liposome mixture to help stabilize the liposome structure and prevent leakage of the liposome inner cargoes. Liposome formulations may primarily consist of: natural phospholipids and lipids, such as 1,2-distearoyl-sn-glycero-3-phosphocholine (DSPC), sphingomyelin, egg phosphatidylcholine, and monosialoganglioside.

Cell

The present invention provides a modified cell comprising the chimeric Cas12i polypeptide or the fusion polypeptide of the present invention and/or a nucleic acid comprising a nucleotide sequence encoding the Cas12i polypeptide or fusion polypeptide of the present invention. The present invention provides a modified cell comprising the chimeric Cas12i polypeptide or the fusion polypeptide of the present invention, wherein the modified cell is a cell that does not normally comprise the Cas12i polypeptide or fusion polypeptide of the present invention. The present invention provides a modified cell (e.g., a genetically modified cell) comprising a nucleic acid, wherein the nucleic acid comprises a nucleotide sequence encoding the chimeric Cas12i polypeptide or the fusion polypeptide of the present invention. The present invention provides a genetically modified cell genetically modified with an mRNA, wherein the mRNA comprises a nucleotide sequence encoding the chimeric Cas12i polypeptide or the fusion polypeptide of the present invention. The present invention provides a genetically modified cell genetically modified with a recombinant expression vector, wherein the recombinant expression vector comprises a nucleotide sequence encoding the chimeric Cas12i polypeptide or the fusion polypeptide of the present invention. The present invention provides a genetically modified cell genetically modified with a recombinant expression vector, wherein the recombinant expression vector comprises: a) a nucleotide sequence encoding the chimeric Cas12i polypeptide or the fusion polypeptide of the present invention; and b) a nucleotide sequence encoding the Cas12i guide RNA of the present invention.

A cell that serves as a recipient may be any one of a variety of cells including, for example, in-vitro cells; in-vivo cells; ex-vivo cells; primary cells; cancer cells; animal cells; plant cells; algal cells; fungal cells; and the like. The cell that serves as a recipient for the chimeric Cas12i polypeptide or the fusion polypeptide of the present invention and/or the nucleic acid comprising the nucleotide sequence encoding the chimeric Cas12i polypeptide or the fusion polypeptide of the present invention and/or the Cas12i guide RNA of the present invention is referred to as a "host cell" or "target cell". The host cell or target cell may be a recipient for the Cas12i system of the present invention. The host cell or target cell may be a recipient for the Cas12i RNP of the present invention. The host cell or target cell may be a recipient for a single component of the Cas12i system of the present invention.

Non-limiting examples of cells (target cells) include: prokaryotic cells, eukaryotic cells, bacterial cells, archaeal cells, cells of unicellular eukaryotic organisms, protozoan cells, plant cells, algal cells (e.g., *Botryococcus braunii, Chlamydomonas reinhardtii, Nannochloropsis gaditana, Chlorella pyrenoidosa, Sargassum patens, C. agardh*, etc.), seaweeds (e.g., kelp)), fungal cells (e.g., yeast cells, cells from mushrooms), animal cells, cells from invertebrates (e.g., fruit flies, cnidarians, echinoderms, nematodes, etc.), cells from vertebrates (e.g., fish, amphibians, reptiles, birds, and mammals), cells from mammals (e.g., ungulates (e.g., pigs, cows, goats, and sheep); rodents (e.g., rats and mice); non-human primates; humans; felines (e.g., cats); canines (e.g., dogs); etc.), and the like. In some embodiments, the cell is a cell that does not originate from a natural organism (e.g., the cell may be a synthetically produced cell, also referred to as an artificial cell).

The cell may be an in-vitro cell (e.g., an established cultured cell line). The cell may be an ex-vivo cell (a cultured cell from an individual). The cell may be an in-vivo cell (e.g., a cell in an individual). The cell may be an isolated cell. The cell may be a cell inside an organism. The cell may be an organism. The cell may be a cell in a cell culture (e.g., an in-vitro cell culture). The cell may be one of a collection of cells. The cell may be a prokaryotic cell or derived from a prokaryotic cell. The cell may be a bacterial cell or may be derived from a bacterial cell. The cell may be an archaeal cell or derived from an archaeal cell. The cell may be a eukaryotic cell or derived from a eukaryotic cell. The cell may be a plant cell or derived from a plant cell. The cell may be an animal cell or derived from an animal cell. The cell may be an invertebrate cell or derived from an invertebrate cell. The cell may be a vertebrate cell or derived from a vertebrate cell. The cell may be a mammalian cell or derived from a mammalian cell. The cell may be a rodent cell or derived from a rodent cell. The cell may be a human cell or derived from a human cell. The cell may be a microbial cell or derived from a microbial cell. The cell may be a fungal cell or derived from a fungal cell. The cell may be an insect cell. The cell may be an arthropod cell. The cell may be a protozoan cell. The cell may be a helminth cell.

Suitable cells include stem cells (e.g., embryonic stem (ES) cells, induced pluripotent stem (iPS) cells; germ cells (e.g., oocytes, sperm, oogonia, spermatogonia, etc.); somatic cells, such as fibroblasts, oligodendrocytes, glial cells, hematopoietic cells, neurons, muscle cells, bone cells, liver cells, pancreatic cells, and the like.

Suitable cells include human embryonic stem cells, embryonic cardiomyocytes, myofibroblasts, mesenchymal stem cells, autologous transplanted expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone marrow-derived progenitor cells, cardiomyocytes, skeletal cells, fetal cells, undifferentiated cells, multipotent progenitor cells, unipotent progenitor cells, monocytes, cardiac myoblasts, skeletal myoblasts, macrophages, capillary endothelial cells, xenogeneic cells, allogeneic cells, and postpartum stem cells.

In some embodiments, the cell is an immune cell, a neuron, an epithelial cell and endothelial cell, or a stem cell. In some embodiments, the immune cell is a T cell, a B cell, a monocyte, a natural killer cell, a dendritic cell, or a macrophage. In some embodiments, the immune cell is a cytotoxic T cell. In some embodiments, the immune cell is a helper T cell. In some embodiments, the immune cell is a regulatory T cell (Treg). In some embodiments, the cell is a stem cell. Stem cells include adult stem cells. Adult stem cells are also referred to as somatic stem cells. In some embodiments, the stem cell is a hematopoietic stem cell (HSC). In other embodiments, the stem cell is a neural stem cell (NSC). In other embodiments, the stem cell is a mesenchymal stem cell (MSC).

Composition or Kit

Another aspect of the present invention relates to a composition or a kit comprising the Cas12i system of the present invention, wherein the Cas12i system may comprise: a) the chimeric Cas12i polypeptide and the Cas12i guide RNA of the present invention; b) the Cas12i fusion polypeptide and the Cas12i guide RNA of the present invention; c) an mRNA encoding the chimeric Cas12i polypeptide of the present invention; and the Cas12i guide RNA; d) an mRNA encoding the Cas12i fusion polypeptide of the present invention, and the Cas12i guide RNA; c) a recombinant expression vector comprising a nucleotide sequence encoding the chimeric Cas12i polypeptide of the present invention and a nucleotide sequence encoding the Cas12i guide RNA; f) a recombinant expression vector comprising a nucleotide sequence encoding the Cas12i fusion polypeptide of the present invention and the nucleotide sequence encoding the Cas12i guide RNA; g) a first recombinant expression vector comprising the nucleotide sequence encoding the chimeric Cas12i polypeptide of the present invention, and a second recombinant expression vector comprising the nucleotide sequence encoding the Cas12i guide RNA; h) a first recombinant expression vector comprising the nucleotide sequence encoding the Cas12i fusion polypeptide of the present invention, and a second recombinant expression vector comprising the nucleotide sequence encoding the Cas12i guide RNA; i) a recombinant expression vector comprising the nucleotide sequence encoding the chimeric Cas12i polypeptide of the present invention, a nucleotide sequence encoding a first Cas12i guide RNA, and a nucleotide sequence encoding a second Cas12i guide RNA; or j) a recombinant expression vector comprising the nucleotide sequence encoding the Cas12i fusion polypeptide of the present invention, a nucleotide sequence encoding a first Cas12i guide RNA, and a nucleotide sequence encoding a second Cas12i guide RNA; or a variant of one of (a) to (j).

The composition or the kit of the present invention may further comprise a pharmaceutically acceptable carrier, such as one or more additional agents, e.g., i) a buffer; ii) a protease inhibitor; iii) a nuclease inhibitor; iv) a reagent required for developing or visualizing a detectable label; v) a positive and/or negative control target DNA; vi) a positive and/or negative control Cas12i guide RNA; and the like. The composition or the kit of the present invention may comprise: a) a component of the Cas12i system of the present invention as described above, or the Cas12i system of the present invention; and b) a therapeutic agent.

The composition or the kit of the present invention may comprise a recombinant expression vector comprising: a) an insertion site for inserting a nucleic acid comprising a nucleotide sequence encoding a moiety of the Cas12i guide RNA, wherein the moiety of the Cas12i guide RNA hybridizes to a target nucleotide sequence in a target nucleic acid; and b) a nucleotide sequence encoding the Cas12i-binding moiety of the Cas12i guide RNA. The composition or the kit of the present invention may comprise a recombinant expression vector comprising: a) an insertion site for inserting a nucleic acid comprising a nucleotide sequence encoding a moiety of the Cas12i guide RNA, wherein the moiety of the Cas12i guide RNA hybridizes to a target nucleotide sequence in a target nucleic acid; b) a nucleotide sequence encoding the Cas12i-binding moiety of the Cas12i guide RNA; and c) a nucleotide sequence encoding the Cas12i polypeptide of the present invention.

Method and Use

The chimeric Cas12i polypeptide of the present invention or the Cas12i fusion polypeptide of the present invention may be used in a variety of methods (e.g., in combination with the Cas12i guide RNA). For example, the chimeric Cas12i polypeptide of the present invention may be used to (i) modify (e.g., methylate, etc.) a target nucleic acid (DNA or RNA; single-stranded or double-stranded); (ii) regulate transcription of the target nucleic acid; (iii) label the target nucleic acid; (iv) bind to the target nucleic acid (e.g., for the purposes of isolation, labeling, imaging, tracking, etc.); (v) modify a polypeptide (e.g., a histone) associated with the target nucleic acid; (vi) perform base pair conversion on the target nucleic acid; and the like. Thus, the present invention provides a method for modifying a target nucleic acid. In some embodiments, the method for modifying the target nucleic acid of the present invention comprises contacting the target nucleic acid with: a) the chimeric Cas12i polypeptide or the fusion polypeptide of the present invention; and b) one or more (e.g., two) Cas12i guide RNAs. In some embodiments, the contacting step is performed in an in-vitro cell. In some embodiments, the contacting step is performed in an in-vivo cell. In some embodiments, the contacting step is performed in an ex-vivo cell.

For example, the present invention provides (but is not limited to) a method for editing the target nucleic acid; a method for regulating transcription of a target from a nucleic acid; a method for isolating the target nucleic acid, a method for binding to the target nucleic acid, a method for imaging the target nucleic acid, a method for modifying the target nucleic acid, and the like.

In some embodiments, the modification comprises increasing or decreasing expression of a target sequence in the target nucleic acid. For example, the modification comprises deaminating a target adenine or a target cytosine in the target nucleic acid to achieve base pair conversion.

As used herein, the term/phrase "contacting the target nucleic acid, for example, with the chimeric Cas12i polypeptide or with the Cas12i fusion polypeptide, etc." encompasses all methods used for contacting the target nucleic acid. For example, the chimeric Cas12i polypeptide may be provided to a cell as a protein, an RNA (encoding the Cas12i polypeptide or fusion polypeptide), or a DNA (encoding the Cas12i polypeptide or fusion polypeptide); while the Cas12i guide RNA may be provided as a guide RNA or a nucleic acid encoding the guide RNA. Thus, when the methods are performed, for example, in a cell (e.g., inside an in-vitro cell, inside an in-vivo cell, or inside an ex-vivo cell), the method comprising contacting the target nucleic acid encompasses introducing any or all of the components in their active/final state (e.g., in one or more protein forms of a chimeric Cas12i polypeptide; in the protein form of a Cas12i fusion polypeptide; in some embodiments, in the RNA form of a guide RNA) into the cell, and also encompasses introducing one or more nucleic acids encoding one or more of the components (e.g., one or more nucleic acids comprising one or more nucleotide sequences encoding the chimeric Cas12i polypeptide or the Cas12i fusion polypeptide, one or more nucleic acids comprising one or more nucleotide sequences encoding one or more guide RNAs, etc.) into the cell. Because the methods may also be performed outside a cell in vitro, the method comprising contacting the target nucleic acid (unless otherwise indicated) encompasses contacting outside the cell in vitro, inside the cell in vitro, inside the cell in vivo, inside the cell ex vivo, etc.

In some embodiments, the method for modifying the target nucleic acid of the present invention comprises introducing into a target cell a Cas12i locus, e.g., a nucleic acid comprising a nucleotide sequence encoding the Cas12i polypeptide and nucleotide sequences of about 1 kilobase (kb) to 5 kb in length surrounding the Cas12i-encoding nucleotide sequence from a cell comprising the Cas12i locus (e.g., in some embodiments, a cell that comprises the Cas12i locus in its natural state), wherein the target cell does not normally (in its natural state) comprise the Cas12i locus. However, one or more spacer sequences, one or more coding guide sequences for the encoded crRNA(s), may be modified, such that one or more target sequences of interest are targeted. Thus, for example, in some embodiments, the method for modifying the target nucleic acid of the present invention comprises introducing into a target cell a Cas12i locus, e.g., a nucleic acid obtained from a source cell (e.g., a cell that comprises the Cas12i locus in its natural state), wherein the nucleic acid has a length of 100 nucleotides (nt) to 5 kb (e.g., 100 nt to 500 nt, 500 nt to 1 kb, 1 kb to 1.5 kb, 1.5 kb to 2 kb, 2 kb to 2.5 kb, 2.5 kb to 3 kb, 3 kb to 3.5 kb, 3.5 kb to 4 kb, or 4 kb to 5 kb) and comprises a nucleotide sequence encoding the Cas12i polypeptide. As described above, in some such cases, one or more spacer sequences, one or more coding guide sequences for the encoded crRNA(s), may be modified, such that one or more target sequences of interest are targeted. In some embodiments, the method comprises introducing into a target cell: i) a Cas12i locus; and ii) a Cas12i gRNA. In some embodiments, the target nucleic acid is in a cell-free composition in vitro. In some embodiments, the target nucleic acid is present in a target cell. In some embodiments, the target nucleic acid is present in a target cell, wherein the target cell is a prokaryotic cell. In some embodiments, the target nucleic acid is present in a target cell, wherein the target cell is a eukaryotic cell. In some embodiments, the target nucleic acid is present in a target cell, wherein the target cell is a mammalian cell. In some embodiments, the target nucleic acid is present in a target cell, wherein the target cell is a plant cell.

In some embodiments, the method for modifying the target nucleic acid of the present invention comprises contacting the target nucleic acid with the Cas12i polypeptide of the present invention or the Cas12i fusion polypeptide of the present invention. In some embodiments, the method for modifying the target nucleic acid of the present invention comprises contacting the target nucleic acid with the Cas12i fusion polypeptide and the Cas12i guide RNA. In some embodiments, the method for modifying the target nucleic acid of the present invention comprises contacting the target nucleic acid with the Cas12i fusion polypeptide, the first Cas12i guide RNA, and the second Cas12i guide RNA.

The chimeric Cas12i polypeptide of the present invention or the Cas12i fusion polypeptide of the present invention, when bound to the Cas12i guide RNA, can bind to the target nucleic acid, and in some embodiments, can bind to and modify the target nucleic acid. The target nucleic acid may be any nucleic acid (e.g., DNA or RNA), may be double-stranded or single-stranded, may be any type of nucleic acid (e.g., chromosomal (genomic DNA), derived from a chromosome, chromosomal DNA, plasmid, viral, extracellular, intracellular, mitochondrial, chloroplast, linear, circular, etc.) and may be from any organism (e.g., as long as the Cas12i guide RNA comprises a nucleotide sequence that hybridizes to a target sequence in the target nucleic acid such that the target nucleic acid can be targeted). The target nucleic acid may be a DNA or an RNA. The target nucleic acid may be double-stranded (e.g., dsDNA or dsRNA) or single-stranded (e.g., ssRNA or ssDNA).

Another aspect of the present invention provides a method for treating a subject diagnosed with a disease associated with or caused by a point mutation, wherein the point mutation can be corrected by the base editor provided herein. For example, in some examples, provided is a method comprising administering to a subject suffering from such a disease (e.g., a cancer associated with the point mutation as described above) an effective amount of an adenosine base editor, wherein the editor corrects the point mutation or introduces an inactivating mutation into a gene associated with the disease. In some embodiments, the disease is a proliferative disease. In some embodiments, the disease is a genetic disease. In some embodiments, the disease is a neoplastic disease. In some embodiments, the disease is a metabolic disease. In some embodiments, the disease is a lysosomal storage disease. Other diseases that can be treated by correcting the point mutation or introducing the inactivating mutation into the gene associated with the disease will be known to those skilled in the art.

In some embodiments, deamination of the mutated A results in a codon encoding a wild-type amino acid. In some embodiments, the contacting is performed in the body of the subject. In some embodiments, the subject has suffered from or has been diagnosed with a disease or disorder. In some embodiments, the disease or disorder is hemoglobinopathy. In some embodiments, the disease or disorder is sickle cell disease. In some embodiments, the disease or disorder is thalassemia. In some embodiments, the disease or disorder is type 1A glycogen storage disease associated with an R83C mutation in a glucose-6-phosphatase-α (G6PC) enzyme, and Stargardt macular dystrophy associated with a G1961E mutation in an ATP-binding cassette sub-family A member 4 (ABCA4) protein. In some embodiments, the disease or disorder is phenylketonuria, von Willebrand disease (vWD), a neoplastic disease associated with mutated PTEN or BRCA1, or Li-Fraumeni syndrome.

Some examples provide a method for using the base editor provided herein. In some embodiments, the base editor is used to introduce a point mutation into a nucleic acid by deaminating a target nucleobase (e.g., an A base). In some embodiments, the deamination of the target nucleobase results in correction of a genetic defect, e.g., results in correction of a point mutation that causes loss of function in a gene product. In some embodiments, the method provided herein is used to introduce an inactivating point mutation into a gene or allele encoding a gene product associated with a disease or disorder. For example, in some embodiments, provided herein is a method for using the base editor to introduce an inactivating point mutation into an oncogene (e.g., in the treatment of a proliferative disease). In some embodiments, the inactivating mutation may result in a premature stop codon in the coding sequence, which leads to expression of a truncated gene product (e.g., a truncated protein that lacks the function of a full-length protein).

In some embodiments, a purpose of the method provided herein is to restore the function of a dysfunctional gene through genome editing. The base editor provided herein can be verified in vitro for gene editing-based human therapy, for example, by correcting a disease-associated mutation in a human cell culture. Those skilled in the art will appreciate that the base editor provided herein can be used to correct any single-point G-to-A or C-to-T mutation.

Other aspects of the present invention relate to a pharmaceutical composition comprising any one of the fusion protein: gRNA complexes described herein. Other aspects of the present invention relate to a pharmaceutical composition comprising any of the polynucleotides or vectors described herein, wherein the polynucleotide or vector comprises a nucleic acid fragment encoding the fusion protein: gRNA complex described herein.

In some embodiments, any of the fusion protein: gRNA complexes described herein is provided as part of the pharmaceutical composition. In some embodiments, the pharmaceutical composition comprises any of the base editors provided herein. In some embodiments, the pharmaceutical composition comprises any of the complexes provided herein. In some embodiments, the pharmaceutical composition comprises a fusion protein: gRNA complex and a pharmaceutically acceptable excipient. The pharmaceutical composition may optionally comprise one or more additional therapeutically active substances.

In some embodiments, the composition provided herein is formulated for delivery to a subject, such as a human subject, to achieve targeted genomic modification within the subject. In some embodiments, a cell is obtained from the subject and contacts with any of the pharmaceutical compositions provided herein. In some embodiments, the cell, removed from the subject and in ex vivo contact with the pharmaceutical composition, is reintroduced into the subject, optionally after the desired genomic modification is achieved or detected in the cell.

The formulation of the pharmaceutical composition described herein may be prepared by any method known in the field of pharmacology. Generally, such a preparation method comprises the steps of combining the active ingredient with an excipient and/or one or more other auxiliary ingredients and then, if necessary and/or desired, shaping and/or packaging the product into the desired single- or multi-dose unit.

In some embodiments, the pharmaceutical composition is formulated for delivery to a subject, e.g., for gene editing. Suitable routes of administration of the pharmaceutical composition described herein include, but are not limited to: topical, subcutaneous, transdermal, intradermal, intralesional, intraarticular, intraperitoneal, intravesical, transmucosal, gingival, submental, intracochlear, transtympanic, intraaural, epidural, intrathecal, intramuscular, intravenous, intravascular, intraosseous, periocular, intratumoral, intracerebral, and lateral ventricle administrations.

In various embodiments, the disclosed editing method results in an on-target DNA base editing efficiency of at least about 35%, 40%, 50%, 60%, 70%, 80%, 85%, 90%, 95%, 98%, or 99% at the target nucleobase pair. The contacting step may result in a DNA base editing efficiency of at least about 60%, 61%, 62%, 63%, 64%, 65%, 66%, 67%, 68%, 69%, 70%, 71%, 72%, 73%, 74%, or 75%. In particular, the contacting step results in a target-based editing efficiency of greater than 75%. In certain examples, a base editing efficiency of 99% may be achieved.

In some embodiments, the disclosed editing method for the base editor results in an actual or average off-target DNA editing frequency of about 2.0% or less, 1.75% or less, 1.5% or less, 1.2% or less, 1% or less, 0.9% or less, 0.8% or less, 0.75% or less, 0.7% or less, 0.65% or less, or 0.6% or less in some examples; the disclosed editing method results in an actual or average off-target DNA editing frequency of 0.5%, less than 0.5%, less than 0.4%, less than 0.35%, less than 0.3%, less than 0.25%, less than 0.2%, or less than 0.1%.

In some embodiments, the base pair intended for editing is 1, 2, 3, 4, 5, 6, 7, 8, 9, 10, 11, 12, 13, 14, 15, 16, 17, 18, 19, or 20 nucleotides upstream of the PAM site. In some examples, the base pair intended for editing is downstream of the PAM site. In some embodiments, the base pair intended for editing is 1, 2, 3, 4, 5, 6, 7, 8, 9, 10, 11, 12, 13, 14, 15, 16, 17, 18, 19, or 20 nucleotides downstream of the PAM site. In some embodiments, the target region comprises a target window, wherein the target window comprises a target nucleobase pair. In some examples, the target window comprises 1-10 nucleotides. In some embodiments, the length of the target window is 1-9, 1-8, 1-7, 1-6, 1-5, 1-4, 1-3, 1-2, or 1 nucleotide. In some embodiments, the length of the target window is 1, 2, 3, 4, 5, 6, 7, 8, 9, 10, 11, 12, 13, 14, 15, 16, 17, 18, 19, or 20 nucleotides. In some examples, the base pair intended for editing is within the target window. In some embodiments, the method is performed using any of the base editors provided herein. In some examples, the target window is a deamination window.

Yet another aspect of the present invention provides use of the fusion protein: gRNA complex provided herein in the preparation of a medicament for treating a disease mediated by a nucleobase A or C mutation. Yet another aspect of the present invention further provides the fusion protein: gRNA complex provided herein for use in the treatment of a disease mediated by a nucleobase A or C mutation. The disease mediated by the nucleobase A mutation may be any one of the treatable diseases mentioned above. The disease mediated by the nucleobase C mutation is, for example, cystic fibrosis, phenylketonuria, epidermolytic hyperkeratosis (EHK), Charcot-Marie-Tooth disease type 4J, neuroblastoma (NB), von Willebrand disease (vWD), myotonia congenita, hereditary renal amyloidosis, dilated cardiomyopathy (DCM), hereditary lymphedema, familial Alzheimer's disease, HIV, prion disease, chronic infantile neurologic cutaneous articular syndrome (CINCA), desmin-related myopathy (DRM), or a neoplastic disease associated with a mutant PI3KCA protein, a mutant CTNNB1 protein, a mutant HRAS protein, or a mutant p53 protein.

Specifically, the fusion protein provided herein can be used to treat various rare diseases, tumors, cancers, inflammations, viral infection diseases, genetic diseases, central nervous system diseases, aging, and a variety of autoimmune diseases, as well as common and chronic diseases. More specifically, the treated disease may be hypertension, hyperlipidemia, hepatitis B virus (HBV), hepatocellular carcinoma (HCC), facioscapulohumeral muscular dystrophy (FSHD), heterozygous familial hypercholesterolemia (HeFH), α-1 antitrypsin deficiency (A1AD), non-arteritic anterior ischemic optic neuropathy (NAION), or Duchenne muscular dystrophy (DMD).

Sequence listing

| SEQ ID NO: | Description | Sequence |
|---|---|---|
| 1 | enCas12i-001 (AA) | MSSAIKSYKSVLRPNERKNQLLKSTIQCLEDGSAFFFKMLQGLFGGITPEIVR<br>FSTEQEKQQQDIALWCAVNWFRPVSQDSLTHTIASDNLVEKFEEYYGGTAS<br>DAIKQYFSASIGESYYWNDCRQQYYDLCRELGVEVSDLTHDLEILCREKCL<br>AVATESNQYNSIISVLFGTGRKEDRSVKLRITKKILEAISNLKEIPKNVAPIQEI<br>ILNVAKATKETFRQVYAGNLGAPSTLERFIAKDGQKEFDLKKLQTDLKKVIR<br>GKSKERDWCCQEELRSYVEQNTIQYDLWAWGEMENKAHTALKIKSTRNYN<br>FAKQRLEQFKRIQSLNNLLVVKKLNDFFDSEFFSGEETYTICVHHLGGKRLS<br>KLYKAWEDDPADPENAIVVLCDDLKNNFKKEPIRNILRYIFTIRQECSAQDIL<br>AAAKYNQQLDRYKSQKANPSVLGNQGFTWRNAVILPEKAQRNDRPNSLDL<br>RIWLYLKLRHPDGRWKKHHIPFYDTRFFQEIYAAGNSPVDTCQFRTPRFGYH<br>LPKLTDQTAIRVNKKHVKAAKTEARIRLAIQQGTLPVSNLKITRISATINSKG<br>QVRIPVKFDVGRQKGTLQIGDRFCGYDQNQTASHAYSLWEVVKEGQYHKE<br>LGCFVRFISSGDIVSITENRGNQFDQLSYEGLAYPQYADWRKKASKFVSLWQ<br>ITKKNKKKEIVTVEAKEKFDAICKYQPRLYKFNKEYAYLLRDIVRGKSLVEL<br>QQIRQEIFRFIEQDCGVTRLGSLSLSTLETVKAVKGIIYSYFSTALNASKNNPIS<br>DEQRKEFDPELFALLEKLELIRTRKKKQKVERIANSLIQTCLENNIKFIRGEGD<br>LSTTNNATKKKANSRSMDWLARGVFNKIRQLAPMHNITLFGCGSLYTSHQD<br>PLVHRNPDKAMRARFEEVNVENIAEWHVRNFSNYLRADSGTGLYYKQATM<br>DFLKHYGLEEHAEGLENKKIKFYDFRKILEDKNLTSVIIPKRGGRIYMATNPV<br>TSDSTPITYAGKTYNRCNADHVAAANIALTVKGIGEQSSDEENPDGSRIKLQ<br>LTS |
| 2 | enCas12i-002 (AA) | MSSAIKSYKSVLRPNERKNQLLKSTIQCLEDGSAFFFKMLQGLFGGITPEIVR<br>FSTEQEKQQQDIALWCAVNWFRPVSQDSLTHTIASDNLVEKFEEYYGGTAS<br>DAIKQYFSASIGESYYWNDCRQQYYDLCRELGVEVSDLTHDLEILCREKCL<br>AVATESNQYNSIISVLFGTGRKEDRSVKLRITKKILEAISNLKEIPKNVAPIQEI<br>ILNVAKATKETFRQVYAGNLGAPSTLERFIAKDGQKEFDLKKLQTDLKKVIR<br>GKSKERDWCCQEELRSYVEQNTIQYDLWAWGEMENKAHTALKIKSTRNYN<br>FAKQRLEQFKRIQSLNNLLVVKKLNDFFDSEFFSGEETYTICVHHLGGKRLS<br>KLYKAWEDDPADPENAIVVLCDDLKNNFKKEPIRNILRYIFTIRQECSAQDIL<br>AAAKYNQQLDRYKSQKANPSVLGNQGFTWRNAVILPEKAQRNDRPNSLDL<br>RIWLYLKLRHPDGRWKKHHIPFYDTRFFQEIYAAGNSPVDTCQFRTPRFGYH<br>LPKLTDQTAIRVNKKHVKAAKTEARIRLAIQQGTLPVSNLKITRISATINSKG<br>QVRIPVKFDVGRQKGTLQIGDRFCGYDQNQTASHAYSLWEVVKEGQYHKE<br>LGCFVRFISSGDIVSITENRGNQFDQLSYEGLAYPQYADWRKKASKFVSLWQ<br>ITKKNKKKEIVTVEAKEKFDAICKYQPRLYKFNKEYAYLLRDIVRGKSLVEL<br>QQIRQEIFRFIEQDCGVTRLGSLSLSTLETVKAVKGIIYSYFSTALNASKNNPIS<br>DEQRKEFDPELFALLEKLELIRTRKKKQKVERIANSLIQTCLENNIKFIRGEGD<br>LSTTNNATKKKANSRSMDWLARGVFNKIRQLAPMHNITLFGCGSLYTSHQD<br>PLVHRNPDKAMRARFEEVNVSNVSEWHMRNFSNYLRADSGTGLYYKQAT<br>LDFLKHYDLEEHADDLEKQNIKFYDFRKILEDKQLTSVIVPKRGGRIYMATN<br>PVTSDSTPVTYAGKTYNRCNADHVAAANIALTVKGIGEQSSDEENPDGSRIK<br>LQLTS |
| 3 | enCas12i-003 (AA) | MSSAIKSYKSVLRPNERKNQLLKSTIQCLEDGSAFFFKMLQGLFGGITPEIVR<br>FSTEQEKQQQDIALWCAVNWFRPVSQDSLTHTIASDNLVEKFEEYYGGTAS<br>DAIKQYFSASIGESYYWNDCRQQYYDLCRELGVEVSDLTHDLEILCREKCL<br>AVATESNQYNSIISVLFGTGRKEDRSVKLRITKKILEAISNLKEIPKNVAPIQEI<br>ILNVAKATKETFRQVYAGNLGAPSTLERFIAKDGQKEFDLKKLQTDLKKVIR<br>GKSKERDWCCQEELRSYVEQNTIQYDLWAWGEMENKAHTALKIKSTRNYN<br>FAKQRLEQFKRIQSLNNLLVVKKLNDFFDSEFFSGEETYTICVHHLGGKRLS<br>KLYKAWEDDPADPENAIVVLCDDLKNNFKKEPIRNILRYIFTIRQECSAQDIL<br>AAAKYNQQLDRYKSQKANPSVLGNQGFTWRNAVILPEKAQRNDRPNSLDL<br>RIWLYLKLRHPDGRWKKHHIPFYDTRFFQEIYAAGNSPVDTCQFRTPRFGYH<br>LPKLTDQTAIRVNKKHVKAAKTEARIRLAIQQGTLPVSNLKITRISATINSKG<br>QVRIPVKFDVGRQKGTLQIGDRFCGYDQNQTASHAYSLWEVVKEGQYHKE<br>LGCFVRFISSGDIVSITENRGNQFDQLSYEGLAYPQYADWRKKASKFVSLWQ<br>ITKKNKKKEIVTVEAKEKFDAICKYQPRLYKFNKEYAYLLRDIVRGKSLVEL<br>QQIRQEIFRFIEQDCGVTRLGSLSLSTLETVKAVKGIIYSYFSTALNASKNNPIS<br>DEQRKEFDPELFALLEKLELIRTRKKKQKVERIANSLIQTCLENNIKFIRGEGD<br>LSTTNNATKKKANSRSMDWLARGVENKIRQLAPMHNITLFGCGSLYTSHQD<br>PLVHRNPDKSFRARWDLVKVKDFGEKHLLTLSRNLTGKGPGTRKYYHQGV<br>EDFLKEYELEDLKEELAKIKKGDPNALPPEVIRNKLKEKLGNENAPVLIPKR<br>GGKYFLSTHNVATGAVKITFNNKERYLCNADHVAAANIALTVKGIGEQSSD<br>EENPDGSRIKLQLTS |
| 4 | enCas12i-004 (AA) | MSSAIKSYKSVLRPNERKNQLLKSTIQCLEDGSAFFFKMLQGLFGGITPEIVR<br>FSTEQEKQQQDIALWCAVNWFRPVSQDSLTHTIASDNLVEKFEEYYGGTAS<br>DAIKQYFSASIGESYYWNDCRQQYYDLCRELGVEVSDLTHDLEILCREKCL<br>AVATESNQYNSIISVLFGTGRKEDRSVKLRITKKILEAISNLKEIPKNVAPIQEI<br>ILNVAKATKETFRQVYAGNLGAPSTLERFIAKDGQKEFDLKKLQTDLKKVIR<br>GKSKERDWCCQEELRSYVEQNTIQYDLWAWGEMENKAHTALKIKSTRNYN<br>FAKQRLEQFKRIQSLNNLLVVKKLNDFFDSEFFSGEETYTICVHHLGGKRLS<br>KLYKAWEDDPADPENAIVVLCDDLKNNFKKEPIRNILRYIFTIRQECSAQDIL<br>AAAKYNQQLDRYKSQKANPSVLGNQGFTWRNAVILPEKAQRNDRPNSLDL<br>RIWLYLKLRHPDGRWKKHHIPFYDTRFFQEIYAAGNSPVDTCQFRTPRFGYH |

-continued

Sequence listing

| SEQ ID NO: | Description | Sequence |
|---|---|---|
| | | LPKLTDQTAIRVNKKHVKAAKTEARIRLAIQQGTLPVSNLKITRISATINSKG<br>QVRIPVKFDVGRQKGTLQIGDRFCGYDQNQTASHAYSLWEVVKEGQYHKE<br>LGCFVRFISSGDIVSITENRGNQFDQLSYEGLAYPQYADWRKKASKFVSLWQ<br>ITKKNKKKEIVTVEAKEKFDAICKYQPRLYKFNKEYAYLLRDIVRGKSLVEL<br>QQIRQEIFRFIEQDCGVTRLGSLSLSTLETVKAVKGIIYSYFSTALNASKNNPIS<br>DEQRKEFDPELFALLEKLELIRTRKKKQKVERIANSLIQTCLENNIKFIRGEGD<br>LSTTNNATKKKANSRSMDWLARGVFNKIRQLAPMHNITLFGCGSLYTSHQD<br>PLVHRNPDKSFRARWRLVKVKDIGEKELLTLSRNLRGKGKGIKKYYHQGVL<br>DFFKEYELEELAGPLAKIKPGDPNAIPPEVLRNKLKEKLGNEDAPVLIPVAGG<br>GIYLSTHNVATGAKKITFNNKERYVCNADHVAAANIALTVKGIGEQSSDEE<br>NPDGSRIKLQLTS |
| 5 | enCas12i-005 (AA) | MSSAIKSYKSVLRPNERKNQLLKSTIQCLEDGSAFFFKMLQGLFGGITPEIVR<br>FSTEQEKQQQDIALWCAVNWFRPVSQDSLTHTIASDNLVEKFEEYYGGTAS<br>DAIKQYFSASIGESYYWNDCRQQYYDLCRELGVEVSDLTHDLEILCREKCL<br>AVATESNQYNSIISVLFGTGRKEDRSVKLRITKKILEAISNLKEIPKNVAPIQEI<br>ILNVAKATKETFRQVYAGNLGAPSTLERFIAKDGQKEFDLKKLQTDLKKVIR<br>GKSKERDWCCQEELRSYVEQNTIQYDLWAWGEMENKAHTALKIKSTRNYN<br>FAKQRLEQFKRIQSLNNLLVVKKLNDFFDSEFFSGEETYTICVHHLGGKRLS<br>KLYKAWEDDPADPENAIVVLCDDLKNNFKKEPIRNILRYIFTIRQECSAQDIL<br>AAAKYNQQLDRYKSQKANPSVLGNQGFTWRNAVILPEKAQRNDRPNSLDL<br>RIWLYLKLRHPDGRWKKHHIPFYDTRFFQEIYAAGNSPVDTCQFRTPRFGYH<br>LPKLTDQTAIRVNKKHVKAAKTEARIRLAIQQGTLPVSNLKITRISATINSKG<br>QVRIPVKFDVGRQKGTLQIGDRFCGYDQNQTASHAYSLWEVVKEGQYHKE<br>LGCFVRFISSGDIVSITENRGNQFDQLSYEGLAYPQYADWRKKASKFVSLWQ<br>ITKKNKKKEIVTVEAKEKFDAICKYQPRLYKFNKEYAYLLRDIVRGKSLVEL<br>QQIRQEIFRFIEQDCGVTRLGSLSLSTLETVKAVKGIIYSYFSTALNASKNNPIS<br>DEQRKEFDPELFALLEKLELIRTRKKKQKVERIANSLIQTCLENNIKFIRGEGD<br>LSTTNNATKKKANSRSMDWLARGVFNKIRQLAPMHNITLFGCGSLYTSHQD<br>PLVHRNPDKKYNARWDLVKVKDIGEGHLLILSRNLRGKGSGIRKYYHQGV<br>LEFFKEYDLEDLAEPLAKIRPGDPNAIPPEVLRERLKEKLGNEDAPVLIPKPG<br>GGVYLSTHNVATGAKKITFNNKERYLCNADHVAAANIALTVKGIGEQSSDE<br>ENPDGSRIKLQLTS |
| 6 | enCas12i-006 (AA) | MSSAIKSYKSVLRPNERKNQLLKSTIQCLEDGSAFFFKMLQGLFGGITPEIVR<br>FSTEQEKQQQDIALWCAVNWFRPVSQDSLTHTIASDNLVEKFEEYYGGTAS<br>DAIKQYFSASIGESYYWNDCRQQYYDLCRELGVEVSDLTHDLEILCREKCL<br>AVATESNQYNSIISVLFGTGRKEDRSVKLRITKKILEAISNLKEIPKNVAPIQEI<br>ILNVAKATKETFRQVYAGNLGAPSTLERFIAKDGQKEFDLKKLQTDLKKVIR<br>GKSKERDWCCQEELRSYVEQNTIQYDLWAWGEMENKAHTALKIKSTRNYN<br>FAKQRLEQFKRIQSLNNLLVVKKLNDFFDSEFFSGEETYTICVHHLGGKRLS<br>KLYKAWEDDPADPENAIVVLCDDLKNNFKKEPIRNILRYIFTIRQECSAQDIL<br>AAAKYNQQLDRYKSQKANPSVLGNQGFTWRNAVILPEKAQRNDRPNSLDL<br>RIWLYLKLRHPDGRWKKHHIPFYDTRFFQEIYAAGNSPVDTCQFRTPRFGYH<br>LPKLTDQTAIRVNKKHVKAAKTEARIRLAIQQGTLPVSNLKITRISATINSKG<br>QVRIPVKFDVGRQKGTLQIGDRFCGYDQNQTASHAYSLWEVVKEGQYHKE<br>LGCFVRFISSGDIVSITENRGNQFDQLSYEGLAYPQYADWRKKASKFVSLWQ<br>ITKKNKKKEIVTVEAKEKFDAICKYQPRLYKFNKEYAYLLRDIVRGKSLVEL<br>QQIRQEIFRFIEQDCGVTRLGSLSLSTLETVKAVKGIIYSYFSTALNASKNNPIS<br>DEQRKEFDPELFALLEKLELIRTRKKKQKVERIANSLIQTCLENNIKFIRGEGD<br>LSTTNNATKKKANSRSMDWLARGVFNKIRQLAPMHNITLFGCGSLYTSHQD<br>PLVHRNPDKSYRARWRLVRVRDFGERHLLTLSRNLTGKGKGTRKYYHQGV<br>LDFFREYDLEDLAGPLAKIRPGDPDAIPPEVLRERLREKLGNDEAPVLIPVRG<br>GPVYLSTHDVATGAKRITFNGKERYLCNADHVAAANIALTVKGIGEQSSDE<br>ENPDGSRIKLQLTS |
| 7 | crRNA-1 | 5'-AGAAATCCGTCTTTCATTGACGG-3' |
| 8 | crRNA-2 | 5'-AGAAATGTGTCCCCAGTTGACAC-3' |
| 9 | crRNA-3 | 5'-AGAAATCCGTCCTTAGTTGACGG-3' |
| 10 | crRNA-4 | 5'-AGACATGTGTCCCCAGTGACAC-3' |
| 11 | crRNA-5 | 5'-AGAAATGTTTCCCCAGTTGAAAC-3' |
| 12 | crRNA-6 | 5'-AGAAATGTGTTCCCAGTTAACAC-3' |
| 13 | crRNA-7 | 5'-AGAAATTTGTCCCCAGTTGACAA-3' |
| 14 | crRNA-8 | 5'-AGAAATCCGTCCTACGTTGACGG-3' |
| 15 | gRNA-1 | 5'-$(N)_n$AGAAATCCGTCTTTCATTGACGG-3' |

-continued

Sequence listing

| SEQ ID NO: | Description | Sequence |
|---|---|---|
| 16 | gRNA-2 | 5'-(N)$_n$AGAAATGTGTCCCCAGTTGACAC-3' |
| 17 | gRNA-3 | 5'-(N)$_n$AGAAATCCGTCCTTAGTTGACGG-3' |
| 18 | gRNA-4 | 5'-(N)$_n$AGACATGTGTCCCCAGTGACAC-3' |
| 19 | gRNA-5 | 5'-(N)$_n$AGAAATGTTTCCCCAGTTGAAAC-3' |
| 20 | gRNA-6 | 5'-(N)$_n$AGAAATGTGTTCCCAGTTAACAC-3' |
| 21 | gRNA-7 | 5'-(N)$_n$AGAAATTTGTCCCCAGTTGACAA-3' |
| 22 | gRNA-8 | 5'-(N)$_n$AGAAATCCGTCCTACGTTGACGG-3' |
| 23 | γ-proteobacteria adenosine deaminase TadA (AA) | MSEVEFSHEYWMRHALTLAKRAWDEREVPVGAVLVHNNRVIGEGWNRPI GRHDPTAHAEIMALRQGGLVMQNYRLIDATLYVTLEPCVMCAGAMIHSRIG RVVFGARDAKTGAAGSLMDVLHHPGMNHRVEITEGILADECAALLSDFFR MRRQEIKAQKKAQSSTD |
| 24 | *Enterobacter* adenosine deaminase TadA (AA) | MRRAFITGVFFLSEVEFSHEYWMRHALTLAKRAWDEREVPVGAVLVHNNR VIGEGWNRPIGRHDPTAHAEIMALRQGGLVMQNYRLIDATLYVTLEPCVMC AGAMIHSRIGRVVFGARDAKTGAAGSLMDVLHHPGMNHRVEITEGILADEC AALLSDFFRMRRQEIKAQKKAQSSTD |
| 25 | *Staphylococcus aureus* TadA (AA) | MGSHMTNDIYFMTLAIEEAKKAAQLGEVPIGAIITKDDEVIARAHNLRETLQ QPTAHAEHIAIERAAKVLGSWRLEGCTLYVTLEPCVMCAGTIVMSRIPRVVY GADDPKGGCSGSLMNLLQQSNFNHRAIVDKGVLKEACSTLLTTFFKNLRAN KKSTN |
| 26 | *Bacillus subtilis* TadA (AA) | MTQDELYMKEAIKEAKKAEEKGEVPIGAVLVINGEIIARAHNLRETEQRSIA HAEMLVIDEACKALGTWRLEGATLYVTLEPCPMCAGAVVLSRVEKVVFGA FDPKGGCSGTLMNLLQEERFNHQAEVVSGVLEEECGGMLSAFFRELRKKKK AARKNLSE |
| 27 | *Salmonella typhimurium* TadA (AA) | MPPAFITGVTSLSDVELDHEYWMRHALTLAKRAWDEREVPVGAVLVHNHR VIGEGWNRPIGRHDPTAHAEIMALRQGGLVLQNYRLLDTTLYVTLEPCVMC AGAMVHSRIGRVVFGARDAKTGAAGSLIDVLHHPGMNHRVEIIEGVLRDEC ATLLSDFFRMRRQEIKALKKADRAEGAGPAV |
| 28 | *Shewanella putrefaciens* TadA (AA) | MDEYWMQVAMQMAEKAEAAGEVPVGAVLVKDGQQIATGYNLSISQHDPT AHAEILCLRSAGKKLENYRLLDATLYITLEPCAMCAGAMVHSRIARVVYGA RDEKTGAAGTVVNLLQHPAFNHQVEVTSGVLAEACSAQLSRFFKRRRDEK KALKLAQRAQQGIE |
| 29 | *Haemophilus influenzae* F3031 TadA (AA) | MDAAKVRSEFDEKMMRYALELADKAEALGEIPVGAVLVDDARNIIGEGWN LSIVQSDPTAHAEIIALRNGAKNIQNYRLLNSTLYVTLEPCTMCAGAILHSRI KRLVFGASDYKTGAIGSRFHFFDDYKMNHTLEITSGVLAEECSQKLSTFFQK RREEKKIEKALLKSLSDK |
| 30 | *Caulobacter crescentus* TadA (AA) | MRTDESEDQDHRMMRLALDAARAAAEAGETPVGAVILDPSTGEVIATAGN GPIAAHDPTAHAEIAAMRAAAAKLGNYRLTDLTLVVTLEPCAMCAGAISHA RIGRVVFGADDPKGGAVVHGPKFFAQPTCHWRPEVTGGVLADESADLLRG FFRARRKAKI |
| 31 | *Geobacter sulfurreducens* TadA (AA) | MSSLKKTPIRDDAYWMGKAIREAAKAAARDEVPIGAVIVRDGAVIGRGHNL REGSNDPSAHAEMIAIRQAARRSANWRLTGATLYVTLEPCLMCMGAIILAR LERVVFGCYDPKGGAAGSLYDLSADPRLNHQVRLSPGVCQEECGTMLSDFF RDLRRRKKAKATPALFIDERKVPPEP |
| 32 | Cytidine deaminase (AA) | MDSLLMNRRKFLYQFKNVRWAKGRRETYLCYVVKRRDSATSFSLDFGYLR NKNGCHVELLFLRYISDWDLDPGRCYRVTWFTSWSPCYDCARHVADFLRG NPNLSLRIFTARLYFCEDRKAEPEGLRRLHRAGVQIAIMTFKDYFYCWNTFV ENHERTFKAWEGLHENSVRLSRQLRRILLPLYEVDDLRDAFRTLGL |
| 33 | Cytidine deaminase AID (AA) | MDSLLMNRRKFLYQFKNVRWAKGRRETYLCYVVKRRDSATSFSLDFGYLR NKNGCHVELLFLRYISDWDLDPGRCYRVTWFTSWSPCYDCARHVADFLRG NPNLSLRIFTARLYFCEDRKAEPEGLRRLHRAGVQIAIMTFKENHERTFKAW EGLHENSVRLSRQLRRILLPLYEVDDLRDAFRTLGL |
| 34 | Cytidine deaminase AID (AA) | MDSLLMNRRKFLYQFKNVRWAKGRRETYLCYVVKRRDSATSFSLDFGYLR NKNGCHVELLFLRYISDWDLDPGRCYRVTWFTSWSPCYDCARHVADFLRG NPNLSLRIFTARLYFCEDRKAEPEGLRRLHRAGVQIAIMTFKDYFYCWNTFV ENHERTFKAWEGLHENSVRLSRQLRRILLPLYEVDDLRDAFRTLGL |

-continued

| SEQ ID NO: | Description | Sequence |
|---|---|---|
| | Sequence listing | |
| 35 | NLS of SV40 virus large T antigen (AA) | PKKKRKV |
| 36 | Nucleoplasm in bipartite NLS (AA) | KRPAATKKAGQAKKKK |
| 37 | c-myc NLS (AA) | PAAKRVKLD |
| 38 | c-myc NLS (AA) | RQRRNELKRSP |
| 39 | hRNPA1 M9 NLS (AA) | NQSSNFGPMKGGNFGGRSSGPYGGGGQYFAKPRNQGGY |
| 40 | IBB domain of importin-α (AA) | RMRIZFKNKGKDTAELRRRRVEVSVELRKAKKDEQILKRRNV |
| 41 | Myoma T protein (AA) | VSRKRPRP |
| 42 | Myoma T protein (AA) | PPKKARED |
| 43 | Human p53 (AA) | PQPKKKPL |
| 44 | Mouse c-abl IV (AA) | SALIKKKKKMAP |
| 45 | Influenza virus NS1 (AA) | DRLRR |
| 46 | Influenza virus NS1 (AA) | PKQKKRK |
| 47 | Hepatitis virus δ antigen (AA) | RKLKKKIKKL |
| 48 | Mouse Mx1 protein (AA) | REKKKFLKRR |
| 49 | Human poly(ADP-ribose) polymerase (AA) | KRKGDEVDGVDEVAKKKSKK |
| 50 | Steroid hormone receptor (human) glucocorticoid (AA) | RKCLQAGMNLEARKTKK |
| 51 | linker | GGSGG |
| 52 | linker | GSGSG |
| 53 | linker | GSGGG |
| 54 | linker | GGGSG |
| 55 | linker | GSSSG |
| 56 | linker | SGGSSGGS |

-continued

Sequence listing

| SEQ ID NO: | Description | Sequence |
| --- | --- | --- |
| 57 | linker | SGSETPGTSESATPES |
| 58 | linker | SGGSSGSETPGTSESATPESSGGS |
| 59 | enCas12i-001 (eukaryotic codon-optimized, nucleotide) | ATGAGCAGCGCCATCAAGAGCTACAAGAGCGTGCTGCGCCCCAACGAGC<br>GCAAGAACCAGCTGCTGAAGAGCACCATCCAGTGCCTGGAGGACGGCA<br>GCGCCTTCTTCTTCAAGATGCTGCAGGGCCTGTTCGGCGGCATCACCCCC<br>GAGATCGTGCGCTTCAGCACCGAGCAGGAGAAGCAGCAGCAGGACATC<br>GCCCTGTGGTGCGCCGTGAACTGGTTCCGCCCCGTGAGCCAGGACAGCC<br>TGACCCACACCATCGCCAGCGACAACCTGGTGGAGAAGTTCGAGGAGTA<br>CTACGGCGGCACCGCCAGCGACGCCATCAAGCAGTACTTCAGCGCCAGC<br>ATCGGCGAGAGCTACTACTGGAACGACTGCCGCCAGCAGTACTACGACC<br>TGTGCCGCGAGCTGGGCGTGGAGGTGAGCGACCTGACCCACGACCTGGA<br>GATCCTGTGCCGCGAGAAGTGCCTGGCCGTGGCCACCGAGAGCAACCAG<br>TACAACAGCATCATCAGCGTGCTGTTCGGCACCGGCAGAAAGGAGGACC<br>GCAGCGTGAAGCTGCGCATCACCAAGAAGATCCTGGAGGCCATCAGCAA<br>CCTGAAGGAGATCCCCAAGAACGTGGCCCCCATCCAGGAGATCATCCTG<br>AACGTGGCCAAGGCCACCAAGGAGACCTTCCGCCAGGTGTACGCCGGCA<br>ACCTGGGCGCCCCCAGCACCCTGGAGAGATTCATCGCCAAGGACGGCCA<br>GAAGGAGTTCGACCTGAAGAAGCTGCAGACCGACCTGAAGAAGGTGAT<br>CCGCGGCAAGAGCAAGGAGCGCGACTGGTGCTGCCAGGAGGAGCTGCG<br>CAGCTACGTGGAGCAGAACACCATCCAGTACGACCTGTGGGCCTGGGGC<br>GAGATGTTCAACAAGGCCCACACCGCCCTGAAGATCAAGAGCACCCGCA<br>ACTACAACTTCGCCAAGCAGCGCCTGGAGCAGTTCAAGAGAATCCAGAG<br>CCTGAACAACCTGCTGGTGGTGAAGAAGCTGAACGACTTCTTCGACAGC<br>GAGTTCTTCAGCGGCGAGGAGACCTACACCATCTGCGTGCACCACCTGG<br>GCGGCAAGAGACTGAGCAAGCTGTACAAGGCCTGGGAGGACGACCCCG<br>CCGACCCCGAGAACGCCATCGTGGTGCTGTGCGACGACCTGAAGAACAA<br>CTTCAAGAAGGAGCCCATCCGCAACATCCTGCGCTACATCTTCACCATCC<br>GCCAGGAGTGCAGCGCCCAGGACATCCTGGCCGCCGCCAAGTACAACCA<br>GCAGCTGGACCGCTACAAGAGCCAGAAGGCCAACCCCAGCGTGCTGGGC<br>AACCAGGGCTTCACCTGGAGAAACGCCGTGATCCTGCCCGAGAAGGCCC<br>AGCGCAACGACCGCCCCAACAGCCTGGACCTGCGCATCTGGCTGTACCT<br>GAAGCTGCGCCACCCCGACGGCCGCTGGAAGAAGCACCACATCCCCTTC<br>TACGACACCCGCTTCTTCCAGGAGATCTACGCCGCCGGCAACAGCCCCG<br>TGGACACCTGCCAGTTCCGCACCCCCCGCTTCGGCTACCACCTGCCCAAG<br>CTGACCGACCAGACCGCCATCCGCGTGAACAAGAAGCACGTGAAGGCCG<br>CCAAGACCGAGGCCCGCATCCGCCTGGCCATCCAGCAGGGCACCCTGCC<br>CGTGAGCAACCTGAAGATCACCAGAATCAGCGCCACCATCAACAGCAAG<br>GGCCAGGTGCGCATCCCCGTGAAGTTCGACGTGGGCCGCCAGAAGGGCA<br>CCCTGCAGATCGGCGACCGCTTCTGCGGCTACGACCAGAACCAGACCGC<br>CAGCCACGCCTACAGCCTGTGGGAGGTGGTGAAGGAGGGCCAGTACCAC<br>AAGGAGCTGGGCTGCTTCGTGCGCTTCATCAGCAGCGGCGACATCGTGA<br>GCATCACCGAGAACCGCGGCAACCAGTTCGACCAGCTGAGCTACGAGGG<br>CCTGGCCTACCCCCAGTACGCCGACTGGCGCAAGAAGGCCAGCAAGTTC<br>GTGAGCCTGTGGCAGATCACCAAGAAGAACAAGAAGAAGGAGATCGTG<br>ACCGTGGAGGCCAAGGAGAAGTTCGACGCCATCTGCAAGTACCAGCCCC<br>GCCTGTACAAGTTCAACAAGGAGTACGCCTACCTGCTGCGCGACATCGT<br>GCGCGGCAAGAGCCTGGTGGAGCTGCAGCAGATCCGCCAGGAGATCTTC<br>CGCTTCATCGAGCAGGACTGCGGCGTGACCCGCCTGGGCAGCCTGAGCC<br>TGAGCACCCTGGAGACCGTGAAGGCCGTGAAGGGCATCATCTACAGCTA<br>CTTCAGCACCGCCCTGAACGCCAGCAAGAACAACCCCATCAGCGACGAG<br>CAGCGCAAGGAGTTCGACCCCGAGCTGTTCGCCCTGCTGGAGAAGCTGG<br>AGCTGATCCGCACCCGCAAGAAGAAGCAGAAGGTGGAGCGCATCGCCA<br>ACAGCCTGATCCAGACCTGCCTGGAGAACAACATCAAGTTCATCCGCGG<br>CGAGGGCGACCTGAGCACCACCAACAACGCCACCAAGAAGAAGGCCAA<br>CAGCCGCAGCATGGACTGGCTGGCCCGCGGCGTGTTCAACAAGATCCGC<br>CAGCTGGCCCCCATGCACAACATCACCCTGTTCGGCTGCGGCAGCCTGTA<br>CACCAGCCACCAGGACCCCCTGGTGCACCGCAACCCCGACAAGGCCATG<br>AGGGCAAGGTTCGAGGAGGTCAACGTGGAGAATATCGCCGAGTGGCAT<br>GTTAGAAACTTCTCAAATTATCTCCGCGCTGACAGCGGGACAGGCCTCTA<br>TTACAAGCAGGCAACCATGGACTTTCTGAAGCACTATGGACTGGAGGAG<br>CACGCAGAGGGGCTGGAAAATAAGAAAATCAAGTTCTATGACTTTCGGA<br>AGATTCTGGAAGATAAAAATCTGACCAGCGTAATCATACCCAAGCGAGG<br>GGGGCGCATCTATATGGCCACCAACCCAGTAACCTCCGACTCAACACCG<br>ATAACCTACGCCGGGAAAACATACAATAGATGCAACGCCGATCACGTGG<br>CCGCCGCCAACATCGCCCTGACCGTGAAGGGCATCGGCGAGCAGAGCAG<br>CGACGAGGAGAACCCCGACGGCAGCCGCATCAAGCTGCAGCTGACCAG<br>C |
| 60 | enCas12i-002 (eukaryotic codon- | ATGAGCAGCGCCATCAAGAGCTACAAGAGCGTGCTGCGCCCCAACGAGC<br>GCAAGAACCAGCTGCTGAAGAGCACCATCCAGTGCCTGGAGGACGGCA<br>GCGCCTTCTTCTTCAAGATGCTGCAGGGCCTGTTCGGCGGCATCACCCCC |

-continued

Sequence listing

| SEQ ID NO: | Description | Sequence |
|---|---|---|
| | optimized, nucleotide) | GAGATCGTGCGCTTCAGCACCGAGCAGGAGAAGCAGCAGCAGGACATC GCCCTGTGGTGCGCCGTGAACTGGTTCCGCCCCGTGAGCCAGGACAGCC TGACCCACACCATCGCCAGCGACAACCTGGTGGAGAAGTTCGAGGAGTA CTACGGCGGCACCGCCAGCGACGCCATCAAGCAGTACTTCAGCGCCAGC ATCGGCGAGAGCTACTACTGGAACGACTGCCGCCAGCAGTACTACGACC TGTGCCGCGAGCTGGGCGTGGAGGTGAGCGACCTGACCCACGACCTGGA GATCCTGTGCCGCGAGAAGTGCCTGGCCGTGGCCACCGAGAGCAACCAG TACAACAGCATCATCAGCGTGCTGTTCGGCACCGGCAGAAAGGAGGACC GCAGCGTGAAGCTGCGCATCACCAAGAAGATCCTGGAGGCCATCAGCAA CCTGAAGGAGATCCCCAAGAACGTGGCCCCCATCCAGGAGATCATCCTG AACGTGGCCAAGGCCACCAAGGAGACCTTCCGCCAGGTGTACGCCGGCA ACCTGGGCGCCCCCAGCACCCTGGAGAGATTCATCGCCAAGGACGGCCA GAAGGAGTTCGACCTGAAGAAGCTGCAGACCGACCTGAAGAAGGTGAT CCGCGGCAAGAGCAAGGAGCGCGACTGGTGCTGCCAGGAGGAGCTGCG CAGCTACGTGGAGCAGAACACCATCCAGTACGACCTGTGGGCCTGGGGC GAGATGTTCAACAAGGCCCACACCGCCCTGAAGATCAAGAGCACCCGCA ACTACAACTTCGCCAAGCAGCGCCTGGAGCAGTTCAAGAGAATCCAGAG CCTGAACAACCTGCTGGTGGTGAAGAAGCTGAACGACTTCTTCGACAGC GAGTTCTTCAGCGGCGAGGAGACCTACACCATCTGCGTGCACCACCTGG GCGGCAAGAGACTGAGCAAGCTGTACAAGGCCTGGGAGGACGACCCCG CCGACCCCGAGAACGCCATCGTGGTGCTGTGCGACGACCTGAAGAACAA CTTCAAGAAGGAGCCCATCCGCAACATCCTGCGCTACATCTTCACCATCC GCCAGGAGTGCAGCGCCCAGGACATCCTGGCCGCCGCCAAGTACAACCA GCAGCTGGACCGCTACAAGAGCCAGAAGGCCAACCCCAGCGTGCTGGGC AACCAGGGCTTCACCTGGAGAAACGCCGTGATCCTGCCCGAGAAGGCCC AGCGCAACGACCGCCCCAACAGCCTGGACCTGCGCATCTGGCTGTACCT GAAGCTGCGCCACCCCGACGGCCGCTGGAAGAAGCACCACATCCCCTTC TACGACACCCGCTTCTTCCAGGAGATCTACGCCGCCGGCAACAGCCCCG TGGACACCTGCCAGTTCCGCACCCCCCGCTTCGGCTACCACCTGCCCAAG CTGACCGACCAGACCGCCATCCGCGTGAACAAGAAGCACGTGAAGGCCG CCAAGACCGAGGCCCGCATCCGCCTGGCCATCCAGCAGGGCACCCTGCC CGTGAGCAACCTGAAGATCACCAGAATCAGCGCCACCATCAACAGCAAG GGCCAGGTGCGCATCCCCGTGAAGTTCGACGTGGGCCGCCAGAAGGGCA CCCTGCAGATCGGCGACCGCTTCTGCGGCTACGACCAGAACCAGACCGC CAGCCACGCCTACAGCCTGTGGGAGGTGGTGAAGGAGGGCCAGTACCAC AAGGAGCTGGGCTGCTTCGTGCGCTTCATCAGCAGCGGCGACATCGTGA GCATCACCGAGAACCGCGGCAACCAGTTCGACCAGCTGAGCTACGAGGG CCTGGCCTACCCCCAGTACGCCGACTGGCGCAAGAAGGCCAGCAAGTTC GTGAGCCTGTGGCAGATCACCAAGAAGAACAAGAAGAAGGAGATCGTG ACCGTGGAGGCCAAGGAGAAGTTCGACGCCATCTGCAAGTACCAGCCCC GCCTGTACAAGTTCAACAAGGAGTACGCCTACCTGCTGCGCGACATCGT GCGCGGCAAGAGCCTGGTGGAGCTGCAGCAGATCCGCCAGGAGATCTTC CGCTTCATCGAGCAGGACTGCGGCGTGACCCGCCTGGGCAGCCTGAGCC TGAGCACCCTGGAGACCGTGAAGGCCGTGAAGGGCATCATCTACAGCTA CTTCAGCACCGCCCTGAACGCCAGCAAGAACAACCCCATCAGCGACGAG CAGCGCAAGGAGTTCGACCCCGAGCTGTTCGCCCTGCTGGAGAAGCTGG AGCTGATCCGCACCCGCAAGAAGAAGCAGAAGGTGGAGCGCATCGCCA ACAGCCTGATCCAGACCTGCCTGGAGAACAACATCAAGTTCATCCGCGG CGAGGGCGACCTGAGCACCACCAACAACGCCACCAAGAAGAAGGCCAA CAGCCGCAGCATGGACTGGCTGGCCCGCGGCGTGTTCAACAAGATCCGC CAGCTGGCCCCCATGCACAACATCACCCTGTTCGGCTGCGGCAGCCTGTA CACCAGCCACCAGGACCCCCTGGTGCACCGCAACCCCGACAAGGCCATG AGAGCCCGGTTTGAGGAAGTGAATGTTAGCAACGTGTCTGAATGGCATA TGAGAAACTTTAGCAATTATTTGAGAGCCGATAGCGGCACTGGTTTGTAT TACAAGCAGGCCACCTTGGATTTTCTGAAGCACTACGACCTTGAGGAAC ACGCAGATGACTTGGAGAAACAGAACATAAAATTCTACGATTTCCGGAA AATTTTGGAAGATAAACAACTGACCTCCGTCATCGTTCCAAAGCGGGGA GGGAGGATCTATATGGCCACTAACCCTGTGACGTCCGATAGTACCCCTGT GACCTACGCAGGAAAGACATACAACCGGTGCAATGCCGATCACGTGGCC GCCGCCAACATCGCCCTGACCGTGAAGGGCATCGGCGAGCAGAGCAGCG ACGAGGAGAACCCCGACGGCAGCCGCATCAAGCTGCAGCTGACCAGC |
| 61 | enCas12i-003 (eukaryotic codon-optimized, nucleotide) | ATGAGCAGCGCCATCAAGAGCTACAAGAGCGTGCTGCGCCCCAACGAGC GCAAGAACCAGCTGCTGAAGAGCACCATCCAGTGCCTGGAGGACGGCA GCGCCTTCTTCTTCAAGATGCTGCAGGGCCTGTTCGGCGGCATCACCCCC GAGATCGTGCGCTTCAGCACCGAGCAGGAGAAGCAGCAGCAGGACATC GCCCTGTGGTGCGCCGTGAACTGGTTCCGCCCCGTGAGCCAGGACAGCC TGACCCACACCATCGCCAGCGACAACCTGGTGGAGAAGTTCGAGGAGTA CTACGGCGGCACCGCCAGCGACGCCATCAAGCAGTACTTCAGCGCCAGC ATCGGCGAGAGCTACTACTGGAACGACTGCCGCCAGCAGTACTACGACC TGTGCCGCGAGCTGGGCGTGGAGGTGAGCGACCTGACCCACGACCTGGA GATCCTGTGCCGCGAGAAGTGCCTGGCCGTGGCCACCGAGAGCAACCAG TACAACAGCATCATCAGCGTGCTGTTCGGCACCGGCAGAAAGGAGGACC GCAGCGTGAAGCTGCGCATCACCAAGAAGATCCTGGAGGCCATCAGCAA |

-continued

Sequence listing

| SEQ ID NO: | Description | Sequence |
|---|---|---|
| | | CCTGAAGGAGATCCCCAAGAACGTGGCCCCCATCCAGGAGATCATCCTG<br>AACGTGGCCAAGGCCACCAAGGAGACCTTCCGCCAGGTGTACGCCGGCA<br>ACCTGGGCGCCCCCAGCACCCTGGAGAGATTCATCGCCAAGGACGGCCA<br>GAAGGAGTTCGACCTGAAGAAGCTGCAGACCGACCTGAAGAAGGTGAT<br>CCGCGGCAAGAGCAAGGAGCGCGACTGGTGCTGCCAGGAGGAGCTGCG<br>CAGCTACGTGGAGCAGAACACCATCCAGTACGACCTGTGGGCCTGGGGC<br>GAGATGTTCAACAAGGCCCACACCGCCCTGAAGATCAAGAGCACCCGCA<br>ACTACAACTTCGCCAAGCAGCGCCTGGAGCAGTTCAAGAGAATCCAGAG<br>CCTGAACAACCTGCTGGTGGTGAAGAAGCTGAACGACTTCTTCGACAGC<br>GAGTTCTTCAGCGGCGAGGAGACCTACACCATCTGCGTGCACCACCTGG<br>GCGGCAAGAGACTGAGCAAGCTGTACAAGGCCTGGGAGGACGACCCCG<br>CCGACCCCGAGAACGCCATCGTGGTGCTGTGCGACGACCTGAAGAACAA<br>CTTCAAGAAGGAGCCCATCCGCAACATCCTGCGCTACATCTTCACCATCC<br>GCCAGGAGTGCAGCGCCCAGGACATCCTGGCCGCCGCCAAGTACAACCA<br>GCAGCTGGACCGCTACAAGAGCCAGAAGGCCAACCCCAGCGTGCTGGGC<br>AACCAGGGCTTCACCTGGAGAAACGCCGTGATCCTGCCCGAGAAGGCCC<br>AGCGCAACGACCGCCCCAACAGCCTGGACCTGCGCATCTGGCTGTACCT<br>GAAGCTGCGCCACCCCGACGGCCGCTGGAAGAAGCACCACATCCCCTTC<br>TACGACACCCGCTTCTTCCAGGAGATCTACGCCGCCGGCAACAGCCCCG<br>TGGACACCTGCCAGTTCCGCACCCCCCGCTTCGGCTACCACCTGCCCAAG<br>CTGACCGACCAGACCGCCATCCGCGTGAACAAGAAGCACGTGAAGGCCG<br>CCAAGACCGAGGCCCGCATCCGCCTGGCCATCCAGCAGGGCACCCTGCC<br>CGTGAGCAACCTGAAGATCACCAGAATCAGCGCCACCATCAACAGCAAG<br>GGCCAGGTGCGCATCCCCGTGAAGTTCGACGTGGGCCGCCAGAAGGGCA<br>CCCTGCAGATCGGCGACCGCTTCTGCGGCTACGACCAGAACCAGACCGC<br>CAGCCACGCCTACAGCCTGTGGGAGGTGGTGAAGGAGGGCCAGTACCAC<br>AAGGAGCTGGGCTGCTTCGTGCGCTTCATCAGCAGCGGCGACATCGTGA<br>GCATCACCGAGAACCGCGGCAACCAGTTCGACCAGCTGAGCTACGAGGG<br>CCTGGCCTACCCCCAGTACGCCGACTGGCGCAAGAAGGCCAGCAAGTTC<br>GTGAGCCTGTGGCAGATCACCAAGAAGAACAAGAAGAAGGAGATCGTG<br>ACCGTGGAGGCCAAGGAGAAGTTCGACGCCATCTGCAAGTACCAGCCCC<br>GCCTGTACAAGTTCAACAAGGAGTACGCCTACCTGCTGCGCGACATCGT<br>GCGCGGCAAGAGCCTGGTGGAGCTGCAGCAGATCCGCCAGGAGATCTTC<br>CGCTTCATCGAGCAGGACTGCGGCGTGACCCGCCTGGGCAGCCTGAGCC<br>TGAGCACCCTGGAGACCGTGAAGGCCGTGAAGGGCATCATCTACAGCTA<br>CTTCAGCACCGCCCTGAACGCCAGCAAGAACAACCCCATCAGCGACGAG<br>CAGCGCAAGGAGTTCGACCCCGAGCTGTTCGCCCTGCTGGAGAAGCTGG<br>AGCTGATCCGCACCCGCAAGAAGAAGCAGAAGGTGGAGCGCATCGCCA<br>ACAGCCTGATCCAGACCTGCCTGGAGAACAACATCAAGTTCATCCGCGG<br>CGAGGGCGACCTGAGCACCACCAACAACGCCACCAAGAAGAAGGCCAA<br>CAGCCGCAGCATGGACTGGCTGGCCCGCGGCGTGTTCAACAAGATCCGC<br>CAGCTGGCCCCCATGCACAACATCACCCTGTTCGGCTGCGGCAGCCTGTA<br>CACCAGCCACCAGGACCCCCTGGTGCACCGCAACCCCGACAAGTCTTTT<br>AGAGCTAGATGGGACCTGGTGAAGGTTAAGGATTTTGGAGAGAAACATC<br>TCCTCACACTGAGCAGGAATCTGACTGGAAAGGGACCAGGCACCCGCAA<br>GTACTACCACCAGGGAGTTGAGGACTTTCTGAAGGAGTATGAGCTGGAG<br>GACCTGAAGGAAGAGCTGGCCAAGATTAAGAAAGGCGACCCAAACGCC<br>CTCCCTCCTGAGGTGATAAGAAATAAACTGAAAGAAAAGCTGGGAAACG<br>AGAACGCACCAGTTCTGATACCTAAGCGCGGTGGAAAGTACTTTCTGTC<br>AACCCATAACGTGGCAACTGGCGCAGTGAAAATCACATTCAACAATAAA<br>GAAAGGTATCTGTGCAACGCCGATCACGTGGCCGCCGCCAACATCGCCC<br>TGACCGTGAAGGGCATCGGCGAGCAGAGCAGCGACGAGGAGAACCCCG<br>ACGGCAGCCGCATCAAGCTGCAGCTGACCAGC |
| 62 | enCas12i-004 (eukaryotic codon-optimized, nucleotide) | ATGAGCAGCGCCATCAAGAGCTACAAGAGCGTGCTGCGCCCCAACGAGC<br>GCAAGAACCAGCTGCTGAAGAGCACCATCCAGTGCCTGGAGGACGGCA<br>GCGCCTTCTTCTTCAAGATGCTGCAGGGCCTGTTCGGCGGCATCACCCCC<br>GAGATCGTGCGCTTCAGCACCGAGCAGGAGAAGCAGCAGCAGGACATC<br>GCCCTGTGGTGCGCCGTGAACTGGTTCCGCCCCGTGAGCCAGGACAGCC<br>TGACCCACACCATCGCCAGCGACAACCTGGTGGAGAAGTTCGAGGAGTA<br>CTACGGCGGCACCGCCAGCGACGCCATCAAGCAGTACTTCAGCGCCAGC<br>ATCGGCGAGAGCTACTACTGGAACGACTGCCGCCAGCAGTACTACGACC<br>TGTGCCGCGAGCTGGGCGTGGAGGTGAGCGACCTGACCCACGACCTGGA<br>GATCCTGTGCCGCGAGAAGTGCCTGGCCGTGGCCACCGAGAGCAACCAG<br>TACAACAGCATCATCAGCGTGCTGTTCGGCACCGGCAGAAAGGAGGACC<br>GCAGCGTGAAGCTGCGCATCACCAAGAAGATCCTGGAGGCCATCAGCAA<br>CCTGAAGGAGATCCCCAAGAACGTGGCCCCCATCCAGGAGATCATCCTG<br>AACGTGGCCAAGGCCACCAAGGAGACCTTCCGCCAGGTGTACGCCGGCA<br>ACCTGGGCGCCCCCAGCACCCTGGAGAGATTCATCGCCAAGGACGGCCA<br>GAAGGAGTTCGACCTGAAGAAGCTGCAGACCGACCTGAAGAAGGTGAT<br>CCGCGGCAAGAGCAAGGAGCGCGACTGGTGCTGCCAGGAGGAGCTGCG<br>CAGCTACGTGGAGCAGAACACCATCCAGTACGACCTGTGGGCCTGGGGC<br>GAGATGTTCAACAAGGCCCACACCGCCCTGAAGATCAAGAGCACCCGCA<br>ACTACAACTTCGCCAAGCAGCGCCTGGAGCAGTTCAAGAGAATCCAGAG |

-continued

Sequence listing

| SEQ ID NO: | Description | Sequence |
|---|---|---|
| | | CCTGAACAACCTGCTGGTGGTGAAGAAGCTGAACGACTTCTTCGACAGC GAGTTCTTCAGCGGCGAGGAGACCTACACCATCTGCGTGCACCACCTGG GCGGCAAGAGACTGAGCAAGCTGTACAAGGCCTGGGAGGACGACCCCG CCGACCCCGAGAACGCCATCGTGGTGCTGTGCGACGACCTGAAGAACAA CTTCAAGAAGGAGCCCATCCGCAACATCCTGCGCTACATCTTCACCATCC GCCAGGAGTGCAGCGCCCAGGACATCCTGGCCGCCGCCAAGTACAACCA GCAGCTGGACCGCTACAAGAGCCAGAAGGCCAACCCCAGCGTGCTGGGC AACCAGGGCTTCACCTGGAGAAACGCCGTGATCCTGCCCGAGAAGGCCC AGCGCAACGACCGCCCCAACAGCCTGGACCTGCGCATCTGGCTGTACCT GAAGCTGCGCCACCCCGACGGCCGCTGGAAGAAGCACCACATCCCCTTC TACGACACCCGCTTCTTCCAGGAGATCTACGCCGCCGGCAACAGCCCCG TGGACACCTGCCAGTTCCGCACCCCCCGCTTCGGCTACCACCTGCCCAAG CTGACCGACCAGACCGCCATCCGCGTGAACAAGAAGCACGTGAAGGCCG CCAAGACCGAGGCCCGCATCCGCCTGGCCATCCAGCAGGGCACCCTGCC CGTGAGCAACCTGAAGATCACCAGAATCAGCGCCACCATCAACAGCAAG GGCCAGGTGCGCATCCCCGTGAAGTTCGACGTGGGCCGCCAGAAGGGCA CCCTGCAGATCGGCGACCGCTTCTGCGGCTACGACCAGAACCAGACCGC CAGCCACGCCTACAGCCTGTGGGAGGTGGTGAAGGAGGGCCAGTACCAC AAGGAGCTGGGCTGCTTCGTGCGCTTCATCAGCAGCGGCGACATCGTGA GCATCACCGAGAACCGCGGCAACCAGTTCGACCAGCTGAGCTACGAGGG CCTGGCCTACCCCCAGTACGCCGACTGGCGCAAGAAGGCCAGCAAGTTC GTGAGCCTGTGGCAGATCACCAAGAAGAACAAGAAGAAGGAGATCGTG ACCGTGGAGGCCAAGGAGAAGTTCGACGCCATCTGCAAGTACCAGCCCC GCCTGTACAAGTTCAACAAGGAGTACGCCTACCTGCTGCGCGACATCGT GCGCGGCAAGAGCCTGGTGGAGCTGCAGCAGATCCGCCAGGAGATCTTC CGCTTCATCGAGCAGGACTGCGGCGTGACCCGCCTGGGCAGCCTGAGCC TGAGCACCCTGGAGACCGTGAAGGCCGTGAAGGGCATCATCTACAGCTA CTTCAGCACCGCCCTGAACGCCAGCAAGAACAACCCCATCAGCGACGAG CAGCGCAAGGAGTTCGACCCCGAGCTGTTCGCCCTGCTGGAGAAGCTGG AGCTGATCCGCACCCGCAAGAAGAAGCAGAAGGTGGAGCGCATCGCCA ACAGCCTGATCCAGACCTGCCTGGAGAACAACATCAAGTTCATCCGCGG CGAGGGCGACCTGAGCACCACCAACAACGCCACCAAGAAGAAGGCCAA CAGCCGCAGCATGGACTGGCTGGCCCGCGGCGTGTTCAACAAGATCCGC CAGCTGGCCCCCATGCACAACATCACCCTGTTCGGCTGCGGCAGCCTGTA CACCAGCCACCAGGACCCCCTGGTGCACCGCAACCCCGACAAGTCTTTT AGAGCTAGATGGAGACTCGTGAAGGTCAAGGACATAGGTGAGAAGGAG CTGCTCACCCTCTCCAGAAACCTGAGAGGGAAAGGGAAGGGAATAAAG AAGTACTATCATCAGGGAGTGCTCGACTTCTTCAAGGAGTACGAGCTCG AAGAGCTGGCCGGACCACTGGCCAAGATTAAGCCTGGTGACCCAAATGC TATACCACCCGAGGTCCTGCGGAATAAACTCAAAGAGAAGCTGGAAAT GAAGATGCACCAGTGCTGATTCCCGTCGCCGGAGGCGGCATCTATCTGA GCACTCACAATGTCGCAACAGGCGCCAAGAAGATCACCTTCAATAACAA AGAGCGGTACGTCTGCAACGCCGATCACGTGGCCGCCGCCAACATCGCC CTGACCGTGAAGGGCATCGGCGAGCAGAGCAGCGACGAGGAGAACCCC GACGGCAGCCCGCATCAAGCTGCAGCTGACCAGC |
| 63 | enCas12i-005 (eukaryotic codon-optimized, nucleotide) | ATGAGCAGCGCCATCAAGAGCTACAAGAGCGTGCTGCGCCCCAACGAGC GCAAGAACCAGCTGCTGAAGAGCACCATCCAGTGCCTGGAGGACGGCA GCGCCTTCTTCTTCAAGATGCTGCAGGGCCTGTTCGGCGGCATCACCCCC GAGATCGTGCGCTTCAGCACCGAGCAGGAGAAGCAGCAGCAGGACATC GCCCTGTGGTGCGCCGTGAACTGGTTCCGCCCCGTGAGCCAGGACAGCC TGACCCACACCATCGCCAGCGACAACCTGGTGGAGAAGTTCGAGGAGTA CTACGGCGGCACCGCCAGCGACGCCATCAAGCAGTACTTCAGCGCCAGC ATCGGCGAGAGCTACTACTGGAACGACTGCCGCCAGCAGTACTACGACC TGTGCCGCGAGCTGGGCGTGGAGGTGAGCGACCTGACCCACGACCTGGA GATCCTGTGCCGCGAGAAGTGCCTGGCCGTGGCCACCGAGAGCAACCAG TACAACAGCATCATCAGCGTGCTGTTCGGCACCGGCAGAAAGGAGGACC GCAGCGTGAAGCTGCGCATCACCAAGAAGATCCTGGAGGCCATCAGCAA CCTGAAGGAGATCCCCAAGAACGTGGCCCCCATCCAGGAGATCATCCTG AACGTGGCCAAGGCCACCAAGGAGACCTTCCGCCAGGTGTACGCCGGCA ACCTGGGCGCCCCCAGCACCCTGGAGAGATTCATCGCCAAGGACGGCCA GAAGGAGTTCGACCTGAAGAAGCTGCAGACCGACCTGAAGAAGGTGAT CCGCGGCAAGAGCAAGGAGCGCGACTGGTGCTGCCAGGAGGAGCTGCG CAGCTACGTGGAGCAGAACACCATCCAGTACGACCTGTGGGCCTGGGGC GAGATGTTCAACAAGGCCCACACCGCCCTGAAGATCAAGAGCACCCGCA ACTACAACTTCGCCAAGCAGCGCCTGGAGCAGTTCAAGAGAATCCAGAG CCTGAACAACCTGCTGGTGGTGAAGAAGCTGAACGACTTCTTCGACAGC GAGTTCTTCAGCGGCGAGGAGACCTACACCATCTGCGTGCACCACCTGG GCGGCAAGAGACTGAGCAAGCTGTACAAGGCCTGGGAGGACGACCCCG CCGACCCCGAGAACGCCATCGTGGTGCTGTGCGACGACCTGAAGAACAA CTTCAAGAAGGAGCCCATCCGCAACATCCTGCGCTACATCTTCACCATCC GCCAGGAGTGCAGCGCCCAGGACATCCTGGCCGCCGCCAAGTACAACCA GCAGCTGGACCGCTACAAGAGCCAGAAGGCCAACCCCAGCGTGCTGGGC AACCAGGGCTTCACCTGGAGAAACGCCGTGATCCTGCCCGAGAAGGCCC |

-continued

Sequence listing

| SEQ ID NO: | Description | Sequence |
|---|---|---|
| | | AGCGCAACGACCGCCCCAACAGCCTGGACCTGCGCATCTGGCTGTACCT |
| | | GAAGCTGCGCCACCCCGACGGCCGCTGGAAGAAGCACCACATCCCCTTC |
| | | TACGACACCCGCTTCTTCCAGGAGATCTACGCCGCCGGCAACAGCCCCG |
| | | TGGACACCTGCCAGTTCCGCACCCCCCGCTTCGGCTACCACCTGCCCAAG |
| | | CTGACCGACCAGACCGCCATCCGCGTGAACAAGAAGCACGTGAAGGCCG |
| | | CCAAGACCGAGGCCCGCATCCGCCTGGCCATCCAGCAGGGCACCCTGCC |
| | | CGTGAGCAACCTGAAGATCACCAGAATCAGCGCCACCATCAACAGCAAG |
| | | GGCCAGGTGCGCATCCCCGTGAAGTTCGACGTGGGCCGCCAGAAGGGCA |
| | | CCCTGCAGATCGGCGACCGCTTCTGCGGCTACGACCAGAACCAGACCGC |
| | | CAGCCACGCCTACAGCCTGTGGGAGGTGGTGAAGGAGGGCCAGTACCAC |
| | | AAGGAGCTGGGCTGCTTCGTGCGCTTCATCAGCAGCGGCGACATCGTGA |
| | | GCATCACCGAGAACCGCGGCAACCAGTTCGACCAGCTGAGCTACGAGGG |
| | | CCTGGCCTACCCCCAGTACGCCGACTGGCGCAAGAAGGCCAGCAAGTTC |
| | | GTGAGCCTGTGGCAGATCACCAAGAAGAACAAGAAGAAGGAGATCGTG |
| | | ACCGTGGAGGCCAAGGAGAAGTTCGACGCCATCTGCAAGTACCAGCCCC |
| | | GCCTGTACAAGTTCAACAAGGAGTACGCCTACCTGCTGCGCGACATCGT |
| | | GCGCGGCAAGAGCCTGGTGGAGCTGCAGCAGATCCGCCAGGAGATCTTC |
| | | CGCTTCATCGAGCAGGACTGCGGCGTGACCCGCCTGGGCAGCCTGAGCC |
| | | TGAGCACCCTGGAGACCGTGAAGGCCGTGAAGGGCATCATCTACAGCTA |
| | | CTTCAGCACCGCCCTGAACGCCAGCAAGAACAACCCCATCAGCGACGAG |
| | | CAGCGCAAGGAGTTCGACCCCGAGCTGTTCGCCCTGCTGGAGAAGCTGG |
| | | AGCTGATCCGCACCCGCAAGAAGAAGCAGAAGGTGGAGCGCATCGCCA |
| | | ACAGCCTGATCCAGACCTGCCTGGAGAACAACATCAAGTTCATCCGCGG |
| | | CGAGGGCGACCTGAGCACCACCAACAACGCCACCAAGAAGAAGGCCAA |
| | | CAGCCGCAGCATGGACTGGCTGGCCCGCGGCGTGTTCAACAAGATCCGC |
| | | CAGCTGGCCCCCATGCACAACATCACCCTGTTCGGCTGCGGCAGCCTGTA |
| | | CACCAGCCACCAGGACCCCCTGGTGCACCGCAACCCCGACAAGAAGTAC |
| | | AATGCTCGGTGGGATCTGGTTAAAGTGAAGGATATTGGTGAGGGCCATC |
| | | TCCTGATTCTGTCAAGAAACCTGCGCGGCAAAGGCTCTGGCATTAGGAA |
| | | ATACTACCATCAGGGCGTCCTGGAGTTCTTTAAAGAGTATGATCTGGAA |
| | | GATCTGGCCGAACCTCTCGCTAAAATTAGACCCGGTGATCCAAACGCCA |
| | | TCCCTCCTGAAGTGCTCAGAGAACGCCTCAAGGAGAAGCTCGGCAACGA |
| | | GGACGCTCCTGTTCTCATCCCTAAGCCTGGAGGAGGCGTGTACCTCAGCA |
| | | CTCATAACGTCGCCACCGGCGCCAAGAAAATCACATTCAACAACAAGGA |
| | | GAGATACCTGTGCAACGCCGATCACGTGGCCGCCGCCAACATCGCCCTG |
| | | ACCGTGAAGGGCATCGGCGAGCAGAGCAGCGACGAGGAGAACCCCGAC |
| | | GGCAGCCGCATCAAGCTGCAGCTGACCAGC |
| 64 | enCas12i-006 | ATGAGCAGCGCCATCAAGAGCTACAAGAGCGTGCTGCGCCCCAACGAGC |
| | (eukaryotic | GCAAGAACCAGCTGCTGAAGAGCACCATCCAGTGCCTGGAGGACGGCA |
| | codon- | GCGCCTTCTTCTTCAAGATGCTGCAGGGCCTGTTCGGCGGCATCACCCCC |
| | optimized, | GAGATCGTGCGCTTCAGCACCGAGCAGGAGAAGCAGCAGCAGGACATC |
| | nucleotide) | GCCCTGTGGTGCGCCGTGAACTGGTTCCGCCCCGTGAGCCAGGACAGCC |
| | | TGACCCACACCATCGCCAGCGACAACCTGGTGGAGAAGTTCGAGGAGTA |
| | | CTACGGCGGCACCGCCAGCGACGCCATCAAGCAGTACTTCAGCGCCAGC |
| | | ATCGGCGAGAGCTACTACTGGAACGACTGCCGCCAGCAGTACTACGACC |
| | | TGTGCCGCGAGCTGGGCGTGGAGGTGAGCGACCTGACCCACGACCTGGA |
| | | GATCCTGTGCCGCGAGAAGTGCCTGGCCGTGGCCACCGAGAGCAACCAG |
| | | TACAACAGCATCATCAGCGTGCTGTTCGGCACCGGCAGAAAGGAGGACC |
| | | GCAGCGTGAAGCTGCGCATCACCAAGAAGATCCTGGAGGCCATCAGCAA |
| | | CCTGAAGGAGATCCCCAAGAACGTGGCCCCCATCCAGGAGATCATCCTG |
| | | AACGTGGCCAAGGCCACCAAGGAGACCTTCCGCCAGGTGTACGCCGGCA |
| | | ACCTGGGCGCCCCCAGCACCCTGGAGAGATTCATCGCCAAGGACGGCCA |
| | | GAAGGAGTTCGACCTGAAGAAGCTGCAGACCGACCTGAAGAAGGTGAT |
| | | CCGCGGCAAGAGCAAGGAGCGCGACTGGTGCTGCCAGGAGGAGCTGCG |
| | | CAGCTACGTGGAGCAGAACACCATCCAGTACGACCTGTGGGCCTGGGGC |
| | | GAGATGTTCAACAAGGCCCACACCGCCCTGAAGATCAAGAGCACCCGCA |
| | | ACTACAACTTCGCCAAGCAGCGCCTGGAGCAGTTCAAGAGAATCCAGAG |
| | | CCTGAACAACCTGCTGGTGGTGAAGAAGCTGAACGACTTCTTCGACAGC |
| | | GAGTTCTTCAGCGGCGAGGAGACCTACACCATCTGCGTGCACCACCTGG |
| | | GCGGCAAGAGACTGAGCAAGCTGTACAAGGCCTGGGAGGACGACCCCG |
| | | CCGACCCCGAGAACGCCATCGTGGTGCTGTGCGACGACCTGAAGAACAA |
| | | CTTCAAGAAGGAGCCCATCCGCAACATCCTGCGCTACATCTTCACCATCC |
| | | GCCAGGAGTGCAGCGCCCAGGACATCCTGGCCGCCGCCAAGTACAACCA |
| | | GCAGCTGGACCGCTACAAGAGCCAGAAGGCCAACCCCAGCGTGCTGGGC |
| | | AACCAGGGCTTCACCTGGAGAAACGCCGTGATCCTGCCCGAGAAGGCCC |
| | | AGCGCAACGACCGCCCCAACAGCCTGGACCTGCGCATCTGGCTGTACCT |
| | | GAAGCTGCGCCACCCCGACGGCCGCTGGAAGAAGCACCACATCCCCTTC |
| | | TACGACACCCGCTTCTTCCAGGAGATCTACGCCGCCGGCAACAGCCCCG |
| | | TGGACACCTGCCAGTTCCGCACCCCCCGCTTCGGCTACCACCTGCCCAAG |
| | | CTGACCGACCAGACCGCCATCCGCGTGAACAAGAAGCACGTGAAGGCCG |
| | | CCAAGACCGAGGCCCGCATCCGCCTGGCCATCCAGCAGGGCACCCTGCC |
| | | CGTGAGCAACCTGAAGATCACCAGAATCAGCGCCACCATCAACAGCAAG |
| | | GGCCAGGTGCGCATCCCCGTGAAGTTCGACGTGGGCCGCCAGAAGGGCA |

-continued

Sequence listing

| SEQ ID NO: | Description | Sequence |
|---|---|---|
| | | CCCTGCAGATCGGCGACCGCTTCTGCGGCTACGACCAGAACCAGACCGC<br>CAGCCACGCCTACAGCCTGTGGGAGGTGGTGAAGGAGGGCCAGTACCAC<br>AAGGAGCTGGGCTGCTTCGTGCGCTTCATCAGCAGCGGCGACATCGTGA<br>GCATCACCGAGAACCGCGGCAACCAGTTCGACCAGCTGAGCTACGAGGG<br>CCTGGCCTACCCCCAGTACGCCGACTGGCGCAAGAAGGCCAGCAAGTTC<br>GTGAGCCTGTGGCAGATCACCAAGAAGAACAAGAAGAAGGAGATCGTG<br>ACCGTGGAGGCCAAGGAGAAGTTCGACGCCATCTGCAAGTACCAGCCCC<br>GCCTGTACAAGTTCAACAAGGAGTACGCCTACCTGCTGCGCGACATCGT<br>GCGCGGCAAGAGCCTGGTGGAGCTGCAGCAGATCCGCCAGGAGATCTTC<br>CGCTTCATCGAGCAGGACTGCGGCGTGACCCGCCTGGGCAGCCTGAGCC<br>TGAGCACCCTGGAGACCGTGAAGGCCGTGAAGGGCATCATCTACAGCTA<br>CTTCAGCACCGCCCTGAACGCCAGCAAGAACAACCCCATCAGCGACGAG<br>CAGCGCAAGGAGTTCGACCCCGAGCTGTTCGCCCTGCTGGAGAAGCTGG<br>AGCTGATCCGCACCCGCAAGAAGAAGCAGAAGGTGGAGCGCATCGCCA<br>ACAGCCTGATCCAGACCTGCCTGGAGAACAACATCAAGTTCATCCGCGG<br>CGAGGGCGACCTGAGCACCACCAACAACGCCACCAAGAAGAAGGCCAA<br>CAGCCGCAGCATGGACTGGCTGGCCCGCGGCGTGTTCAACAAGATCCGC<br>CAGCTGGCCCCCATGCACAACATCACCCTGTTCGGCTGCGGCAGCCTGTA<br>CACCAGCCACCAGGACCCCCTGGTGCACCGCAACCCCGACAAGTCTTAT<br>AGAGCTAGGTGGAGACTGGTTAGGGTTAGAGATTTTGGCGAGAGACACC<br>TGCTGACCCTGTCCAGAAACCTCACCGGGAAGGGTAAGGGCACCAGGAA<br>GTATTATCATCAGGGCGTGCTCGATTTCTTCAGGGAATACGATCTGGAGG<br>ATCTGGCTGGGCCACTGGCTAAAATAAGACCAGGCGACCCTGATGCCAT<br>ACCTCCTGAAGTTCTGCGGGAGCGGCTGCGGGAAAAGCTCGGGAACGAC<br>GAAGCTCCAGTGCTCATTCCTGTGAGAGGAGGTCCTGTGTACCTCAGCAC<br>ACATGATGTTGCAACCGGCGCCAAAAGAATTACATTCAATGGCAAGGAG<br>CGCTACCTGTGCAACGCCGATCACGTGGCCGCCGCCAACATCGCCCTGA<br>CCGTGAAGGGCATCGGCGAGCAGAGCAGCGACGAGGAGAACCCCGACG<br>GCAGCCGCATCAAGCTGCAGCTGACCAGC |
| 65 | denCas12i-001<br>(D1009A,<br>underlined)<br>(AA) | MSSAIKSYKSVLRPNERKNQLLKSTIQCLEDGSAFFFKMLQGLFGGITPEIVR<br>FSTEQEKQQQDIALWCAVNWFRPVSQDSLTHTIASDNLVEKFEEYYGGTAS<br>DAIKQYFSASIGESYYWNDCRQQYYDLCRELGVEVSDLTHDLEILCREKCL<br>AVATESNQYNSIISVLFGTGRKEDRSVKLRITKKILEAISNLKEIPKNVAPIQEI<br>ILNVAKATKETFRQVYAGNLGAPSTLERFIAKDGQKEFDLKKLQTDLKKVIR<br>GKSKERDWCCQEELRSYVEQNTIQYDLWAWGEMENKAHTALKIKSTRNYN<br>FAKQRLEQFKRIQSLNNLLVVKKLNDFFDSEFFSGEETYTICVHHLGGKRLS<br>KLYKAWEDDPADPENAIVVLCDDLKNNFKKEPIRNILRYIFTIRQECSAQDIL<br>AAAKYNQQLDRYKSQKANPSVLGNQGFTWRNAVILPEKAQRNDRPNSLDL<br>RIWLYLKLRHPDGRWKKHHIPFYDTRFFQEIYAAGNSPVDTCQFRTPRFGYH<br>LPKLTDQTAIRVNKKHVKAAKTEARIRLAIQQGTLPVSNLKITRISATINSKG<br>QVRIPVKFDVGRQKGTLQIGDRFCGYDQNQTASHAYSLWEVVKEGQYHKE<br>LGCFVRFISSGDIVSITENRGNQFDQLSYEGLAYPQYADWRKKASKFVSLWQ<br>ITKKNKKKEIVTVEAKEKFDAICKYQPRLYKFNKEYAYLLRDIVRGKSLVEL<br>QQIRQEIFRFIEQDCGVTRLGSLSLSTLETVKAVKGIIYSYFSTALNASKNNPIS<br>DEQRKEFDPELFALLEKLELIRTRKKKQKVERIANSLIQTCLENNIKFIRGEGD<br>LSTTNNATKKKANSRSMDWLARGVFNKIRQLAPMHNITLFGCGSLYTSHQD<br>PLVHRNPDKAMRARFEEVNVENIAEWHVRNFSNYLRADSGTGLYYKQATM<br>DFLKHYGLEEHAEGLENKKIKFYDFRKILEDKNLTSVIIPKRGGRIYMATNPV<br>TSDSTPITYAGKTYNRCNAAHVAAANIALTVKGIGEQSSDEENPDGSRIKLQ<br>LTS |
| 66 | denCas12i-002<br>(D1009A)<br>(AA) | MSSAIKSYKSVLRPNERKNQLLKSTIQCLEDGSAFFFKMLQGLFGGITPEIVR<br>FSTEQEKQQQDIALWCAVNWFRPVSQDSLTHTIASDNLVEKFEEYYGGTAS<br>DAIKQYFSASIGESYYWNDCRQQYYDLCRELGVEVSDLTHDLEILCREKCL<br>AVATESNQYNSIISVLFGTGRKEDRSVKLRITKKILEAISNLKEIPKNVAPIQEI<br>ILNVAKATKETFRQVYAGNLGAPSTLERFIAKDGQKEFDLKKLQTDLKKVIR<br>GKSKERDWCCQEELRSYVEQNTIQYDLWAWGEMENKAHTALKIKSTRNYN<br>FAKQRLEQFKRIQSLNNLLVVKKLNDFFDSEFFSGEETYTICVHHLGGKRLS<br>KLYKAWEDDPADPENAIVVLCDDLKNNFKKEPIRNILRYIFTIRQECSAQDIL<br>AAAKYNQQLDRYKSQKANPSVLGNQGFTWRNAVILPEKAQRNDRPNSLDL<br>RIWLYLKLRHPDGRWKKHHIPFYDTRFFQEIYAAGNSPVDTCQFRTPRFGYH<br>LPKLTDQTAIRVNKKHVKAAKTEARIRLAIQQGTLPVSNLKITRISATINSKG<br>QVRIPVKFDVGRQKGTLQIGDRFCGYDQNQTASHAYSLWEVVKEGQYHKE<br>LGCFVRFISSGDIVSITENRGNQFDQLSYEGLAYPQYADWRKKASKFVSLWQ<br>ITKKNKKKEIVTVEAKEKFDAICKYQPRLYKFNKEYAYLLRDIVRGKSLVEL<br>QQIRQEIFRFIEQDCGVTRLGSLSLSTLETVKAVKGIIYSYFSTALNASKNNPIS<br>DEQRKEFDPELFALLEKLELIRTRKKKQKVERIANSLIQTCLENNIKFIRGEGD<br>LSTTNNATKKKANSRSMDWLARGVFNKIRQLAPMHNITLFGCGSLYTSHQD<br>PLVHRNPDKAMRARFEEVNVSNVSEWHMRNFSNYLRADSGTGLYYKQAT<br>LDFLKHYDLEEHADDLEKQNIKFYDFRKILEDKQLTSVIVPKRGGRIYMATN<br>PVTSDSTPVTYAGKTYNRCNAAHVAAANIALTVKGIGEQSSDEENPDGSRIK<br>LQLTS |

-continued

| Sequence listing | | |
|---|---|---|
| SEQ ID NO: | Description | Sequence |
| 67 | NUC domain of enCas12i-001 | RARFEEVNVENIAEWHVRNFSNYLRADSGTGLYYKQATMDFLKHYGLEEH AEGLENKKIKFYDFRKILEDKNLTSVIIPKRGGRIYMATNPVTSDSTPITYAG KTYNRCN |
| 68 | NUC domain of enCas12i-002 | RARFEEVNVSNVSEWHMRNFSNYLRADSGTGLYYKQATLDFLKHYDLEEH ADDLEKQNIKFYDFRKILEDKQLTSVIVPKRGGRIYMATNPVTSDSTPVTYA GKTYNRCN |
| 69 | NUC domain of enCas12i-003 | SFRARWDLVKVKDFGEKHLLTLSRNLTGKGPGTRKYYHQGVEDFLKEYEL EDLKEELAKIKKGDPNALPPEVIRNKLKEKLGNENAPVLIPKRGGKYFLSTH NVATGAVKITFNNKERYL |
| 70 | NUC domain of enCas12i-004 | SFRARWRLVKVKDIGEKELLTLSRNLRGKGKGIKKYYHQGVLDFFKEYELE ELAGPLAKIKPGDPNAIPPEVLRNKLKEKLGNEDAPVLIPVAGGGIYLSTHNV ATGAKKITFNNKERYV |
| 71 | NUC domain of enCas12i-005 | KYNARWDLVKVKDIGEGHLLILSRNLRGKGSGIRKYYHQGVLEFFKEYDLE DLAEPLAKIRPGDPNAIPPEVLRERLKEKLGNEDAPVLIPKPGGGVYLSTHNV ATGAKKITENNKERYL |
| 72 | NUC domain of enCas12i-006 | SYRARWRLVRVRDFGERHLLTLSRNLTGKGKGTRKYYHQGVLDFFREYDL EDLAGPLAKIRPGDPDAIPPEVLRERLREKLGNDEAPVLIPVRGGPVYLSTHD VATGAKRITFNGKERYL |
| 73 | CCR5-Target gRNA | 5'-AGGCCAAAGAATTCCTGGAA-3' |
| 74 | BCL11A-Target gRNA | 5'-TCACAGGCTCCAGGAAGGGT-3' |
| 75 | RNF2-Target gRNA | 5'-TTCAACATATCCAAACAAAT-3' |
| 76 | CCR5-F primer | 5'-TCTGCTTCGGTGTCGAAATGAG-3' |
| 77 | CCR5-R primer | 5'-TGCAGAAGCGTTTGGCAATGTG-3' |
| 78 | BCL11A-F primer | 5'-GCTGAAAAGCGATACAGGGC-3' |
| 79 | BCL11A-R primer | 5'-ATCACCAAGAGAGCCTTCCG-3' |
| 80 | RNF2-F primer | 5'-TTTATAACAGTGGTGGTGAGGCT-3' |
| 81 | RNF2-R primer | 5'-TTCTCAAACCCTGGAAAGCACT-3' |
| 82 | Reverse complementary sequence of RNF2-Target gRNA | 5'-ATTTGTTTGGATATGTTGAA-3' |
| 83 | XTEN linker | SGGSSGGSSGSETPGTSESATPESSGGSSGGS |
| 84 | TTR-Target gRNA | 5'-TTGTATAATAGGAAAGGGAA-3' |
| 85 | TRE-eGFP Target | 5'-TCTATCACTGATAGGGAGTG-3' |
| 86 | XTEN80 linker | GGPSSGAPPPSGGSPAGSPTSTEEGTSESATPESGPGTSTEPSEGSAPGSPAGS PTSTEEGTSTEPSEGSAPGTSTEPSE |
| 87 | linker | SGGSGGSGGS |
| 88 | SV40 NLS-denCas12i-001-nucleoplasmin | PKKKRKVMSSAIKSYKSVLRPNERKNQLLKSTIQCLEDGSAFFFKMLQGLFG GITPEIVRFSTEQEKQQQDIALWCAVNWFRPVSQDSLTHTIASDNLVEKFEE YYGGTASDAIKQYFSASIGESYYWNDCRQQYYDLCRELGVEVSDLTHDLEI LCREKCLAVATESNQYNSIISVLFGTGRKEDRSVKLRITKKILEAISNLKEIPK |

-continued

Sequence listing

| SEQ ID NO: | Description | Sequence |
|---|---|---|
| | NLS-VPR (VP64-p65-RTA) | NVAPIQEIILNVAKATKETFRQVYAGNLGAPSTLERFIAKDGQKEFDLKKLQ TDLKKVIRGKSKERDWCCQEELRSYVEQNTIQYDLWAWGEMENKAHTAL KIKSTRNYNFAKQRLEQFKRIQSLNNLLVVKKLNDFFDSEFFSGEETYTICVH HLGGKRLSKLYKAWEDDPADPENAIVVLCDDLKNNFKKEPIRNILRYIFTIR QECSAQDILAAAKYNQQLDRYKSQKANPSVLGNQGFTWRNAVILPEKAQR NDRPNSLDLRIWLYLKLRHPDGRWKKHHIPFYDTRFFQEIYAAGNSPVDTC QFRTPRFGYHLPKLTDQTAIRVNKKHVKAAKTEARIRLAIQQGTLPVSNLKI TRISATINSKGQVRIPVKFDVGRQKGTLQIGDRFCGYDQNQTASHAYSLWEV VKEGQYHKELGCFVRFISSGDIVSITENRGNQFDQLSYEGLAYPQYADWRK KASKFVSLWQITKKNKKKEIVTVEAKEKFDAICKYQPRLYKFNKEYAYLLR DIVRGKSLVELQQIRQEIFRFIEQDCGVTRLGSLSLSTLETVKAVKGIIYSYFS TALNASKNNPISDEQRKEFDPELFALLEKLELIRTRKKKQKVERIANSLIQTC LENNIKFIRGEGDLSTTNNATKKKANSRSMDWLARGVFNKIRQLAPMHNIT LFGCGSLYTSHQDPLVHRNPDKAMRARFEEVNVENIAEWHVRNFSNYLRA DSGTGLYYKQATMDFLKHYGLEEHAEGLENKKIKFYDFRKILEDKNLTSVII PKRGGRIYMATNPVTSDSTPITYAGKTYNRCNAAHVAAANIALTVKGIGEQ SSDEENPDGSRIKLQLTSKRPAATKKAGQAKKKKEASGSGRADALDDFDLD MLGSDALDDFDLDMLGSDALDDFDLDMLGSDALDDFDLDMLINSRSSGSP KKKRKVGSQYLPDTDDRHRIEEKRKRTYETFKSIMKKSPFSGPTDPRPPPRRI AVPSRSSASVPKPAPQPYPFTSSLSTINYDEFPTMVFPSGQISQASALAPAPPQ VLPQAPAPAPAPAMVSALAQAPAPVPVLAPGPPQAVAPPAPKPTQAGEGTL SEALLQLQFDDEDLGALLGNSTDPAVFTDLASVDNSEFQQLLNQGIPVAPHT TEPMLMEYPEAITRLVTGAQRPPDPAPAPLGAPGLPNGLLSGDEDFSSIADM DFSALLGSGSGSRDSREGMFLPKPEAGSAISDVFEGREVCQPKRIRPFHPPGS PWANRPLPASLAPTPTGPVHEPVGSLTPAPVPQPLDPAPAVTPEASHLLEDPD EETSQAVKALREMADTVIPQKEEAAICGQMDLSHPPPRGHLDELTTTLESMT EDLNLDSPLTPELNEILDTFLNDECLLHAMHISTGLSIFDTSLF |
| 89 | SV40 NLS-denCas12i-002-nucleoplasmin NLS-VPR (VP64-p65-RTA) | PKKKRKVMSSAIKSYKSVLRPNERKNQLLKSTIQCLEDGSAFFFKMLQGLFG GITPEIVRFSTEQEKQQQDIALWCAVNWFRPVSQDSLTHTIASDNLVEKFEE YYGGTASDAIKQYFSASIGESYYWNDCRQQYYDLCRELGVEVSDLTHDLEI LCREKCLAVATESNQYNSIISVLFGTGRKEDRSVKLRITKKILEAISNLKEIPK NVAPIQEIILNVAKATKETFRQVYAGNLGAPSTLERFIAKDGQKEFDLKKLQ TDLKKVIRGKSKERDWCCQEELRSYVEQNTIQYDLWAWGEMENKAHTAL KIKSTRNYNFAKQRLEQFKRIQSLNNLLVVKKLNDFFDSEFFSGEETYTICVH HLGGKRLSKLYKAWEDDPADPENAIVVLCDDLKNNFKKEPIRNILRYIFTIR QECSAQDILAAAKYNQQLDRYKSQKANPSVLGNQGFTWRNAVILPEKAQR NDRPNSLDLRIWLYLKLRHPDGRWKKHHIPFYDTRFFQEIYAAGNSPVDTC QFRTPRFGYHLPKLTDQTAIRVNKKHVKAAKTEARIRLAIQQGTLPVSNLKI TRISATINSKGQVRIPVKFDVGRQKGTLQIGDRFCGYDQNQTASHAYSLWEV VKEGQYHKELGCFVRFISSGDIVSITENRGNQFDQLSYEGLAYPQYADWRK KASKFVSLWQITKKNKKKEIVTVEAKEKFDAICKYQPRLYKFNKEYAYLLR DIVRGKSLVELQQIRQEIFRFIEQDCGVTRLGSLSLSTLETVKAVKGIIYSYFS TALNASKNNPISDEQRKEFDPELFALLEKLELIRTRKKKQKVERIANSLIQTC LENNIKFIRGEGDLSTTNNATKKKANSRSMDWLARGVFNKIRQLAPMHNIT LFGCGSLYTSHQDPLVHRNPDKAMRARFEEVNVSNVSEWHMRNFSNYLRA DSGTGLYYKQATLDFLKHYDLEEHADDLEKQNIKFYDFRKILEDKQLTSVIV PKRGGRIYMATNPVTSDSTPVTYAGKTYNRCNAAHVAAANIALTVKGIGEQ SSDEENPDGSRIKLQLTSKRPAATKKAGQAKKKKEASGSGRADALDDFDLD MLGSDALDDFDLDMLGSDALDDFDLDMLGSDALDDFDLDMLINSRSSGSP KKKRKVGSQYLPDTDDRHRIEEKRKRTYETFKSIMKKSPFSGPTDPRPPPRRI AVPSRSSASVPKPAPQPYPFTSSLSTINYDEFPTMVFPSGQISQASALAPAPPQ VLPQAPAPAPAPAMVSALAQAPAPVPVLAPGPPQAVAPPAPKPTQAGEGTL SEALLQLQFDDEDLGALLGNSTDPAVFTDLASVDNSEFQQLLNQGIPVAPHT TEPMLMEYPEAITRLVTGAQRPPDPAPAPLGAPGLPNGLLSGDEDFSSIADM DFSALLGSGSGSRDSREGMFLPKPEAGSAISDVFEGREVCQPKRIRPFHPPGS PWANRPLPASLAPTPTGPVHEPVGSLTPAPVPQPLDPAPAVTPEASHLLEDPD EETSQAVKALREMADTVIPQKEEAAICGQMDLSHPPPRGHLDELTTTLESMT EDLNLDSPLTPELNEILDTFLNDECLLHAMHISTGLSIFDTSLF |
| 90 | SV40 NLS-denCas12i-001-nucleoplasmin NLS-VPRmini (VP64-p65-RTA truncation) | PKKKRKVMSSAIKSYKSVLRPNERKNQLLKSTIQCLEDGSAFFFKMLQGLFG GITPEIVRFSTEQEKQQQDIALWCAVNWFRPVSQDSLTHTIASDNLVEKFEE YYGGTASDAIKQYFSASIGESYYWNDCRQQYYDLCRELGVEVSDLTHDLEI LCREKCLAVATESNQYNSIISVLFGTGRKEDRSVKLRITKKILEAISNLKEIPK NVAPIQEIILNVAKATKETFRQVYAGNLGAPSTLERFIAKDGQKEFDLKKLQ TDLKKVIRGKSKERDWCCQEELRSYVEQNTIQYDLWAWGEMENKAHTAL KIKSTRNYNFAKQRLEQFKRIQSLNNLLVVKKLNDFFDSEFFSGEETYTICVH HLGGKRLSKLYKAWEDDPADPENAIVVLCDDLKNNFKKEPIRNILRYIFTIR QECSAQDILAAAKYNQQLDRYKSQKANPSVLGNQGFTWRNAVILPEKAQR NDRPNSLDLRIWLYLKLRHPDGRWKKHHIPFYDTRFFQEIYAAGNSPVDTC QFRTPRFGYHLPKLTDQTAIRVNKKHVKAAKTEARIRLAIQQGTLPVSNLKI TRISATINSKGQVRIPVKFDVGRQKGTLQIGDRFCGYDQNQTASHAYSLWEV VKEGQYHKELGCFVRFISSGDIVSITENRGNQFDQLSYEGLAYPQYADWRK KASKFVSLWQITKKNKKKEIVTVEAKEKFDAICKYQPRLYKFNKEYAYLLR |

-continued

Sequence listing

| SEQ ID NO: | Description | Sequence |
|---|---|---|
| | | DIVRGKSLVELQQIRQEIFRFIEQDCGVTRLGSLSLSTLETVKAVKGIIYSYFS<br>TALNASKNNPISDEQRKEFDPELFALLEKLELIRTRKKKQKVERIANSLIQTC<br>LENNIKFIRGEGDLSTTNNATKKKANSRSMDWLARGVFNKIRQLAPMHNIT<br>LFGCGSLYTSHQDPLVHRNPDKAMRARFEEVNVENIAEWHVRNFSNYLRA<br>DSGTGLYYKQATMDFLKHYGLEEHAEGLENKKIKFYDFRKILEDKNLTSVII<br>PKRGGRIYMATNPVTSDSTPITYAGKTYNRCNAAHVAAANIALTVKGIGEQ<br>SSDEENPDGSRIKLQLTSKRPAATKKAGQAKKKKDALDDFDLDMLGSDAL<br>DDFDLDMLGSDALDDFDLDMLGSDALDDFDLDMLINSRSSGSPKKKRKVG<br>SGGGSGGSGSVLPQAPAPAPAPAMVSALAQAPAPVPVLAPGPPQAVAPPAP<br>KPTQAGEGTLSEALLQLQFDDEDLGALLGNSTDPAVFTDLASVDNSEFQQL<br>LNQGIPVAPHTTEPMLMEYPEAITRLVTGAQRPPDPAPAPLGAPGLPNGLLS<br>GDEDFSSIADMDFSALLSGGGSGGSGSDLSHPPPRGHLDELTTTLESMTEDL<br>NLDSPLTPELNEILDTFLNDECLLHAMHISTGLSIFDTSLF |
| 91 | SV40 NLS-denCas 12i-002-nucleoplasmin NLS-VPRmini (VP64-p65-RTA truncation) | PKKKRKVMSSAIKSYKSVLRPNERKNQLLKSTIQCLEDGSAFFFKMLQGLFG<br>GITPEIVRFSTEQEKQQQDIALWCAVNWFRPVSQDSLTHTIASDNLVEKFEE<br>YYGGTASDAIKQYFSASIGESYYWNDCRQQYYDLCRELGVEVSDLTHDLEI<br>LCREKCLAVATESNQYNSIISVLFGTGRKEDRSVKLRITKKILEAISNLKEIPK<br>NVAPIQEIILNVAKATKETFRQVYAGNLGAPSTLERFIAKDGQKEFDLKKLQ<br>TDLKKVIRGKSKERDWCCQEELRSYVEQNTIQYDLWAWGEMENKAHTAL<br>KIKSTRNYNFAKQRLEQFKRIQSLNNLLVVKKLNDFFDSEFFSGEETYTICVH<br>HLGGKRLSKLYKAWEDDPADPENAIVVLCDDLKNNFKKEPIRNILRYIFTIR<br>QECSAQDILAAAKYNQQLDRYKSQKANPSVLGNQGFTWRNAVILPEKAQR<br>NDRPNSLDLRIWLYLKLRHPDGRWKKHHIPFYDTRFFQEIYAAGNSPVDTC<br>QFRTPRFGYHLPKLTDQTAIRVNKKHVKAAKTEARIRLAIQQGTLPVSNLKI<br>TRISATINSKGQVRIPVKFDVGRQKGTLQIGDRFCGYDQNQTASHAYSLWEV<br>VKEGQYHKELGCFVRFISSGDIVSITENRGNQFDQLSYEGLAYPQYADWRK<br>KASKFVSLWQITKKNKKKEIVTVEAKEKFDAICKYQPRLYKFNKEYAYLLR<br>DIVRGKSLVELQQIRQEIFRFIEQDCGVTRLGSLSLSTLETVKAVKGIIYSYFS<br>TALNASKNNPISDEQRKEFDPELFALLEKLELIRTRKKKQKVERIANSLIQTC<br>LENNIKFIRGEGDLSTTNNATKKKANSRSMDWLARGVFNKIRQLAPMHNIT<br>LFGCGSLYTSHQDPLVHRNPDKAMRARFEEVNVSNVSEWHMRNFSNYLRA<br>DSGTGLYYKQATLDFLKHYDLEEHADDLEKQNIKFYDFRKILEDKQLTSVIV<br>PKRGGRIYMATNPVTSDSTPVTYAGKTYNRCNAAHVAAANIALTVKGIGEQ<br>SSDEENPDGSRIKLQLTSKRPAATKKAGQAKKKKDALDDFDLDMLGSDAL<br>DDFDLDMLGSDALDDFDLDMLGSDALDDFDLDMLINSRSSGSPKKKRKVG<br>SGGGSGGSGSVLPQAPAPAPAPAMVSALAQAPAPVPVLAPGPPQAVAPPAP<br>KPTQAGEGTLSEALLQLQFDDEDLGALLGNSTDPAVFTDLASVDNSEFQQL<br>LNQGIPVAPHTTEPMLMEYPEAITRLVTGAQRPPDPAPAPLGAPGLPNGLLS<br>GDEDFSSIADMDFSALLSGGGSGGSGSDLSHPPPRGHLDELTTTLESMTEDL<br>NLDSPLTPELNEILDTFLNDECLLHAMHISTGLSIFDTSLF |
| 92 | DNMT3A-DNMT3L-XTEN80 linker-denCas12i-001-SV40 NLS-KRAB | MNHDQEFDPPKVYPPVPAEKRKPIRVLSLFDGIATGLLVLKDLGIQVDRYIA<br>SEVCEDSITVGMVRHQGKIMYVGDVRSVTQKHIQEWGPFDLVIGGSPCNDL<br>SIVNPARKGLYEGTGRLFFEFYRLLHDARPKEGDDRPFFWLFENVVAMGVS<br>DKRDISRFLESNPVMIDAKEVSAAHRARYFWGNLPGMNRPLASTVNDKLEL<br>QECLEHGRIAKFSKVRTITTRSNSIKQGKDQHFPVFMNEKEDILWCTEMERV<br>FGFPVHYTDVSNMSRLARQRLLGRSWSVPVIRHLFAPLKEYFACVSSGNSN<br>ANSRGPSFSSGLVPLSLRGSHMGPMEIYKTVSAWKRQPVRVLSLFRNIDKVL<br>KSLGFLESGSGSGGGTLKYVEDVTNVVRRDVEKWGPFDLVYGSTQPLGSSC<br>DRCPGWYMFQFHRILQYALPRQESQRPFFWIFMDNLLLTEDDQETTTRFLQT<br>EAVTLQDVRGRDYQNAMRVWSNIPGLKSKHAPLTPKEEEYLQAQVRSRSK<br>LDAPKVDLLVKNCLLPLREYFKYFSQNSLPLGGPSSGAPPPSGGSPAGSPTST<br>EEGTSESATPESGPGTSTEPSEGSAPGSPAGSPTSTEEGTSTEPSEGSAPGTSTE<br>PSEMSSAIKSYKSVLRPNERKNQLLKSTIQCLEDGSAFFFKMLQGLFGGITPEI<br>VRFSTEQEKQQQDIALWCAVNWFRPVSQDSLTHTIASDNLVEKFEEYYGGT<br>ASDAIKQYFSASIGESYYWNDCRQQYYDLCRELGVEVSDLTHDLEILCREKC<br>LAVATESNQYNSIISVLFGTGRKEDRSVKLRITKKILEAISNLKEIPKNVAPIQ<br>EIILNVAKATKETFRQVYAGNLGAPSTLERFIAKDGQKEFDLKKLQTDLKKV<br>IRGKSKERDWCCQEELRSYVEQNTIQYDLWAWGEMENKAHTALKIKSTRN<br>YNFAKQRLEQFKRIQSLNNLLVVKKLNDFFDSEFFSGEETYTICVHHLGGKR<br>LSKLYKAWEDDPADPENAIVVLCDDLKNNFKKEPIRNILRYIFTIRQECSAQD<br>ILAAAKYNQQLDRYKSQKANPSVLGNQGFTWRNAVILPEKAQRNDRPNSL<br>DLRIWLYLKLRHPDGRWKKHHIPFYDTRFFQEIYAAGNSPVDTCQFRTPRFG<br>YHLPKLTDQTAIRVNKKHVKAAKTEARIRLAIQQGTLPVSNLKITRISATINS<br>KGQVRIPVKFDVGRQKGTLQIGDRFCGYDQNQTASHAYSLWEVVKEGQYH<br>KELGCFVRFISSGDIVSITENRGNQFDQLSYEGLAYPQYADWRKKASKFVSL<br>WQITKKNKKKEIVTVEAKEKFDAICKYQPRLYKFNKEYAYLLRDIVRGKSL<br>VELQQIRQEIFRFIEQDCGVTRLGSLSLSTLETVKAVKGIIYSYFSTALNASKN<br>NPISDEQRKEFDPELFALLEKLELIRTRKKKQKVERIANSLIQTCLENNIKFIR<br>GEGDLSTTNNATKKKANSRSMDWLARGVFNKIRQLAPMHNITLFGCGSLYT<br>SHQDPLVHRNPDKAMRARFEEVNVENIAEWHVRNFSNYLRADSGTGLYYK<br>QATMDFLKHYGLEEHAEGLENKKIKFYDFRKILEDKNLTSVIIPKRGGRIYM<br>ATNPVTSDSTPITYAGKTYNRCNAAHVAAANIALTVKGIGEQSSDEENPDGS |

-continued

Sequence listing

| SEQ ID NO: | Description | Sequence |
|---|---|---|
| | | RIKLQLTSPKKKRKVDGIGSGSNGSSGSGGGGGMDAKSLTAWSRTLVTFKD<br>VFVDFTREEWKLLDTAQQIVYRNVMLENYKNLVSLGYQLTKPDVILRLEKG<br>EEP |
| 93 | DNMT3A-DNMT3L-XTEN80 linker-denCas12i-002-SV40 NLS-KRAB | MNHDQEFDPPKVYPPVPAEKRKPIRVLSLFDGIATGLLVLKDLGIQVDRYIA<br>SEVCEDSITVGMVRHQGKIMYVGDVRSVTQKHIQEWGPFDLVIGGSPCNDL<br>SIVNPARKGLYEGTGRLFFEFYRLLHDARPKEGDDRPFFWLFENVVAMGVS<br>DKRDISRFLESNPVMIDAKEVSAAHRARYFWGNLPGMNRPLASTVNDKLEL<br>QECLEHGRIAKFSKVRTITTRSNSIKQGKDQHFPVFMNEKEDILWCTEMERV<br>FGFPVHYTDVSNMSRLARQRLLGRSWSVPVIRHLFAPLKEYFACVSSGNSN<br>ANSRGPSFSSGLVPLSLRGSHMGPMEIYKTVSAWKRQPVRVLSLFRNIDKVL<br>KSLGFLESGSGSGGGTLKYVEDVTNVVRRDVEKWGPFDLVYGSTQPLGSSC<br>DRCPGWYMFQFHRILQYALPRQESQRPFFWIFMDNLLLTEDDQETTTRFLQT<br>EAVTLQDVRGRDYQNAMRVWSNIPGLKSKHAPLTPKEEEYLQAQVRSRSK<br>LDAPKVDLLVKNCLLPLREYFKYFSQNSLPLGGPSSGAPPPSGGSPAGSPTST<br>EEGTSESATPESGPGTSTEPSEGSAPGSPAGSPTSTEEGTSTEPSEGSAPGTSTE<br>PSEMSSAIKSYKSVLRPNERKNQLLKSTIQCLEDGSAFFFKMLQGLFGGITPEI<br>VRFSTEQEKQQQDIALWCAVNWFRPVSQDSLTHTIASDNLVEKFEEYYGGT<br>ASDAIKQYFSASIGESYYWNDCRQQYYDLCRELGVEVSDLTHDLEILCREKC<br>LAVATESNQYNSIISVLFGTGRKEDRSVKLRITKKILEAISNLKEIPKNVAPIQ<br>EIILNVAKATKETFRQVYAGNLGAPSTLERFIAKDGQKEFDLKKLQTDLKKV<br>IRGKSKERDWCCQEELRSYVEQNTIQYDLWAWGEMENKAHTALKIKSTRN<br>YNFAKQRLEQFKRIQSLNNLLVVKKLNDFFDSEFFSGEETYTICVHHLGGKR<br>LSKLYKAWEDDPADPENAIVVLCDDLKNNFKKEPIRNILRYIFTIRQECSAQD<br>ILAAAKYNQQLDRYKSQKANPSVLGNQGFTWRNAVILPEKAQRNDRPNSL<br>DLRIWLYLKLRHPDGRWKKHHIPFYDTRFFQEIYAAGNSPVDTCQFRTPRFG<br>YHLPKLTDQTAIRVNKKHVKAAKTEARIRLAIQQGTLPVSNLKITRISATINS<br>KGQVRIPVKFDVGRQKGTLQIGDRFCGYDQNQTASHAYSLWEVVKEGQYH<br>KELGCFVRFISSGDIVSITENRGNQFDQLSYEGLAYPQYADWRKKASKFVSL<br>WQITKKNKKKEIVTVEAKEKFDAICKYQPRLYKFNKEYAYLLRDIVRGKSL<br>VELQQIRQEIFRFIEQDCGVTRLGSLSLSTLETVKAVKGIIYSYFSTALNASKN<br>NPISDEQRKEFDPELFALLEKLELIRTRKKKQKVERIANSLIQTCLENNIKFIR<br>GEGDLSTTNNATKKKANSRSMDWLARGVFNKIRQLAPMHNITLFGCGSLYT<br>SHQDPLVHRNPDKAMRARFEEVNVSNVSEWHMRNFSNYLRADSGTGLYY<br>KQATLDFLKHYDLEEHADDLEKQNIKFYDFRKILEDKQLTSVIVPKRGGRIY<br>MATNPVTSDSTPVTYAGKTYNRCNAAHVAAANIALTVKGIGEQSSDEENPD<br>GSRIKLQLTSPKKKRKVDGIGSGSNGSSGSGGGGGMDAKSLTAWSRTLVTF<br>KDVFVDFTREEWKLLDTAQQIVYRNVMLENYKNLVSLGYQLTKPDVILRLE<br>KGEEP |
| 94 | SV40 NLS-TadA-8e-XTEN linker-denCas12i-001 | PKKKRKVSEVEFSHEYWMRHALTLAKRARDEREVPVGAVLVLNNRVIGEG<br>WNRAIGLHDPTAHAEIMALRQGGLVMQNYRLIDATLYVTFEPCVMCAGAM<br>IHSRIGRVVFGVRNSKRGAAGSLMNVLNYPGMNHRVEITEGILADECAALL<br>CDFYRMPRQVFNAQKKAQSSINSGGSSGGSSGSETPGTSESATPESSGGSSG<br>GSMSSAIKSYKSVLRPNERKNQLLKSTIQCLEDGSAFFFKMLQGLFGGITPEI<br>VRFSTEQEKQQQDIALWCAVNWFRPVSQDSLTHTIASDNLVEKFEEYYGGT<br>ASDAIKQYFSASIGESYYWNDCRQQYYDLCRELGVEVSDLTHDLEILCREKC<br>LAVATESNQYNSIISVLFGTGRKEDRSVKLRITKKILEAISNLKEIPKNVAPIQ<br>EIILNVAKATKETFRQVYAGNLGAPSTLERFIAKDGQKEFDLKKLQTDLKKV<br>IRGKSKERDWCCQEELRSYVEQNTIQYDLWAWGEMENKAHTALKIKSTRN<br>YNFAKQRLEQFKRIQSLNNLLVVKKLNDFFDSEFFSGEETYTICVHHLGGKR<br>LSKLYKAWEDDPADPENAIVVLCDDLKNNFKKEPIRNILRYIFTIRQECSAQD<br>ILAAAKYNQQLDRYKSQKANPSVLGNQGFTWRNAVILPEKAQRNDRPNSL<br>DLRIWLYLKLRHPDGRWKKHHIPFYDTRFFQEIYAAGNSPVDTCQFRTPRFG<br>YHLPKLTDQTAIRVNKKHVKAAKTEARIRLAIQQGTLPVSNLKITRISATINS<br>KGQVRIPVKFDVGRQKGTLQIGDRFCGYDQNQTASHAYSLWEVVKEGQYH<br>KELGCFVRFISSGDIVSITENRGNQFDQLSYEGLAYPQYADWRKKASKFVSL<br>WQITKKNKKKEIVTVEAKEKFDAICKYQPRLYKFNKEYAYLLRDIVRGKSL<br>VELQQIRQEIFRFIEQDCGVTRLGSLSLSTLETVKAVKGIIYSYFSTALNASKN<br>NPISDEQRKEFDPELFALLEKLELIRTRKKKQKVERIANSLIQTCLENNIKFIR<br>GEGDLSTTNNATKKKANSRSMDWLARGVFNKIRQLAPMHNITLFGCGSLYT<br>SHQDPLVHRNPDKAMRARFEEVNVENIAEWHVRNFSNYLRADSGTGLYYK<br>QATMDFLKHYGLEEHAEGLENKKIKFYDFRKILEDKNLTSVIIPKRGGRIYM<br>ATNPVTSDSTPITYAGKTYNRCNAAHVAAANIALTVKGIGEQSSDEENPDGS<br>RIKLQLTS |
| 95 | SV40 NLS-TadA-8e-XTEN linker-denCas12i-002 | PKKKRKVSEVEFSHEYWMRHALTLAKRARDEREVPVGAVLVLNNRVIGEG<br>WNRAIGLHDPTAHAEIMALRQGGLVMQNYRLIDATLYVTFEPCVMCAGAM<br>IHSRIGRVVFGVRNSKRGAAGSLMNVLNYPGMNHRVEITEGILADECAALL<br>CDFYRMPRQVFNAQKKAQSSINSGGSSGGSSGSETPGTSESATPESSGGSSG<br>GSMSSAIKSYKSVLRPNERKNQLLKSTIQCLEDGSAFFFKMLQGLFGGITPEI<br>VRFSTEQEKQQQDIALWCAVNWFRPVSQDSLTHTIASDNLVEKFEEYYGGT<br>ASDAIKQYFSASIGESYYWNDCRQQYYDLCRELGVEVSDLTHDLEILCREKC<br>LAVATESNQYNSIISVLFGTGRKEDRSVKLRITKKILEAISNLKEIPKNVAPIQ |

-continued

Sequence listing

| SEQ ID NO: | Description | Sequence |
|---|---|---|
| | | EIILNVAKATKETFRQVYAGNLGAPSTLERFIAKDGQKEFDLKKLQTDLKKV<br>IRGKSKERDWCCQEELRSYVEQNTIQYDLWAWGEMENKAHTALKIKSTRN<br>YNFAKQRLEQFKRIQSLNNLLVVKKLNDFFDSEFFSGEETYTICVHHLGGKR<br>LSKLYKAWEDDPADPENAIVVLCDDLKNNFKKEPIRNILRYIFTIRQECSAQD<br>ILAAAKYNQQLDRYKSQKANPSVLGNQGFTWRNAVILPEKAQRNDRPNSL<br>DLRIWLYLKLRHPDGRWKKHHIPFYDTRFFQEIYAAGNSPVDTCQFRTPRFG<br>YHLPKLTDQTAIRVNKKHVKAAKTEARIRLAIQQGTLPVSNLKITRISATINS<br>KGQVRIPVKFDVGRQKGTLQIGDRFCGYDQNQTASHAYSLWEVVKEGQYH<br>KELGCFVRFISSGDIVSITENRGNQFDQLSYEGLAYPQYADWRKKASKFVSL<br>WQITKKNKKKEIVTVEAKEKFDAICKYQPRLYKFNKEYAYLLRDIVRGKSL<br>VELQQIRQEIFRFIEQDCGVTRLGSLSLSTLETVKAVKGIIYSYFSTALNASKN<br>NPISDEQRKEFDPELFALLEKLELIRTRKKKQKVERIANSLIQTCLENNIKFIR<br>GEGDLSTTNNATKKKANSRSMDWLARGVFNKIRQLAPMHNITLFGCGSLYT<br>SHQDPLVHRNPDKAMRARFEEVNVSNVSEWHMRNFSNYLRADSGTGLYY<br>KQATLDFLKHYDLEEHADDLEKQNIKFYDFRKILEDKQLTSVIVPKRGGRIY<br>MATNPVTSDSTPVTYAGKTYNRCNAAHVAAANIALTVKGIGEQSSDEENPD<br>GSRIKLQLTS |
| 96 | SV40<br>NLS-APOBEC-<br>1-XTEN<br>linker-<br>denCas12i-001-<br>IUG-UGI | PKKKRKVSSETGPVAVDPTLRRRIEPHEFEVFFDPRELRKETCLLYEINWGG<br>RHSIWRHTSQNTNKHVEVNFIEKFTTERYFCPNTRCSITWFLSWSPCGECSR<br>AITEFLSRYPHVTLFIYIARLYHHADPRNRQGLRDLISSGVTIQIMTEQESGYC<br>WRNFVNYSPSNEAHWPRYPHLWVRLYVLELYCIILGLPPCLNILRRKQPQLT<br>FFTIALQSCHYQRLPPHILWATGLKSGGSSGGSSGSETPGTSESATPESSGGSS<br>GGSMSSAIKSYKSVLRPNERKNQLLKSTIQCLEDGSAFFFKMLQGLFGGITPE<br>IVRFSTEQEKQQQDIALWCAVNWFRPVSQDSLTHTIASDNLVEKFEEYYGGT<br>ASDAIKQYFSASIGESYYWNDCRQQYYDLCRELGVEVSDLTHDLEILCREKC<br>LAVATESNQYNSIISVLFGTGRKEDRSVKLRITKKILEAISNLKEIPKNVAPIQ<br>EIILNVAKATKETFRQVYAGNLGAPSTLERFIAKDGQKEFDLKKLQTDLKKV<br>IRGKSKERDWCCQEELRSYVEQNTIQYDLWAWGEMFNKAHTALKIKSTRN<br>YNFAKQRLEQFKRIQSLNNLLVVKKLNDFFDSEFFSGEETYTICVHHLGGKR<br>LSKLYKAWEDDPADPENAIVVLCDDLKNNFKKEPIRNILRYIFTIRQECSAQD<br>ILAAAKYNQQLDRYKSQKANPSVLGNQGFTWRNAVILPEKAQRNDRPNSL<br>DLRIWLYLKLRHPDGRWKKHHIPFYDTRFFQEIYAAGNSPVDTCQFRTPRFG<br>YHLPKLTDQTAIRVNKKHVKAAKTEARIRLAIQQGTLPVSNLKITRISATINS<br>KGQVRIPVKFDVGRQKGTLQIGDRFCGYDQNQTASHAYSLWEVVKEGQYH<br>KELGCFVRFISSGDIVSITENRGNQFDQLSYEGLAYPQYADWRKKASKFVSL<br>WQITKKNKKKEIVTVEAKEKFDAICKYQPRLYKFNKEYAYLLRDIVRGKSL<br>VELQQIRQEIFRFIEQDCGVTRLGSLSLSTLETVKAVKGIIYSYFSTALNASKN<br>NPISDEQRKEFDPELFALLEKLELIRTRKKKQKVERIANSLIQTCLENNIKFIR<br>GEGDLSTTNNATKKKANSRSMDWLARGVFNKIRQLAPMHNITLFGCGSLYT<br>SHQDPLVHRNPDKAMRARFEEVNVENIAEWHVRNFSNYLRADSGTGLYYK<br>QATMDFLKHYGLEEHAEGLENKKIKFYDFRKILEDKNLTSVIIPKRGGRIYM<br>ATNPVTSDSTPITYAGKTYNRCNAAHVAAANIALTVKGIGEQSSDEENPDGS<br>RIKLQLTSSGGSGGSGGSTNLSDIIEKETGKQLVIQESILMLPEEVEEVIGNKP<br>ESDILVHTAYDESTDENVMLLTSDAPEYKPWALVIQDSNGENKIKMLSGGS<br>GGSGGSTNLSDIIEKETGKQLVIQESILMLPEEVEEVIGNKPESDILVHTAYDE<br>STDENVMLLTSDAPEYKPWALVIQDSNGENKIKML |
| 97 | SV40<br>NLS-APOBEC-<br>1-XTEN<br>linker-<br>denCas12i-002-<br>UGI-UGI | PKKKRKVSSETGPVAVDPTLRRRIEPHEFEVFFDPRELRKETCLLYEINWGG<br>RHSIWRHTSQNTNKHVEVNFIEKFTTERYFCPNTRCSITWFLSWSPCGECSR<br>AITEFLSRYPHVTLFIYIARLYHHADPRNRQGLRDLISSGVTIQIMTEQESGYC<br>WRNFVNYSPSNEAHWPRYPHLWVRLYVLELYCIILGLPPCLNILRRKQPQLT<br>FFTIALQSCHYQRLPPHILWATGLKSGGSSGGSSGSETPGTSESATPESSGGSS<br>GGSMSSAIKSYKSVLRPNERKNQLLKSTIQCLEDGSAFFFKMLQGLFGGITPE<br>IVRFSTEQEKQQQDIALWCAVNWFRPVSQDSLTHTIASDNLVEKFEEYYGGT<br>ASDAIKQYFSASIGESYYWNDCRQQYYDLCRELGVEVSDLTHDLEILCREKC<br>LAVATESNQYNSIISVLFGTGRKEDRSVKLRITKKILEAISNLKEIPKNVAPIQ<br>EIILNVAKATKETFRQVYAGNLGAPSTLERFIAKDGQKEFDLKKLQTDLKKV<br>IRGKSKERDWCCQEELRSYVEQNTIQYDLWAWGEMENKAHTALKIKSTRN<br>YNFAKQRLEQFKRIQSLNNLLVVKKLNDFFDSEFFSGEETYTICVHHLGGKR<br>LSKLYKAWEDDPADPENAIVVLCDDLKNNFKKEPIRNILRYIFTIRQECSAQD<br>ILAAAKYNQQLDRYKSQKANPSVLGNQGFTWRNAVILPEKAQRNDRPNSL<br>DLRIWLYLKLRHPDGRWKKHHIPFYDTRFFQEIYAAGNSPVDTCQFRTPRFG<br>YHLPKLTDQTAIRVNKKHVKAAKTEARIRLAIQQGTLPVSNLKITRISATINS<br>KGQVRIPVKFDVGRQKGTLQIGDRFCGYDQNQTASHAYSLWEVVKEGQYH<br>KELGCFVRFISSGDIVSITENRGNQFDQLSYEGLAYPQYADWRKKASKFVSL<br>WQITKKNKKKEIVTVEAKEKFDAICKYQPRLYKFNKEYAYLLRDIVRGKSL<br>VELQQIRQEIFRFIEQDCGVTRLGSLSLSTLETVKAVKGIIYSYFSTALNASKN<br>NPISDEQRKEFDPELFALLEKLELIRTRKKKQKVERIANSLIQTCLENNIKFIR<br>GEGDLSTTNNATKKKANSRSMDWLARGVFNKIRQLAPMHNITLFGCGSLYT<br>SHQDPLVHRNPDKAMRARFEEVNVSNVSEWHMRNFSNYLRADSGTGLYY<br>KQATLDFLKHYDLEEHADDLEKQNIKFYDFRKILEDKQLTSVIVPKRGGRIY<br>MATNPVTSDSTPVTYAGKTYNRCNAAHVAAANIALTVKGIGEQSSDEENPD<br>GSRIKLQLTSSGGSGGSGGSTNLSDIIEKETGKQLVIQESILMLPEEVEEVIGN |

-continued

| Sequence listing | | |
|---|---|---|
| SEQ ID NO: | Description | Sequence |
| | | KPESDILVHTAYDESTDENVMLLTSDAPEYKPWALVIQDSNGENKIKMLSG<br>GSGGSGGSTNLSDIIEKETGKQLVIQESILMLPEEVEEVIGNKPESDILVHTAY<br>DESTDENVMLLTSDAPEYKPWALVIQDSNGENKIKML |
| 98 | TRE Target with PAM sequence | 5'-TTCTCTATCACTGATAGGGAGTG-3' |

EXAMPLES

Example 1. Prediction of crRNA of enCas12i Effector Protein

A common software was adopted to predict the crRNA of the chimeric Cas12i protein provided by the present invention, and the sequences of the predicted crRNA-1 to crRNA-8 (FIG. 1) are set forth in SEQ ID NOs: 7 to 14, respectively.

A base editor linking fragment, formed by linking the nucleotides of denCas12i-001 (D1009A, eukaryotic codon-optimized) via an XTEN linker (SGGSSGGSSGSETPGT-SESATPESSGGSSGGS, SEQ ID NO: 83) to an adenine deaminase TadA-8e (derived from the deaminase TadA-8e of ABE8e, see Richter, Michelle F et al., "Phage-assisted evolution of an adenine base editor with improved Cas domain compatibility and activity.", Nature biotechnology vol. 38, 7 (2020): 883-891. doi: 10.1038/s41587-020-0453-z), was constructed into a eukaryotic expression vector pX330. Expression of denCas12i-001 was initiated by a chicken β-actin promoter. An eGFP gene (used for performing cell sorting) was linked downstream of this base editor via a self-cleaving polypeptide 2A (P2A), while an sgRNA sequence (the sgRNA sequence contained two segments, namely Target gRNA and crRNA, respectively) was constructed downstream of a U6 promoter. The target gene for the targeting segments of this sgRNA was namely RNF2, RNF2-Target gRNA (5'-TTCAACATATCCAAACAAAT-3', SEQ ID NO: 75). The crRNAs were crRNA-1, crRNA-2, crRNA-3, and crRNA-8. Recombinant vectors were then formed, which were respectively marked as: pX330-ABE8e-crRNA1-RNF2-Target gRNA (vector 1), pX330-ABE8e-crRNA2-RNF2-Target gRNA (vector 2), pX330-ABE8e-crRNA3-RNF2-Target gRNA (vector 3), and pX330-ABE8e-crRNA8-RNF2-Target gRNA (vector 4). The maps of the vectors are shown in FIG. 2.

Subsequently, the above adenine base editor vectors 1~4 were separately transfected into human HEK293T cells, and then the cells were cultured at 37° C. with 5% carbon dioxide. After 72 hours of transfection, flow cytometry sorting was performed. eGFP-positive cells were collected by fluorescence-activated cell sorting (FACS). After the cell sorting, the cells were cultured for another 48 h, and the editing efficiency of the adenine base editors on the RNF2 target was determined by sequencing, with the results shown in FIG. 3. The results show that the sgRNAs formed by crRNA-1, crRNA-2, crRNA-3, and crRNA-8 with the targeting segment could all edit base A to base G on the target, with the editing site being at the 9th position, and the editing efficiency being about 7%-46%; crRNA-1 to crRNA-8 were all presumed to be effective because the sequences and secondary structures of crRNA-1 to crRNA-8 were highly similar. The following examples all adopted crRNA-1.

Example 2. High-Throughput PAM-SCANR Experiment Based on *Escherichia coli*

The method referred to Leenay, Ryan T et al., "Identifying and Visualizing Functional PAM Diversity across CRISPR-Cas Systems.", Molecular cell vol. 62, 1 (2016): 137-47. doi: 10.1016/j.molcel.2016.02.031, and this experiment was adopted to confirm and analyze the base preferences of PAMs for the enCas12i-001 effector protein (FIG. 4A) and the enCas12i-001-N229R mutant (FIG. 4B). The experimental results are shown in FIG. 4, which revealed that the effector protein had a broad genomic targeting range and could efficiently recognize PAM sequences rich in T/A and the like; specifically, the binding of the enCas12i effector protein to the target dsDNA depended on 5'-TTN PAM (N=A, T, C, or G), 5'-ATN (N=A, T, C, or G), 5'-TAN (N=A, T, C, or G), or 5'-AAN (N=A, T, C, or G). For the following examples, the chosen PAM was 5'-TTC.

Example 3. Expression and Purification of enCas12i Effector Protein

To obtain the enCas12i-001 effector protein, the recombinant plasmid pET-enCas12i encoding the enCas12i-001 effector protein was transformed into *Escherichia coli* (Arctic Express (DE3)) for expression. This strain was grown in LB broth supplemented with antibiotics. The bacteria were grown at 37° C. until the $OD_{600}$ reached 0.5. Then, the growth temperature was reduced to 16° C., and expression was induced for 20 h. The cells were pelleted and resuspended in a loading buffer (20 mM $KH_2PO_4$, pH 7.0, 0.5 M NaCl, 10 mM imidazole, 5% glycerol), and then disrupted by sonication. The cell debris was removed by centrifugation. The supernatant was loaded onto a 5-mL HiTrap chelating HP column charged with $Ni^{2+}$ (GE Healthcare), and then elution was performed using a linear increasing concentration gradient of imidazole. Fractions containing the enCas12i-001 effector protein were combined and subsequently loaded onto a heparin column, and then elution was performed using a linear increasing concentration gradient of NaCl (from 0.5 M to 1 M NaCl). Fractions containing the enCas12i-001 effector protein were combined, dialyzed against 10 mM Bis-Tris-HCl pH 7.0, 300 mM KCl, 1 mM EDTA, 1 mM DTT, and 50% (v/v) glycerol, and then stored at −20° C. The enCas12i-001 effector protein could be successfully expressed.

Example 4. Determination of Cleavage Performance by T7 Endonuclease 1 (T7E1)

4.1. In this experiment, a commonly used T7E1 experiment was adopted to test the cleavage activity of the effector protein. Multiple eukaryotic expression vectors targeting different genes were constructed, with the targeted genes being CCR5, BCL11A, and RNF2, respectively. The Target gRNA sequences of the targets are as follows, and the crRNAs in the sgRNAs were crRNA-1. The targets were located within these genes.

CCR5-Target gRNA: 5'-AGGCCAAAGAATTCCTG-GAA-3' (SEQ ID NO: 73);

BCL11A-Target gRNA; 5'-TCACAGGCTCCAG-GAAGGGT-3' (SEQ ID NO: 74); RNF2-Target gRNA: 5'-TTCAACATATCCAAACAAAT-3' (SEQ ID NO: 75).

The structures of the maps of the eukaryotic expression vectors are shown in Table 1, FIG. 5, and FIG. 6.

4.2. T7E1 experiment: The above plasmids expressing the Cas12 effector protein and sgRNA (vectors 5-14) were separately transfected into HEK293T cells. After 72 h, the DNA of the transgenic cells was extracted for detection. PCR amplification was performed on dsDNA fragments containing the target sites at different genomic loci (CCR5, BCL11A, and RNF2) using the corresponding primer pairs (as shown in Table 2). The PCR products were purified by gel extraction. The purified PCR products were each used, followed by the addition of $ddH_2O$. Then, the mixture was denatured and annealed to form a heteroduplex dsDNA. Then, the mixture was treated with NEB buffer 2 containing salt ions and T7EI (NEB) endonuclease at 37° C. Then, the cleavage results of the PCR products were detected by 3% agarose gel electrophoresis analysis. The results are shown in the electrophoretogram of FIG. 7.

In the electrophoretogram of FIG. 7, the electrophoresis nucleic acid Marker was a 2000-bp DNA ladder, the length of the target fragment of the CCR5 target was about 305 bp, and after T7E1 digestion of the mutation at the cleavage site, the two resulting segments were about 128 bp and 177 bp in length, respectively (marked as cleaved in the figure); the length of the target fragment of the BCL11A target was about 324 bp, and after T7E1 digestion of the mutation at the cleavage site, the two resulting segments were about 120 bp and 204 bp in length, respectively (marked as cleaved in the figure); the length of the target fragment of the RNF2 target was about 430 bp, and after T7E1 digestion of the mutation at the cleavage site, the two resulting segments were about 151 bp and 279 bp in length, respectively (marked as cleaved in the figure). In the electrophoretogram, the lane marked as M represents Marker, the lanes marked as 1, 5, and 9 represent blank controls (i.e., results for transfection with vector 14), the lanes marked as 2-4 respectively represent results for transfection with vectors 5-7, the lanes marked as 6-8 respectively represent results for transfection with vectors 8-10, and the lanes marked as 10-12 respectively represent results for transfection with vectors 11-13. The results in FIG. 7 show that: the blank control lanes only contained uncleaved bands, while the other lanes all contained distinct cleaved bands, with the cleaved band at the RNF2 site being the most distinct. If the enCas12i effector protein has the activity of specifically cleaving dsDNA, resulting in the presence of incompletely matched dsDNAs in the system after editing by the effector protein, T7E1 can recognize these incompletely matched dsDNAs and digest and cleave the same, leading to the appearance of multiple T7E1-cleaved bands in the system, and vice versa. The two short cleaved bands in FIG. 7 indicate that: the enCas12i effector protein had the activity of specifically cleaving dsDNA in vivo.

Specifically, the vectors were constructed as follows.

Cleaved vector: The eukaryotic codon-optimized nucleotides of the enCas12i-001 and enCas12i-002 effector proteins (SEQ ID NO: 59 and SEQ ID NO: 60) were separately constructed into a eukaryotic expression vector pX330. Expression of the two effector proteins was initiated by a chicken β-actin promoter, while an sgRNA sequence (the sgRNA sequence contained two segments, namely crRNA-1 and Target gRNA, respectively) was constructed downstream of a U6 promoter. The target genes for the targeting segments of this sgRNA were CCR5, BCL11A, and RNF2, specifically CCR5-Target gRNA, BCL11A-Target gRNA, and RNF2-Target gRNA). Cleaved vectors were then formed, which were respectively marked as: pX330-enCas12i-002-CCR5-Target gRNA (vector 5), pX330-enCas12i-001-CCR5-Target gRNA (vector 6), pX330-enCas12i-002-BCL11A-Target gRNA (vector 8), pX330-enCas12i-001-BCL11A-Target gRNA (vector 9), pX330-enCas12i-002-RNF2-Target gRNA (vector 11), and pX330-enCas12i-001-RNF2-Target gRNA (vector 12).

Positive control vector: The existing Cas12i$^{Max}$ nucleotide (reference: Chen Y, Hu Y, Wang X, et al., Synergistic engineering of CRISPR-Cas nucleases enables robust mammalian genome editing. Innovation (Camb). 2022; 3 (4): 100264. Published 2022 May 26. doi: 10.1016/j.xinn.2022.100264) was constructed into a eukaryotic expression vector pX330. Expression of the Cas12i$^{Max}$ was initiated by a chicken β-actin promoter, while an sgRNA sequence (the sgRNA sequence contained two segments, namely crRNA-1 and Target gRNA, respectively) was constructed downstream of a U6 promoter. The target genes for the targeting segments of this sgRNA were CCR5, BCL11A, and RNF2, specifically CCR5-Target gRNA, BCL11A-Target gRNA, and RNF2-Target gRNA. Positive cleaved vectors were then formed, which were respectively marked as: pX330-Cas12i$^{Max}$-CCR5-Target gRNA (vector 7), pX330-Cas12i$^{Max}$-BCL11A-Target gRNA (vector 10), and pX330-Cas12i$^{Max}$-RNF2-Target gRNA (vector 13).

Positive empty vector: The above Cas12i$^{Max}$ nucleotide was constructed into a eukaryotic expression vector pX330. Expression of the Cas12i$^{Max}$ was initiated by a chicken β-actin promoter, while crRNA-1 was constructed downstream of a U6 promoter without constructing the Target gRNA. A positive empty vector was then formed, which was marked as: pX330-Cas12i$^{Max}$_crRNA (vector 14).

TABLE 1

(see FIG. 5 and FIG. 6 for the maps of the vectors)

| Electrophoresis lane No. (from left to right) | Name of vector | sgRNA crRNA | sgRNA target gRNA | Effector protein |
|---|---|---|---|---|
| 1 | Vector 14: pX330-Cas12i$^{Max}$-crRNA | crRNA-1 | None | Cas12i$^{Max}$ |
| 2 | Vector 5: pX330-enCas12i-002-CCR5-Target gRNA | crRNA-1 | CCR5-Target gRNA | enCas12i-002 |
| 3 | Vector 6: pX330-enCas12i-001-CCR5-Target gRNA | crRNA-1 | CCR5-Target gRNA | enCas12i-001 |
| 4 | Vector 7: pX330-Cas12i$^{Max}$-CCR5-Target gRNA | crRNA-1 | CCR5-Target gRNA | Cas12i$^{Max}$ |
| 5 | Vector 14: pX330-Cas12i$^{Max}$-crRNA | crRNA-1 | None | Cas12i$^{Max}$ |

TABLE 1-continued (see FIG. 5 and FIG. 6 for the maps of the vectors)

| Electro-phoresis lane No. (from left to right) | Name of vector | sgRNA crRNA | sgRNA target gRNA | Effector protein |
|---|---|---|---|---|
| 6 | Vector 8: pX330-enCas12i-002-BCL11A-Target gRNA | crRNA-1 | BCL11A-Target gRNA | enCas12i-002 |
| 7 | Vector 9: pX330-enCas12i-001-BCL11A-Target gRNA | crRNA-1 | BCL11A-Target gRNA | enCas12i-001 |
| 8 | Vector 10: pX330-Cas12i$^{Max}$-BCL11A-Target gRNA | crRNA-1 | BCL11A-Target gRNA | Cas12i$^{Max}$ |
| 9 | Vector 14: pX330-Cas12i$^{Max}$-crRNA | crRNA-1 | None | Cas12i$^{Max}$ |
| 10 | Vector 11: pX330-enCas12i-002-RNF2-Target gRNA | crRNA-1 | RNF2-Target gRNA | enCas12i-002 |
| 11 | Vector 12: pX330-enCas12i-001-RNF2-Target gRNA | crRNA-1 | RNF2-Target gRNA | enCas12i-001 |
| 12 | Vector 13: pX330-Cas12i$^{Max}$-RNF2-Target gRNA | crRNA-1 | RNF2-Target gRNA | Cas12i$^{Max}$ |

TABLE 2

(primer pairs for PCR amplification in the T7E1 experiment)

| Name of primer | Sequence (5'→3') | SEQ ID NO: |
|---|---|---|
| CCR5-F | TCTGCTTCGGTGTCGAAATGAG | 76 |
| CCR5-R | TGCAGAAGCGTTTGGCAATGTG | 77 |
| BCL11A-F | GCTGAAAAGCGATACAGGGC | 78 |
| BCL11A-R | ATCACCAAGAGAGCCTTCCG | 79 |
| RNF2-F | TTTATAACAGTGGTGGTGAGGCT | 80 |
| RNF2-R | TTCTCAAACCCTGGAAAGCACT | 81 |

Example 5. Verification of Cleavage Activity of enCas12i Effector Proteins in Human Cell Line In order to further confirm the dsDNA cleavage activity of the enCas12i effector proteins in mammalian cells, this experiment adopted sequencing for verification. As shown in Table 3, the vector structures were formed by separately constructing the eukaryotic codon-optimized nucleotides of the enCas12i-001 effector protein (SEQ ID NO: 59), the enCas12i-002 effector protein (SEQ ID NO: 60), and the existing Cas12i$^{Max}$, along with an RNF2 gene-targeting sgRNA, into a eukaryotic expression vector pX330. The target RNF2-Target gRNA sequence was: 5'-TTCAA-CATATCCAAACAAAT-3' (SEQ ID NO: 75), and the reverse complementary sequence of RNF2-Target gRNA was: 5'-ATTTGTTTGGATATGTTGAA-3' (SEQ ID NO: 82). The crRNA in the sgRNA was crRNA-1, and expression of the sgRNA was initiated by a U6 promoter. Expression of the enCas12i effector proteins was initiated by a chicken β-actin promoter. An eGFP gene (used for performing cell sorting) was linked downstream of an enCas12i nucleotide or a Cas12i$^{Max}$ nucleotide via a self-cleaving polypeptide 2A (P2A). Recombinant vectors were then formed, which were respectively marked as: pX330-Cas12i$^{Max}$-crRNA-eGFP (vector 15, containing no Target gRNA and serving as a blank control), pX330-Cas12i$^{Max}$-RNF2-eGFP (vector 16, serving as a positive control), pX330-enCas12i-001-RNF2-eGFP (vector 17), and pX330-enCas12i-002-RNF2-eGFP (vector 18).

Figure 9A:
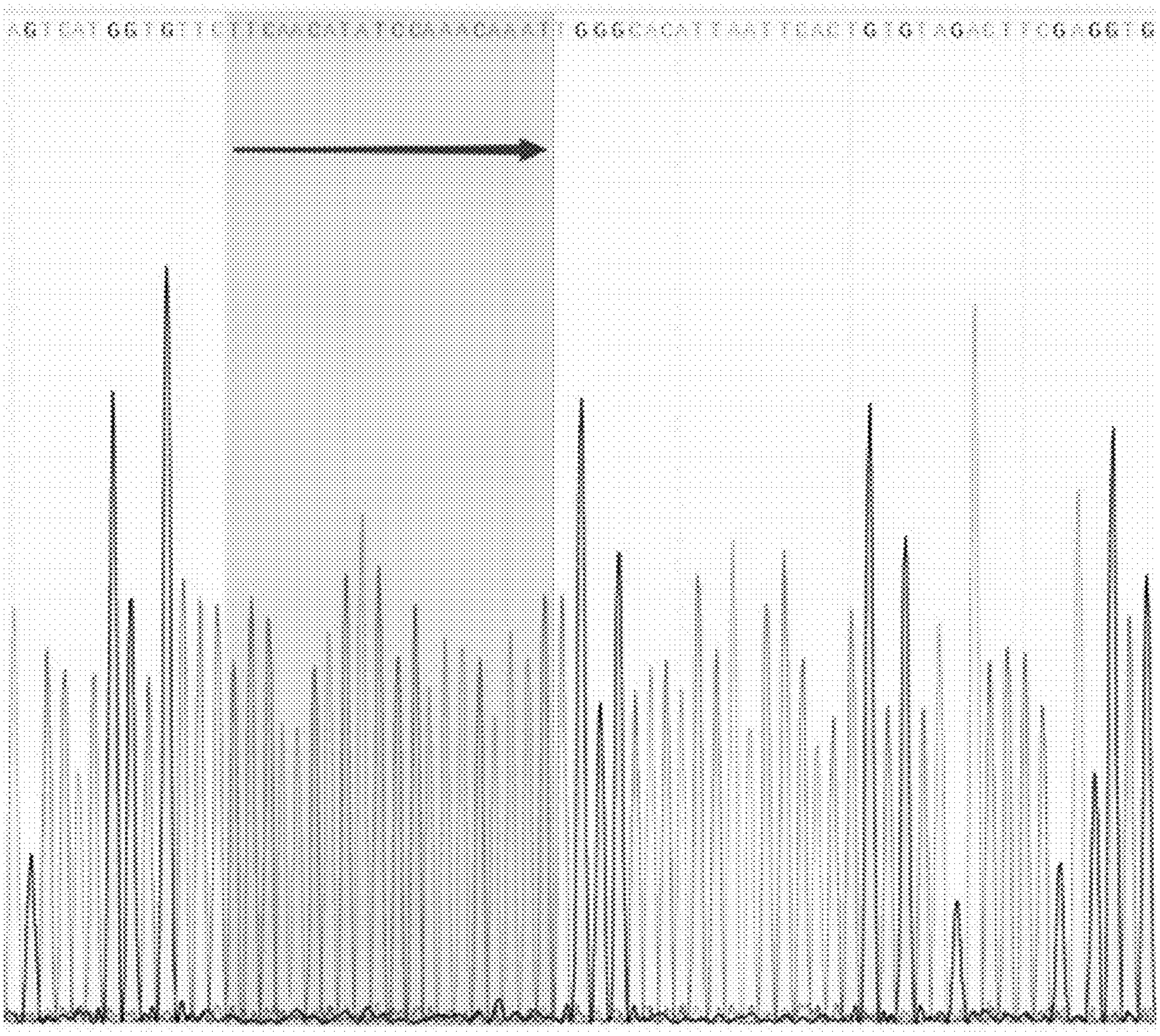
FIG. 9 and FIG. 10 show the cleavage activity of the enCas12i effector proteins of the present invention in eukaryotic cells by sequencing results.
Figure 9B:
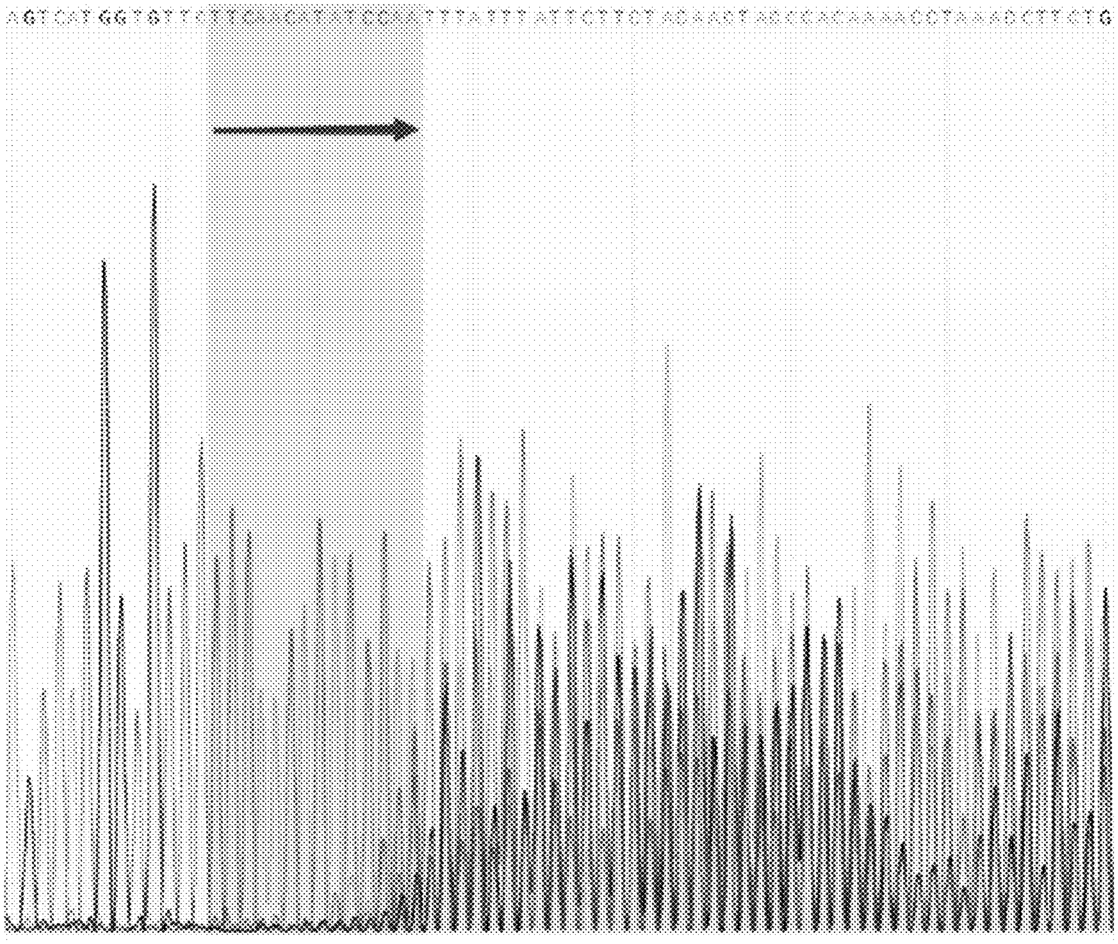
Figure 9C:
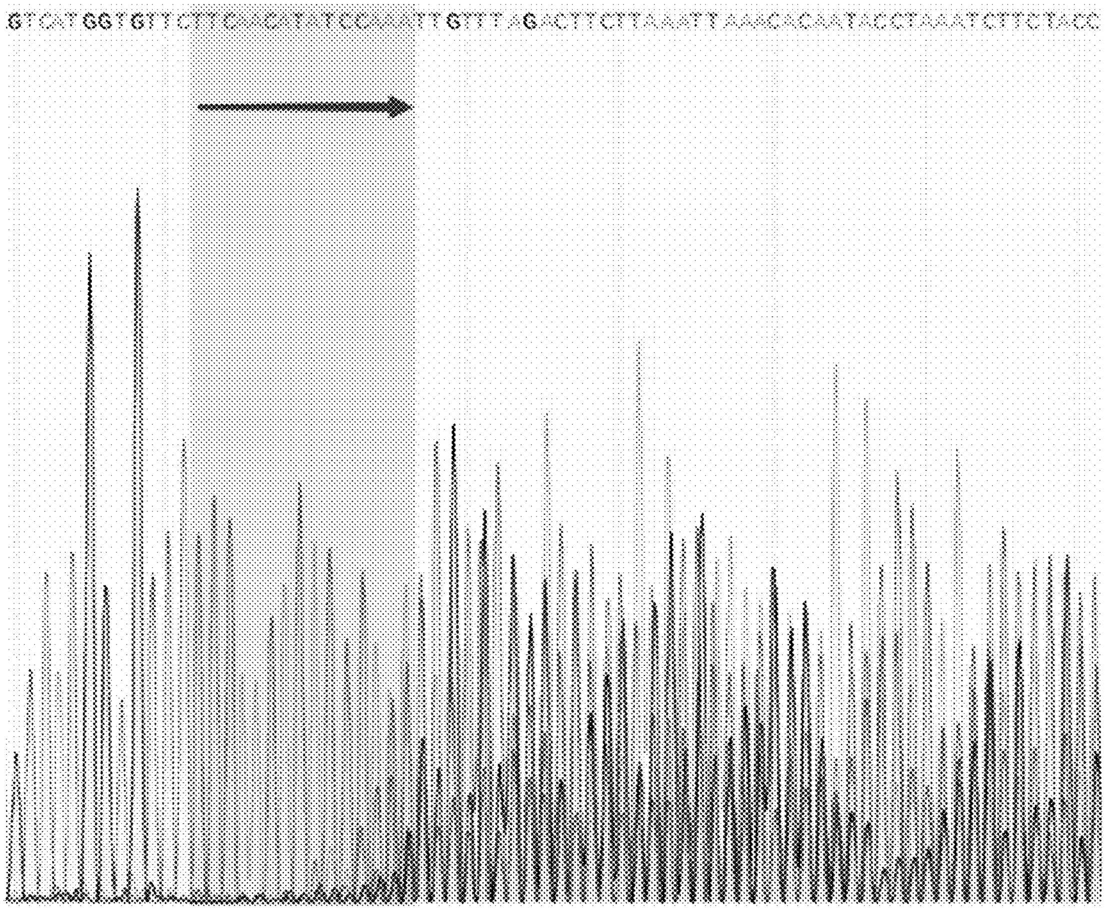
Figure 10:
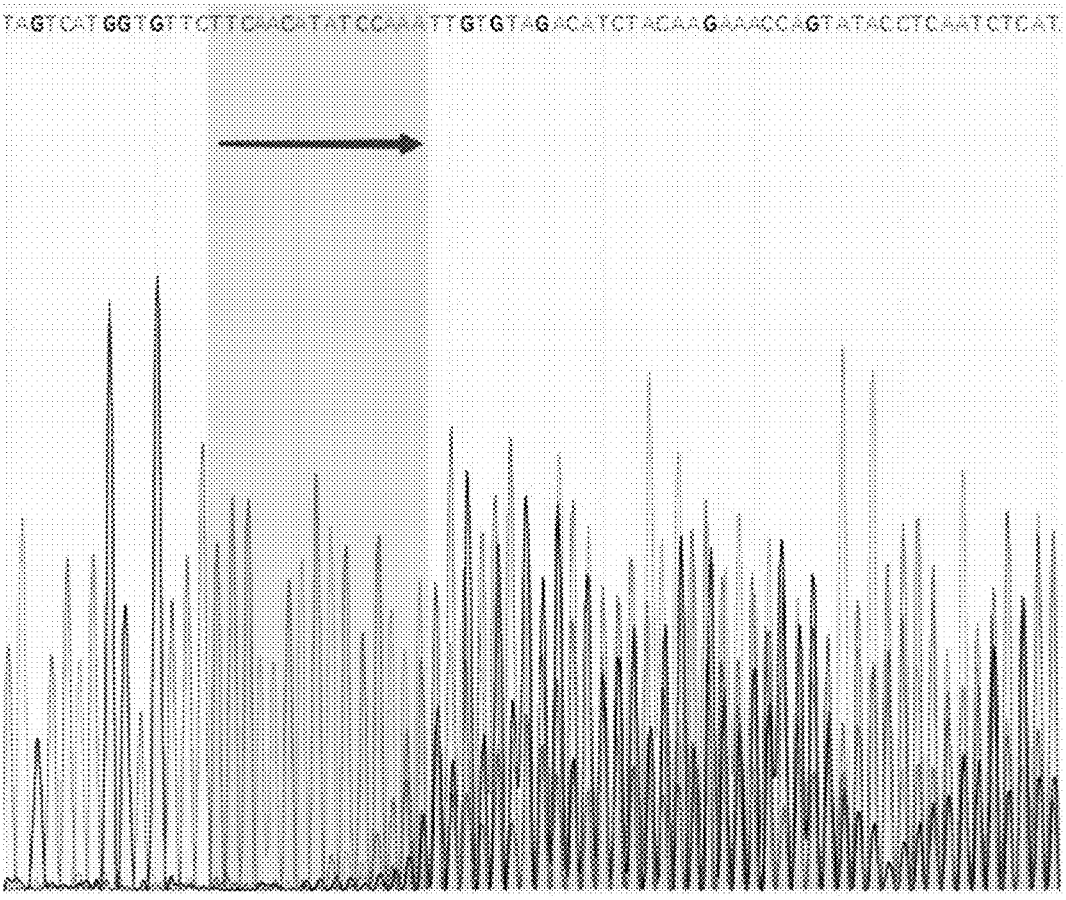

The above vectors (vectors 15-18) were separately transfected into human HEK293T cells. The cells were cultured at 37° C. with 5% carbon dioxide. After 72 hours of transfection, eGFP-positive cells were collected by fluorescence-activated cell sorting (FACS). After the cell sorting, the cells were cultured for another 48 h. Subsequently, the genome of the sorted cells was extracted, and sequencing was performed by using the above primers (RNF2-F and RNF2-R). The results are shown in FIG. 9 and FIG. 10. From the sequencing results, it can be seen that in the blank control in FIG. 9A, the arrowed region represents the reverse complementary sequence of RNF2-Target gRNA; the peak shapes upstream and downstream of this target sequence were relatively intact, showing predominantly single peak shapes with only baseline noise; there are no frameshift mutation peak shapes downstream (in the direction of the arrow) of the reverse complementary sequence of RNF2-Target gRNA. The sequencing peak shapes of enCas12i-001 (FIG. 9C) and enCas12i-002 (FIG. 10) were consistent with those of the positive control Cas12i$^{Max}$ (FIG. 9B), both of which had continuous stable overlapping peaks downstream (in the direction of the arrow) of the RNF2 target sequence, i.e., downstream of the reading frame, indicating that the enCas12i effector proteins of this patent performed cleavage at the RNF2 target, so that the reading frame downstream sequence downstream (in the direction of the arrow) of the RNF2 target underwent a frameshift mutation, leading to a change in the reading frame and thus resulting in continuous stable overlapping peaks downstream of the site. The results demonstrate that the enCas12i effector proteins of the present invention had cleavage activity in eukaryotic cells.

TABLE 3

(the structures of vectors 15-18 are shown in FIG. 8)

| | sgRNA | | |
|---|---|---|---|
| Name of vector | crRNA | target gRNA | Effector protein |
| Vector 15: pX330-Cas12i$^{Max}$-crRNA-eGFP | crRNA-1 | None | Cas12i$^{Max}$ |
| Vector 16: pX330-Cas12i$^{Max}$-RNF2-eGFP | crRNA-1 | RNF2-Target gRNA | Cas12i$^{Max}$ |
| Vector 17: pX330-enCas12i-001-RNF2-eGFP | crRNA-1 | RNF2-Target gRNA | enCas12i-001 |
| Vector 18: pX330-enCas12i-002-RNF2-eGFP | crRNA-1 | RNF2-Target gRNA | enCas12i-002 |

Example 6. Verification of Base Editing Activity of Base Editors (ABEs) Constructed by enCas12i Effector Proteins and Adenosine Deaminase The base editor (ABE) constructed by the CRISPR-Cas protein and adenosine deaminase can effectively cause the conversion of A:T base pairs to G:C base pairs or the conversion of C:G base pairs to T:A base pairs in DNA. Therefore, the editing capacity of the denCas12i in a human cell line can be detected by the base editor, and the editing effect of the base editor can be measured. Corresponding vectors were constructed according to sgRNAs described in Table 4.

Experimental groups: Base editor linking fragments, formed by separately linking the eukaryotic codon-optimized nucleotides of denCas12i-001 to denCas12i-002 (D1009A) and denCas12i-003 to denCas12i-006 via XTEN an linker (D1019A) (SGGSSGGSSGSETPGTSESAT-PESSGGSSGGS, SEQ ID NO: 83) to the above adenine deaminase TadA-8e, were each constructed into a eukaryotic expression vector pX330. Expression of the base editor was initiated by a chicken β-actin promoter. An eGFP gene (used for performing cell sorting) was linked downstream of this base editor via a self-cleaving polypeptide 2A (P2A), while sgRNA sequences (crRNA-1 and RNF2-Target gRNA, or crRNA-1 and TTR-Target gRNA) were constructed downstream of a U6 promoter in the eukaryotic expression vector. Recombinant adenine base editor vectors were then formed, which were respectively marked as: pX330-ABE8e-denCas12i-001-RNF2-eGFP (vector 19), pX330-ABE8e-denCas12i-002-RNF2-eGFP (vector 20), pX330-ABE8e-denCas12i-003-RNF2-eGFP (vector 21), pX330-ABE8e-denCas12i-004-RNF2-eGFP (vector 22), pX330-ABE8e-denCas12i-005-RNF2-eGFP (vector 23), pX330-ABE8e-denCas12i-006-RNF2-eGFP (vector 24), pX330-ABE8e-denCas12i-001-TTR-eGFP (vector 25), pX330-ABE8e-denCas12i-002-TTR-eGFP (vector 26), pX330-ABE8e-denCas12i-003-TTR-eGFP (vector 27), pX330-ABE8e-denCas12i-004-TTR-eGFP (vector 28), pX330-ABE8e-denCas12i-005-TTR-eGFP (vector 29), and pX330-ABE8e-denCas12i-006-TTR-eGFP (vector 30).

Editing targets: The sequences of RNF2-Target gRNA and TTR-Target gRNA are as follows:

```
RNF2-Target gRNA:
                                       (SEQ ID NO: 75)
5'-TTCAACATATCCAAACAAAT-3.

TTR-Target gRNA:
                                       (SEQ ID NO: 84)
5'-TTGTATAATAGGAAAGGGAA-3'.
```

TABLE 4

(the structures of vectors 19-30 are shown in FIG. 11 and FIG. 12)

| Name of vector | sgRNA crRNA | sgRNA target gRNA | Effector protein |
|---|---|---|---|
| Vector 19: pX330-ABE8e-denCas12i-001-RNF2-eGFP | crRNA-1 | RNF2-Target gRNA | denCas12i-001 |
| Vector 20: pX330-ABE8e-denCas12i-002-RNF2-eGFP | crRNA-1 | RNF2-Target gRNA | denCas12i-002 |
| Vector 21: pX330-ABE8e-denCas12i-003-RNF2-eGFP | crRNA-1 | RNF2-Target gRNA | denCas12i-003 |
| Vector 22: pX330-ABE8e-denCas12i-004-RNF2-eGFP | crRNA-1 | RNF2-Target gRNA | denCas12i-004 |
| Vector 23: pX330-ABE8e-denCas12i-005-RNF2-eGFP | crRNA-1 | RNF2-Target gRNA | denCas12i-005 |
| Vector 24: pX330-ABE8e-denCas12i-006-RNF2-eGFP | crRNA-1 | RNF2-Target gRNA | denCas12i-006 |
| Vector 25: pX330-ABE8e-denCas12i-001-TTR-eGFP | crRNA-1 | TTR-Target gRNA | denCas12i-001 |
| Vector 26: pX330-ABE8e-denCas12i-002-TTR-eGFP | crRNA-1 | TTR-Target gRNA | denCas12i-002 |
| Vector 27: pX330-ABE8e-denCas12i-003-TTR-eGFP | crRNA-1 | TTR-Target gRNA | denCas12i-003 |
| Vector 28: pX330-ABE8e-denCas12i-004-TTR-eGFP | crRNA-1 | TTR-Target gRNA | denCas12i-004 |
| Vector 29: pX330-ABE8e-denCas12i-005-TTR-eGFP | crRNA-1 | TTR-Target gRNA | denCas12i-005 |
| Vector 30: pX330-ABE8e-denCas12i-006-TTR-eGFP | crRNA-1 | TTR-Target gRNA | denCas12i-006 |

Figure 13:
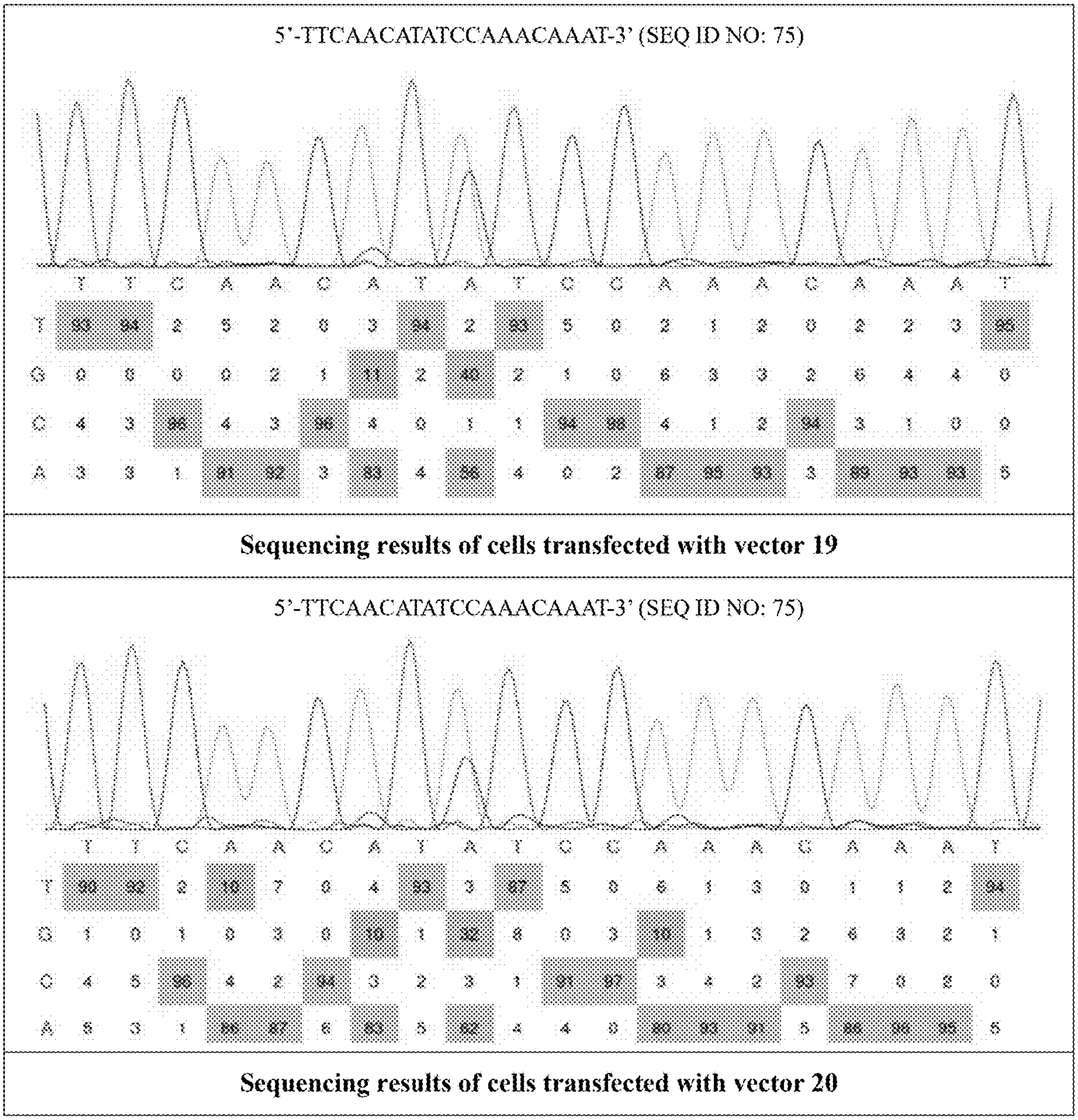

Subsequently, the above adenine base editor vectors 19-30 were separately transfected into human HEK293T cells, and then the cells were cultured at 37° C. with 5% carbon dioxide. After 72 hours of transfection, flow cytometry sorting was performed. eGFP-positive cells were collected by fluorescence-activated cell sorting (FACS). After the cell sorting, the cells were cultured for another 48 h, and the editing efficiency of the adenine base editors on the RNF2 target and the TTR target was determined by sequencing, with the results shown in FIG. 13, FIG. 14, and FIG. 15. The results show that all six effector proteins, denCas12i-001 to denCas12i-006, could edit base A to base G on the targets. The editing efficiency of the adenine base editors formed by the enCas12i effector proteins provided by the present invention was 20%-40%, and the editing windows were at the 7th, 8th, 9th, and 10th positions from the start of the targets. In terms of the RNF2 target, the editing windows for enCas12i-001 and enCas12i-002 were at the 7th and 9th positions, while the editing windows for enCas12i-003 to denCas12i-006 were also at the 7th and 9th positions. In terms of the TTR target, the editing windows for enCas12i-001 and enCas12i-002 were at the 7th and 10th positions, while the editing windows for enCas12i-003 to denCas12i-006 were at the 7th, 8th, and 10th positions. The following experiment adopted the enCas12i-001 effector protein.

Example 7. Verification of DNA Binding and Cleavage Activity of enCas12i Mutants A large number of experiments have verified that the amino acids at the 229th, 924th, and 925th positions of the enCas12i effector protein can affect the DNA binding and cleavage activity of the effector protein. Therefore, this experiment aimed to verify the nuclease activity of an enCas12i-001-N229R mutant, an enCas12i-001-D924R mutant, and an enCas12i-001-S925R mutant.

Figure 16:
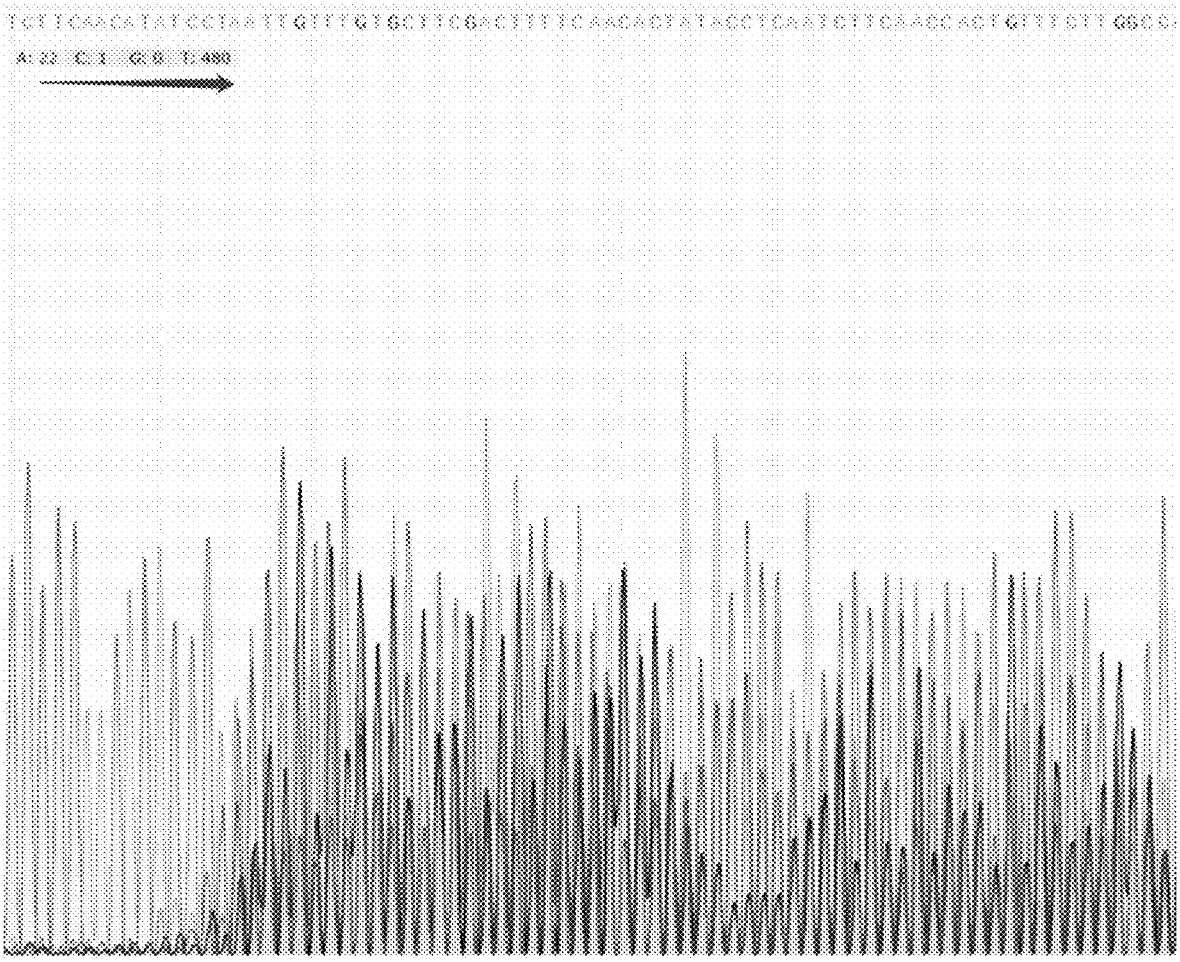
FIG. 16 and FIG. 17 show the cleavage activity of mutants of the enCas12i effector protein of the present invention in eukaryotic cells by sequencing results.
Figure 17:
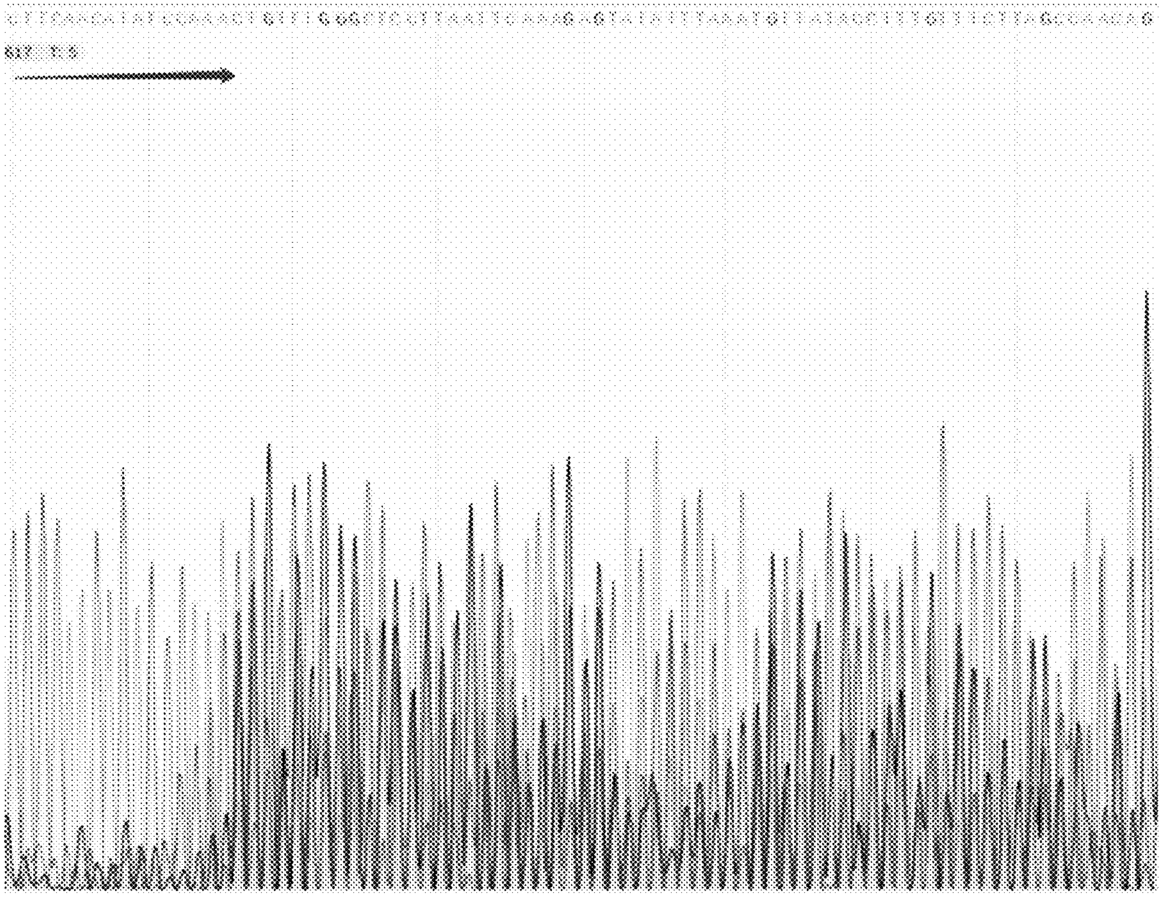

7.1. Referring to the method in Example 5, the pX330-enCas12i-001-N229R-RNF2-eGFP, pX330-enCas12i-001-D924R-RNF2-eGFP, and pX330-enCas12i-001-S925R-RNF2-eGFP vectors were constructed. These vectors were separately transfected into 293T cells, and then the cells were cultured, sorted, and subjected to target amplification and sequencing analysis. The results are shown in FIG. 16 and FIG. 17. In the results, the arrows indicate the RNF2 target (5'-TTCAACATATCCAAACAAAT-3', SEQ ID NO: 75). The reading frame downstream sequence downstream (in the direction of the arrow) of the RNF2 target underwent a frameshift mutation, leading to a change in the reading frame and thus resulting in continuous stable overlapping peaks downstream of the site. The results demonstrate that the enCas12i effector protein of the present invention had cleavage activity in eukaryotic cells.

7.2. Referring to the method in Example 6, the pX330-ABE8e-denCas12i-001-N229R-RNF2-eGFP, pX330-ABE8e-denCas12i-001-D924R-RNF2-eGFP, pX330-ABE8e-denCas12i-001-S925R-RNF2-eGFP, pX330-ABE8e-denCas12i-001-N229R-TTR-eGFP, pX330-ABE8e-denCas12i-001-D924R-TTR-eGFP, and pX330-ABE8e-denCas12i-001-S925R-TTR-eGFP vectors were constructed. These vectors were separately transfected into 293T cells, and then the cells were cultured, sorted, and subjected to target amplification and sequencing analysis. The results are shown in FIG. 18 and FIG. 19. The results show that the enCas12i mutants (enCas12i-N229R, enCas12i-D924R, and enCas12i-S925R) could edit base A to base G on the targets (RNF2 and TTR). For RNF2, the three mutants all exhibited the highest editing efficiency at the 9th position, with N229R showing the highest efficiency. For TTR, the three mutants exhibited editing efficiency at the 7th and 10th positions. The following experiment was performed by adopting enCas12i-001-N229R.

Example 8. Effect Testing of Epigenetic Activators Constructed Based on enCas12i-001 and enCas12i-001-N229R in Human Cell Line To test whether the enCas12i effector protein of the present invention can bind to dsDNA and induce transcriptional activation in mammalian cells, in this example, the rtTA (reverse tetracycline-controlled transactivator) expression cassette and the eGFP expression cassette controlled by a minimal CMV promoter (PminiCMV), along with six copies of a tetracycline response element (TRE, 5'-TTCTCTATCACTGATAGGGAGTG-3', SEQ ID NO: 98, containing 5'-TTC-3' PAM and the target sequence of enCas12i-001 or enCas12i-001-N229R), were constructed onto a lentivirus vector to obtain a TRE-eGFP reporter system (FIG. 20A). The reporter system vector was then transfected into HEK293T cells, resulting in stable 293T cells containing the reporter system.

Figure 20B:
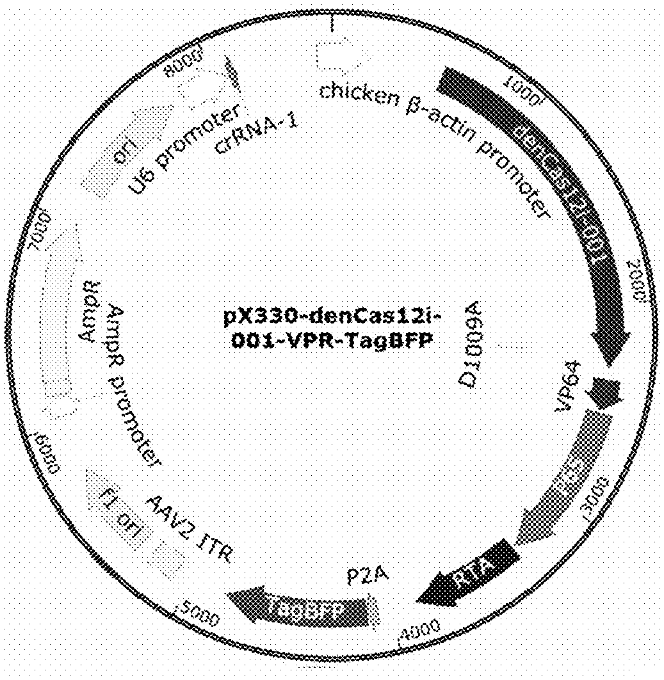
FIG. 20 shows schematic diagrams of expression vectors for epigenetic activators constructed based on enCas12i-001 and enCas12i-001-N229R.
Figure 20C:
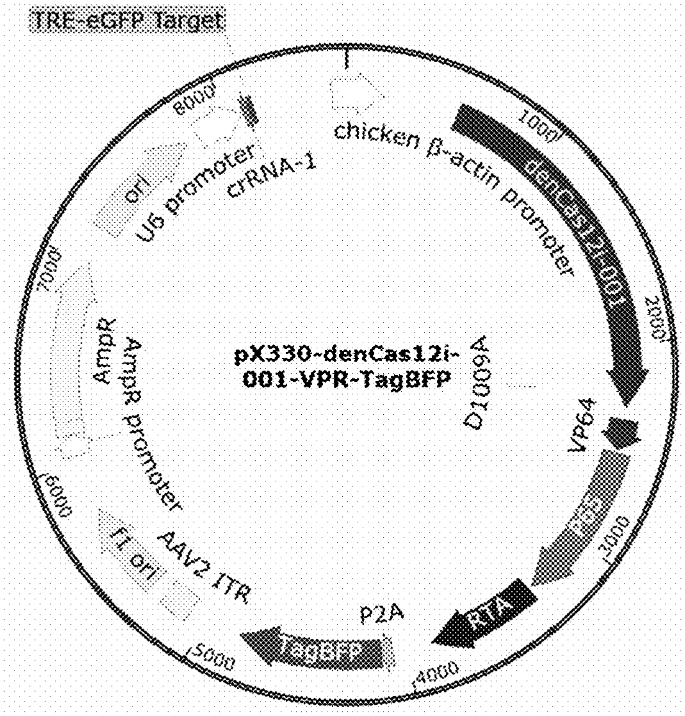
Figure 20D:
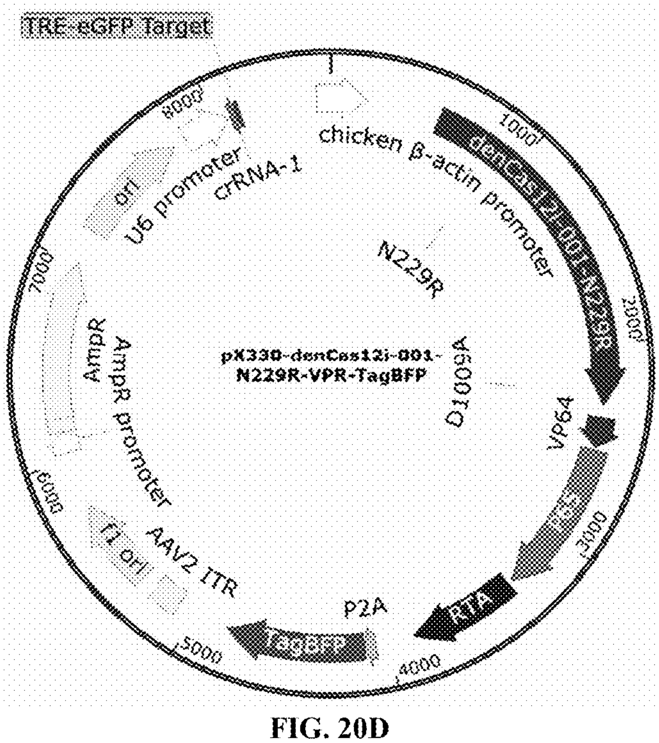
Figure 21A:
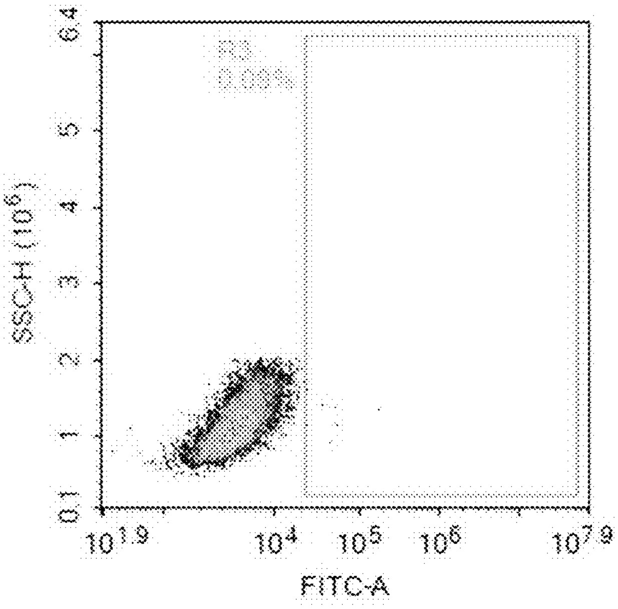
FIG. 21 shows the expression of GFP fluorescence in 293T cells transfected with the epigenetic activators of the present invention.
Figure 21B:
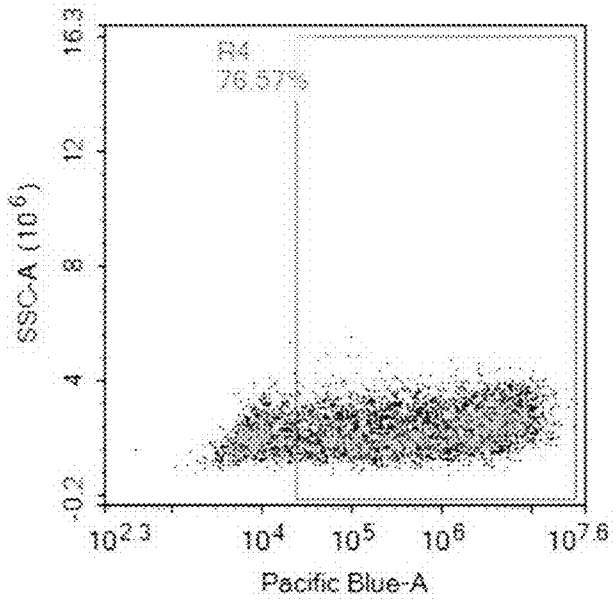
Figure 21C:
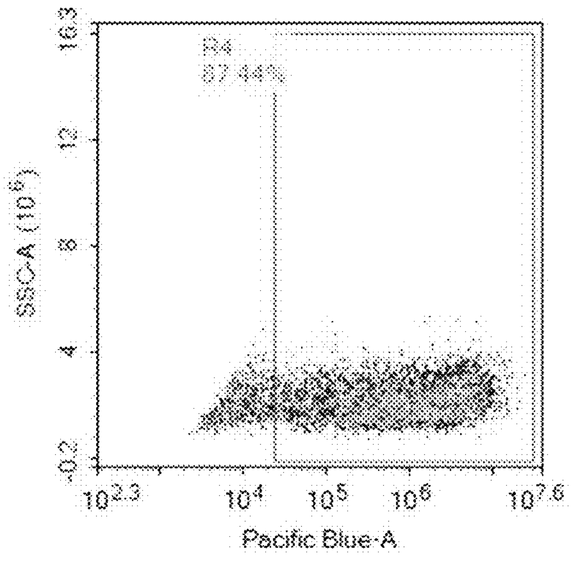

Meanwhile, a transcriptional activator VP64-p65-Rta58 was fused into each of codon-optimized denCas12i-001 and denCas12i-001-N229R, forming denCas12i-001-VPR and denCas12i-001-N229R-VPR, respectively. The two fusions were each combined with the crRNA-1 and the gRNA targeting the TRE sequence (i.e., TRE-eGFP Target, 5'-TCTATCACTGATAGGGAGTG-3', SEQ ID NO: 85), and then constructed onto a eukaryotic vector containing a blue fluorescent protein TagBFP, forming plasmids named as pX330-denCas12i-001-VPR-TagBFP and pX330-denCas12i-001-N229R-VPR-TagBFP, respectively (FIG. 20B to FIG. 20D; FIG. 20B represents a control empty vector containing denCas12i-001-VPR but lacking TRE-eGFP Target, and FIGS. 20C to 20D represent the experimental groups, with FIG. 20C containing denCas12i-001-VPR and TRE-eGFP Target, and FIG. 20D containing denCas12i-001-N229R-VPR and TRE-eGFP Target). These plasmids were separately transfected into the above 293T cells containing the reporter system. The simultaneous expression of TagBFP and GFP fluorescent proteins was detected by FACS flow cytometry, and the results are shown in FIG. 21. FIG. 21A shows the GFP fluorescence results in TagBFP-expressing cells after transfection with the control empty vector, FIG. 21B shows the GFP fluorescence results in TagBFP-expressing cells after transfection with the pX330-denCas12i-001-VPR-TagBFP vector, and FIG. 21C shows the GFP fluorescence results in TagBFP-expressing cells after transfection with the pX330-denCas12i-001-N229R-VPR-TagBFP vector. From the results, it can be seen that the cells in the control empty vector group showed no eGFP fluorescence, and the percentage of eGFP-positive cells in the denCas12i-VPR experimental groups of the present invention was significantly increased, indicating that both denCas12i-001-VPR and denCas12i-001-N229R-VPR successfully targeted TRE-eGFP Target for transcriptional activation of eGFP. This indicates that the enCas12i-001 and enCas12i-001-N229R of the present invention could be used for epigenetic editors. From the data, it can be seen that the activation efficiency of the epigenetic activator composed of enCas12i-001-N229R was higher.

The above experiments indicate that the point mutation of N229R in the enCas12i effector protein could significantly improve the cleavage and binding activity of enCas12i.

What is claimed is:

1. An engineered chimeric Cas12i polypeptide, wherein the engineered chimeric Cas12i polypeptide is capable of binding to a nucleic acid, and wherein the engineered chimeric Cas12i polypeptide comprises, from N-terminus to C-terminus, a first peptide segment, a second peptide segment, and a third peptide segment connected in sequence, wherein:

- the first peptide segment comprises an amino acid sequence having at least 80% sequence identity to the amino acid sequence of aa 1 to 897 of SEQ ID NO: 1 or aa 1 to 895 of SEQ ID NO: 3;
- the second peptide segment comprises an amino acid sequence having at least 80% sequence identity to the amino acid sequence set forth in any one of SEQ ID NOs: 67 to 72; and
- the third peptide segment comprises an amino acid sequence having at least 80% sequence identity to the amino acid sequence of aa 1008 to 1044 of SEQ ID NO: 1 or aa 1016 to 1054 of SEQ ID NO: 3.

2. The engineered chimeric Cas12i polypeptide according to claim 1, wherein the engineered chimeric Cas12i polypeptide is capable of cleaving the nucleic acid.

3. The engineered chimeric Cas12i polypeptide according to claim 1, wherein the engineered chimeric Cas12i polypeptide is mutated to have one or more of the following characteristics:

- (i) partial or complete inactivation of nucleic acid cleavage activity, or an enhancement of nucleic acid cleavage activity; and
- (ii) an enhancement of nucleic acid binding activity.

4. The engineered chimeric Cas12i polypeptide according to claim 1, wherein the engineered chimeric Cas12i polypeptide, according to the sequence numbering set forth in SEQ ID NO: 1, has an amino acid substitution at position D1009.

5. The engineered chimeric Cas12i polypeptide according to claim 4, wherein the amino acid substitution at position D1009 is a substitution with alanine.

6. The engineered chimeric Cas12i polypeptide according to claim 1, wherein the engineered chimeric Cas12i polypeptide, according to the sequence numbering set forth in SEQ ID NO: 1, has an amino acid substitution at position N229.

7. The engineered chimeric Cas12i polypeptide according to claim 6, wherein the engineered chimeric Cas12i polypeptide

- (i) comprises an amino acid sequence having at least 95% sequence identity to the amino acid sequence set forth in SEQ ID NO: 1; and
- (ii) has an amino acid substitution, at at least one of the two positions D924 and S925.

8. The engineered chimeric Cas12i polypeptide according to claim 7, wherein the amino acid substitution at position D924 or S925 is a substitution with lysine, arginine, or histidine.

9. The engineered chimeric Cas12i polypeptide according to claim 7, wherein the amino acid substitution at position D924 or S925 is a substitution with arginine.

10. The engineered chimeric Cas12i polypeptide according to claim 6, wherein the amino acid substitution at position N229 is a substitution with lysine, arginine, or histidine.

11. The engineered chimeric Cas12i polypeptide according to claim 6, wherein the amino acid substitution at position N229 is a substitution with arginine.

12. A CRISPR-Cas system, comprising:

- (a) a Cas12i polypeptide selected from the engineered chimeric Cas12i polypeptide according to claim 1; and
- (b) a guide RNA complexed with the Cas12i polypeptide to guide the Cas12i polypeptide to bind to a target nucleic acid.

13. The CRISPR-Cas system according to claim 12, wherein the guide RNA comprises a guide segment hybridizing with the target nucleic acid and a repeat segment binding to the Cas12i polypeptide, and the guide RNA does not comprise and does not bind to a tracrRNA.

14. The CRISPR-Cas system according to claim 13, wherein the repeat segment of the guide RNA comprises the nucleotide sequence set forth in any one of SEQ ID NOS: 7, 8, 9, and 14.

15. The CRISPR-Cas system according to claim 13, wherein the repeat segment of the guide RNA is the nucleotide sequence set forth in any one of SEQ ID NOs: 7 to 14 7, 8, 9 and 14.

16. A method for modifying a target nucleic acid, comprising contacting the target nucleic acid with the CRISPR- Cas system according to claim 12 or a complex comprising the CRISPR-Cas system, wherein the contacting results in a modification of the target nucleic acid, and wherein the target nucleic acid is a double-stranded DNA.

17. The method according to claim 16, wherein the contacting occurs outside a cell in vitro, inside a cultured cell, or inside an in-vivo cell.

18. The method according to claim 17, wherein the cell is a eukaryotic cell.

19. The method according to claim 17, wherein the cell is a human cell.

20. The method according to claim 16, wherein the modification comprises increasing or decreasing expression of a target sequence in the target nucleic acid, or the modification comprises deaminating a target adenine or a target cytosine in the target nucleic acid to achieve base pair conversion.

21. A fusion polypeptide, comprising a Cas12i polypeptide fused to one or more heterologous polypeptides, wherein the Cas12i polypeptide is selected from the engineered chimeric Cas12i polypeptide according to claim 1.

22. The fusion polypeptide according to claim 21, wherein the one or more heterologous polypeptides are each independently an epitope tag or a nuclear localization signal, or have one or more of the following enzymatic activities: reverse transcriptase activity, nuclease activity, methyltransferase activity, demethylase activity, acetyltransferase activity, deacetylase activity, kinase activity, phosphatase activity, ubiquitin ligase activity, deubiquitination activity, adenylation activity, deadenylation activity, SUMOylation activity, deSUMOylation activity, ribosylation activity, deribosylation activity, myristoylation activity, demyristoylation activity, glycosylation activity and deglycosylation activity, DNA repair activity, DNA damage activity, deaminase activity, dismutase activity, alkylation activity, depurination activity, oxidation activity, pyrimidine dimer formation activity, integrase activity, transposase activity, recombinase activity, polymerase activity, ligase activity, helicase activity, photolyase activity, and glycosylase activity.

23. The fusion polypeptide according to claim 22, wherein the enzymatic activity domain has one or more of the following enzymatic activities: deaminase activity, methyltransferase activity, demethylase activity, acetyltransferase activity, and deacetylase activity.

24. The fusion polypeptide according to claim 21, wherein the one or more heterologous polypeptides are independently a transcriptional repression domain, a transcriptional activation domain, or a deaminase domain.

25. The fusion polypeptide according to claim 24, wherein the transcriptional activation domain comprises a domain formed by an enzyme selected from the following: a transcriptional activator, a histone lysine methyltransferase, a histone lysine demethylase, a histone acetyltransferase, and a DNA demethylase.

26. The fusion polypeptide according to claim 24, wherein the transcriptional repression domain comprises a domain selected from the following: a transcriptional repressor, a ZIM3 domain, a KOX1 repression domain, a Mad mSIN3 interaction domain (SID), an ERF repressor domain (ERD), an SRDX repression domain, a histone lysine methyltransferase, a histone lysine demethylase, a histone lysine deacetylase, a DNA methylase, and a peripheral recruitment element.

27. The fusion polypeptide according to claim 24, wherein the transcriptional activation domain comprises VP64; P65; RTA; truncated P65; truncated RTA; or one or more fusion forms thereof or therebetween.

28. The fusion polypeptide according to claim 24, wherein the transcriptional repression domain is selected from a KRAB catalytic domain, a DNA methyltransferase, or a combination thereof.

29. The fusion polypeptide according to claim 24, wherein a structure of the fusion polypeptide is selected from:

$NH_2$-[Cas12i]-[transcriptional regulatory domain]-COOH;

$NH_2$-[transcriptional regulatory domain]-[Cas12i]—COOH;

$NH_2$-[Cas12i]-[transcriptional activation domain]-COOH;

$NH_2$-[transcriptional activation domain]-[Cas12i]—COOH;

$NH_2$—[NLS]-[Cas12i]-[transcriptional activation domain]-COOH;

$NH_2$-[Cas12i]-[transcriptional activation domain]-[NLS]—COOH;

$NH_2$—[NLS]-[Cas12i]-[transcriptional activation domain]-[NLS]—COOH;

$NH_2$—[NLS]-[transcriptional activation domain]-[Cas12i]—COOH;

$NH_2$-[transcriptional activation domain]-[Cas12i]-[NLS]—COOH;

$NH_2$—[NLS]-[transcriptional activation domain]-[Cas12i]-[NLS]—COOH;

$NH_2$-[Cas12i]-[VP64-P65-RTA fusion protein]-COOH;

$NH_2$—[VP64-P65-RTA fusion protein]-[Cas12i]—COOH;

$NH_2$—[NLS]-[Cas12i]-[VP64-P65-RTA fusion protein]-COOH;

$NH_2$-[Cas12i]-[VP64-P65-RTA fusion protein]-[NLS]—COOH;

$NH_2$—[NLS]-[Cas12i]-[VP64-P65-RTA fusion protein]-[NLS]—COOH;

$NH_2$—[NLS]-[VP64-P65-RTA fusion protein]-[Cas12i]—COOH;

$NH_2$—[VP64-P65-RTA fusion protein]-[Cas12i]-[NLS]—COOH;

$NH_2$—[NLS]-[Cas12i]-[VP64-P65-RTA fusion protein]-[NLS]—COOH;

$NH_2$-[Cas12i]-[transcriptional inhibition domain]-COOH;

$NH_2$-[transcriptional inhibition domain]-[Cas12i]—COOH;

$NH_2$—[NLS]-[Cas12i]-[transcriptional inhibition domain]-COOH;

$NH_2$-[Cas12i]-[transcriptional inhibition domain]-[NLS]—COOH;

$NH_2$—[NLS]-[Cas12i]-[transcriptional inhibition domain]-[NLS]—COOH;

$NH_2$—[NLS]-[transcriptional inhibition domain]-[Cas12i]—COOH;

$NH_2$-[transcriptional inhibition domain]-[Cas12i]-[NLS]—COOH;

$NH_2$—[NLS]-[transcriptional inhibition domain]-[Cas12i]-[NLS]—COOH;

$NH_2$-[Cas12i]-[first transcriptional inhibition domain]-[second transcriptional inhibition domain]-COOH;

$NH_2$-[Cas12i]-[second transcriptional inhibition domain]-[first transcriptional inhibition domain]-COOH;

$NH_2$-[first transcriptional inhibition domain]-[second transcriptional inhibition domain]-[Cas12i]—COOH;

$NH_2$-[second transcriptional inhibition domain]-[first transcriptional inhibition domain]-[Cas12i]—COOH;

$NH_2$-[first transcriptional inhibition domain]-[Cas12i]-[second transcriptional inhibition domain]-COOH;

$NH_2$-[second transcriptional inhibition domain]-[Cas12i]-[first transcriptional inhibition domain]-COOH;

$NH_2$—[NLS]-[Cas12i]-[KRAB catalytic domain]-[DNMT3A-DNMT3L]-COOH;

$NH_2$-[Cas12i]-[KRAB catalytic domain]-[DNMT3A-DNMT3L]-[NLS]—COOH;

$NH_2$—[NLS]-[Cas12i]-[KRAB catalytic domain]-[DNMT3A-DNMT3L]-[NLS]—COOH;

$NH_2$—[NLS]-[KRAB catalytic domain]-[DNMT3A-DNMT3L]-[Cas12i]—COOH;

$NH_2$—[KRAB catalytic domain]-[DNMT3A-DNMT3L]-[Cas12i]-[NLS]—COOH;

$NH_2$—[NLS]-[KRAB catalytic domain]-[DNMT3A-DNMT3L]-[Cas12i]-[NLS]—COOH;

$NH_2$—[NLS]-[KRAB catalytic domain]-[Cas12i]-[DNMT3A-DNMT3L]-COOH;

$NH_2$—[KRAB catalytic domain]-[Cas12i]-[DNMT3A-DNMT3L]-[NLS]—COOH;

$NH_2$—[NLS]-[KRAB catalytic domain]-[Cas12i]-[DNMT3A-DNMT3L]-[NLS]—COOH;

$NH_2$—[NLS]-[DNMT3A-DNMT3L]-[Cas12i]-[KRAB catalytic domain]-COOH;

$NH_2$-[DNMT3A-DNMT3L]-[Cas12i]-[KRAB catalytic domain]-[NLS]—COOH; and $NH_2$—[NLS]-[DNMT3A-DNMT3L]-[Cas12i]-[KRAB catalytic domain]-[NLS]—COOH.

30. The fusion polypeptide according to claim 24, wherein the deaminase domain comprises an adenosine deaminase domain, a cytidine deaminase domain, or a combination thereof.

31. The fusion polypeptide according to claim 30, wherein the cytidine deaminase is selected from an activation-induced cytidine deaminase (AID), an apolipoprotein B mRNA editing complex (APOBEC), and PmCDA1.

32. The fusion polypeptide according to claim 30, wherein the adenosine deaminase domain is TadA, ecTadA, saTadA, ecTadA7.10, TadA-8c, TadA8.17, TadA8.20, TadA9, or a combination thereof.

33. The fusion polypeptide according to claim 30, wherein a structure of the fusion polypeptide is selected from:

$NH_2$-[adenosine deaminase domain]-[Cas12i]—COOH;

$NH_2$-[Cas12i]-[adenosine deaminase domain]-COOH;

$NH_2$-[first adenosine deaminase domain]-[second adenosine deaminase domain]-[Cas12i]—COOH;

$NH_2$-[first adenosine deaminase domain]-[Cas12i]-[second adenosine deaminase domain]-COOH;

$NH_2$-[Cas12i]-[first adenosine deaminase domain]-[second adenosine deaminase domain]-COOH;

$NH_2$-[second adenosine deaminase domain]-[first adenosine deaminase domain]-[Cas12i]—COOH;

$NH_2$-[second adenosine deaminase domain]-[Cas12i]-[first adenosine deaminase domain]-COOH;

$NH_2$-[Cas12i]-[second adenosine deaminase domain]-[first adenosine deaminase domain]-COOH;

$NH_2$-[adenosine deaminase domain]-[Cas12i]-[NLS]—COOH;

$NH_2$-[Cas12i]-[adenosine deaminase domain]-[NLS]—COOH;

$NH_2$—[NLS]-[adenosine deaminase domain]-[Cas12i]—COOH;

$NH_2$—[NLS]-[Cas12i]-[adenosine deaminase domain]-COOH;

$NH_2$—[NLS]-[adenosine deaminase domain]-[Cas12i]-[NLS]—COOH;

$NH_2$—[NLS]-[Cas12i]-[adenosine deaminase domain]-[NLS]—COOH;

$NH_2$-[cytidine deaminase domain]-[Cas12i]-[uracil glycosylase inhibitor (UGI)]—COOH;

$NH_2$-[uracil glycosylase inhibitor (UGI)]-[Cas12i]-[cytidine deaminase domain]-COOH;

$NH_2$—[NLS]-[cytidine deaminase domain]-[Cas12i]-[uracil glycosylase inhibitor (UGI)]—COOH;

$NH_2$—[NLS]-[uracil glycosylase inhibitor (UGI)]-[Cas12i]-[cytidine deaminase domain]-COOH;

$NH_2$-[cytidine deaminase domain]-[Cas12i]-[uracil glycosylase inhibitor (UGI)]-[NLS]—COOH;

$NH_2$-[uracil glycosylase inhibitor (UGI)]-[Cas12i]-[cytidine deaminase domain]-[NLS]—COOH;

$NH_2$—[NLS]-[cytidine deaminase domain]-[Cas12i]-[uracil glycosylase inhibitor (UGI)]-[NLS]—COOH; and $NH_2$—[NLS]-[uracil glycosylase inhibitor (UGI)]-[Cas12i]-[cytidine deaminase domain]-[NLS]—COOH.

34. A complex, comprising the fusion polypeptide according to claim 21 and a guide RNA, wherein the guide RNA is complexed with the fusion polypeptide to guide the fusion polypeptide to bind to a target nucleic acid.

35. The complex according to claim 34, wherein the complex is an epigenetic editor comprising a fusion polypeptide that comprises the amino acid sequence set forth in any one of SEQ ID NOs: 88 to 93.

36. The complex according to claim 34, wherein the complex is a base editor comprising a fusion polypeptide that comprises the amino acid sequence set forth in any one of SEQ ID NOs: 94 to 97.

37. The complex according to claim 34, wherein the guide RNA comprises a guide segment hybridizing with the target nucleic acid and a repeat segment binding to the fusion polypeptide, and the guide RNA does not comprise and does not bind to a tracrRNA.

38. The complex according to claim 37, wherein the repeat segment of the guide RNA comprises the nucleotide sequence set forth in any one of SEQ ID NOs: 7, 8, 9 and 14.

39. A delivery system, comprising an engineered chimeric Cas12i polypeptide, a CRISPR-Cas system comprising the chimeric Cas12i polypeptide, a fusion polypeptide comprising the chimeric Cas12i polypeptide, a complex comprising the chimeric Cas12i polypeptide, a nucleic acid encoding the chimeric Cas12i polypeptide, a vector comprising the nucleic acid encoding the chimeric Cas12i polypeptide, or a vector system comprising the nucleic acid encoding the chimeric Cas12i polypeptide, wherein the engineered chimeric Cas12i polypeptide comprises, from N-terminus to C-terminus, a first peptide segment, a second peptide segment, and a third peptide segment connected in sequence, wherein:

the first peptide segment comprises an amino acid sequence having at least 80% sequence identity to the amino acid sequence of aa 1 to 897 of SEQ ID NO: 1 or aa 1 to 895 of SEQ ID NO: 3;

the second peptide segment comprises an amino acid sequence having at least 80% sequence identity to the amino acid sequence set forth in any one of SEQ ID NOs: 67 to 72; and the third peptide segment comprises an amino acid sequence having at least 80% sequence identity to the amino acid sequence of aa 1008 to 1044 of SEQ ID NO: 1 or aa 1016 to 1054 of SEQ ID NO: 3.

40. The delivery system according to claim 39, wherein the delivery system comprises a liposome, a nanoparticle, or an exosome.

41. A cell, comprising an engineered chimeric Cas12i polypeptide, a CRISPR-Cas system comprising the chimeric Cas12i polypeptide, a fusion polypeptide comprising the chimeric Cas12i polypeptide, a complex comprising the chimeric Cas12i polypeptide, a nucleic acid encoding the chimeric Cas12i polypeptide, a vector comprising the nucleic acid encoding the chimeric Cas12i polypeptide, a vector system comprising the nucleic acid encoding the chimeric Cas12i polypeptide, or a delivery system comprising the chimeric Cas12i polypeptide or the nucleic acid encoding the same, wherein the engineered chimeric Cas12i polypeptide comprises, from N-terminus to C-terminus, a first peptide segment, a second peptide segment, and a third peptide segment connected in sequence, wherein:

the first peptide segment comprises an amino acid sequence having at least 80% sequence identity to the amino acid sequence of aa 1 to 897 of SEQ ID NO: 1 or aa 1 to 895 of SEQ ID NO: 3;

the second peptide segment comprises an amino acid sequence having at least 80% sequence identity to the amino acid sequence set forth in any one of SEQ ID NOs: 67 to 72; and the third peptide segment comprises an amino acid sequence having at least 80% sequence identity to the amino acid sequence of aa 1008 to 1044 of SEQ ID NO: 1 or aa 1016 to 1054 of SEQ ID NO: 3.

42. The cell according to claim 41, wherein the cell is a eukaryotic cell.

43. The cell according to claim 41, wherein the cell is a human cell.

44. A composition or a kit, comprising an engineered chimeric Cas12i polypeptide, a CRISPR-Cas system comprising the chimeric Cas12i polypeptide, a fusion polypeptide comprising the chimeric Cas12i polypeptide, a complex comprising the chimeric Cas12i polypeptide, a nucleic acid encoding the chimeric Cas12i polypeptide, a vector comprising the nucleic acid encoding the chimeric Cas12i polypeptide, a vector system comprising the nucleic acid encoding the chimeric Cas12i polypeptide, a delivery system comprising the chimeric Cas12i polypeptide or the nucleic acid encoding the same, or a cell comprising the chimeric Cas12i polypeptide or the nucleic acid encoding the same; and a pharmaceutically acceptable carrier;

wherein the engineered chimeric Cas12i polypeptide comprises, from N-terminus to C-terminus, a first peptide segment, a second peptide segment, and a third peptide segment connected in sequence, wherein:

the first peptide segment comprises an amino acid sequence having at least 80% sequence identity to the amino acid sequence of aa 1 to 897 of SEQ ID NO: 1 or aa 1 to 895 of SEQ ID NO: 3;

the second peptide segment comprises an amino acid sequence having at least 80% sequence identity to the amino acid sequence set forth in any one of SEQ ID NOs: 67 to 72; and the third peptide segment comprises an amino acid sequence having at least 80% sequence identity to the amino acid sequence of aa 1008 to 1044 of SEQ ID NO: 1 or aa 1016 to 1054 of SEQ ID NO: 3.

45. The engineered chimeric Cas12i polypeptide according to claim 1, wherein the engineered chimeric Cas12i polypeptide has an amino acid sequence set forth in any one of SEQ ID NOs: 1 to 6.

46. A nucleic acid, comprising a polynucleotide, wherein the polynucleotide encodes (i) an engineered chimeric Cas12i polypeptide or (ii) a fusion polypeptide comprising the engineered chimeric Cas12i polypeptide, wherein the engineered chimeric Cas12i polypeptide comprises, from N-terminus to C-terminus, a first peptide segment, a second peptide segment, and a third peptide segment connected in sequence, wherein:

the first peptide segment comprises an amino acid sequence having at least 80% sequence identity to the amino acid sequence of aa 1 to 897 of SEQ ID NO: 1 or aa 1 to 895 of SEQ ID NO: 3;

the second peptide segment comprises an amino acid sequence having at least 80% sequence identity to the amino acid sequence set forth in any one of SEQ ID NOs: 67 to 72; and the third peptide segment comprises an amino acid sequence having at least 80% sequence identity to the amino acid sequence of aa 1008 to 1044 of SEQ ID NO: 1 or aa 1016 to 1054 of SEQ ID NO: 3.

47. A vector, comprising the nucleic acid according to claim 46.

48. The vector according to claim 47, wherein the vector is a plasmid or a viral vector.

49. The vector according to claim 48, wherein the viral vector is an adeno-associated virus vector, an adenovirus vector, a retrovirus vector, a lentivirus vector, or a herpes simplex virus vector.

50. The nucleic acid according to claim 46, wherein the polynucleotide is codon-optimized for expression in a prokaryotic or eukaryotic cell.

51. The nucleic acid according to claim 46, wherein the polynucleotide comprises or is the nucleotide sequence set forth in any one of SEQ ID NOs: 59 to 64.

52. A vector system, comprising a first vector and a second vector different from the first vector, wherein the first vector comprises the nucleic acid according to claim 46; the second vector comprises a nucleic acid comprising a guide RNA or a nucleotide sequence encoding the guide RNA, wherein the guide RNA comprises a repeat segment comprising the nucleotide sequence set forth in any one of SEQ ID NOs: 7, 8, 9 and 14.

53. The vector system according to claim 52, wherein the first vector and the second vector are each independently a plasmid or a viral vector.

54. The vector system according to claim 53, wherein the viral vector is an adeno-associated virus vector, an adenovirus vector, a retrovirus vector, a lentivirus vector, or a herpes simplex virus vector.

* * * * *

SEQUENCE LISTING

```
Sequence total quantity: 105
SEQ ID NO: 1            moltype = AA  length = 1044
FEATURE                 Location/Qualifiers
source                  1..1044
                        mol_type = protein
                        organism = synthetic construct
SEQUENCE: 1
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQYNSIISV LFGTGRKEDR  180
SVKLRITKKI LEAISNLKEI PKNVAPIQEI ILNVAKATKE TFRQVYAGNL GAPSTLERFI  240
AKDGQKEFDL KKLQTDLKKV IRGKSKERDW CCQEELRSYV EQNTIQYDLW AWGEMFNKAH  300
TALKIKSTRN YNFAKQRLEQ FKRIQSLNNL LVVKKLNDFF DSEFFSGEET YTICVHHLGG  360
KRLSKLYKAW EDDPADPENA IVVLCDDLKN NFKKEPIRNI LRYIFTIRQE CSAQDILAAA  420
KYNQQLDRYK SQKANPSVLG NQGFTWRNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITRISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMRAR  900
FEEVNVENIA EWHVRNFSNY LRADSGTGLY YKQATMDFLK HYGLEEHAEG LENKKIKFYD  960
FRKILEDKNL TSVIIPKRGG RIYMATNPVT SDSTPITYAG KTYNRCNADH VAAANIALTV  1020
KGIGEQSSDE ENPDGSRIKL QLTS                                         1044

SEQ ID NO: 2            moltype = AA  length = 1044
FEATURE                 Location/Qualifiers
source                  1..1044
                        mol_type = protein
                        organism = synthetic construct
SEQUENCE: 2
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQYNSIISV LFGTGRKEDR  180
SVKLRITKKI LEAISNLKEI PKNVAPIQEI ILNVAKATKE TFRQVYAGNL GAPSTLERFI  240
AKDGQKEFDL KKLQTDLKKV IRGKSKERDW CCQEELRSYV EQNTIQYDLW AWGEMFNKAH  300
TALKIKSTRN YNFAKQRLEQ FKRIQSLNNL LVVKKLNDFF DSEFFSGEET YTICVHHLGG  360
KRLSKLYKAW EDDPADPENA IVVLCDDLKN NFKKEPIRNI LRYIFTIRQE CSAQDILAAA  420
KYNQQLDRYK SQKANPSVLG NQGFTWRNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITRISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMRAR  900
```

-continued

```
FEEVNVSNVS EWHMRNFSNY LRADSGTGLY YKQATLDFLK HYDLEEHADD LEKQNIKFYD  960
FRKILEDKQL TSVIVPKRGG RIYMATNPVT SDSTPVTYAG KTYNRCNADH VAAANIALTV  1020
KGIGEQSSDE ENPDGSRIKL QLTS                                        1044

SEQ ID NO: 3            moltype = AA  length = 1054
FEATURE                 Location/Qualifiers
source                  1..1054
                        mol_type = protein
                        organism = synthetic construct
SEQUENCE: 3
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQYNSIISV LFGTGRKEDR  180
SVKLRITKKI LEAISNLKEI PKNVAPIQEI ILNVAKATKE TFRQVYAGNL GAPSTLERFI  240
AKDGQKEFDL KKLQTDLKKV IRGKSKERDW CCQEELRSYV EQNTIQYDLW AWGEMFNKAH  300
TALKIKSTRN YNFAKQRLEQ FKRIQSLNNL LVVKKLNDFF DSEFFSGEET YTICVHHLGG  360
KRLSKLYKAW EDDPADPENA IVVLCDDLKN NFKKEPIRNI LRYIFTIRQE CSAQDILAAA  420
KYNQQLDRYK SQKANPSVLG NQGFTWRNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITRISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKSFRAR  900
WDLVKVKDFG EKHLLTLSRN LTGKGPGTRK YYHQGVEDFL KEYELEDLKE ELAKIKKGDP  960
NALPPEVIRN KLKEKLGNEN APVLIPKRGG KYFLSTHNVA TGAVKITFNN KERYLCNADH  1020
VAAANIALTV KGIGEQSSDE ENPDGSRIKL QLTS                             1054

SEQ ID NO: 4            moltype = AA  length = 1054
FEATURE                 Location/Qualifiers
source                  1..1054
                        mol_type = protein
                        organism = synthetic construct
SEQUENCE: 4
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQYNSIISV LFGTGRKEDR  180
SVKLRITKKI LEAISNLKEI PKNVAPIQEI ILNVAKATKE TFRQVYAGNL GAPSTLERFI  240
AKDGQKEFDL KKLQTDLKKV IRGKSKERDW CCQEELRSYV EQNTIQYDLW AWGEMFNKAH  300
TALKIKSTRN YNFAKQRLEQ FKRIQSLNNL LVVKKLNDFF DSEFFSGEET YTICVHHLGG  360
KRLSKLYKAW EDDPADPENA IVVLCDDLKN NFKKEPIRNI LRYIFTIRQE CSAQDILAAA  420
KYNQQLDRYK SQKANPSVLG NQGFTWRNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITRISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKSFRAR  900
WRLVKVKDIG EKELLTLSRN LRGKGKGIKK YYHQGVLDFF KEYELEELAG PLAKIKPGDP  960
NAIPPEVLRN KLKEKLGNED APVLIPVAGG GIYLSTHNVA TGAKKITFNN KERYVCNADH  1020
VAAANIALTV KGIGEQSSDE ENPDGSRIKL QLTS                             1054

SEQ ID NO: 5            moltype = AA  length = 1054
FEATURE                 Location/Qualifiers
source                  1..1054
                        mol_type = protein
                        organism = synthetic construct
SEQUENCE: 5
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQYNSIISV LFGTGRKEDR  180
SVKLRITKKI LEAISNLKEI PKNVAPIQEI ILNVAKATKE TFRQVYAGNL GAPSTLERFI  240
AKDGQKEFDL KKLQTDLKKV IRGKSKERDW CCQEELRSYV EQNTIQYDLW AWGEMFNKAH  300
TALKIKSTRN YNFAKQRLEQ FKRIQSLNNL LVVKKLNDFF DSEFFSGEET YTICVHHLGG  360
KRLSKLYKAW EDDPADPENA IVVLCDDLKN NFKKEPIRNI LRYIFTIRQE CSAQDILAAA  420
KYNQQLDRYK SQKANPSVLG NQGFTWRNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITRISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKKYNAR  900
WDLVKVKDIG EGHLLILSRN LRGKGSGIRK YYHQGVLEFF KEYDLEDLAE PLAKIRPGDP  960
NAIPPEVLRE RLKEKLGNED APVLIPKPGG GVYLSTHNVA TGAKKITFNN KERYLCNADH  1020
VAAANIALTV KGIGEQSSDE ENPDGSRIKL QLTS                             1054
```

```
SEQ ID NO: 6            moltype = AA  length = 1054
FEATURE                 Location/Qualifiers
source                  1..1054
                        mol_type = protein
                        organism = synthetic construct
SEQUENCE: 6
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQYNSIISV LFGTGRKEDR  180
SVKLRITKKI LEAISNLKEI PKNVAPIQEI ILNVAKATKE TFRQVYAGNL GAPSTLERFI  240
AKDGQKEFDL KKLQTDLKKV IRGKSKERDW CCQEELRSYV EQNTIQYDLW AWGEMFNKAH  300
TALKIKSTRN YNFAKQRLEQ FKRIQSLNNL LVVKKLNDFF DSEFFSGEET YTICVHHLGG  360
KRLSKLYKAW EDDPADPENA IVVLCDDLKN NFKKEPIRNI LRYIFTIRQE CSAQDILAAA  420
KYNQQLDRYK SQKANPSVLG NQGFTWRNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITRISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKSYRAR  900
WRLVRVRDFG ERHLLTLSRN LTGKGKGTRK YYHQGVLDFF REYDLEDLAG PLAKIRPGDP  960
DAIPPEVLRE RLREKLGNDE APVLIPVRGG PVYLSTHDVA TGAKRITFNG KERYLCNADH  1020
VAAANIALTV KGIGEQSSDE ENPDGSRIKL QLTS                              1054

SEQ ID NO: 7            moltype = RNA  length = 23
FEATURE                 Location/Qualifiers
source                  1..23
                        mol_type = other RNA
                        organism = synthetic construct
SEQUENCE: 7
agaaatccgt ctttcattga cgg                                          23

SEQ ID NO: 8            moltype = RNA  length = 23
FEATURE                 Location/Qualifiers
source                  1..23
                        mol_type = other RNA
                        organism = synthetic construct
SEQUENCE: 8
agaaatgtgt ccccagttga cac                                          23

SEQ ID NO: 9            moltype = RNA  length = 23
FEATURE                 Location/Qualifiers
source                  1..23
                        mol_type = other RNA
                        organism = synthetic construct
SEQUENCE: 9
agaaatccgt ccttagttga cgg                                          23

SEQ ID NO: 10           moltype = RNA  length = 22
FEATURE                 Location/Qualifiers
source                  1..22
                        mol_type = other RNA
                        organism = synthetic construct
SEQUENCE: 10
agacatgtgt ccccagtgac ac                                           22

SEQ ID NO: 11           moltype = RNA  length = 23
FEATURE                 Location/Qualifiers
source                  1..23
                        mol_type = other RNA
                        organism = synthetic construct
SEQUENCE: 11
agaaatgttt ccccagttga aac                                          23

SEQ ID NO: 12           moltype = RNA  length = 23
FEATURE                 Location/Qualifiers
source                  1..23
                        mol_type = other RNA
                        organism = synthetic construct
SEQUENCE: 12
agaaatgtgt tcccagttaa cac                                          23

SEQ ID NO: 13           moltype = RNA  length = 23
FEATURE                 Location/Qualifiers
source                  1..23
                        mol_type = other RNA
                        organism = synthetic construct
SEQUENCE: 13
```

```
agaaatttgt ccccagttga caa                                           23

SEQ ID NO: 14          moltype = RNA  length = 23
FEATURE                Location/Qualifiers
source                 1..23
                       mol_type = other RNA
                       organism = synthetic construct
SEQUENCE: 14
agaaatccgt cctacgttga cgg                                           23

SEQ ID NO: 15          moltype = RNA  length = 24
FEATURE                Location/Qualifiers
source                 1..24
                       mol_type = other RNA
                       organism = synthetic construct
SEQUENCE: 15
nagaaatccg tctttcattg acgg                                          24

SEQ ID NO: 16          moltype = RNA  length = 24
FEATURE                Location/Qualifiers
source                 1..24
                       mol_type = other RNA
                       organism = synthetic construct
SEQUENCE: 16
nagaaatgtg tccccagttg acac                                          24

SEQ ID NO: 17          moltype = RNA  length = 24
FEATURE                Location/Qualifiers
source                 1..24
                       mol_type = other RNA
                       organism = synthetic construct
SEQUENCE: 17
nagaaatccg tccttagttg acgg                                          24

SEQ ID NO: 18          moltype = RNA  length = 23
FEATURE                Location/Qualifiers
source                 1..23
                       mol_type = other RNA
                       organism = synthetic construct
SEQUENCE: 18
nagacatgtg tccccagtga cac                                           23

SEQ ID NO: 19          moltype = RNA  length = 24
FEATURE                Location/Qualifiers
source                 1..24
                       mol_type = other RNA
                       organism = synthetic construct
SEQUENCE: 19
nagaaatgtt tccccagttg aaac                                          24

SEQ ID NO: 20          moltype = RNA  length = 24
FEATURE                Location/Qualifiers
source                 1..24
                       mol_type = other RNA
                       organism = synthetic construct
SEQUENCE: 20
nagaaatgtg ttcccagtta acac                                          24

SEQ ID NO: 21          moltype = RNA  length = 24
FEATURE                Location/Qualifiers
source                 1..24
                       mol_type = other RNA
                       organism = synthetic construct
SEQUENCE: 21
nagaaatttg tccccagttg acaa                                          24

SEQ ID NO: 22          moltype = RNA  length = 24
FEATURE                Location/Qualifiers
source                 1..24
                       mol_type = other RNA
                       organism = synthetic construct
SEQUENCE: 22
nagaaatccg tcctacgttg acgg                                          24

SEQ ID NO: 23          moltype = AA  length = 167
FEATURE                Location/Qualifiers
source                 1..167
                       mol_type = protein
                       organism = synthetic construct
```

```
SEQUENCE: 23
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTD                167

SEQ ID NO: 24          moltype = AA  length = 178
FEATURE                Location/Qualifiers
source                 1..178
                       mol_type = protein
                       organism = synthetic construct
SEQUENCE: 24
MRRAFITGVF FLSEVEFSHE YWMRHALTLA KRAWDEREVP VGAVLVHNNR VIGEGWNRPI  60
GRHDPTAHAE IMALRQGGLV MQNYRLIDAT LYVTLEPCVM CAGAMIHSRI GRVVFGARDA  120
KTGAAGSLMD VLHHPGMNHR VEITEGILAD ECAALLSDFF RMRRQEIKAQ KKAQSSTD    178

SEQ ID NO: 25          moltype = AA  length = 160
FEATURE                Location/Qualifiers
source                 1..160
                       mol_type = protein
                       organism = synthetic construct
SEQUENCE: 25
MGSHMTNDIY FMTLAIEEAK KAAQLGEVPI GAIITKDDEV IARAHNLRET LQQPTAHAEH  60
IAIERAAKVL GSWRLEGCTL YVTLEPCVMC AGTIVMSRIP RVVYGADDPK GGCSGSLMNL  120
LQQSNFNHRA IVDKGVLKEA CSTLLTTFFK NLRANKKSTN                        160

SEQ ID NO: 26          moltype = AA  length = 161
FEATURE                Location/Qualifiers
source                 1..161
                       mol_type = protein
                       organism = synthetic construct
SEQUENCE: 26
MTQDELYMKE AIKEAKKAEE KGEVPIGAVL VINGEIIARA HNLRETEQRS IAHAEMLVID  60
EACKALGTWR LEGATLYVTL EPCPMCAGAV VLSRVEKVVF GAFDPKGGCS GTLMNLLQEE  120
RFNHQAEVVS GVLEEECGGM LSAFFRELRK KKKAARKNLS E                      161

SEQ ID NO: 27          moltype = AA  length = 183
FEATURE                Location/Qualifiers
source                 1..183
                       mol_type = protein
                       organism = synthetic construct
SEQUENCE: 27
MPPAFITGVT SLSDVELDHE YWMRHALTLA KRAWDEREVP VGAVLVHNHR VIGEGWNRPI  60
GRHDPTAHAE IMALRQGGLV LQNYRLLDTT LYVTLEPCVM CAGAMVHSRI GRVVFGARDA  120
KTGAAGSLID VLHHPGMNHR VEIIEGVLRD ECATLLSDFF RMRRQEIKAL KKADRAEGAG  180
PAV                                                                183

SEQ ID NO: 28          moltype = AA  length = 164
FEATURE                Location/Qualifiers
source                 1..164
                       mol_type = protein
                       organism = synthetic construct
SEQUENCE: 28
MDEYWMQVAM QMAEKAEAAG EVPVGAVLVK DGQQIATGYN LSISQHDPTA HAEILCLRSA  60
GKKLENYRLL DATLYITLEP CAMCAGAMVH SRIARVVYGA RDEKTGAAGT VVNLLQHPAF  120
NHQVEVTSGV LAEACSAQLS RFFKRRRDEK KALKLAQRAQ QGIE                   164

SEQ ID NO: 29          moltype = AA  length = 173
FEATURE                Location/Qualifiers
source                 1..173
                       mol_type = protein
                       organism = synthetic construct
SEQUENCE: 29
MDAAKVRSEF DEKMMRYALE LADKAEALGE IPVGAVLVDD ARNIIGEGWN LSIVQSDPTA  60
HAEIIALRNG AKNIQNYRLL NSTLYVTLEP CTMCAGAILH SRIKRLVFGA SDYKTGAIGS  120
RFHFFDDYKM NHTLEITSGV LAEECSQKLS TFFQKRREEK KIEKALLKSL SDK          173

SEQ ID NO: 30          moltype = AA  length = 161
FEATURE                Location/Qualifiers
source                 1..161
                       mol_type = protein
                       organism = synthetic construct
SEQUENCE: 30
MRTDESEDQD HRMMRLALDA ARAAAEAGET PVGAVILDPS TGEVIATAGN GPIAAHDPTA  60
HAEIAAMRAA AAKLGNYRLT DLTLVVTLEP CAMCAGAISH ARIGRVVFGA DDPKGGAVVH  120
GPKFFAQPTC HWRPEVTGGV LADESADLLR GFFRARRKAK I                      161

SEQ ID NO: 31          moltype = AA  length = 179
FEATURE                Location/Qualifiers
source                 1..179
```

```
                        mol_type = protein
                        organism = synthetic construct
SEQUENCE: 31
MSSLKKTPIR DDAYWMGKAI REAAKAAARD EVPIGAVIVR DGAVIGRGHN LREGSNDPSA  60
HAEMIAIRQA ARRSANWRLT GATLYVTLEP CLMCMGAIIL ARLERVVFGC YDPKGGAAGS  120
LYDLSADPRL NHQVRLSPGV CQEECGTMLS DFFRDLRRRK KAKATPALFI DERKVPPEP   179

SEQ ID NO: 32           moltype = AA  length = 198
FEATURE                 Location/Qualifiers
source                  1..198
                        mol_type = protein
                        organism = synthetic construct
SEQUENCE: 32
MDSLLMNRRK FLYQFKNVRW AKGRRETYLC YVVKRRDSAT SFSLDFGYLR NKNGCHVELL  60
FLRYISDWDL DPGRCYRVTW FTSWSPCYDC ARHVADFLRG NPNLSLRIFT ARLYFCEDRK  120
AEPEGLRRLH RAGVQIAIMT FKDYFYCWNT FVENHERTFK AWEGLHENSV RLSRQLRRIL  180
LPLYEVDDLR DAFRTLGL                                               198

SEQ ID NO: 33           moltype = AA  length = 188
FEATURE                 Location/Qualifiers
source                  1..188
                        mol_type = protein
                        organism = synthetic construct
SEQUENCE: 33
MDSLLMNRRK FLYQFKNVRW AKGRRETYLC YVVKRRDSAT SFSLDFGYLR NKNGCHVELL  60
FLRYISDWDL DPGRCYRVTW FTSWSPCYDC ARHVADFLRG NPNLSLRIFT ARLYFCEDRK  120
AEPEGLRRLH RAGVQIAIMT FKENHERTFK AWEGLHENSV RLSRQLRRIL LPLYEVDDLR  180
DAFRTLGL                                                          188

SEQ ID NO: 34           moltype = AA  length = 198
FEATURE                 Location/Qualifiers
source                  1..198
                        mol_type = protein
                        organism = synthetic construct
SEQUENCE: 34
MDSLLMNRRK FLYQFKNVRW AKGRRETYLC YVVKRRDSAT SFSLDFGYLR NKNGCHVELL  60
FLRYISDWDL DPGRCYRVTW FTSWSPCYDC ARHVADFLRG NPNLSLRIFT ARLYFCEDRK  120
AEPEGLRRLH RAGVQIAIMT FKDYFYCWNT FVENHERTFK AWEGLHENSV RLSRQLRRIL  180
LPLYEVDDLR DAFRTLGL                                               198

SEQ ID NO: 35           moltype = AA  length = 7
FEATURE                 Location/Qualifiers
source                  1..7
                        mol_type = protein
                        organism = synthetic construct
SEQUENCE: 35
PKKKRKV                                                           7

SEQ ID NO: 36           moltype = AA  length = 16
FEATURE                 Location/Qualifiers
source                  1..16
                        mol_type = protein
                        organism = synthetic construct
SEQUENCE: 36
KRPAATKKAG QAKKKK                                                 16

SEQ ID NO: 37           moltype = AA  length = 9
FEATURE                 Location/Qualifiers
source                  1..9
                        mol_type = protein
                        organism = synthetic construct
SEQUENCE: 37
PAAKRVKLD                                                         9

SEQ ID NO: 38           moltype = AA  length = 11
FEATURE                 Location/Qualifiers
source                  1..11
                        mol_type = protein
                        organism = synthetic construct
SEQUENCE: 38
RQRRNELKRS P                                                      11

SEQ ID NO: 39           moltype = AA  length = 38
FEATURE                 Location/Qualifiers
source                  1..38
                        mol_type = protein
                        organism = synthetic construct
SEQUENCE: 39
NQSSNFGPMK GGNFGGRSSG PYGGGGQYFA KPRNQGGY                         38
```

```
SEQ ID NO: 40           moltype = AA  length = 42
FEATURE                 Location/Qualifiers
source                  1..42
                        mol_type = protein
                        organism = synthetic construct
SEQUENCE: 40
RMRIZFKNKG KDTAELRRRR VEVSVELRKA KKDEQILKRR NV                  42

SEQ ID NO: 41           moltype = AA  length = 8
FEATURE                 Location/Qualifiers
source                  1..8
                        mol_type = protein
                        organism = synthetic construct
SEQUENCE: 41
VSRKRPRP                                                        8

SEQ ID NO: 42           moltype = AA  length = 8
FEATURE                 Location/Qualifiers
source                  1..8
                        mol_type = protein
                        organism = synthetic construct
SEQUENCE: 42
PPKKARED                                                        8

SEQ ID NO: 43           moltype = AA  length = 8
FEATURE                 Location/Qualifiers
source                  1..8
                        mol_type = protein
                        organism = synthetic construct
SEQUENCE: 43
PQPKKKPL                                                        8

SEQ ID NO: 44           moltype = AA  length = 12
FEATURE                 Location/Qualifiers
source                  1..12
                        mol_type = protein
                        organism = synthetic construct
SEQUENCE: 44
SALIKKKKKM AP                                                   12

SEQ ID NO: 45           moltype = AA  length = 5
FEATURE                 Location/Qualifiers
source                  1..5
                        mol_type = protein
                        organism = synthetic construct
SEQUENCE: 45
DRLRR                                                           5

SEQ ID NO: 46           moltype = AA  length = 7
FEATURE                 Location/Qualifiers
source                  1..7
                        mol_type = protein
                        organism = synthetic construct
SEQUENCE: 46
PKQKKRK                                                         7

SEQ ID NO: 47           moltype = AA  length = 10
FEATURE                 Location/Qualifiers
source                  1..10
                        mol_type = protein
                        organism = synthetic construct
SEQUENCE: 47
RKLKKKIKKL                                                      10

SEQ ID NO: 48           moltype = AA  length = 10
FEATURE                 Location/Qualifiers
source                  1..10
                        mol_type = protein
                        organism = synthetic construct
SEQUENCE: 48
REKKKFLKRR                                                      10

SEQ ID NO: 49           moltype = AA  length = 20
FEATURE                 Location/Qualifiers
source                  1..20
                        mol_type = protein
                        organism = synthetic construct
SEQUENCE: 49
```

```
KRKGDEVDGV DEVAKKKSKK                                             20

SEQ ID NO: 50           moltype = AA  length = 17
FEATURE                 Location/Qualifiers
source                  1..17
                        mol_type = protein
                        organism = synthetic construct
SEQUENCE: 50
RKCLQAGMNL EARKTKK                                                17

SEQ ID NO: 51           moltype = AA  length = 5
FEATURE                 Location/Qualifiers
source                  1..5
                        mol_type = protein
                        organism = synthetic construct
SEQUENCE: 51
GGSGG                                                             5

SEQ ID NO: 52           moltype = AA  length = 5
FEATURE                 Location/Qualifiers
source                  1..5
                        mol_type = protein
                        organism = synthetic construct
SEQUENCE: 52
GSGSG                                                             5

SEQ ID NO: 53           moltype = AA  length = 5
FEATURE                 Location/Qualifiers
source                  1..5
                        mol_type = protein
                        organism = synthetic construct
SEQUENCE: 53
GSGGG                                                             5

SEQ ID NO: 54           moltype = AA  length = 5
FEATURE                 Location/Qualifiers
source                  1..5
                        mol_type = protein
                        organism = synthetic construct
SEQUENCE: 54
GGGSG                                                             5

SEQ ID NO: 55           moltype = AA  length = 5
FEATURE                 Location/Qualifiers
source                  1..5
                        mol_type = protein
                        organism = synthetic construct
SEQUENCE: 55
GSSSG                                                             5

SEQ ID NO: 56           moltype = AA  length = 8
FEATURE                 Location/Qualifiers
source                  1..8
                        mol_type = protein
                        organism = synthetic construct
SEQUENCE: 56
SGGSSGGS                                                          8

SEQ ID NO: 57           moltype = AA  length = 16
FEATURE                 Location/Qualifiers
source                  1..16
                        mol_type = protein
                        organism = synthetic construct
SEQUENCE: 57
SGSETPGTSE SATPES                                                 16

SEQ ID NO: 58           moltype = AA  length = 24
FEATURE                 Location/Qualifiers
source                  1..24
                        mol_type = protein
                        organism = synthetic construct
SEQUENCE: 58
SGGSSGSETP GTSESATPES SGGS                                        24

SEQ ID NO: 59           moltype = DNA  length = 3132
FEATURE                 Location/Qualifiers
source                  1..3132
                        mol_type = other DNA
                        organism = synthetic construct
```

```
SEQUENCE: 59
atgagcagcg ccatcaagag ctacaagagc gtgctgcgcc ccaacgagcg caagaaccag  60
ctgctgaaga gcaccatcca gtgcctggag gacggcagcg ccttcttctt caagatgctg  120
cagggcctgt tcggcggcat cacccccgag atcgtgcgct tcagcaccga gcaggagaag  180
cagcagcagg acatcgccct gtggtgcgcc gtgaactggt tccgccccgt gagccaggac  240
agcctgaccc acaccatcgc cagcgacaac ctggtggaga agttcgagga gtactacggc  300
ggcaccgcca gcgacgccat caagcagtac ttcagcgcca gcatcggcga gagctactac  360
tggaacgact gccgccagca gtactacgac ctgtgccgcg agctgggcgt ggaggtgagc  420
gacctgaccc acgacctgga gatcctgtgc cgcgagaagt gcctggccgt ggccaccgag  480
agcaaccagt acaacagcat catcagcgtg ctgttcggca ccggcagaaa ggaggaccgc  540
agcgtgaagc tgcgcatcac caagaagatc ctggaggcca tcagcaacct gaaggagatc  600
cccaagaacg tggcccccat ccaggagatc atcctgaacg tggccaaggc caccaaggag  660
accttccgcc aggtgtacgc cggcaacctg ggcgccccca gcaccctgga gagattcatc  720
gccaaggacg gccagaagga gttcgacctg aagaagctgc agaccgacct gaagaaggtg  780
atccgcggca agagcaagga gcgcgactgg tgctgccagg aggagctgcg cagctacgtg  840
gagcagaaca ccatccagta cgacctgtgg gcctggggcg agatgttcaa caaggcccac  900
accgccctga agatcaagag cacccgcaac tacaacttcg ccaagcagcg cctggagcag  960
ttcaagagaa tccagagcct gaacaacctg ctggtggtga agaagctgaa cgacttcttc  1020
gacagcgagt tcttcagcgg cgaggagacc tacaccatct gcgtgcacca cctgggcggc  1080
aagagactga gcaagctgta caaggcctgg gaggacgacc ccgccgaccc cgagaacgcc  1140
atcgtggtgc tgtgcgacga cctgaagaac aacttcaaga aggagcccat ccgcaacatc  1200
ctgcgctaca tcttcaccat ccgccaggag tgcagcgccc aggacatcct ggccgccgcc  1260
aagtacaacc agcagctgga ccgctacaag agccagaagg ccaaccccag cgtgctgggc  1320
aaccagggct tcacctggag aaacgccgtg atcctgcccg agaaggccca gcgcaacgac  1380
cgccccaaca gcctggacct gcgcatctgg ctgtacctga agctgcgcca ccccgacggc  1440
cgctggaaga agcaccacat cccettctac gacacccgct tcttccagga gatctacgcc  1500
gccggcaaca gccccgtgga cacctgccag ttccgcaccc cccgcttcgg ctaccacctg  1560
cccaagctga ccgaccagac cgccatccgc gtgaacaaga agcacgtgaa ggccgccaag  1620
accgaggccc gcatccgcct ggccatccag cagggcaccc tgcccgtgag caacctgaag  1680
atcaccagaa tcagcgccac catcaacagc aagggccagg tgcgcatccc cgtgaagttc  1740
gacgtgggcc gccagaaggg caccctgcag atcggcgacc gcttctgcgg ctacgaccag  1800
aaccagaccg ccagccacgc ctacagcctg tgggaggtgg tgaaggaggg ccagtaccac  1860
aaggagctgg gctgcttcgt gcgcttcatc agcagcggcg acatcgtgag catcaccgag  1920
aaccgcggca accagttcga ccagctgagc tacgagggcc tggcctaccc ccagtacgcc  1980
gactggcgca agaaggccag caagttcgtg agcctgtggc agatcaccaa gaagaacaag  2040
aagaaggaga tcgtgaccgt ggaggccaag gagaagttcg acgccatctg caagtaccag  2100
ccccgcctgt acaagttcaa caaggagtac gcctacctgc tgcgcgacat cgtgcgcggc  2160
aagagcctgg tggagctgca gcagatccgc caggagatct tccgcttcat cgagcaggac  2220
tgcggcgtga cccgcctggg cagcctgagc ctgagcaccc tggagaccgt gaaggccgtg  2280
aagggcatca tctacagcta cttcagcacc gccctgaacg ccagcaagaa caaccccatc  2340
agcgacgagc agcgcaagga gttcgacccc gagctgttcg ccctgctgga gaagctggag  2400
ctgatccgca cccgcaagaa gaagcagaag gtggagcgca tcgccaacag cctgatccag  2460
acctgcctgg agaacaacat caagttcatc cgcggcgagg gcgacctgag caccaccaac  2520
aacgccacca agaagaaggc caacagccgc agcatggact ggctggcccg cggcgtgttc  2580
aacaagatcc gccagctggc ccccatgcac aacatcaccc tgttcggctg cggcagcctg  2640
tacaccagcc accaggaccc cctggtgcac cgcaaccccg acaaggccat gaggg caagg  2700
ttcgaggagg tcaacgtgga gaatatcgcc gagtggcatg ttagaaactt ctcaaattat  2760
ctccgcgctg acagcgggac aggcctctat tacaagcagg caaccatgga ctttctgaag  2820
cactatggac tggaggagca cgcagagggg ctggaaaata agaaaatcaa gttctatgac  2880
tttcggaaga ttctggaaga taaaaatctg accagcgtaa tcatacccaa gcgagggggg  2940
cgcatctata tggccaccaa cccagtaacc tccgactcaa caccgataac ctacgccggg  3000
aaaacataca atagatgcaa cgccgatcac gtggccgccg ccaacatcgc cctgaccgtg  3060
aagggcatcg gcgagcagag cagcgacgag gagaaccccg acggcagccg catcaagctg  3120
cagctgacca gc                                                      3132
```

```
SEQ ID NO: 60          moltype = DNA  length = 3132
FEATURE                Location/Qualifiers
source                 1..3132
                       mol_type = other DNA
                       organism = synthetic construct
SEQUENCE: 60
atgagcagcg ccatcaagag ctacaagagc gtgctgcgcc ccaacgagcg caagaaccag  60
ctgctgaaga gcaccatcca gtgcctggag gacggcagcg ccttcttctt caagatgctg  120
cagggcctgt tcggcggcat cacccccgag atcgtgcgct tcagcaccga gcaggagaag  180
cagcagcagg acatcgccct gtggtgcgcc gtgaactggt tccgccccgt gagccaggac  240
agcctgaccc acaccatcgc cagcgacaac ctggtggaga agttcgagga gtactacggc  300
ggcaccgcca gcgacgccat caagcagtac ttcagcgcca gcatcggcga gagctactac  360
tggaacgact gccgccagca gtactacgac ctgtgccgcg agctgggcgt ggaggtgagc  420
gacctgaccc acgacctgga gatcctgtgc cgcgagaagt gcctggccgt ggccaccgag  480
agcaaccagt acaacagcat catcagcgtg ctgttcggca ccggcagaaa ggaggaccgc  540
agcgtgaagc tgcgcatcac caagaagatc ctggaggcca tcagcaacct gaaggagatc  600
cccaagaacg tggcccccat ccaggagatc atcctgaacg tggccaaggc caccaaggag  660
accttccgcc aggtgtacgc cggcaacctg ggcgccccca gcaccctgga gagattcatc  720
gccaaggacg gccagaagga gttcgacctg aagaagctgc agaccgacct gaagaaggtg  780
atccgcggca agagcaagga gcgcgactgg tgctgccagg aggagctgcg cagctacgtg  840
gagcagaaca ccatccagta cgacctgtgg gcctggggcg agatgttcaa caaggcccac  900
accgccctga agatcaagag cacccgcaac tacaacttcg ccaagcagcg cctggagcag  960
ttcaagagaa tccagagcct gaacaacctg ctggtggtga agaagctgaa cgacttcttc  1020
gacagcgagt tcttcagcgg cgaggagacc tacaccatct gcgtgcacca cctgggcggc  1080
```

```
aagagactga gcaagctgta caaggcctgg gaggacgacc ccgccgaccc cgagaacgcc  1140
atcgtggtgc tgtgcgacga cctgaagaac aacttcaaga aggagcccat ccgcaacatc  1200
ctgcgctaca tcttcaccat ccgccaggag tgcagcgccc aggacatcct ggccgccgcc  1260
aagtacaacc agcagctgga ccgctacaag agccagaagg ccaaccccag cgtgctgggc  1320
aaccagggct tcacctggag aaacgccgtg atcctgcccg agaaggccca gcgcaacgac  1380
cgccccaaca gcctggacct gcgcatctgg ctgtacctga agctgcgcca ccccgacggc  1440
cgctggaaga agcaccacat cccccttctac gacacccgct tcttccagga gatctacgcc  1500
gccggcaaca gccccgtgga cacctgccag ttccgcaccc cccgcttcgg ctaccacctg  1560
cccaagctga ccgaccagac cgccatccgc gtgaacaaga agcacgtgaa ggccgccaag  1620
accgaggccc gcatccgcct ggccatccag cagggcaccc tgcccgtgag caacctgaag  1680
atcaccagaa tcagcgccac catcaacagc aagggccagg tgcgcatccc cgtgaagttc  1740
gacgtgggcc gccagaaggg caccctgcag atcggcgacc gcttctgcgg ctacgaccag  1800
aaccagaccg ccagccacgc ctacagcctg tgggaggtgg tgaaggaggg ccagtaccac  1860
aaggagctgg gctgcttcgt gcgcttcatc agcagcggcg acatcgtgag catcaccgag  1920
aaccgcggca accagttcga ccagctgagc tacgagggcc tggcctaccc ccagtacgcc  1980
gactggcgca agaaggccag caagttcgtg agcctgtggc agatcaccaa gaagaacaag  2040
aagaaggaga tcgtgaccgt ggaggccaag gagaagttcg acgccatctg caagtaccag  2100
ccccgcctgt acaagttcaa caaggagtac gcctacctgc tgcgcgacat cgtgcgcggc  2160
aagagcctgg tggagctgca gcagatccgc caggagatct tccgcttcat cgagcaggac  2220
tgcggcgtga cccgcctggg cagcctgagc ctgagcaccc tggagaccgt gaaggccgtg  2280
aagggcatca tctacagcta cttcagcacc gccctgaacg ccagcaagaa caaccccatc  2340
agcgacgagc agcgcaagga gttcgacccc gagctgttcg ccctgctgga gaagctggag  2400
ctgatccgca cccgcaagaa gaagcagaag gtggagcgca tcgccaacag cctgatccag  2460
acctgcctgg agaacaacat caagttcatc cgcggcgagg gcgacctgag caccaccaac  2520
aacgccacca agaagaaggc caacagccgc agcatggact ggctggcccg cggcgtgttc  2580
aacaagatcc gccagctggc ccccatgcac aacatcaccc tgttcggctg cggcagcctg  2640
tacaccagcc accaggaccc cctggtgcac cgcaaccccg acaaggccat gagagcccgg  2700
tttgaggaag tgaatgttag caacgtgtct gaatggcata tgagaaactt tagcaattat  2760
ttgagagccg atagcggcac tggtttgtat tacaagcagg ccaccttgga ttttctgaag  2820
cactacgacc ttgaggaaca cgcagatgac ttggagaaac agaacataaa attctacgat  2880
ttccggaaaa ttttggaaga taaacaactg acctccgtca tcgttccaaa gcggggaggg  2940
aggatctata tggccactaa ccctgtgacg tccgatagta cccctgtgac ctacgcagga  3000
aagacataca accggtgcaa tgccgatcac gtggccgccg ccaacatcgc cctgaccgtg  3060
aagggcatcg gcgagcagag cagcgacgag gagaaccccg acggcagccg catcaagctg  3120
cagctgacca gc                                                      3132

SEQ ID NO: 61           moltype = DNA  length = 3162
FEATURE                 Location/Qualifiers
source                  1..3162
                        mol_type = other DNA
                        organism = synthetic construct
SEQUENCE: 61
atgagcagcg ccatcaagag ctacaagagc gtgctgcgcc ccaacgagcg caagaaccag  60
ctgctgaaga gcaccatcca gtgcctggag gacggcagcg ccttcttctt caagatgctg  120
cagggcctgt tcggcggcat cacccccgag atcgtgcgct tcagcaccga gcaggagaag  180
cagcagcagg acatcgccct gtggtgcgcc gtgaactggt tccgccccgt gagccaggac  240
agcctgaccc acaccatcgc cagcgacaac ctggtggaga agttcgagga gtactacggc  300
ggcaccgcca gcgacgccat caagcagtac ttcagcgcca gcatcggcga gagctactac  360
tggaacgact gccgccagca gtactacgac ctgtgccgcg agctgggcgt ggaggtgagc  420
gacctgaccc acgacctgga gatcctgtgc cgcgagaagt gcctggccgt ggccaccgag  480
agcaaccagt acaacagcat catcagcgtg ctgttcggca ccggcagaaa ggaggaccgc  540
agcgtgaagc tgcgcatcac caagaagatc ctggaggcca tcagcaacct gaaggagatc  600
cccaagaacg tggcccccat ccaggagatc atcctgaacg tggccaaggc caccaaggag  660
accttccgcc aggtgtacgc cggcaacctg ggcgccccca gcaccctgga gagattcatc  720
gccaaggacg gccagaagga gttcgacctg aagaagctgc agaccgacct gaagaaggtg  780
atccgcggca agagcaagga gcgcgactgg tgctgccagg aggagctgcg cagctacgtg  840
gagcagaaca ccatccagta cgacctgtgg gcctggggcg agatgttcaa caaggcccac  900
accgccctga agatcaagag cacccgcaac tacaacttcg ccaagcagcg cctggagcag  960
ttcaagagaa tccagagcct gaacaacctg ctggtggtga agaagctgaa cgacttcttc  1020
gacagcgagt tcttcagcgg cgaggagacc tacaccatct gcgtgcacca cctgggcggc  1080
aagagactga gcaagctgta caaggcctgg gaggacgacc ccgccgaccc cgagaacgcc  1140
atcgtggtgc tgtgcgacga cctgaagaac aacttcaaga aggagcccat ccgcaacatc  1200
ctgcgctaca tcttcaccat ccgccaggag tgcagcgccc aggacatcct ggccgccgcc  1260
aagtacaacc agcagctgga ccgctacaag agccagaagg ccaaccccag cgtgctgggc  1320
aaccagggct tcacctggag aaacgccgtg atcctgcccg agaaggccca gcgcaacgac  1380
cgccccaaca gcctggacct gcgcatctgg ctgtacctga agctgcgcca ccccgacggc  1440
cgctggaaga agcaccacat cccccttctac gacacccgct tcttccagga gatctacgcc  1500
gccggcaaca gccccgtgga cacctgccag ttccgcaccc cccgcttcgg ctaccacctg  1560
cccaagctga ccgaccagac cgccatccgc gtgaacaaga agcacgtgaa ggccgccaag  1620
accgaggccc gcatccgcct ggccatccag cagggcaccc tgcccgtgag caacctgaag  1680
atcaccagaa tcagcgccac catcaacagc aagggccagg tgcgcatccc cgtgaagttc  1740
gacgtgggcc gccagaaggg caccctgcag atcggcgacc gcttctgcgg ctacgaccag  1800
aaccagaccg ccagccacgc ctacagcctg tgggaggtgg tgaaggaggg ccagtaccac  1860
aaggagctgg gctgcttcgt gcgcttcatc agcagcggcg acatcgtgag catcaccgag  1920
aaccgcggca accagttcga ccagctgagc tacgagggcc tggcctaccc ccagtacgcc  1980
gactggcgca agaaggccag caagttcgtg agcctgtggc agatcaccaa gaagaacaag  2040
aagaaggaga tcgtgaccgt ggaggccaag gagaagttcg acgccatctg caagtaccag  2100
ccccgcctgt acaagttcaa caaggagtac gcctacctgc tgcgcgacat cgtgcgcggc  2160
aagagcctgg tggagctgca gcagatccgc caggagatct tccgcttcat cgagcaggac  2220
```

```
tgcggcgtga cccgcctggg cagcctgagc ctgagcaccc tggagaccgt gaaggccgtg  2280
aagggcatca tctacagcta cttcagcacc gccctgaacg ccagcaagaa caaccccatc  2340
agcgacgagc agcgcaagga gttcgacccc gagctgttcg ccctgctgga gaagctggag  2400
ctgatccgca cccgcaagaa gaagcagaag gtggagcgca tcgccaacag cctgatccag  2460
acctgcctgg agaacaacat caagttcatc cgcggcgagg gcgacctgag caccaccaac  2520
aacgccacca agaagaaggc caacagccgc agcatggact ggctggcccg cggcgtgttc  2580
aacaagatcc gccagctggc ccccatgcac aacatcaccc tgttcggctg cggcagcctg  2640
tacaccagcc accaggaccc cctggtgcac cgcaaccccg acaagtcttt tagagctaga  2700
tgggacctgg tgaaggttaa ggattttgga gagaaacatc tcctcacact gagcaggaat  2760
ctgactggaa agggaccagg cacccgcaag tactaccacc agggagttga ggactttctg  2820
aaggagtatg agctggagga cctgaaggaa gagctggcca agattaagaa aggcgaccca  2880
aacgccctcc ctcctgaggt gataagaaat aaactgaaag aaaagctggg aaacgagaac  2940
gcaccagttc tgatacctaa gcgcggtgga aagtactttc tgtcaaccca taacgtggca  3000
actggcgcag tgaaaatcac attcaacaat aaagaaaggt atctgtgcaa cgccgatcac  3060
gtggccgccg ccaacatcgc cctgaccgtg aagggcatcg gcgagcagag cagcgacgag  3120
gagaaccccg acggcagccg catcaagctg cagctgacca gc                    3162
```

```
SEQ ID NO: 62          moltype = DNA  length = 3162
FEATURE                Location/Qualifiers
source                 1..3162
                       mol_type = other DNA
                       organism = synthetic construct
SEQUENCE: 62
atgagcagcg ccatcaagag ctacaagagc gtgctgcgcc ccaacgagcg caagaaccag  60
ctgctgaaga gcaccatcca gtgcctggag gacggcagcg ccttcttctt caagatgctg  120
cagggcctgt tcggcggcat cacccccgag atcgtgcgct tcagcaccga gcaggagaag  180
cagcagcagg acatcgccct gtggtgcgcc gtgaactggt tccgccccgt gagccaggac  240
agcctgaccc acaccatcgc cagcgacaac ctggtggaga agttcgagga gtactacggc  300
ggcaccgcca gcgacgccat caagcagtac ttcagcgcca gcatcggcga gagctactac  360
tggaacgact gccgccagca gtactacgac ctgtgccgcg agctgggcgt ggaggtgagc  420
gacctgaccc acgacctgga gatcctgtgc cgcgagaagt gcctggccgt ggccaccgag  480
agcaaccagt acaacagcat catcagcgtg ctgttcggca ccggcagaaa ggaggaccgc  540
agcgtgaagc tgcgcatcac caagaagatc ctggaggcca tcagcaacct gaaggagatc  600
cccaagaacg tggcccccat ccaggagatc atcctgaacg tggccaaggc caccaaggag  660
accttccgcc aggtgtacgc cggcaacctg ggcgccccca gcaccctgga gagattcatc  720
gccaaggacg gccagaagga gttcgacctg aagaagctgc agaccgacct gaagaaggtg  780
atccgcggca agagcaagga gcgcgactgg tgctgccagg aggagctgcg cagctacgtg  840
gagcagaaca ccatccagta cgacctgtgg gcctggggcg agatgttcaa caaggcccac  900
accgccctga agatcaagag cacccgcaac tacaacttcg ccaagcagcg cctggagcag  960
ttcaagagaa tccagagcct gaacaacctg ctggtggtga agaagctgaa cgacttcttc  1020
gacagcgagt tcttcagcgg cgaggagacc tacaccatct gcgtgcacca cctgggcggc  1080
aagagactga gcaagctgta caaggcctgg gaggacgacc ccgccgaccc cgagaacgcc  1140
atcgtggtgc tgtgcgacga cctgaagaac aacttcaaga aggagcccat ccgcaacatc  1200
ctgcgctaca tcttcaccat ccgccaggag tgcagcgccc aggacatcct ggccgccgcc  1260
aagtacaacc agcagctgga ccgctacaag agccagaagg ccaaccccag cgtgctgggc  1320
aaccagggct tcacctggag aaacgccgtg atcctgcccg agaaggccca gcgcaacgac  1380
cgccccaaca gcctggacct gcgcatctgg ctgtacctga agctgcgcca ccccgacggc  1440
cgctggaaga agcaccacat ccccttctac gacacccgct tcttccagga gatctacgcc  1500
gccggcaaca gccccgtgga cacctgccag ttccgcaccc cccgcttcgg ctaccacctg  1560
cccaagctga ccgaccagac cgccatccgc gtgaacaaga agcacgtgaa ggccgccaag  1620
accgaggccc gcatccgcct ggccatccag cagggcaccc tgcccgtgag caacctgaag  1680
atcaccagaa tcagcgccac catcaacagc aagggccagg tgcgcatccc cgtgaagttc  1740
gacgtgggcc gccagaaggg caccctgcag atcggcgacc gcttctgcgg ctacgaccag  1800
aaccagaccg ccagccacgc ctacagcctg tgggaggtgg tgaaggaggg ccagtaccac  1860
aaggagctgg gctgcttcgt gcgcttcatc agcagcggcg acatcgtgag catcaccgag  1920
aaccgcggca accagttcga ccagctgagc tacgagggcc tggcctaccc ccagtacgcc  1980
gactggcgca agaaggccag caagttcgtg agcctgtggc agatcaccaa gaagaacaag  2040
aagaaggaga tcgtgaccgt ggaggccaag gagaagttcg acgccatctg caagtaccag  2100
ccccgcctgt acaagttcaa caaggagtac gcctacctgc tgcgcgacat cgtgcgcggc  2160
aagagcctgg tggagctgca gcagatccgc caggagatct tccgcttcat cgagcaggac  2220
tgcggcgtga cccgcctggg cagcctgagc ctgagcaccc tggagaccgt gaaggccgtg  2280
aagggcatca tctacagcta cttcagcacc gccctgaacg ccagcaagaa caaccccatc  2340
agcgacgagc agcgcaagga gttcgacccc gagctgttcg ccctgctgga gaagctggag  2400
ctgatccgca cccgcaagaa gaagcagaag gtggagcgca tcgccaacag cctgatccag  2460
acctgcctgg agaacaacat caagttcatc cgcggcgagg gcgacctgag caccaccaac  2520
aacgccacca agaagaaggc caacagccgc agcatggact ggctggcccg cggcgtgttc  2580
aacaagatcc gccagctggc ccccatgcac aacatcaccc tgttcggctg cggcagcctg  2640
tacaccagcc accaggaccc cctggtgcac cgcaaccccg acaagtcttt tagagctaga  2700
tggagactcg tgaaggtcaa ggacataggt gagaaggagc tgctcaccct ctccagaaac  2760
ctgagaggga aagggaaggg aataaagaag tactatcatc agggagtgct cgacttcttc  2820
aaggagtacg agctcgaaga gctggccgga ccactggcca agattaagcc tggtgaccca  2880
aatgctatac cacccgaggt cctgcggaat aaactcaaag agaagctggg aaatgaagat  2940
gcaccagtgc tgattcccgt cgccggaggc ggcatctatc tgagcactca caatgtcgca  3000
acaggcgcca agaagatcac cttcaataac aaagagcggt acgtctgcaa cgccgatcac  3060
gtggccgccg ccaacatcgc cctgaccgtg aagggcatcg gcgagcagag cagcgacgag  3120
gagaaccccg acggcagccg catcaagctg cagctgacca gc                    3162
```

```
SEQ ID NO: 63          moltype = DNA  length = 3162
FEATURE                Location/Qualifiers
```

```
source                1..3162
                      mol_type = other DNA
                      organism = synthetic construct
SEQUENCE: 63
atgagcagcg ccatcaagag ctacaagagc gtgctgcgcc ccaacgagcg caagaaccag  60
ctgctgaaga gcaccatcca gtgcctggag gacggcagcg ccttcttctt caagatgctg  120
cagggcctgt tcggcggcat cacccccgag atcgtgcgct tcagcaccga gcaggagaag  180
cagcagcagg acatcgccct gtggtgcgcc gtgaactggt tccgccccgt gagccaggac  240
agcctgaccc acaccatcgc cagcgacaac ctggtggaga agttcgagga gtactacggc  300
ggcaccgcca gcgacgccat caagcagtac ttcagcgcca gcatcggcga gagctactac  360
tggaacgact gccgccagca gtactacgac ctgtgccgcg agctgggcgt ggaggtgagc  420
gacctgaccc acgacctgga gatcctgtgc cgcgagaagt gcctggccgt ggccaccgag  480
agcaaccagt acaacagcat catcagcgtg ctgttcggca ccggcagaaa ggaggaccgc  540
agcgtgaagc tgcgcatcac caagaagatc ctggaggcca tcagcaacct gaaggagatc  600
cccaagaacg tggcccccat ccaggagatc atcctgaacg tggccaaggc caccaaggag  660
accttccgcc aggtgtacgc cggcaacctg ggcgccccca gcaccctgga gagattcatc  720
gccaaggacg gccagaagga gttcgacctg aagaagctgc agaccgacct gaagaaggtg  780
atccgcggca agagcaagga gcgcgactgg tgctgccagg aggagctgcg cagctacgtg  840
gagcagaaca ccatccagta cgacctgtgg gcctggggcg agatgttcaa caaggcccac  900
accgccctga agatcaagag cacccgcaac tacaacttcg ccaagcagcg cctggagcag  960
ttcaagagaa tccagagcct gaacaacctg ctggtggtga agaagctgaa cgacttcttc  1020
gacagcgagt tcttcagcgg cgaggagacc tacaccatct gcgtgcacca cctgggcggc  1080
aagagactga gcaagctgta caaggcctgg gaggacgacc ccgccgaccc cgagaacgcc  1140
atcgtggtgc tgtgcgacga cctgaagaac aacttcaaga aggagcccat ccgcaacatc  1200
ctgcgctaca tcttcaccat ccgccaggag tgcagcgccc aggacatcct ggccgccgcc  1260
aagtacaacc agcagctgga ccgctacaag agccagaagg ccaaccccag cgtgctgggc  1320
aaccagggct tcacctggag aaacgccgtg atcctgcccg agaaggccca gcgcaacgac  1380
cgccccaaca gcctggacct gcgcatctgg ctgtacctga agctgcgcca ccccgacggc  1440
cgctggaaga agcaccacat ccccttctac gacacccgct tcttccagga gatctacgcc  1500
gccggcaaca gccccgtgga cacctgccag ttccgcaccc cccgcttcgg ctaccacctg  1560
cccaagctga ccgaccagac cgccatccgc gtgaacaaga agcacgtgaa ggccgccaag  1620
accgaggccc gcatccgcct ggccatccag cagggcaccc tgcccgtgag caacctgaag  1680
atcaccagaa tcagcgccac catcaacagc aagggccagg tgcgcatccc cgtgaagttc  1740
gacgtgggcc gccagaaggg caccctgcag atcggcgacc gcttctgcgg ctacgaccag  1800
aaccagaccg ccagccacgc ctacagcctg tgggaggtgg tgaaggaggg ccagtaccac  1860
aaggagctgg gctgcttcgt gcgcttcatc agcagcggcg acatcgtgag catcaccgag  1920
aaccgcggca accagttcga ccagctgagc tacgagggcc tggcctaccc ccagtacgcc  1980
gactggcgca agaaggccag caagttcgtg agcctgtggc agatcaccaa gaagaacaag  2040
aagaaggaga tcgtgaccgt ggaggccaag gagaagttcg acgccatctg caagtaccag  2100
ccccgcctgt acaagttcaa caaggagtac gcctacctgc tgcgcgacat cgtgcgcggc  2160
aagagcctgg tggagctgca gcagatccgc caggagatct tccgcttcat cgagcaggac  2220
tgcggcgtga cccgcctggg cagcctgagc ctgagcaccc tggagaccgt gaaggccgtg  2280
aagggcatca tctacagcta cttcagcacc gccctgaacg ccagcaagaa caaccccatc  2340
agcgacgagc agcgcaagga gttcgacccc gagctgttcg ccctgctgga gaagctggag  2400
ctgatccgca cccgcaagaa gaagcagaag gtggagcgca tcgccaacag cctgatccag  2460
acctgcctgg agaacaacat caagttcatc cgcggcgagg gcgacctgag caccaccaac  2520
aacgccacca agaagaaggc caacagccgc agcatggact ggctggcccg cggcgtgttc  2580
aacaagatcc gccagctggc ccccatgcac aacatcaccc tgttcggctg cggcagcctg  2640
tacaccagcc accaggaccc cctggtgcac cgcaaccccg acaagaagta caatgctcgg  2700
tgggatctgg ttaaagtgaa ggatattggt gagggccatc tcctgattct gtcaagaaac  2760
ctgcgcggca aaggctctgg cattaggaaa tactaccatc agggcgtcct ggagttcttt  2820
aaagagtatg atctggaaga tctggccgaa cctctcgcta aaattagacc cggtgatcca  2880
aacgccatcc ctcctgaagt gctcagagaa cgcctcaagg agaagctcgg caacgaggac  2940
gctcctgttc tcatccctaa gcctggagga ggcgtgtacc tcagcactca taacgtcgcc  3000
accggcgcca agaaaatcac attcaacaac aaggagagat acctgtgcaa cgccgatcac  3060
gtggccgccg ccaacatcgc cctgaccgtg aagggcatcg gcgagcagag cagcgacgag  3120
gagaaccccg acggcagccg catcaagctg cagctgacca gc                    3162

SEQ ID NO: 64         moltype = DNA  length = 3162
FEATURE               Location/Qualifiers
source                1..3162
                      mol_type = other DNA
                      organism = synthetic construct
SEQUENCE: 64
atgagcagcg ccatcaagag ctacaagagc gtgctgcgcc ccaacgagcg caagaaccag  60
ctgctgaaga gcaccatcca gtgcctggag gacggcagcg ccttcttctt caagatgctg  120
cagggcctgt tcggcggcat cacccccgag atcgtgcgct tcagcaccga gcaggagaag  180
cagcagcagg acatcgccct gtggtgcgcc gtgaactggt tccgccccgt gagccaggac  240
agcctgaccc acaccatcgc cagcgacaac ctggtggaga agttcgagga gtactacggc  300
ggcaccgcca gcgacgccat caagcagtac ttcagcgcca gcatcggcga gagctactac  360
tggaacgact gccgccagca gtactacgac ctgtgccgcg agctgggcgt ggaggtgagc  420
gacctgaccc acgacctgga gatcctgtgc cgcgagaagt gcctggccgt ggccaccgag  480
agcaaccagt acaacagcat catcagcgtg ctgttcggca ccggcagaaa ggaggaccgc  540
agcgtgaagc tgcgcatcac caagaagatc ctggaggcca tcagcaacct gaaggagatc  600
cccaagaacg tggcccccat ccaggagatc atcctgaacg tggccaaggc caccaaggag  660
accttccgcc aggtgtacgc cggcaacctg ggcgccccca gcaccctgga gagattcatc  720
gccaaggacg gccagaagga gttcgacctg aagaagctgc agaccgacct gaagaaggtg  780
atccgcggca agagcaagga gcgcgactgg tgctgccagg aggagctgcg cagctacgtg  840
gagcagaaca ccatccagta cgacctgtgg gcctggggcg agatgttcaa caaggcccac  900
```

-continued

```
accgccctga agatcaagag cacccgcaac tacaacttcg ccaagcagcg cctggagcag  960
ttcaagagaa tccagagcct gaacaacctg ctggtggtga agaagctgaa cgacttcttc  1020
gacagcgagt tcttcagcgg cgaggagacc tacaccatct gcgtgcacca cctgggcggc  1080
aagagactga gcaagctgta caaggcctgg gaggacgacc ccgccgaccc cgagaacgcc  1140
atcgtggtgc tgtgcgacga cctgaagaac aacttcaaga aggagcccat ccgcaacatc  1200
ctgcgctaca tcttcaccat ccgccaggag tgcagcgccc aggacatcct ggccgccgcc  1260
aagtacaacc agcagctgga ccgctacaag agccagaagg ccaaccccag cgtgctgggc  1320
aaccagggct tcacctggag aaacgccgtg atcctgcccg agaaggccca gcgcaacgac  1380
cgccccaaca gcctggacct gcgcatctgg ctgtacctga agctgcgcca ccccgacggc  1440
cgctggaaga agcaccacat ccccttctac gacacccgct tcttccagga gatctacgcc  1500
gccggcaaca gccccgtgga cacctgccag ttccgcaccc cccgcttcgg ctaccacctg  1560
cccaagctga ccgaccagac cgccatccgc gtgaacaaga agcacgtgaa ggccgccaag  1620
accgaggccc gcatccgcct ggccatccag cagggcaccc tgcccgtgag caacctgaag  1680
atcaccagaa tcagcgccac catcaacagc aagggccagg tgcgcatccc cgtgaagttc  1740
gacgtgggcc gccagaaggg caccctgcag atcggcgacc gcttctgcgg ctacgaccag  1800
aaccagaccg ccagccacgc ctacagcctg tgggaggtgg tgaaggaggg ccagtaccac  1860
aaggagctgg gctgcttcgt gcgcttcatc agcagcggcg acatcgtgag catcaccgag  1920
aaccgcggca accagttcga ccagctgagc tacgagggcc tggcctaccc ccagtacgcc  1980
gactggcgca agaaggccag caagttcgtg agcctgtggc agatcaccaa gaagaacaag  2040
aagaaggaga tcgtgaccgt ggaggccaag gagaagttcg acgccatctg caagtaccag  2100
ccccgcctgt acaagttcaa caaggagtac gcctacctgc tgcgcgacat cgtgcgcggc  2160
aagagcctgg tggagctgca gcagatccgc caggagatct tccgcttcat cgagcaggac  2220
tgcggcgtga cccgcctggg cagcctgagc ctgagcaccc tggagaccgt gaaggccgtg  2280
aagggcatca tctacagcta cttcagcacc gccctgaacg ccagcaagaa caaccccatc  2340
agcgacgagc agcgcaagga gttcgacccc gagctgttcg ccctgctgga gaagctggag  2400
ctgatccgca cccgcaagaa gaagcagaag gtggagcgca tcgccaacag cctgatccag  2460
acctgcctgg agaacaacat caagttcatc cgcggcgagg gcgacctgag caccaccaac  2520
aacgccacca agaagaaggc caacagccgc agcatggact ggctggcccg cggcgtgttc  2580
aacaagatcc gccagctggc ccccatgcac aacatcaccc tgttcggctg cggcagcctg  2640
tacaccagcc accaggaccc cctggtgcac cgcaaccccg acaagtctta tagagctagg  2700
tggagactgg ttagggttag agattttggc gagagacacc tgctgaccct gtccagaaac  2760
ctcaccggga agggtaaggg caccaggaag tattatcatc agggcgtgct cgatttcttc  2820
agggaatacg atctggagga tctggctggg ccactggcta aaataagacc aggcgaccct  2880
gatgccatac ctcctgaagt tctgcgggag cggctgcggg aaaagctcgg gaacgacgaa  2940
gctccagtgc tcattcctgt gagaggaggt cctgtgtacc tcagcacaca tgatgttgca  3000
accggcgcca aaagaattac attcaatggc aaggagcgct acctgtgcaa cgccgatcac  3060
gtggccgccg ccaacatcgc cctgaccgtg aagggcatcg gcgagcagag cagcgacgag  3120
gagaaccccg acggcagccg catcaagctg cagctgacca gc                     3162

SEQ ID NO: 65           moltype = AA  length = 1044
FEATURE                 Location/Qualifiers
source                  1..1044
                        mol_type = protein
                        organism = synthetic construct
SEQUENCE: 65
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQYNSIISV LFGTGRKEDR  180
SVKLRITKKI LEAISNLKEI PKNVAPIQEI ILNVAKATKE TFRQVYAGNL GAPSTLERFI  240
AKDGQKEFDL KKLQTDLKKV IRGKSKERDW CCQEELRSYV EQNTIQYDLW AWGEMFNKAH  300
TALKIKSTRN YNFAKQRLEQ FKRIQSLNNL LVVKKLNDFF DSEFFSGEET YTICVHHLGG  360
KRLSKLYKAW EDDPADPENA IVVLCDDLKN NFKKEPIRNI LRYIFTIRQE CSAQDILAAA  420
KYNQQLDRYK SQKANPSVLG NQGFTWRNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITRISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMRAR  900
FEEVNVENIA EWHVRNFSNY LRADSGTGLY YKQATMDFLK HYGLEEHAEG LENKKIKFYD  960
FRKILEDKNL TSVIIPKRGG RIYMATNPVT SDSTPITYAG KTYNRCNAAH VAAANIALTV  1020
KGIGEQSSDE ENPDGSRIKL QLTS                                         1044

SEQ ID NO: 66           moltype = AA  length = 1044
FEATURE                 Location/Qualifiers
source                  1..1044
                        mol_type = protein
                        organism = synthetic construct
SEQUENCE: 66
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQYNSIISV LFGTGRKEDR  180
SVKLRITKKI LEAISNLKEI PKNVAPIQEI ILNVAKATKE TFRQVYAGNL GAPSTLERFI  240
AKDGQKEFDL KKLQTDLKKV IRGKSKERDW CCQEELRSYV EQNTIQYDLW AWGEMFNKAH  300
TALKIKSTRN YNFAKQRLEQ FKRIQSLNNL LVVKKLNDFF DSEFFSGEET YTICVHHLGG  360
KRLSKLYKAW EDDPADPENA IVVLCDDLKN NFKKEPIRNI LRYIFTIRQE CSAQDILAAA  420
KYNQQLDRYK SQKANPSVLG NQGFTWRNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
```

```
TEARIRLAIQ QGTLPVSNLK ITRISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMRAR  900
FEEVNVSNVS EWHMRNFSNY LRADSGTGLY YKQATLDFLK HYDLEEHADD LEKQNIKFYD  960
FRKILEDKQL TSVIVPKRGG RIYMATNPVT SDSTPVTYAG KTYNRCNAAH VAAANIALTV  1020
KGIGEQSSDE ENPDGSRIKL QLTS                                          1044

SEQ ID NO: 67           moltype = AA  length = 110
FEATURE                 Location/Qualifiers
source                  1..110
                        mol_type = protein
                        organism = synthetic construct
SEQUENCE: 67
RARFEEVNVE NIAEWHVRNF SNYLRADSGT GLYYKQATMD FLKHYGLEEH AEGLENKKIK  60
FYDFRKILED KNLTSVIIPK RGGRIYMATN PVTSDSTPIT YAGKTYNRCN             110

SEQ ID NO: 68           moltype = AA  length = 110
FEATURE                 Location/Qualifiers
source                  1..110
                        mol_type = protein
                        organism = synthetic construct
SEQUENCE: 68
RARFEEVNVS NVSEWHMRNF SNYLRADSGT GLYYKQATLD FLKHYDLEEH ADDLEKQNIK  60
FYDFRKILED KQLTSVIVPK RGGRIYMATN PVTSDSTPVT YAGKTYNRCN             110

SEQ ID NO: 69           moltype = AA  length = 120
FEATURE                 Location/Qualifiers
source                  1..120
                        mol_type = protein
                        organism = synthetic construct
SEQUENCE: 69
SFRARWDLVK VKDFGEKHLL TLSRNLTGKG PGTRKYYHQG VEDFLKEYEL EDLKEELAKI  60
KKGDPNALPP EVIRNKLKEK LGNENAPVLI PKRGGKYFLS THNVATGAVK ITFNNKERYL  120

SEQ ID NO: 70           moltype = AA  length = 120
FEATURE                 Location/Qualifiers
source                  1..120
                        mol_type = protein
                        organism = synthetic construct
SEQUENCE: 70
SFRARWRLVK VKDIGEKELL TLSRNLRGKG KGIKKYYHQG VLDFFKEYEL EELAGPLAKI  60
KPGDPNAIPP EVLRNKLKEK LGNEDAPVLI PVAGGGIYLS THNVATGAKK ITFNNKERYV  120

SEQ ID NO: 71           moltype = AA  length = 120
FEATURE                 Location/Qualifiers
source                  1..120
                        mol_type = protein
                        organism = synthetic construct
SEQUENCE: 71
KYNARWDLVK VKDIGEGHLL ILSRNLRGKG SGIRKYYHQG VLEFFKEYDL EDLAEPLAKI  60
RPGDPNAIPP EVLRERLKEK LGNEDAPVLI PKPGGGVYLS THNVATGAKK ITFNNKERYL  120

SEQ ID NO: 72           moltype = AA  length = 120
FEATURE                 Location/Qualifiers
source                  1..120
                        mol_type = protein
                        organism = synthetic construct
SEQUENCE: 72
SYRARWRLVR VRDFGERHLL TLSRNLTGKG KGTRKYYHQG VLDFFREYDL EDLAGPLAKI  60
RPGDPDAIPP EVLRERLREK LGNDEAPVLI PVRGGPVYLS THDVATGAKR ITFNGKERYL  120

SEQ ID NO: 73           moltype = RNA  length = 20
FEATURE                 Location/Qualifiers
source                  1..20
                        mol_type = other RNA
                        organism = synthetic construct
SEQUENCE: 73
aggccaaaga attcctggaa                                              20

SEQ ID NO: 74           moltype = RNA  length = 20
FEATURE                 Location/Qualifiers
source                  1..20
                        mol_type = other RNA
                        organism = synthetic construct
SEQUENCE: 74
tcacaggctc caggaagggt                                              20
```

```
SEQ ID NO: 75          moltype = RNA  length = 20
FEATURE                Location/Qualifiers
source                 1..20
                       mol_type = other RNA
                       organism = synthetic construct
SEQUENCE: 75
ttcaacatat ccaaacaaat                                        20

SEQ ID NO: 76          moltype = DNA  length = 22
FEATURE                Location/Qualifiers
source                 1..22
                       mol_type = other DNA
                       organism = synthetic construct
SEQUENCE: 76
tctgcttcgg tgtcgaaatg ag                                     22

SEQ ID NO: 77          moltype = DNA  length = 22
FEATURE                Location/Qualifiers
source                 1..22
                       mol_type = other DNA
                       organism = synthetic construct
SEQUENCE: 77
tgcagaagcg tttggcaatg tg                                     22

SEQ ID NO: 78          moltype = DNA  length = 20
FEATURE                Location/Qualifiers
source                 1..20
                       mol_type = other DNA
                       organism = synthetic construct
SEQUENCE: 78
gctgaaaagc gatacagggc                                        20

SEQ ID NO: 79          moltype = DNA  length = 20
FEATURE                Location/Qualifiers
source                 1..20
                       mol_type = other DNA
                       organism = synthetic construct
SEQUENCE: 79
atcaccaaga gagccttccg                                        20

SEQ ID NO: 80          moltype = DNA  length = 23
FEATURE                Location/Qualifiers
source                 1..23
                       mol_type = other DNA
                       organism = synthetic construct
SEQUENCE: 80
tttataacag tggtggtgag gct                                    23

SEQ ID NO: 81          moltype = DNA  length = 22
FEATURE                Location/Qualifiers
source                 1..22
                       mol_type = other DNA
                       organism = synthetic construct
SEQUENCE: 81
ttctcaaacc ctggaaagca ct                                     22

SEQ ID NO: 82          moltype = RNA  length = 20
FEATURE                Location/Qualifiers
source                 1..20
                       mol_type = other RNA
                       organism = synthetic construct
SEQUENCE: 82
atttgtttgg atatgttgaa                                        20

SEQ ID NO: 83          moltype = AA  length = 32
FEATURE                Location/Qualifiers
source                 1..32
                       mol_type = protein
                       organism = synthetic construct
SEQUENCE: 83
SGGSSGGSSG SETPGTSESA TPESSGGSSG GS                          32

SEQ ID NO: 84          moltype = RNA  length = 20
FEATURE                Location/Qualifiers
source                 1..20
                       mol_type = other RNA
                       organism = synthetic construct
SEQUENCE: 84
```

```
ttgtataata ggaaagggaa                                             20

SEQ ID NO: 85          moltype = RNA  length = 20
FEATURE                Location/Qualifiers
source                 1..20
                       mol_type = other RNA
                       organism = synthetic construct
SEQUENCE: 85
tctatcactg atagggagtg                                             20

SEQ ID NO: 86          moltype = AA  length = 80
FEATURE                Location/Qualifiers
source                 1..80
                       mol_type = protein
                       organism = synthetic construct
SEQUENCE: 86
GGPSSGAPPP SGGSPAGSPT STEEGTSESA TPESGPGTST EPSEGSAPGS PAGSPTSTEE  60
GTSTEPSEGS APGTSTEPSE                                             80

SEQ ID NO: 87          moltype = AA  length = 10
FEATURE                Location/Qualifiers
source                 1..10
                       mol_type = protein
                       organism = synthetic construct
SEQUENCE: 87
SGGSGGSGGS                                                        10

SEQ ID NO: 88          moltype = AA  length = 1598
FEATURE                Location/Qualifiers
source                 1..1598
                       mol_type = protein
                       organism = synthetic construct
SEQUENCE: 88
PKKKRKVMSS AIKSYKSVLR PNERKNQLLK STIQCLEDGS AFFFKMLQGL FGGITPEIVR  60
FSTEQEKQQQ DIALWCAVNW FRPVSQDSLT HTIASDNLVE KFEEYYGGTA SDAIKQYFSA  120
SIGESYYWND CRQQYYDLCR ELGVEVSDLT HDLEILCREK CLAVATESNQ YNSIISVLFG  180
TGRKEDRSVK LRITKKILEA ISNLKEIPKN VAPIQEIILN VAKATKETFR QVYAGNLGAP  240
STLERFIAKD GQKEFDLKKL QTDLKKVIRG KSKERDWCCQ EELRSYVEQN TIQYDLWAWG  300
EMFNKAHTAL KIKSTRNYNF AKQRLEQFKR IQSLNNLLVV KKLNDFFDSE FFSGEETYTI  360
CVHHLGGKRL SKLYKAWEDD PADPENAIVV LCDDLKNNFK KEPIRNILRY IFTIRQECSA  420
QDILAAAKYN QQLDRYKSQK ANPSVLGNQG FTWRNAVILP EKAQRNDRPN SLDLRIWLYL  480
KLRHPDGRWK KHHIPFYDTR FFQEIYAAGN SPVDTCQFRT PRFGYHLPKL TDQTAIRVNK  540
KHVKAAKTEA RIRLAIQQGT LPVSNLKITR ISATINSKGQ VRIPVKFDVG RQKGTLQIGD  600
RFCGYDQNQT ASHAYSLWEV VKEGQYHKEL GCFVRFISSG DIVSITENRG NQFDQLSYEG  660
LAYPQYADWR KKASKFVSLW QITKKNKKKE IVTVEAKEKF DAICKYQPRL YKFNKEYAYL  720
LRDIVRGKSL VELQQIRQEI FRFIEQDCGV TRLGSLSLST LETVKAVKGI IYSYFSTALN  780
ASKNNPISDE QRKEFDPELF ALLEKLELIR TRKKKQKVER IANSLIQTCL ENNIKFIRGE  840
GDLSTTNNAT KKKANSRSMD WLARGVFNKI RQLAPMHNIT LFGCGSLYTS HQDPLVHRNP  900
DKAMRARFEE VNVENIAEWH VRNFSNYLRA DSGTGLYYKQ ATMDFLKHYG LEEHAEGLEN  960
KKIKFYDFRK ILEDKNLTSV IIPKRGGRIY MATNPVTSDS TPITYAGKTY NRCNAAHVAA  1020
ANIALTVKGI GEQSSDEENP DGSRIKLQLT SKRPAATKKA GQAKKKKEAS GSGRADALDD  1080
FDLDMLGSDA LDDFDLDMLG SDALDDFDLD MLGSDALDDF DLDMLINSRS SGSPKKKRKV  1140
GSQYLPDTDD RHRIEEKRKR TYETFKSIMK KSPFSGPTDP RPPPRRIAVP SRSSASVPKP  1200
APQPYPFTSS LSTINYDEFP TMVFPSGQIS QASALAPAPP QVLPQAPAPA PAPAMVSALA  1260
QAPAPVPVLA PGPPQAVAPP APKPTQAGEG TLSEALLQLQ FDDEDLGALL GNSTDPAVFT  1320
DLASVDNSEF QQLLNQGIPV APHTTEPMLM EYPEAITRLV TGAQRPPDPA PAPLGAPGLP  1380
NGLLSGDEDF SSIADMDFSA LLGSGSGSRD SREGMFLPKP EAGSAISDVF EGREVCQPKR  1440
IRPFHPPGSP WANRPLPASL APTPTGPVHE PVGSLTPAPV PQPLDPAPAV TPEASHLLED  1500
PDEETSQAVK ALREMADTVI PQKEEAAICG QMDLSHPPPR GHLDELTTTL ESMTEDLNLD  1560
SPLTPELNEI LDTFLNDECL LHAMHISTGL SIFDTSLF                         1598

SEQ ID NO: 89          moltype = AA  length = 1598
FEATURE                Location/Qualifiers
source                 1..1598
                       mol_type = protein
                       organism = synthetic construct
SEQUENCE: 89
PKKKRKVMSS AIKSYKSVLR PNERKNQLLK STIQCLEDGS AFFFKMLQGL FGGITPEIVR  60
FSTEQEKQQQ DIALWCAVNW FRPVSQDSLT HTIASDNLVE KFEEYYGGTA SDAIKQYFSA  120
SIGESYYWND CRQQYYDLCR ELGVEVSDLT HDLEILCREK CLAVATESNQ YNSIISVLFG  180
TGRKEDRSVK LRITKKILEA ISNLKEIPKN VAPIQEIILN VAKATKETFR QVYAGNLGAP  240
STLERFIAKD GQKEFDLKKL QTDLKKVIRG KSKERDWCCQ EELRSYVEQN TIQYDLWAWG  300
EMFNKAHTAL KIKSTRNYNF AKQRLEQFKR IQSLNNLLVV KKLNDFFDSE FFSGEETYTI  360
CVHHLGGKRL SKLYKAWEDD PADPENAIVV LCDDLKNNFK KEPIRNILRY IFTIRQECSA  420
QDILAAAKYN QQLDRYKSQK ANPSVLGNQG FTWRNAVILP EKAQRNDRPN SLDLRIWLYL  480
KLRHPDGRWK KHHIPFYDTR FFQEIYAAGN SPVDTCQFRT PRFGYHLPKL TDQTAIRVNK  540
KHVKAAKTEA RIRLAIQQGT LPVSNLKITR ISATINSKGQ VRIPVKFDVG RQKGTLQIGD  600
RFCGYDQNQT ASHAYSLWEV VKEGQYHKEL GCFVRFISSG DIVSITENRG NQFDQLSYEG  660
LAYPQYADWR KKASKFVSLW QITKKNKKKE IVTVEAKEKF DAICKYQPRL YKFNKEYAYL  720
```

```
LRDIVRGKSL VELQQIRQEI FRFIEQDCGV TRLGSLSLST LETVKAVKGI IYSYFSTALN  780
ASKNNPISDE QRKEFDPELF ALLEKLELIR TRKKKQKVER IANSLIQTCL ENNIKFIRGE  840
GDLSTTNNAT KKKANSRSMD WLARGVFNKI RQLAPMHNIT LFGCGSLYTS HQDPLVHRNP  900
DKAMRARFEE VNVSNVSEWH MRNFSNYLRA DSGTGLYYKQ ATLDFLKHYD LEEHADDLEK  960
QNIKFYDFRK ILEDKQLTSV IVPKRGGRIY MATNPVTSDS TPVTYAGKTY NRCNAAHVAA  1020
ANIALTVKGI GEQSSDEENP DGSRIKLQLT SKRPAATKKA GQAKKKKEAS GSGRADALDD  1080
FDLDMLGSDA LDDFDLDMLG SDALDDFDLD MLGSDALDDF DLDMLINSRS SGSPKKKRKV  1140
GSQYLPDTDD RHRIEEKRKR TYETFKSIMK KSPFSGPTDP RPPPRRIAVP SRSSASVPKP  1200
APQPYPFTSS LSTINYDEFP TMVFPSGQIS QASALAPAPP QVLPQAPAPA PAPAMVSALA  1260
QAPAPVPVLA PGPPQAVAPP APKPTQAGEG TLSEALLQLQ FDDEDLGALL GNSTDPAVFT  1320
DLASVDNSEF QQLLNQGIPV APHTTEPMLM EYPEAITRLV TGAQRPPDPA PAPLGAPGLP  1380
NGLLSGDEDF SSIADMDFSA LLGSGSGSRD SREGMFLPKP EAGSAISDVF EGREVCQPKR  1440
IRPFHPPGSP WANRPLPASL APTPTGPVHE PVGSLTPAPV PQPLDPAPAV TPEASHLLED  1500
PDEETSQAVK ALREMADTVI PQKEEAAICG QMDLSHPPPR GHLDELTTTL ESMTEDLNLD  1560
SPLTPELNEI LDTFLNDECL LHAMHISTGL SIFDTSLF                          1598

SEQ ID NO: 90          moltype = AA  length = 1380
FEATURE                Location/Qualifiers
source                 1..1380
                       mol_type = protein
                       organism = synthetic construct
SEQUENCE: 90
PKKKRKVMSS AIKSYKSVLR PNERKNQLLK STIQCLEDGS AFFFKMLQGL FGGITPEIVR  60
FSTEQEKQQQ DIALWCAVNW FRPVSQDSLT HTIASDNLVE KFEEYYGGTA SDAIKQYFSA  120
SIGESYYWND CRQQYYDLCR ELGVEVSDLT HDLEILCREK CLAVATESNQ YNSIISVLFG  180
TGRKEDRSVK LRITKKILEA ISNLKEIPKN VAPIQEIILN VAKATKETFR QVYAGNLGAP  240
STLERFIAKD GQKEFDLKKL QTDLKKVIRG KSKERDWCCQ EELRSYVEQN TIQYDLWAWG  300
EMFNKAHTAL KIKSTRNYNF AKQRLEQFKR IQSLNNLLVV KKLNDFFDSE FFSGEETYTI  360
CVHHLGGKRL SKLYKAWEDD PADPENAIVV LCDDLKNNFK KEPIRNILRY IFTIRQECSA  420
QDILAAAKYN QQLDRYKSQK ANPSVLGNQG FTWRNAVILP EKAQRNDRPN SLDLRIWLYL  480
KLRHPDGRWK KHHIPFYDTR FFQEIYAAGN SPVDTCQFRT PRFGYHLPKL TDQTAIRVNK  540
KHVKAAKTEA RIRLAIQQGT LPVSNLKITR ISATINSKGQ VRIPVKFDVG RQKGTLQIGD  600
RFCGYDQNQT ASHAYSLWEV VKEGQYHKEL GCFVRFISSG DIVSITENRG NQFDQLSYEG  660
LAYPQYADWR KKASKFVSLW QITKKNKKKE IVTVEAKEKF DAICKYQPRL YKFNKEYAYL  720
LRDIVRGKSL VELQQIRQEI FRFIEQDCGV TRLGSLSLST LETVKAVKGI IYSYFSTALN  780
ASKNNPISDE QRKEFDPELF ALLEKLELIR TRKKKQKVER IANSLIQTCL ENNIKFIRGE  840
GDLSTTNNAT KKKANSRSMD WLARGVFNKI RQLAPMHNIT LFGCGSLYTS HQDPLVHRNP  900
DKAMRARFEE VNVENIAEWH VRNFSNYLRA DSGTGLYYKQ ATMDFLKHYG LEEHAEGLEN  960
KKIKFYDFRK ILEDKNLTSV IIPKRGGRIY MATNPVTSDS TPITYAGKTY NRCNAAHVAA  1020
ANIALTVKGI GEQSSDEENP DGSRIKLQLT SKRPAATKKA GQAKKKKDAL DDFDLDMLGS  1080
DALDDFDLDM LGSDALDDFD LDMLGSDALD DFDLDMLINS RSSGSPKKKR KVGSGGGSGG  1140
SGSVLPQAPA PAPAPAMVSA LAQAPAPVPV LAPGPPQAVA PPAPKPTQAG EGTLSEALLQ  1200
LQFDDEDLGA LLGNSTDPAV FTDLASVDNS EFQQLLNQGI PVAPHTTEPM LMEYPEAITR  1260
LVTGAQRPPD PAPAPLGAPG LPNGLLSGDE DFSSIADMDF SALLSGGGSG GSGSDLSHPP  1320
PRGHLDELTT TLESMTEDLN LDSPLTPELN EILDTFLNDE CLLHAMHIST GLSIFDTSLF  1380

SEQ ID NO: 91          moltype = AA  length = 1380
FEATURE                Location/Qualifiers
source                 1..1380
                       mol_type = protein
                       organism = synthetic construct
SEQUENCE: 91
PKKKRKVMSS AIKSYKSVLR PNERKNQLLK STIQCLEDGS AFFFKMLQGL FGGITPEIVR  60
FSTEQEKQQQ DIALWCAVNW FRPVSQDSLT HTIASDNLVE KFEEYYGGTA SDAIKQYFSA  120
SIGESYYWND CRQQYYDLCR ELGVEVSDLT HDLEILCREK CLAVATESNQ YNSIISVLFG  180
TGRKEDRSVK LRITKKILEA ISNLKEIPKN VAPIQEIILN VAKATKETFR QVYAGNLGAP  240
STLERFIAKD GQKEFDLKKL QTDLKKVIRG KSKERDWCCQ EELRSYVEQN TIQYDLWAWG  300
EMFNKAHTAL KIKSTRNYNF AKQRLEQFKR IQSLNNLLVV KKLNDFFDSE FFSGEETYTI  360
CVHHLGGKRL SKLYKAWEDD PADPENAIVV LCDDLKNNFK KEPIRNILRY IFTIRQECSA  420
QDILAAAKYN QQLDRYKSQK ANPSVLGNQG FTWRNAVILP EKAQRNDRPN SLDLRIWLYL  480
KLRHPDGRWK KHHIPFYDTR FFQEIYAAGN SPVDTCQFRT PRFGYHLPKL TDQTAIRVNK  540
KHVKAAKTEA RIRLAIQQGT LPVSNLKITR ISATINSKGQ VRIPVKFDVG RQKGTLQIGD  600
RFCGYDQNQT ASHAYSLWEV VKEGQYHKEL GCFVRFISSG DIVSITENRG NQFDQLSYEG  660
LAYPQYADWR KKASKFVSLW QITKKNKKKE IVTVEAKEKF DAICKYQPRL YKFNKEYAYL  720
LRDIVRGKSL VELQQIRQEI FRFIEQDCGV TRLGSLSLST LETVKAVKGI IYSYFSTALN  780
ASKNNPISDE QRKEFDPELF ALLEKLELIR TRKKKQKVER IANSLIQTCL ENNIKFIRGE  840
GDLSTTNNAT KKKANSRSMD WLARGVFNKI RQLAPMHNIT LFGCGSLYTS HQDPLVHRNP  900
DKAMRARFEE VNVSNVSEWH MRNFSNYLRA DSGTGLYYKQ ATLDFLKHYD LEEHADDLEK  960
QNIKFYDFRK ILEDKQLTSV IVPKRGGRIY MATNPVTSDS TPVTYAGKTY NRCNAAHVAA  1020
ANIALTVKGI GEQSSDEENP DGSRIKLQLT SKRPAATKKA GQAKKKKDAL DDFDLDMLGS  1080
DALDDFDLDM LGSDALDDFD LDMLGSDALD DFDLDMLINS RSSGSPKKKR KVGSGGGSGG  1140
SGSVLPQAPA PAPAPAMVSA LAQAPAPVPV LAPGPPQAVA PPAPKPTQAG EGTLSEALLQ  1200
LQFDDEDLGA LLGNSTDPAV FTDLASVDNS EFQQLLNQGI PVAPHTTEPM LMEYPEAITR  1260
LVTGAQRPPD PAPAPLGAPG LPNGLLSGDE DFSSIADMDF SALLSGGGSG GSGSDLSHPP  1320
PRGHLDELTT TLESMTEDLN LDSPLTPELN EILDTFLNDE CLLHAMHIST GLSIFDTSLF  1380

SEQ ID NO: 92          moltype = AA  length = 1765
FEATURE                Location/Qualifiers
source                 1..1765
```

```
                        mol_type = protein
                        organism = synthetic construct
SEQUENCE: 92
MNHDQEFDPP KVYPPVPAEK RKPIRVLSLF DGIATGLLVL KDLGIQVDRY IASEVCEDSI  60
TVGMVRHQGK IMYVGDVRSV TQKHIQEWGP FDLVIGGSPC NDLSIVNPAR KGLYEGTGRL  120
FFEFYRLLHD ARPKEGDDRP FFWLFENVVA MGVSDKRDIS RFLESNPVMI DAKEVSAAHR  180
ARYFWGNLPG MNRPLASTVN DKLELQECLE HGRIAKFSKV RTITTRSNSI KQGKDQHFPV  240
FMNEKEDILW CTEMERVFGF PVHYTDVSNM SRLARQRLLG RSWSVPVIRH LFAPLKEYFA  300
CVSSGNSNAN SRGPSFSSGL VPLSLRGSHM GPMEIYKTVS AWKRQPVRVL SLFRNIDKVL  360
KSLGFLESGS GSGGGTLKYV EDVTNVVRRD VEKWGPFDLV YGSTQPLGSS CDRCPGWYMF  420
QFHRILQYAL PRQESQRPFF WIFMDNLLLT EDDQETTTRF LQTEAVTLQD VRGRDYQNAM  480
RVWSNIPGLK SKHAPLTPKE EEYLQAQVRS RSKLDAPKVD LLVKNCLLPL REYFKYFSQN  540
SLPLGGPSSG APPPSGGSPA GSPTSTEEGT SESATPESGP GTSTEPSEGS APGSPAGSPT  600
STEEGTSTEP SEGSAPGTST EPSEMSSAIK SYKSVLRPNE RKNQLLKSTI QCLEDGSAFF  660
FKMLQGLFGG ITPEIVRFST EQEKQQQDIA LWCAVNWFRP VSQDSLTHTI ASDNLVEKFE  720
EYYGGTASDA IKQYFSASIG ESYYWNDCRQ QYYDLCRELG VEVSDLTHDL EILCREKCLA  780
VATESNQYNS IISVLFGTGR KEDRSVKLRI TKKILEAISN LKEIPKNVAP IQEIILNVAK  840
ATKETFRQVY AGNLGAPSTL ERFIAKDGQK EFDLKKLQTD LKKVIRGKSK ERDWCCQEEL  900
RSYVEQNTIQ YDLWAWGEMF NKAHTALKIK STRNYNFAKQ RLEQFKRIQS LNNLLVVKKL  960
NDFFDSEFFS GEETYTICVH HLGGKRLSKL YKAWEDDPAD PENAIVVLCD DLKNNFKKEP  1020
IRNILRYIFT IRQECSAQDI LAAAKYNQQL DRYKSQKANP SVLGNQGFTW RNAVILPEKA  1080
QRNDRPNSLD LRIWLYLKLR HPDGRWKKHH IPFYDTRFFQ EIYAAGNSPV DTCQFRTPRF  1140
GYHLPKLTDQ TAIRVNKKHV KAAKTEARIR LAIQQGTLPV SNLKITRISA TINSKGQVRI  1200
PVKFDVGRQK GTLQIGDRFC GYDQNQTASH AYSLWEVVKE GQYHKELGCF VRFISSGDIV  1260
SITENRGNQF DQLSYEGLAY PQYADWRKKA SKFVSLWQIT KKNKKKEIVT VEAKEKFDAI  1320
CKYQPRLYKF NKEYAYLLRD IVRGKSLVEL QQIRQEIFRF IEQDCGVTRL GSLSLSTLET  1380
VKAVKGIIYS YFSTALNASK NNPISDEQRK EFDPELFALL EKLELIRTRK KKQKVERIAN  1440
SLIQTCLENN IKFIRGEGDL STTNNATKKK ANSRSMDWLA RGVFNKIRQL APMHNITLFG  1500
CGSLYTSHQD PLVHRNPDKA MRARFEEVNV ENIAEWHVRN FSNYLRADSG TGLYYKQATM  1560
DFLKHYGLEE HAEGLENKKI KFYDFRKILE DKNLTSVIIP KRGGRIYMAT NPVTSDSTPI  1620
TYAGKTYNRC NAAHVAAANI ALTVKGIGEQ SSDEENPDGS RIKLQLTSPK KKRKVDGIGS  1680
GSNGSSGSGG GGGMDAKSLT AWSRTLVTFK DVFVDFTREE WKLLDTAQQI VYRNVMLENY  1740
KNLVSLGYQL TKPDVILRLE KGEEP                                       1765

SEQ ID NO: 93           moltype = AA  length = 1765
FEATURE                 Location/Qualifiers
source                  1..1765
                        mol_type = protein
                        organism = synthetic construct
SEQUENCE: 93
MNHDQEFDPP KVYPPVPAEK RKPIRVLSLF DGIATGLLVL KDLGIQVDRY IASEVCEDSI  60
TVGMVRHQGK IMYVGDVRSV TQKHIQEWGP FDLVIGGSPC NDLSIVNPAR KGLYEGTGRL  120
FFEFYRLLHD ARPKEGDDRP FFWLFENVVA MGVSDKRDIS RFLESNPVMI DAKEVSAAHR  180
ARYFWGNLPG MNRPLASTVN DKLELQECLE HGRIAKFSKV RTITTRSNSI KQGKDQHFPV  240
FMNEKEDILW CTEMERVFGF PVHYTDVSNM SRLARQRLLG RSWSVPVIRH LFAPLKEYFA  300
CVSSGNSNAN SRGPSFSSGL VPLSLRGSHM GPMEIYKTVS AWKRQPVRVL SLFRNIDKVL  360
KSLGFLESGS GSGGGTLKYV EDVTNVVRRD VEKWGPFDLV YGSTQPLGSS CDRCPGWYMF  420
QFHRILQYAL PRQESQRPFF WIFMDNLLLT EDDQETTTRF LQTEAVTLQD VRGRDYQNAM  480
RVWSNIPGLK SKHAPLTPKE EEYLQAQVRS RSKLDAPKVD LLVKNCLLPL REYFKYFSQN  540
SLPLGGPSSG APPPSGGSPA GSPTSTEEGT SESATPESGP GTSTEPSEGS APGSPAGSPT  600
STEEGTSTEP SEGSAPGTST EPSEMSSAIK SYKSVLRPNE RKNQLLKSTI QCLEDGSAFF  660
FKMLQGLFGG ITPEIVRFST EQEKQQQDIA LWCAVNWFRP VSQDSLTHTI ASDNLVEKFE  720
EYYGGTASDA IKQYFSASIG ESYYWNDCRQ QYYDLCRELG VEVSDLTHDL EILCREKCLA  780
VATESNQYNS IISVLFGTGR KEDRSVKLRI TKKILEAISN LKEIPKNVAP IQEIILNVAK  840
ATKETFRQVY AGNLGAPSTL ERFIAKDGQK EFDLKKLQTD LKKVIRGKSK ERDWCCQEEL  900
RSYVEQNTIQ YDLWAWGEMF NKAHTALKIK STRNYNFAKQ RLEQFKRIQS LNNLLVVKKL  960
NDFFDSEFFS GEETYTICVH HLGGKRLSKL YKAWEDDPAD PENAIVVLCD DLKNNFKKEP  1020
IRNILRYIFT IRQECSAQDI LAAAKYNQQL DRYKSQKANP SVLGNQGFTW RNAVILPEKA  1080
QRNDRPNSLD LRIWLYLKLR HPDGRWKKHH IPFYDTRFFQ EIYAAGNSPV DTCQFRTPRF  1140
GYHLPKLTDQ TAIRVNKKHV KAAKTEARIR LAIQQGTLPV SNLKITRISA TINSKGQVRI  1200
PVKFDVGRQK GTLQIGDRFC GYDQNQTASH AYSLWEVVKE GQYHKELGCF VRFISSGDIV  1260
SITENRGNQF DQLSYEGLAY PQYADWRKKA SKFVSLWQIT KKNKKKEIVT VEAKEKFDAI  1320
CKYQPRLYKF NKEYAYLLRD IVRGKSLVEL QQIRQEIFRF IEQDCGVTRL GSLSLSTLET  1380
VKAVKGIIYS YFSTALNASK NNPISDEQRK EFDPELFALL EKLELIRTRK KKQKVERIAN  1440
SLIQTCLENN IKFIRGEGDL STTNNATKKK ANSRSMDWLA RGVFNKIRQL APMHNITLFG  1500
CGSLYTSHQD PLVHRNPDKA MRARFEEVNV SNVSEWHMRN FSNYLRADSG TGLYYKQATL  1560
DFLKHYDLEE HADDLEKQNI KFYDFRKILE DKQLTSVIVP KRGGRIYMAT NPVTSDSTPV  1620
TYAGKTYNRC NAAHVAAANI ALTVKGIGEQ SSDEENPDGS RIKLQLTSPK KKRKVDGIGS  1680
GSNGSSGSGG GGGMDAKSLT AWSRTLVTFK DVFVDFTREE WKLLDTAQQI VYRNVMLENY  1740
KNLVSLGYQL TKPDVILRLE KGEEP                                       1765

SEQ ID NO: 94           moltype = AA  length = 1249
FEATURE                 Location/Qualifiers
source                  1..1249
                        mol_type = protein
                        organism = synthetic construct
SEQUENCE: 94
PKKKRKVSEV EFSHEYWMRH ALTLAKRARD EREVPVGAVL VLNNRVIGEG WNRAIGLHDP  60
TAHAEIMALR QGGLVMQNYR LIDATLYVTF EPCVMCAGAM IHSRIGRVVF GVRNSKRGAA  120
```

-continued

```
GSLMNVLNYP GMNHRVEITE GILADECAAL LCDFYRMPRQ VFNAQKKAQS SINSGGSSGG  180
SSGSETPGTS ESATPESSGG SSGGSMSSAI KSYKSVLRPN ERKNQLLKST IQCLEDGSAF  240
FFKMLQGLFG GITPEIVRFS TEQEKQQQDI ALWCAVNWFR PVSQDSLTHT IASDNLVEKF  300
EEYYGGTASD AIKQYFSASI GESYYWNDCR QQYYDLCREL GVEVSDLTHD LEILCREKCL  360
AVATESNQYN SIISVLFGTG RKEDRSVKLR ITKKILEAIS NLKEIPKNVA PIQEIILNVA  420
KATKETFRQV YAGNLGAPST LERFIAKDGQ KEFDLKKLQT DLKKVIRGKS KERDWCCQEE  480
LRSYVEQNTI QYDLWAWGEM FNKAHTALKI KSTRNYNFAK QRLEQFKRIQ SLNNLLVVKK  540
LNDFFDSEFF SGEETYTICV HHLGGKRLSK LYKAWEDDPA DPENAIVVLC DDLKNNFKKE  600
PIRNILRYIF TIRQECSAQD ILAAAKYNQQ LDRYKSQKAN PSVLGNQGFT WRNAVILPEK  660
AQRNDRPNSL DLRIWLYLKL RHPDGRWKKH HIPFYDTRFF QEIYAAGNSP VDTCQFRTPR  720
FGYHLPKLTD QTAIRVNKKH VKAAKTEARI RLAIQQGTLP VSNLKITRIS ATINSKGQVR  780
IPVKFDVGRQ KGTLQIGDRF CGYDQNQTAS HAYSLWEVVK EGQYHKELGC FVRFISSGDI  840
VSITENRGNQ FDQLSYEGLA YPQYADWRKK ASKFVSLWQI TKKNKKKEIV TVEAKEKFDA  900
ICKYQPRLYK FNKEYAYLLR DIVRGKSLVE LQQIRQEIFR FIEQDCGVTR LGSLSLSTLE  960
TVKAVKGIIY SYFSTALNAS KNNPISDEQR KEFDPELFAL LEKLELIRTR KKKQKVERIA  1020
NSLIQTCLEN NIKFIRGEGD LSTTNNATKK KANSRSMDWL ARGVFNKIRQ LAPMHNITLF  1080
GCGSLYTSHQ DPLVHRNPDK AMRARFEEVN VENIAEWHVR NFSNYLRADS GTGLYYKQAT  1140
MDFLKHYGLE EHAEGLENKK IKFYDFRKIL EDKNLTSVII PKRGGRIYMA TNPVTSDSTP  1200
ITYAGKTYNR CNAAHVAAAN IALTVKGIGE QSSDEENPDG SRIKLQLTS             1249

SEQ ID NO: 95          moltype = AA  length = 1249
FEATURE                Location/Qualifiers
source                 1..1249
                       mol_type = protein
                       organism = synthetic construct
SEQUENCE: 95
PKKKRKVSEV EFSHEYWMRH ALTLAKRARD EREVPVGAVL VLNNRVIGEG WNRAIGLHDP  60
TAHAEIMALR QGGLVMQNYR LIDATLYVTF EPCVMCAGAM IHSRIGRVVF GVRNSKRGAA  120
GSLMNVLNYP GMNHRVEITE GILADECAAL LCDFYRMPRQ VFNAQKKAQS SINSGGSSGG  180
SSGSETPGTS ESATPESSGG SSGGSMSSAI KSYKSVLRPN ERKNQLLKST IQCLEDGSAF  240
FFKMLQGLFG GITPEIVRFS TEQEKQQQDI ALWCAVNWFR PVSQDSLTHT IASDNLVEKF  300
EEYYGGTASD AIKQYFSASI GESYYWNDCR QQYYDLCREL GVEVSDLTHD LEILCREKCL  360
AVATESNQYN SIISVLFGTG RKEDRSVKLR ITKKILEAIS NLKEIPKNVA PIQEIILNVA  420
KATKETFRQV YAGNLGAPST LERFIAKDGQ KEFDLKKLQT DLKKVIRGKS KERDWCCQEE  480
LRSYVEQNTI QYDLWAWGEM FNKAHTALKI KSTRNYNFAK QRLEQFKRIQ SLNNLLVVKK  540
LNDFFDSEFF SGEETYTICV HHLGGKRLSK LYKAWEDDPA DPENAIVVLC DDLKNNFKKE  600
PIRNILRYIF TIRQECSAQD ILAAAKYNQQ LDRYKSQKAN PSVLGNQGFT WRNAVILPEK  660
AQRNDRPNSL DLRIWLYLKL RHPDGRWKKH HIPFYDTRFF QEIYAAGNSP VDTCQFRTPR  720
FGYHLPKLTD QTAIRVNKKH VKAAKTEARI RLAIQQGTLP VSNLKITRIS ATINSKGQVR  780
IPVKFDVGRQ KGTLQIGDRF CGYDQNQTAS HAYSLWEVVK EGQYHKELGC FVRFISSGDI  840
VSITENRGNQ FDQLSYEGLA YPQYADWRKK ASKFVSLWQI TKKNKKKEIV TVEAKEKFDA  900
ICKYQPRLYK FNKEYAYLLR DIVRGKSLVE LQQIRQEIFR FIEQDCGVTR LGSLSLSTLE  960
TVKAVKGIIY SYFSTALNAS KNNPISDEQR KEFDPELFAL LEKLELIRTR KKKQKVERIA  1020
NSLIQTCLEN NIKFIRGEGD LSTTNNATKK KANSRSMDWL ARGVFNKIRQ LAPMHNITLF  1080
GCGSLYTSHQ DPLVHRNPDK AMRARFEEVN VSNVSEWHMR NFSNYLRADS GTGLYYKQAT  1140
LDFLKHYDLE EHADDLEKQN IKFYDFRKIL EDKQLTSVIV PKRGGRIYMA TNPVTSDSTP  1200
VTYAGKTYNR CNAAHVAAAN IALTVKGIGE QSSDEENPDG SRIKLQLTS             1249

SEQ ID NO: 96          moltype = AA  length = 1497
FEATURE                Location/Qualifiers
source                 1..1497
                       mol_type = protein
                       organism = synthetic construct
SEQUENCE: 96
PKKKRKVSSE TGPVAVDPTL RRRIEPHEFE VFFDPRELRK ETCLLYEINW GGRHSIWRHT  60
SQNTNKHVEV NFIEKFTTER YFCPNTRCSI TWFLSWSPCG ECSRAITEFL SRYPHVTLFI  120
YIARLYHHAD PRNRQGLRDL ISSGVTIQIM TEQESGYCWR NFVNYSPSNE AHWPRYPHLW  180
VRLYVLELYC IILGLPPCLN ILRRKQPQLT FFTIALQSCH YQRLPPHILW ATGLKSGGSS  240
GGSSGSETPG TSESATPESS GGSSGGSMSS AIKSYKSVLR PNERKNQLLK STIQCLEDGS  300
AFFFKMLQGL FGGITPEIVR FSTEQEKQQQ DIALWCAVNW FRPVSQDSLT HTIASDNLVE  360
KFEEYYGGTA SDAIKQYFSA SIGESYYWND CRQQYYDLCR ELGVEVSDLT HDLEILCREK  420
CLAVATESNQ YNSIISVLFG TGRKEDRSVK LRITKKILEA ISNLKEIPKN VAPIQEIILN  480
VAKATKETFR QVYAGNLGAP STLERFIAKD GQKEFDLKKL QTDLKKVIRG KSKERDWCCQ  540
EELRSYVEQN TIQYDLWAWG EMFNKAHTAL KIKSTRNYNF AKQRLEQFKR IQSLNNLLVV  600
KKLNDFFDSE FFSGEETYTI CVHHLGGKRL SKLYKAWEDD PADPENAIVV LCDDLKNNFK  660
KEPIRNILRY IFTIRQECSA QDILAAAKYN QQLDRYKSQK ANPSVLGNQG FTWRNAVILP  720
EKAQRNDRPN SLDLRIWLYL KLRHPDGRWK KHHIPFYDTR FFQEIYAAGN SPVDTCQFRT  780
PRFGYHLPKL TDQTAIRVNK KHVKAAKTEA RIRLAIQQGT LPVSNLKITR ISATINSKGQ  840
VRIPVKFDVG RQKGTLQIGD RFCGYDQNQT ASHAYSLWEV VKEGQYHKEL GCFVRFISSG  900
DIVSITENRG NQFDQLSYEG LAYPQYADWR KKASKFVSLW QITKKNKKKE IVTVEAKEKF  960
DAICKYQPRL YKFNKEYAYL LRDIVRGKSL VELQQIRQEI FRFIEQDCGV TRLGSLSLST  1020
LETVKAVKGI IYSYFSTALN ASKNNPISDE QRKEFDPELF ALLEKLELIR TRKKKQKVER  1080
IANSLIQTCL ENNIKFIRGE GDLSTTNNAT KKKANSRSMD WLARGVFNKI RQLAPMHNIT  1140
LFGCGSLYTS HQDPLVHRNP DKAMRARFEE VNVENIAEWH VRNFSNYLRA DSGTGLYYKQ  1200
ATMDFLKHYG LEEHAEGLEN KKIKFYDFRK ILEDKNLTSV IIPKRGGRIY MATNPVTSDS  1260
TPITYAGKTY NRCNAAHVAA ANIALTVKGI GEQSSDEENP DGSRIKLQLT SSGGSGGSGG  1320
STNLSDIIEK ETGKQLVIQE SILMLPEEVE EVIGNKPESD ILVHTAYDES TDENVMLLTS  1380
DAPEYKPWAL VIQDSNGENK IKMLSGGSGG SGGSTNLSDI IEKETGKQLV IQESILMLPE  1440
EVEEVIGNKP ESDILVHTAY DESTDENVML LTSDAPEYKP WALVIQDSNG ENKIKML     1497
```

```
SEQ ID NO: 97          moltype = AA  length = 1497
FEATURE                Location/Qualifiers
source                 1..1497
                       mol_type = protein
                       organism = synthetic construct
SEQUENCE: 97
PKKKRKVSSE TGPVAVDPTL RRRIEPHEFE VFFDPRELRK ETCLLYEINW GGRHSIWRHT  60
SQNTNKHVEV NFIEKFTTER YFCPNTRCSI TWFLSWSPCG ECSRAITEFL SRYPHVTLFI  120
YIARLYHHAD PRNRQGLRDL ISSGVTIQIM TEQESGYCWR NFVNYSPSNE AHWPRYPHLW  180
VRLYVLELYC IILGLPPCLN ILRRKQPQLT FFTIALQSCH YQRLPPHILW ATGLKSGGSS  240
GGSSGSETPG TSESATPESS GGSSGGSMSS AIKSYKSVLR PNERKNQLLK STIQCLEDGS  300
AFFFKMLQGL FGGITPEIVR FSTEQEKQQQ DIALWCAVNW FRPVSQDSLT HTIASDNLVE  360
KFEEYYGGTA SDAIKQYFSA SIGESYYWND CRQQYYDLCR ELGVEVSDLT HDLEILCREK  420
CLAVATESNQ YNSIISVLFG TGRKEDRSVK LRITKKILEA ISNLKEIPKN VAPIQEIILN  480
VAKATKETFR QVYAGNLGAP STLERFIAKD GQKEFDLKKL QTDLKKVIRG KSKERDWCCQ  540
EELRSYVEQN TIQYDLWAWG EMFNKAHTAL KIKSTRNYNF AKQRLEQFKR IQSLNNLLVV  600
KKLNDFFDSE FFSGEETYTI CVHHLGGKRL SKLYKAWEDD PADPENAIVV LCDDLKNNFK  660
KEPIRNILRY IFTIRQECSA QDILAAAKYN QQLDRYKSQK ANPSVLGNQG FTWRNAVILP  720
EKAQRNDRPN SLDLRIWLYL KLRHPDGRWK KHHIPFYDTR FFQEIYAAGN SPVDTCQFRT  780
PRFGYHLPKL TDQTAIRVNK KHVKAAKTEA RIRLAIQQGT LPVSNLKITR ISATINSKGQ  840
VRIPVKFDVG RQKGTLQIGD RFCGYDQNQT ASHAYSLWEV VKEGQYHKEL GCFVRFISSG  900
DIVSITENRG NQFDQLSYEG LAYPQYADWR KKASKFVSLW QITKKNKKKE IVTVEAKEKF  960
DAICKYQPRL YKFNKEYAYL LRDIVRGKSL VELQQIRQEI FRFIEQDCGV TRLGSLSLST  1020
LETVKAVKGI IYSYFSTALN ASKNNPISDE QRKEFDPELF ALLEKLELIR TRKKKQKVER  1080
IANSLIQTCL ENNIKFIRGE GDLSTTNNAT KKKANSRSMD WLARGVFNKI RQLAPMHNIT  1140
LFGCGSLYTS HQDPLVHRNP DKAMRARFEE VNVSNVSEWH MRNFSNYLRA DSGTGLYYKQ  1200
ATLDFLKHYD LEEHADDLEK QNIKFYDFRK ILEDKQLTSV IVPKRGGRIY MATNPVTSDS  1260
TPVTYAGKTY NRCNAAHVAA ANIALTVKGI GEQSSDEENP DGSRIKLQLT SSGGSGGSGG  1320
STNLSDIIEK ETGKQLVIQE SILMLPEEVE EVIGNKPESD ILVHTAYDES TDENVMLLTS  1380
DAPEYKPWAL VIQDSNGENK IKMLSGGSGG SGGSTNLSDI IEKETGKQLV IQESILMLPE  1440
EVEEVIGNKP ESDILVHTAY DESTDENVML LTSDAPEYKP WALVIQDSNG ENKIKML     1497

SEQ ID NO: 98          moltype = DNA  length = 23
FEATURE                Location/Qualifiers
source                 1..23
                       mol_type = other DNA
                       organism = synthetic construct
SEQUENCE: 98
ttctctatca ctgataggga gtg                                          23

SEQ ID NO: 99          moltype = DNA  length = 68
FEATURE                Location/Qualifiers
source                 1..68
                       mol_type = other DNA
                       organism = Homo sapiens
SEQUENCE: 99
agtcatggtg ttcttcaaca tatccaaaca aattgggcac attaattcac tgtgtagact  60
tcgaggtg                                                           68

SEQ ID NO: 100         moltype = DNA  length = 71
FEATURE                Location/Qualifiers
source                 1..71
                       mol_type = other DNA
                       organism = Homo sapiens
SEQUENCE: 100
agtcatggtg ttcttcaaca tatccaattt atttattctt ctacaactac ccacaaaacc  60
taaaccttct g                                                       71

SEQ ID NO: 101         moltype = DNA  length = 72
FEATURE                Location/Qualifiers
source                 1..72
                       mol_type = other DNA
                       organism = Homo sapiens
SEQUENCE: 101
gtcatggtgt tcttcaacat atccaaattg tttagacttc ttaaattaaa cacaatacct  60
aaatcttcta cc                                                      72

SEQ ID NO: 102         moltype = DNA  length = 71
FEATURE                Location/Qualifiers
source                 1..71
                       mol_type = other DNA
                       organism = Homo sapiens
SEQUENCE: 102
tagtcatggt gttcttcaac atatccaaat tgtgtagaca tctacaagaa accagtatac  60
ctcaatctca t                                                       71

SEQ ID NO: 103         moltype = DNA  length = 76
FEATURE                Location/Qualifiers
```

-continued

```
source               1..76
                     mol_type = other DNA
                     organism = Homo sapiens
SEQUENCE: 103
tcttcaacat atcctaattg tttgtgcttc gacttttcaa cactatacct caatcttcaa  60
ccactgtttc ttggcc                                                  76

SEQ ID NO: 104       moltype = DNA  length = 87
FEATURE              Location/Qualifiers
source               1..87
                     mol_type = other DNA
                     organism = Homo sapiens
SEQUENCE: 104
tcttcaacat atcctaattg tttgtgcttc gacttttcaa cactatacct caatcttcaa  60
ccactgtttc ttggccaaca gtaattg                                      87

SEQ ID NO: 105       moltype = DNA  length = 80
FEATURE              Location/Qualifiers
source               1..80
                     mol_type = other DNA
                     organism = Homo sapiens
SEQUENCE: 105
cttcaacata tccaaactgt ttgggctcct taattcaaag agtatattta aatgttatac  60
ctttgtttct tagccaacag                                              80
```